United States Patent
Vrijbloed et al.

(10) Patent No.: US 7,582,604 B2
(45) Date of Patent: Sep. 1, 2009

(54) TEMPLATE-FIXED PEPTIDOMIMETICS WITH ANTIBACTERIAL ACTIVITY

(75) Inventors: Jan Wim Vrijbloed, Zurich (CH); Daniel Obrecht, Battwil (CH); John Anthony Robinson, Wermatswil (CH); Odile Sellier, Sausheim (FR); Marc Kessler, Bischheim (FR)

(73) Assignees: Polyphor Ltd., Allschwil (CH); Universität Zürich, Zürich (CH)

( * ) Notice: Subject to any disclaimer, the term of this patent is extended or adjusted under 35 U.S.C. 154(b) by 289 days.

(21) Appl. No.: 11/062,021

(22) Filed: Feb. 18, 2005

(65) Prior Publication Data

US 2005/0239693 A1     Oct. 27, 2005

Related U.S. Application Data

(63) Continuation of application No. PCT/EP02/09278, filed on Aug. 20, 2002.

(51) Int. Cl.
*A61K 38/12* (2006.01)
*C07K 7/64* (2006.01)

(52) U.S. Cl. ............................................ 514/9; 530/317
(58) Field of Classification Search ........................ None
See application file for complete search history.

(56) References Cited

U.S. PATENT DOCUMENTS

| 7,253,146 B2 * | 8/2007 | Obrecht et al. ................. 514/11 |
| 2004/0171066 A1 * | 9/2004 | Obrecht et al. ................ 435/7.1 |

FOREIGN PATENT DOCUMENTS

| WO | WO 98/16549 A1 | 4/1998 |
| WO | WO 01/16161 A1 | 3/2001 |
| WO | WO 02/70547 A1 | 9/2002 |

OTHER PUBLICATIONS

R.B. Merrifield. "Solid-Phase Peptide Synthesis." in Advances in Enzymology vol. 32. (1969) pp. 221-296.*

Aumelas et al.; Synthesis and solution structure of the antimicrobial peptide protegrin-1; Eur. J. Biochem., vol. 237, 1996, pp. 575-583.
Robinson; The Design, Synthesis and Conformation of Some New β-Hairpin Mimetics: Novel Reagents for Drug and Vaccine Discovery; Synlett, No. 4, 1999, pp. 429-441.
International Search Report for International Application No. PCT/EP02/09278, mailed Mar. 31, 2003.
International Preliminary Examination Report for International Application No. PCT1EP02/09278, dated May 19, 2004.
Gibbs, Alan C., et al., "Probing the Structural Determinants of Type II' Beta-Turn Formation in Peptides and Proteins", Journal of the American Chemical Society, vol. 124, No. 7, 1203-1213, 2002.
Späth, et al., "Stabilization of a Beta-Hairpin Conformation in a Cyclic Peptide Using the Templating Effect of a Heterochiral Diproline Unit", Helvetica Chimica Acta, vol. 81, 1726-1738, (1998).
Jiang, et al., "Combinatorial Biomimetic Chemistry: Parallel Synthesis of a Small Library of Beta-Hairpin Mimetics Based on Loop II from Human Platelet-Derived Growth Factor B", Helvetica Chimica Acta, vol. 83, 3097-3112, (2000).
Ripka, W.C., et al., "Protein Beta-Turn Mimetics II: Design, Synthesis, and Evaluation in the Cyclic Peptide Gramicidin S", Tetrahedron, vol. 49, No. 17, 3609-3628, (1993).

* cited by examiner

*Primary Examiner*—Andrew D Kosar
(74) *Attorney, Agent, or Firm*—Hoffmann & Baron, LLP

(57) ABSTRACT

Template-fixed β-hairpin peptidomimetics of the general formula (I), wherein Z is a template-fixed chain of 12 α-amino acid residues which, depend on their positions in the chain (counted starting from the N-terminal amino acid) are Gly, or Pro, or of certain types which, as the remaining symbols in the above formula, are defined in the description and the claims, and salts thereof, have the property to selectively inhibit the growth of or to kill microorganisms such as *Pseudomonas aeruginosa* and *Acinetobacter*. They can be used as disinfectants for foodstuff, cosmetics, medicaments or other nutrient-containing materials, or as medicaments or treat or prevent infections. In a specific embodiment, the template is based on the D-Pro-L-Pro dipeptide. These β-hairpin peptidomimetics can be manufactured by processes which are based on a mixed solid- and solution phase synthetic strategy.

13 Claims, No Drawings

SEQUENCE LISTING

```
<160> NUMBER OF SEQ ID NOS: 8

<210> SEQ ID NO 1
<211> LENGTH: 14
<212> TYPE: PRT
<213> ORGANISM: Artificial Sequence
<220> FEATURE:
<223> OTHER INFORMATION: antimicrobial cyclic peptide sequence based on
      Protegrin 1 peptide
<220> FEATURE:
<221> NAME/KEY: MISC_FEATURE
<222> LOCATION: (13)..(13)
<223> OTHER INFORMATION: Pro in postion 13 is a D-Pro

<400> SEQUENCE: 1

Arg Trp Leu Lys Lys Arg Arg Trp Leu Tyr Tyr Arg Pro Pro
1               5                   10

<210> SEQ ID NO 2
<211> LENGTH: 14
<212> TYPE: PRT
<213> ORGANISM: Artificial Sequence
<220> FEATURE:
<223> OTHER INFORMATION: antimicrobial cyclic peptide sequence based on
```

```
                Protegrin 1 peptide
<220> FEATURE:
<221> NAME/KEY: MISC_FEATURE
<222> LOCATION: (13)..(13)
<223> OTHER INFORMATION: Pro in position 13 is a D-Pro

<400> SEQUENCE: 2

Arg Trp Leu Lys Lys Arg Arg Trp Lys Tyr Val Arg Pro Pro
1               5                   10

<210> SEQ ID NO 3
<211> LENGTH: 14
<212> TYPE: PRT
<213> ORGANISM: Artificial Sequence
<220> FEATURE:
<223> OTHER INFORMATION: antimicrobial cyclic peptide sequence based on
      Protegrin 1 peptide
<220> FEATURE:
<221> NAME/KEY: MISC_FEATURE
<222> LOCATION: (13)..(13)
<223> OTHER INFORMATION: Pro in position 13 is D-Pro

<400> SEQUENCE: 3

Arg Trp Leu Lys Lys Arg Arg Trp Lys Thr Tyr Arg Pro Pro
1               5                   10

<210> SEQ ID NO 4
<211> LENGTH: 14
<212> TYPE: PRT
<213> ORGANISM: Artificial Sequence
<220> FEATURE:
<223> OTHER INFORMATION: antimicrobial cyclic peptide sequence based on
      Protegrin 1 peptide
<220> FEATURE:
<221> NAME/KEY: MISC_FEATURE
<222> LOCATION: (13)..(13)
<223> OTHER INFORMATION: Pro in position 13 is a D-Pro

<400> SEQUENCE: 4

Arg Trp Leu Lys Lys Arg Arg Trp Lys Gln Tyr Arg Pro Pro
1               5                   10

<210> SEQ ID NO 5
<211> LENGTH: 14
<212> TYPE: PRT
<213> ORGANISM: Artificial sequence
<220> FEATURE:
<223> OTHER INFORMATION: antimicrobial cyclic peptide sequence based on
      Protegrin 1 peptide
<220> FEATURE:
<221> NAME/KEY: MISC_FEATURE
<222> LOCATION: (13)..(13)
<223> OTHER INFORMATION: Pro in position 13 is D-Pro

<400> SEQUENCE: 5

Arg Trp Leu Val Lys Arg Arg Trp Lys Tyr Tyr Arg Pro Pro
1               5                   10

<210> SEQ ID NO 6
<211> LENGTH: 14
<212> TYPE: PRT
<213> ORGANISM: Artificial sequence
<220> FEATURE:
<223> OTHER INFORMATION: antimicrobial cyclic peptide sequence based on
      Protegrin 1 peptide
<220> FEATURE:
<221> NAME/KEY: MISC_FEATURE
<222> LOCATION: (13)..(13)
<223> OTHER INFORMATION: Pro in position 13 is D-Pro

<400> SEQUENCE: 6
```

```
Arg Trp Leu Lys Lys Arg Arg Trp Val Tyr Tyr Arg Pro Pro
1               5                   10

<210> SEQ ID NO 7
<211> LENGTH: 14
<212> TYPE: PRT
<213> ORGANISM: Artificial sequence
<220> FEATURE:
<223> OTHER INFORMATION: antimicrobial cyclic peptide sequence based on
      Protegrin 1 peptide
<220> FEATURE:
<221> NAME/KEY: MISC_FEATURE
<222> LOCATION: (13)..(13)
<223> OTHER INFORMATION: Pro in position 13 is a D-Pro

<400> SEQUENCE: 7

Arg Trp Leu Lys Lys Arg Arg Trp Lys Tyr Gln Arg Pro Pro
1               5                   10

<210> SEQ ID NO 8
<211> LENGTH: 14
<212> TYPE: PRT
<213> ORGANISM: Artificial sequence
<220> FEATURE:
<223> OTHER INFORMATION: antimicrobial cyclic peptide sequence based on
      Protegrin 1 peptide
<220> FEATURE:
<221> NAME/KEY: MISC_FEATURE
<222> LOCATION: (13)..(13)
<223> OTHER INFORMATION: Pro in position 13 is D-Pro

<400> SEQUENCE: 8

Arg Trp Leu Lys Lys Arg Arg Trp Lys Tyr Leu Arg Pro Pro
1               5                   10
```

TEMPLATE-FIXED PEPTIDOMIMETICS WITH ANTIBACTERIAL ACTIVITY

CROSS REFERENCE TO RELATED APPLICATION

This application is a continuation of International Application No. PCT/EP/2002/009278, filed Aug. 20, 2002.

The present invention provides template-fixed β-hairpin peptidomimetics incorporating a template-fixed chain of 12 α-amino acid residues which, depending on their positions in the chain, are Gly or Pro, or of certain types, as defined herein below. These template-fixed β-hairpin mimetics have a selective antimicrobial activity. In addition, the present invention provides efficient synthetic processes by which these compounds can, if desired, be made in parallel library-format. These β-hairpin peptidomimetics show improved efficacy, bioavailability, half-life and most importantly a significantly enhanced ratio between antibacterial activity on the one hand, and hemolysis of red blood cells on the other.

The growing problem of microbial resistance to established antibiotics has stimulated intense interest in developing novel antimicrobial agents with new modes of action (H. Breithaupt, *Nat. Biotechnol.* 1999, 17, 1165-1169). One emerging class of antibiotics is based on naturally occurring cationic peptides (T. Ganz, R. I. Lehrer, *Mol. Medicine Today* 1999, 5, 292-297; R. M. Epand, H. J. Vogel, *Biochim. Biophys. Acta* 1999,1462, 11-28). These include disulfide-bridged β-hairpin and β-sheet peptides (such as the protegrins [V. N. M.; O. V. Shamova, H. A. Korneva, R. I. Lehrer, *FEBS Lett.* 1993, 327, 231-236], tachyplesins [T. Nakamura, H. Furunaka, T. Miyata, F. Tokunaga, T. Muta, S. Iwanaga, M. Niwa, T. Takao, Y. Shimonishi, Y. *J. Biol. Chem.* 1988, 263, 16709-16713], and the defensins [R. I. Lehrer, A. K. Lichtenstein, T. Ganz, *Annu. Rev. Immunol.* 1993, 11, 105-128], amphipathic α-helical peptides (e.g. cecropins, dermaseptins, magainins, and mellitins [A. Tossi, L. Sandri, A. Giangaspero, *Biopolymers* 2000, 55, 4-30]), as well as other linear and loop-structured peptides. Although the mechanisms of action of antimicrobial cationic peptides are not yet fully understood, their primary site of interaction is the microbial cell membrane (H. W. Huang, Biochemistry 2000, 39, 8347-8352). Upon exposure to these agents, the cell membrane undergoes permeabilization, which is followed by rapid cell death. However, more complex mechanisms of action, for example, involving receptor-mediated signaling, cannot presently be ruled out (M. Wu, E. Maier, R. Benz, R. E. Hancock, *Biochemistry* 1999, 38, 7235-7242).

The antimicrobial activities of many of these cationic peptides usually correlate with their preferred secondary structures, observed either in aqueous solution or in membrane-like environments (N. Sitaram, R. Nagaraj, *Biochim. Biophys. Acta* 1999, 1462, 29-54). Structural studies by nuclear magnetic resonance (NMR) spectroscopy have shown that cationic peptides such as protegrin 1 (A. Aumelas, M. Mangoni, C. Roumestand, L. Chiche, E. Despaux, G. Grassy, B. Calas, A. Chavanieu, A. *Eur. J. Biochem.* 1996, 237, 575-583; R. L. Fahrner, T. Dieckmann, S. S. L. Harwig, R. I. Lehrer, D. Eisenberg, J. Feigon, *J. Chem. Biol.* 1996, 3, 543-550) and tachyplesin I (K. Kawano, T. Yoneya, T. Miyata, K. Yoshikawa, F. Tokunaga, Y. Terada, S. J. Iwanaga, S. *J. Biol. Chem.* 1990, 265, 15365-15367) adopt well defined β-hairpin conformations, due to the constraining effect of two disulfide bridges. In protegrin analogues lacking one or both of these disulfide bonds, the stability of the β-hairpin conformation is diminished, and the antimicrobial activity is reduced (J. Chen, T. J. Falla, H. J. Liu, M. A. Hurst, C. A. Fujii, D. A. Mosca, J. R. EmbreeD. J. Loury, P. A. Radel, C. C. Chang, L. Gu, J. C. Fiddes, *Biopolymers* 2000, 55, 88-98; S. L. Harwig, A. Waring, H. J. Yang, Y. Cho, L. Tan, R. I. Lehrer, R. J. *Eur. J. Biochem.* 1996, 240, 352-357; M. E. Mangoni, A. Aumelas, P. Charnet, C. Roumestand, L. Chiche, E. Despaux, G. Grassy, B. Calas, A. Chavanieu, *FEBS Lett.* 1996, 383, 93-98; H. Tamamura, T. Murakami, S. Noriuchi, K. Sugihara, A. Otaka, W. Takada, T. Ibuka, M. Waki, N. Tamamoto, N. Fujii, *Chem. Pharm. Bull.* 1995, 43, 853-858). Similar observations have been made in analogues of tachyplesin I (H. Tamamura, R. Ikoma, M. Niwa, S. Funakoshi, T. Murakami, N. Fujii, *Chem. Pharm. Bull.* 1993, 41, 978-980) and in hairpin-loop mimetics of rabbit defensin NP-2 (S. Thennarasu, R. Nagaraj, *Biochem. Biophys. Res. Comm.* 1999, 254, 281-283). These results show that the β-hairpin structure plays an important role in the antimicrobial activity and stability of these protegrin-like peptides. In the case of the cationic peptides preferring α-helical structures, the amphililic structure of the helix appears to play a key role in determining antimicrobial activity (A. Tossi, L. Sandri, A. Giangaspero, A. *Biopolymers* 2000, 55, 4-30). Gramicidin S is a backbone-cyclic peptide with a well defined β-hairpin structure (S. E. Hull, R. Karlsson, P. Main, M. M. Woolfson, E. J. Dodson, *Nature* 1978, 275, 206-275) that displays potent antimicrobial activity against gram-positive and gram-negative bacteria (L. H. Kondejewski, S. W. Farmer, D. S. Wishart, R. E. Hancock, R. S. Hodges, *Int. J. Peptide Prot. Res.* 1996, 47, 460-466). The high hemolytic activity of gramicidin S has, however, hindered its widespread use as an antibiotic. Recent structural studies by NMR have indicated that the high hemolytic activity apparently correlates with the highly amphipathic nature of this cyclic β-hairpin-like molecule, but that it is possible to dissociate antimicrobial and hemolytic activities by modulating the conformation and amphiphilicity (L. H. Kondejewski, M. Jelokhani-Niaraki, S. W. Farmer, B. Lix, M. Kay, B. D. Sykes, R. E. Hancock, R. S. Hodges, *J. Biol. Chem.* 1999, 274, 13181-13192; C. McInnes L. H. Kondejewski, R. S. Hodges, B. D. Sykes, *J. Biol. Chem.* 2000, 275, 14287-14294).

A new cyclic antimicrobial peptide RTD-1 was reported recently from primate leukocytes (Y.-Q. Tang, J. Yuan, G. Ösapay, K. Ösapay, D. Tran, C. J. Miller, A. J. Oellette, M. E. Selsted, *Science* 1999, 286, 498-502. This peptide contains three disulfide bridges, which act to constrain the cyclic peptide backbone into a hairpin geometry. Cleavage of the three disulfide bonds leads to a significant loss of antimicrobial activity. Analogues of protegrins (J. P. Tarn, C. Wu, J.-L. Yang, *Eur. J. Biochem.* 2000, 267, 3289-3300) and tachyplesins (J.-P. Tam, Y.-A. Lu, J.-L. Yang, *Biochemistry* 2000, 39, 7159-7169; N. Sitaram, R. Nagaraij, *Biochem. Biophys. Res. Comm.* 2000, 267, 783-790) containing a cyclic peptide backbone, as well as multiple disulfide bridges to enforce a amphiphilic hairpin structure, have also been reported. In these cases, removal of all the cystine constraints does not always lead to a large loss of antimicrobial activity, but does modulate the membranolytic selectivity (J. P. Tam, C. Wu, J.-L. Yang, *Eur. J. Biochem.* 2000, 267, 3289-3300).

A key issue in the design of new selective cationic antimicrobial peptides are bioavailability, stability and reduced haemolytic activity. The naturally occurring protegrins and tachyplesins exert a significant hemolytic activity against human red blood cells. This is also the case for protegrin analogues such as IB367 (J. Chen, T. J. Falla, H. J. Liu, M. A. Hurst, C. A. Fujii, D. A. Mosca, J. R. Embree, D. J. Loury, P. A. Radel, C. C. Chang, L. Gu, J. C. Fiddes, *Biopolymers* 2000, 55, 88-98; C. Chang, L. Gu, J. Chen, U.S. Pat. No. 5,916,872, 1999). This high hemolytic activity essentially obviates its use in vivo, and represents a serious disadvantage in clinical applications. Also, the antibiotic activity of analogues often decreases significantly with increasing salt concentration, such that under in vivo conditions (ca. 100-150 mM NaCl) the antimicrobial activity may be severely reduced.

Protegrin 1 exhibits potent and similar activity against gram-positive and gram-negative bacteria as well as fungi in both low- and high-salt assays. This broad antimicrobial activity combined with a rapid mode of action, and their ability to kill bacteria resistant to other classes of antibiotics, make them attractive targets for development of clinically useful antibiotics. The activity against gram-positive bacteria is typically higher than against gram-negative bacteria. However, protegrin 1 also exhibits a high hemolytic activity against human red blood cells, and hence a low selectivity towards microbial cells. Oriented CD experiments (W. T. Heller, A. J. Waring, R. I. Lehrer, H. W. Huang, *Biochemistry* 1998, 37, 17331-17338) indicate that protegrin 1 may exist in two different states as it interacts with membranes, and these states are strongly influenced by lipid composition. Studies of cyclic protegrin analogues (J.-P. Tam, C. Wu, J.-L. Yang, *Eur. J. Biochem.* 2000, 267, 3289-3300) have revealed, that an increase in the conformational rigidity, resulting from backbone cyclization and multiple disulfide bridges, may confer membranolytic selectivity that dissociates antimicrobial activity from hemolytic activity, at least in the series of compounds studied.

Protegrin 1 is an 18 residues linear peptide, with an amidated carboxyl terminus and two disulfide bridges. Tachyplesin I contains 17 residues, also has an amidated carboxyl terminus and contains two disulfide bridges. Recently described backbone-cyclic protegrin and tachyplesin analogues typically contain 18 residues and up to three disulfide bridges (J. P. Tam, C. Wu, J.-L. Yang, *Eur. J. Biochem.* 2000, 267, 3289-3300; J. P. Tam, Y.-A. Lu, J.-L. Yang, *Biochemistry* 2000, 39, 7159-7169; N. Sitaram, R. Nagaraij, *Biochem. Biophys. Res. Comm.* 2000, 267, 783-790).

Cathelicidin, a 37-residue linear helical-type cationic peptide, and analogues are currently under investigation as inhaled therapeutic agents for *cystic fibrosis* (CF) lung disease (L. Saiman, S. Tabibi, T. D. Starner, P. San Gabriel, P. L. Winokur, H. P. Jia, P. B. McGray, Jr., B. F. Tack, *Antimicrob. Agents and Chemother.* 2001, 45, 2838-2844; R. E. W. Hancock, R. Lehrer, *Trends Biotechnol.* 1998, 16, 82-88). Over 80% of CF patients become chronically infected with *pseudomonas aeruginosa* (C. A. Demko, P. J. Biard, P. B. Davies, *J. Clin. Epidemiol.* 1995, 48, 1041-1049; E. M. Kerem, R. Gold, H. Levinson, *J. Pediatr.* 1990, 116, 714-719). Other antimicrobial peptides against Pseudomonads (Y. H. Yau, B. Ho, N. S. Tan, M. L. Ng, J. L. Ding, *Antimicrob. Agents and Chemother.* 2001, 45, 2820-2825 and herein cited references), like FALL-39, SMAP-29, and lepidopteran cecropin display a few of the desired attributes like potent antimicrobial activity over a wide range of pH, rapid killing rate, and low hemolytic activity.

In the compounds described below, a new strategy is introduced to stabilize β-hairpin conformations in backbone-cyclic cationic peptide mimetics exhibiting selective antimicrobial activity. This involves transplanting the cationic and hydrophobic hairpin sequence onto a template, whose function is to restrain the peptide loop backbone into a hairpin geometry.

Template-bound hairpin mimetic peptides have been described in the literature (D, Obrecht, M. Altorfer, J. A. Robinson, *Adv. Med. Chem.* 1999, 4, 1-68; J. A. Robinson, *Syn. Lett.* 2000, 4, 429-441), but such molecules have not previously been evaluated for development of selective antimicrobial peptides. However, the ability to generate β-hairpin peptidomimetics using combinatorial and parallel synthesis methods has now been established (L. Jiang, K. Moehle, B. Dhanapal, D. Obrecht, J. A. Robinson, *Helv. Chim. Acta.* 2000, 83, 3097-3112). These methods allow the synthesis and screening of large hairpin mimetic libraries, which in turn considerably facilitates structure-activity studies, and hence the discovery of new molecules with potent selective antimicrobial and very low hemolytic activity to human red blood cells. The present strategy allows to synthesize β-hairpin peptidomimetics with novel selectivities towards various multi-drug resistant *pseudomonas-* or *acinetobacter* strains.

The β-hairpin peptidomimetics of the present invention are compounds of the general formula

(I)

wherein

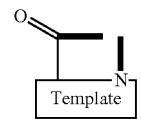

is a group of one of the formulae

(a1)

(a2)

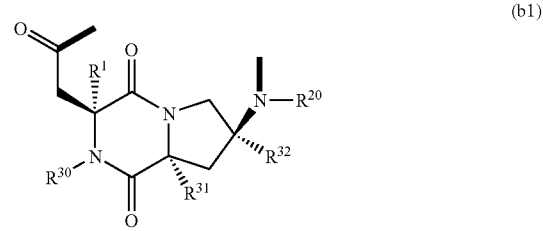

(b1)

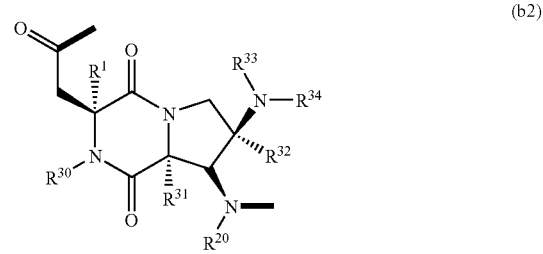

(b2)

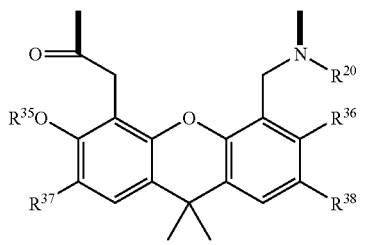
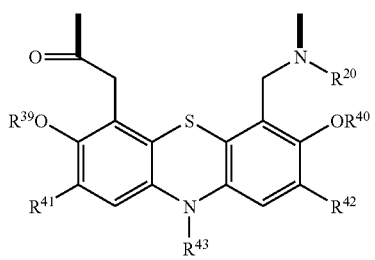
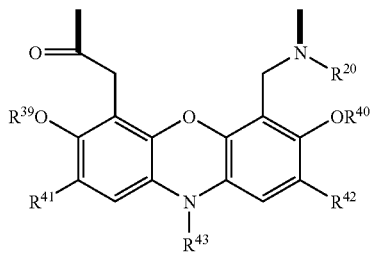
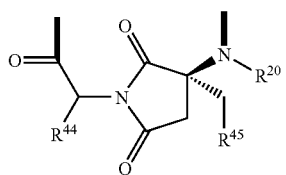
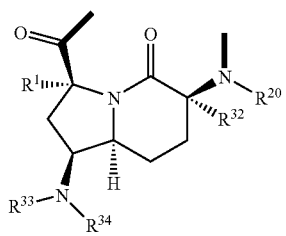
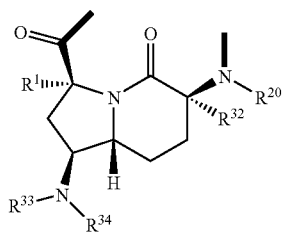
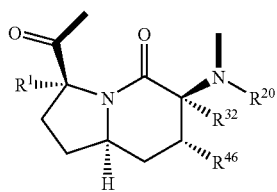
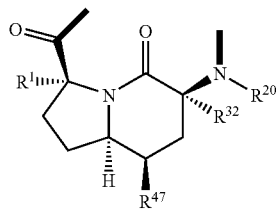
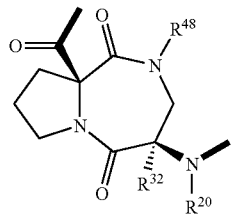
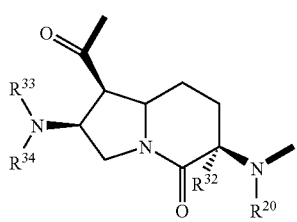
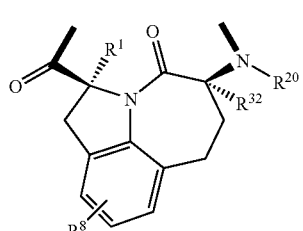
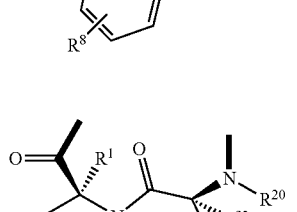
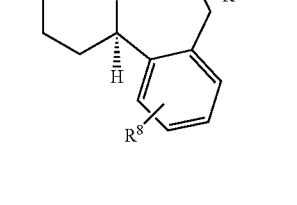
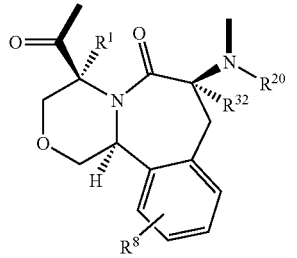

-continued
(i3)
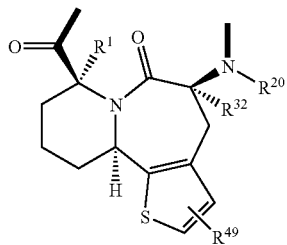
(i4)
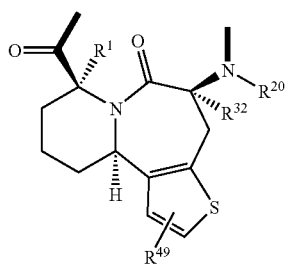
(j)
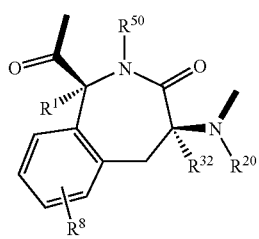
(k)
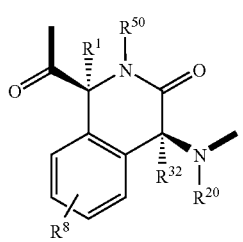
(l)
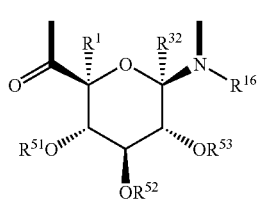
(m)
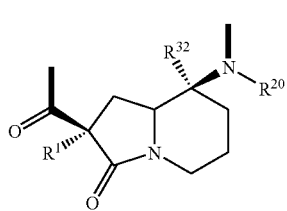
-continued
(n)
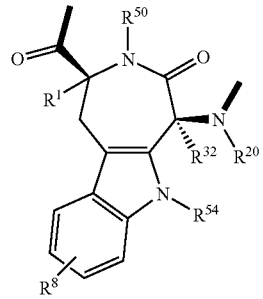
(o)
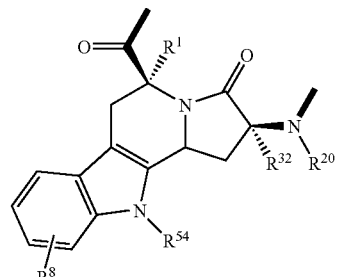
and
(p)
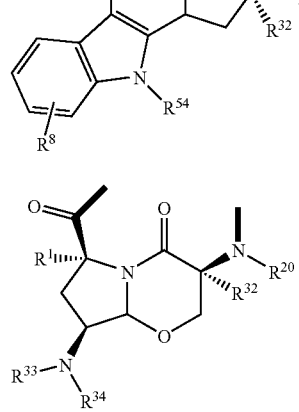
wherein
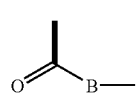
is the residue of an L-α-amino acid with B being a residue of formula —NR$^{20}$CH(R$^{71}$)— or the enantiomer of one of the groups A1 to A69 as defined hereinafter;
is a group of one of the formulae
A1
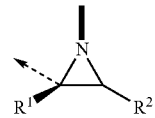
A2
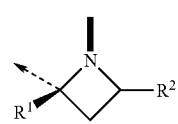

-continued
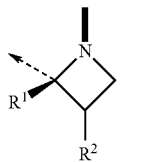 A3
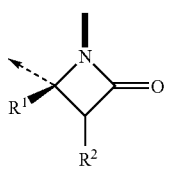 A4
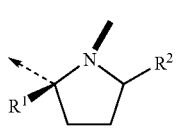 A5
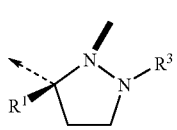 A6
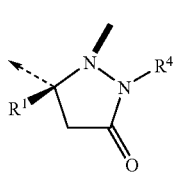 A7
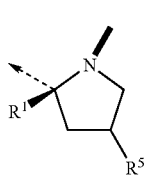 A8
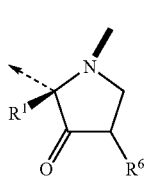 A9
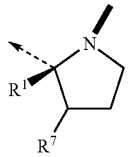 A10
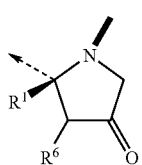 A11
-continued
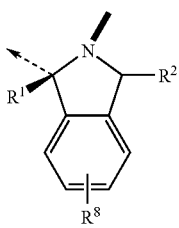 A12
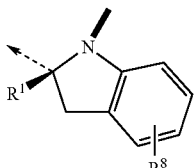 A13
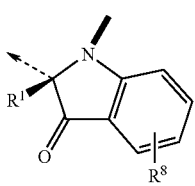 A14
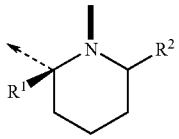 A15
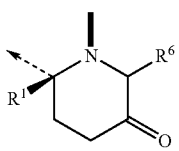 A16
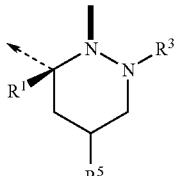 A17
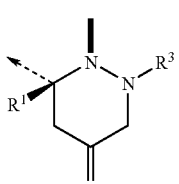 A18
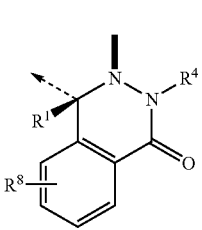 A19

-continued
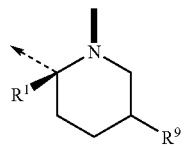 A20
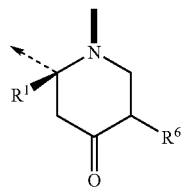 A21
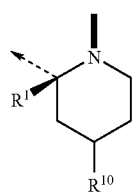 A22
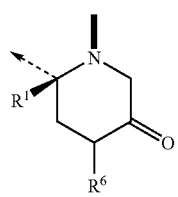 A23
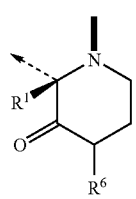 A24
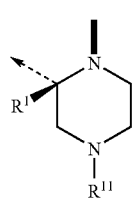 A25
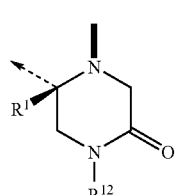 A26
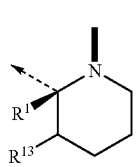 A27
-continued
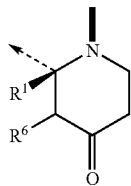 A28
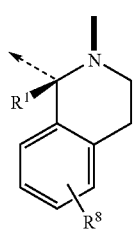 A29
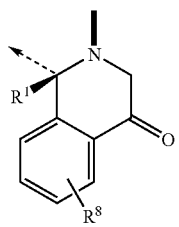 A30
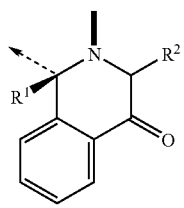 A31
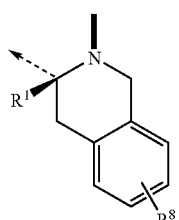 A32
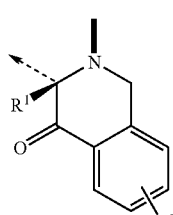 A33
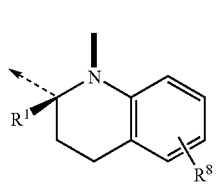 A34

-continued
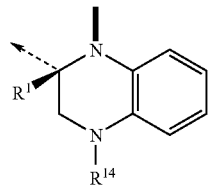 A35
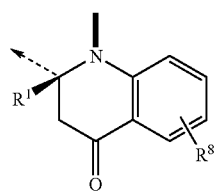 A36
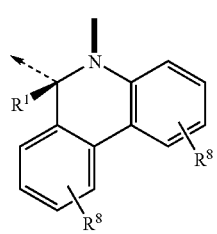 A37
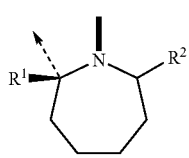 A38
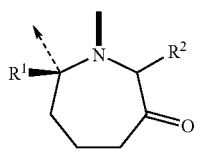 A39
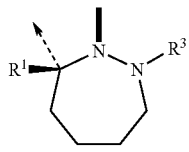 A40
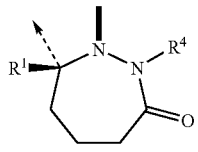 A41
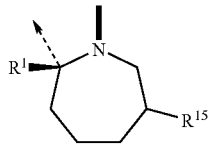 A42
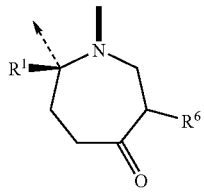 A43
-continued
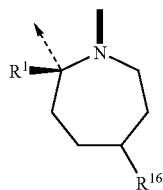 A44
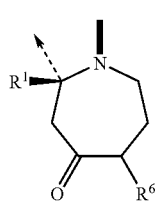 A45
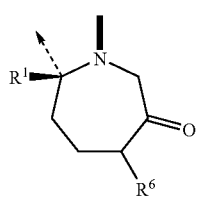 A46
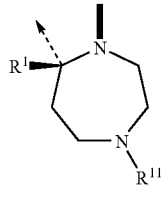 A47
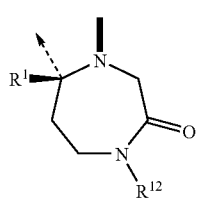 A48
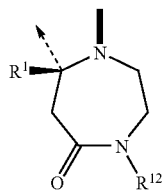 A49
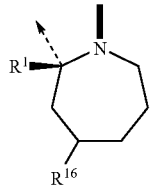 A50
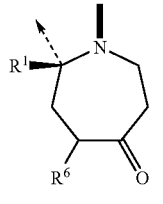 A51

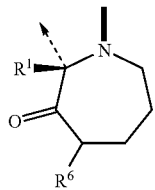
A52
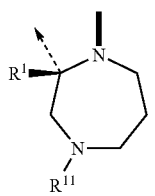
A53
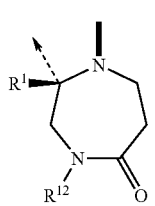
A54
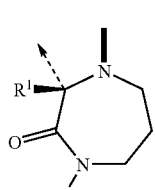
A55
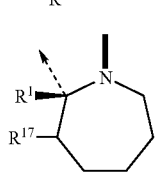
A56
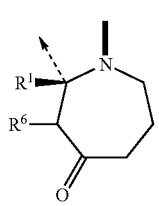
A57
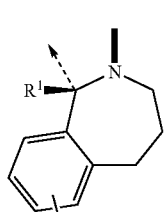
A58
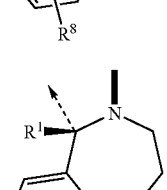
A59
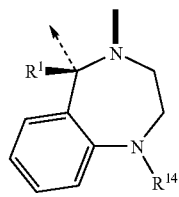
A60
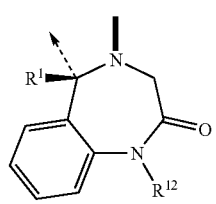
A61
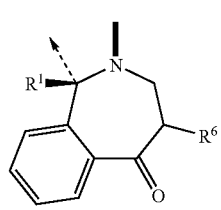
A62
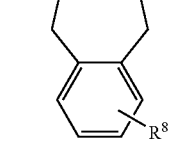
A63
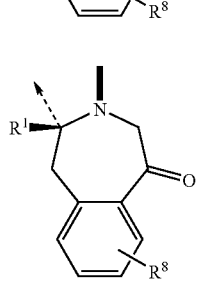
A64
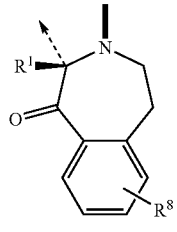
A65
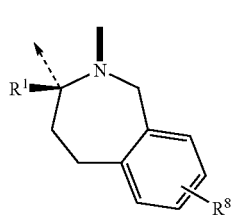
A66

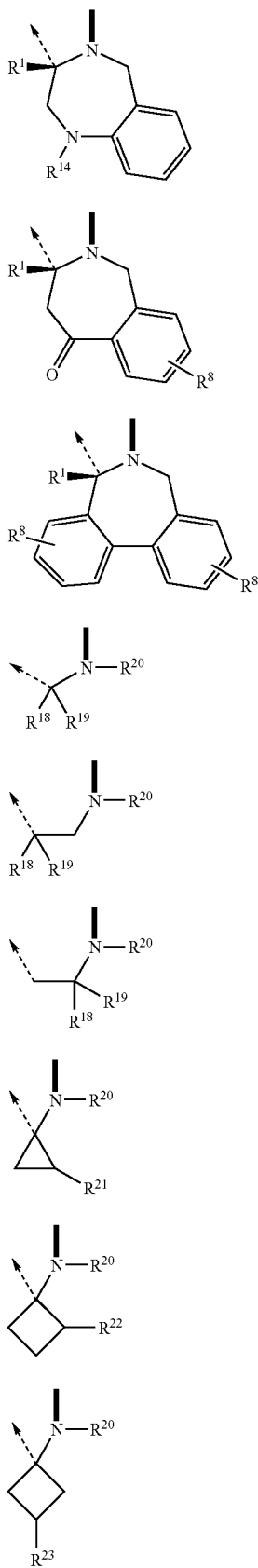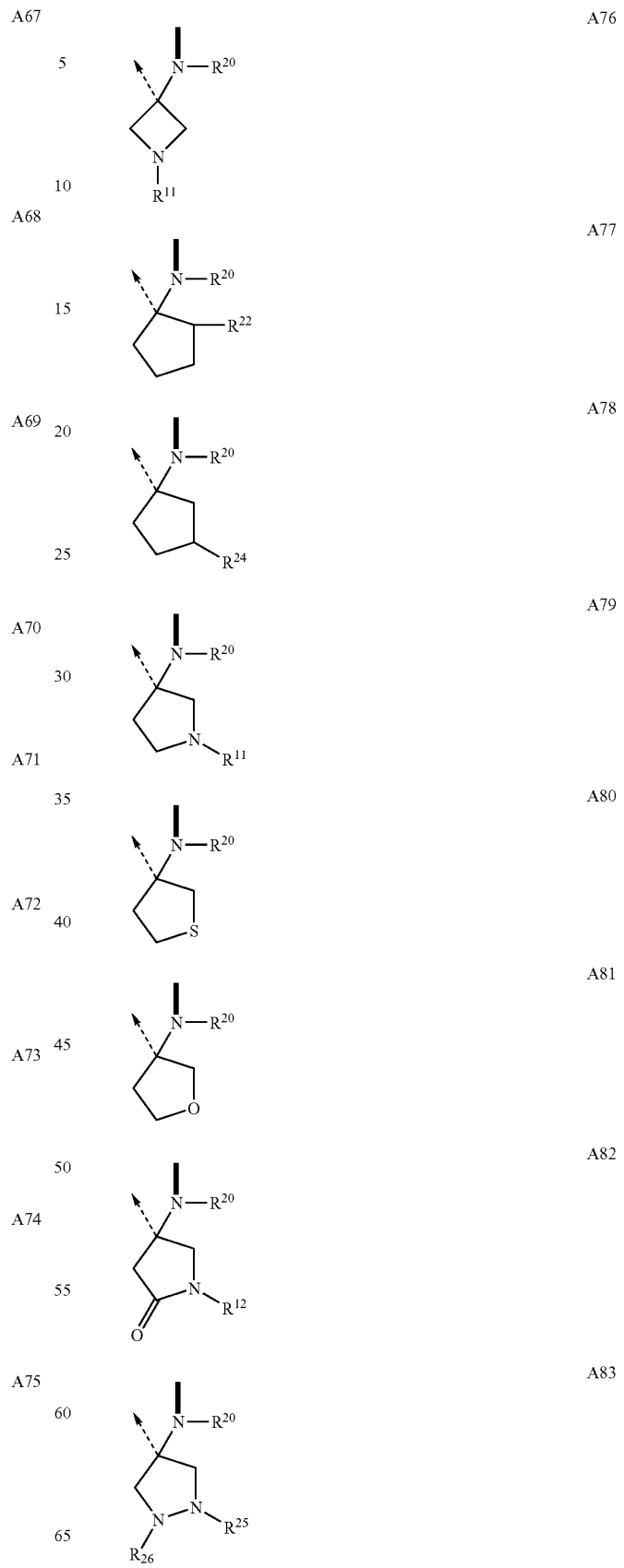

-continued
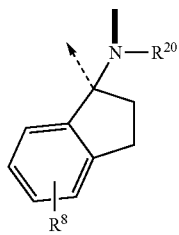 A84
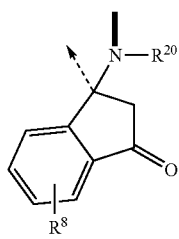 A85
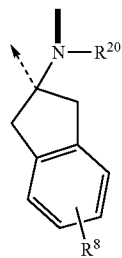 A86
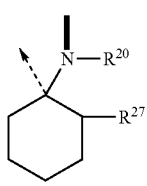 A87
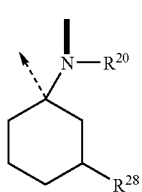 A88
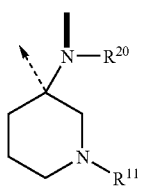 A89
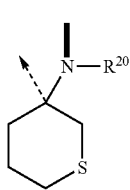 A90
-continued
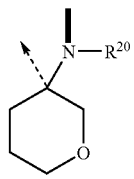 A91
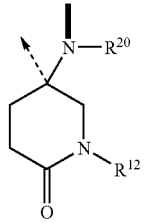 A92
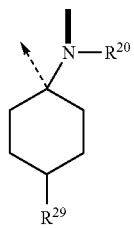 A93
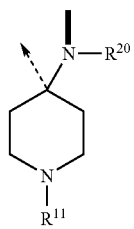 A94
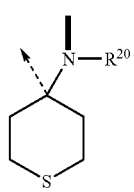 A95
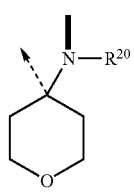 A96
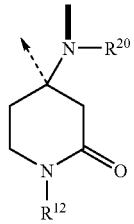 A97

-continued

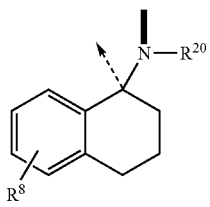
A98

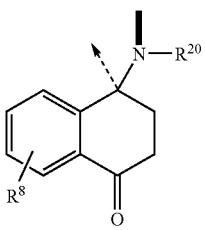
A99

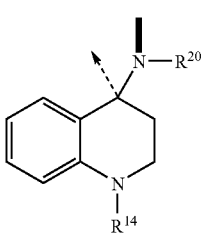
A100

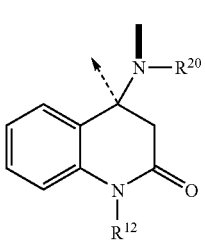
A101

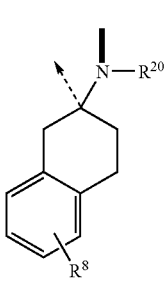
A102

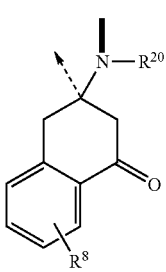
A103 and

-continued

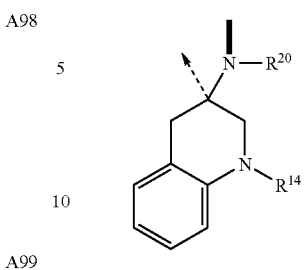
A104

$R^1$ is H; lower alkyl; or aryl-lower alkyl;

$R^2$ is H; alkyl; alkenyl; —$(CH_2)_m(CHR^{61})_sOR^{55}$; —$(CH_2)_m(CHR^{61})_sSR^{56}$; —$(CH_2)_m(CHR^{61})_sNR^{33}R^{34}$; —$(CH_2)_m(CHR^{61})_sOCONR^{33}R^{75}$; —$(CH_2)_m(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_s C_6H_4R^8$;

$R^3$ is H; alkyl; alkenyl; —$(CH_2)_m(CHR^{61})_sOR^{55}$; —$(CH_2)_m(CHR^{61})_sSR^{56}$; —$(CH_2)_m(CHR^{61})_sNR^{33}R^{34}$; —$(CH_2)_m(CHR^{61})_sOCONR^{33}R^{75}$; —$(CH_2)_m(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_sR^{62}$; or —$(CH_2)_o(CHR^{61})_s C_6H_4R^8$;

$R^4$ is H; alkyl; alkenyl; —$(CH_2)_m(CHR^{61})_sOR^{55}$; —$(CH_2)_m(CHR^{61})SR^{56}$; —$(CH_2)_m(CHR^{61})_sNR^{33}R^{34}$; —$(CH_2)_m(CHR^{61})_sOCONR^{33}R^{75}$; —$(CH_2)_m(CHR^{61})_sNR^{20}CONR^{33}R^{82}$; —$(CH_2)_p(CHR^{61})_sCOOR^{57}$; —$(CH_2)_p(CHR^{61})_sCONR^{58}R^{59}$; —$(CH_2)_p(CHR^{61})_sPO(OR^{60})_2$; —$(CH_2)_p(CHR^{61})_2SO_2R^{62}$; or —$(CH_2)_o(CHR^{61})_s C_6H_4R^8$;

$R^5$ is alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$; —$(CH_2)_o(CHR^{61})_sOCONR^{33}R^{75}$; —$(CH_2)_o(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_s C_6H_4R^8$;

$R^6$ is H; alkyl; alkenyl; —$(CH_2)_o(CHR^{61})_sOR^{55}$; —$(CH_2)_m(CHR^{61})_sSR^{56}$; —$(CH_2)_o(CHR^{61})_sNR^{33}R^{34}$; —$(CH_2)_o(CHR^{61})_sOCONR^{33}R^{75}$; —$(CH_2)_o(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_s C_6H_4R^8$;

$R^7$ is alkyl; alkenyl; —$(CH_2)_q(CHR^{61})_sOR^{55}$; —$(CH_2)_q(CHR^{61})_sNR^{33}R^{34}$; —$(CH_2)_q(CHR^{61})OCONR^{33}R^{75}$; —$(CH_2)_q(CHR^{61})_sNR^{20}CONR^{33}R^{82}$; —$(CH_2)_r(CHR^{61})_sCOOR^{57}$; —$(CH_2)_r(CHR^{61})_sCONR^{58}R^{59}$; —$(CH_2)_r(CHR^{61})_sPO(OR^{60})_2$; —$(CH_2)_r(CHR^{61})_sSO_2R^{62}$; or —$(CH_2)_s(CHR^{61})_s C_6H_4R^8$;

$R^8$ is H; Cl; F; $CF_3$; $NO_2$; lower alkyl; lower alkenyl; aryl; aryl-lower alkyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$; —$(CH_2)_o(CHR^{61})_sOCONR^{33}R^{75}$; —$(CH_2)_o(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})COR^{64}$;

$R^9$ is alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$; —$(CH_2)_o(CHR^{61})_sOCONR^{33}R^{75}$; —$(CH_2)_o(CHR^{61})_sNR^{20}CONR^{33}R^{82}$; —$(CH_2)_o(CHR^{61})_sCOOR^{57}$;

—(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{10}$ is alkyl; alkenyl; —(CH$_2$)$_o$(CHR$^{61}$)$_s$OR$^{55}$; —(CH$_2$)$_o$(CHR$^{61}$)$_s$SR$^{56}$; —(CH$_2$)$_o$(CHR$^{61}$)$_s$NR$^{33}$R$^{34}$; —(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$; —(CH$_2$)$_m$(CHR$^{61}$)COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_m$(CHR$^{61}$)SO$_2$R$^{62}$; or —(CH$_2$)$_o$(CHR$^{61}$)$_s$C$_6$H$_4$R$^8$;

R$^{11}$ is H; alkyl; alkenyl; —(CH$_2$)$_m$(CHR$^{61}$)$_s$OR$^{55}$; —(CH$_2$)$_m$(CHR$^{61}$)$_s$NR$^{33}$R$^{34}$; —(CH$_2$)$_m$(CHR$^{61}$)$_s$OCONR$^{33}$R$^{75}$; —(CH$_2$)$_m$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_m$SO$_2$R$^{62}$; or —(CH$_2$)$_o$(CHR$^{61}$)$_s$C$_6$H$_4$R$^8$;

R$^{12}$ is H; alkyl; alkenyl; —(CH$_2$)$_m$(CHR$^{61}$)$_s$OR$^{55}$; —(CH$_2$)$_m$(CHR$^{61}$)$_s$SR$^{56}$; —(CH$_2$)$_m$(CHR$^{61}$)$_s$NR$^{33}$R$^{34}$; —(CH$_2$)$_m$(CHR$^{61}$)$_s$OCONR$^{33}$R$^{75}$; —(CH$_2$)$_m$(CHR$^{61}$)NR$^{20}$CONR$^{33}$R$^{82}$; —(CH$_2$)$_s$(CHR$^{61}$)$_s$COOR$^{57}$; —(CH$_2$)$_r$(CHR$^{61}$)$_s$CONR$^{58}$R$^{59}$; —(CH$_2$)$_r$(CHR$^{61}$)$_s$PO(OR$^{60}$)$_2$; —(CH$_2$)$_r$(CHR$^{61}$)$_s$SO$_2$R$^{62}$; or —(CH$_2$)$_r$(CHR$^{61}$)$_s$C$_6$H$_4$R$^8$;

R$^{13}$ is alkyl; alkenyl; —(CH$_2$)$_q$(CHR$^{61}$)$_s$OR$^{55}$; —(CH$_2$)$_q$(CHR$^{61}$)SR$^{56}$; —(CH$_2$)$_q$(CHR$^{61}$)$_s$NR$^{33}$R$^{34}$; —(CH$_2$)$_q$(CHR$^{61}$)$_s$OCONR$^{33}$R$^{15}$; —(CH$_2$)$_q$(CHR$^{61}$)$_s$NR$^{20}$CONR$^{33}$R$^{82}$; —(CH$_2$)$_q$(CHR$^{61}$)$_s$COOR$^{57}$; —(CH$_2$)$_q$(CHR$^{61}$)$_s$CONR$^{58}$R$^{59}$; —(CH$_2$)$_q$(CHR$^{61}$)$_s$PO(OR$^{60}$)$_2$; —(CH$_2$)$_q$(CHR$^{61}$)$_s$SO$_2$R$^{62}$; or —(CH$_2$)$_q$(CHR$^{61}$)$_s$C$_6$H$_4$R$^8$;

R$^{14}$ is H; alkyl; alkenyl; —(CH$_2$)$_m$(CHR$^{61}$)$_s$OR$^{55}$; —(CH$_2$)$_m$(CHR$^{61}$)$_s$NR$^{33}$R$^{34}$; —(CH$_2$)$_m$(CHR$^{61}$)$_s$OCONR$^{33}$R$^{75}$; —(CH$_2$)$_m$(CHR$^{61}$)$_s$NR$^{20}$CONR$^{33}$R$^{82}$; —(CH$_2$)$_q$(CHR$^{61}$)$_s$COOR$^5$; —(CH$_2$)$_q$(CHR$^{61}$)$_s$CONR$^{58}$R$^{59}$; —(CH$_2$)$_q$(CHR$^{61}$)$_s$PO(OR$^{60}$)$_2$; —(CH$_2$)$_q$(CHR$^{61}$)$_s$SOR$^{62}$; or —(CH$_2$)$_q$(CHR$^{61}$)s C$_6$H$_4$R$^8$;

R$^{15}$ is alkyl; alkenyl; —(CH$_2$)$_o$(CHR$^{61}$)$_s$OR$^{55}$; —(CH$_2$)$_o$(CHR$^{61}$)$_s$SR$^{56}$; —(CH$_2$)$_o$(CHR$^{61}$)$_s$NR$^{33}$R$^{34}$; —(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$; —(CH$_2$)$_o$(CHR$^{61}$)$_2$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^6$; or —(CH$_2$)$_o$(CHR$^6$)$_s$C$_6$H$_4$R$^8$;

R$^{16}$ is alkyl; alkenyl; —(CH$_2$)$_o$(CHR$^{61}$)$_s$OR$^{55}$; —(CH$_2$)$_o$(CHR$^{61}$)$_s$SR$^{56}$; —(CH$_2$)$_o$(CHR$^{61}$)$_s$NR$^{33}$R$^{34}$; —(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)s SO$_2$R$^{62}$; or —(CH$_2$)$_o$(CHR$^{61}$)$_s$C$_6$H$_4$R$^8$;

R$^{17}$ is alkyl; alkenyl; —(CH$_2$)$_q$(CHR$^{61}$)$_s$OR$^{55}$; —(CH$_2$)$_q$(CHR$^{61}$)$_s$SR$^{56}$; —(CH$_2$)$_q$(CHR$^{61}$)$_s$NR$^{33}$R$^{34}$; —(CH$_2$)$_q$(CHR$^{61}$)$_s$OCONR$^{33}$R$^{75}$; —(CH$_2$)$_q$(CHR$^{61}$)$_s$NR$^{20}$CONR$^{33}$R$^{82}$; —(CH$_2$)$_q$(CHR$^{61}$)$_s$COOR$^{57}$; —(CH$_2$)$_q$(CHR$^{61}$)$_s$CONR$^{58}$R$^{59}$; —(CH$_2$)$_q$(CHR$^{61}$)$_s$PO(OR$^6$)$_2$; —(CH$_2$)$_q$(CHR$^{61}$)s SO$_2$R$^{62}$; or —(CH$_2$)$_q$(CHR$^{61}$)$_s$C$_6$H$_4$R$^8$;

R$^{18}$ is alkyl; alkenyl; —(CH$_2$)$_p$(CHR$^{61}$)OR$^{55}$; —(CH$_2$)$_m$(CHR$^{61}$)$_s$SR$^{56}$; —(CH$_2$)$_p$(CHR$^{61}$)$_s$NR$^{33}$R$^{34}$; —(CH$_2$)$_m$(CHR$^{61}$)$_s$OCONR$^{33}$R$^{75}$; —(CH$_2$)$_m$(CHR$^{61}$)$_s$NR$^{20}$CONR$^{33}$R$^{34}$; —(CH$_2$)$_m$(CHR$^{61}$)$_s$COOR$^{57}$; —(CH$_2$)$_p$(CHR$^{61}$)$_s$CONR$^{58}$R$^{59}$; —(CH$_2$)$_p$(CHR$^{61}$)$_s$PO(OR$^{60}$)$_2$; —(CH$_2$)$_p$(CHR$^{61}$)$_s$SO$_2$R$^{62}$; or —(CH$_2$)$_o$(CHR$^{61}$)$_s$C$_6$H$_4$R$^8$;

R$^{19}$ is lower alkyl; —(CH$_2$)$_p$(CHR$^{61}$)$_s$OR$^{55}$; —(CH$_2$)$_p$(CHR$^{61}$)SR$^{56}$; —(CH$_2$)$_p$(CHR$^{61}$)$_s$NR$^{33}$R$^{34}$; —(CH$_1$)$_p$(CHR$^{61}$)$_s$OCONR$^{33}$R$^{75}$; —(CH$_2$)$_p$(CHR$^{61}$)$_s$NR$^{20}$CONR$^{33}$R$^{82}$; —(CH$_2$)$_p$(CHR$^{61}$)$_s$COOR$^{57}$; (CH$_2$)$_p$(CHR$^{61}$)$_s$CONR$^{58}$R$^{59}$; —(CH$_2$)$_p$(CHR$^{61}$)$_s$PO(OR$^{60}$)$_2$; —(CH$_2$)$_m$(CHR$^{61}$) SO$_2$R$^{62}$; or —(CH$_2$)$_o$(CHR$^{61}$)$_s$C$_6$H$_4$R$^8$; or R$^{18}$ and R$^{19}$ taken together can form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—;

R$^{20}$ is H; alkyl; alkenyl; or aryl-lower alkyl;

R$^{21}$ is H; alkyl; alkenyl; —(CH$_2$)$_o$(CHR$^{61}$)$_s$OR$^{15}$; —(CH$_2$)$_o$(CHR$^{61}$)$_s$SR$^{56}$; —(CH$_2$)$_m$(CHR$^{61}$)$_s$NR$^{33}$R$^{34}$; —(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_1$R$^8$;

R$^{22}$ is H; alkyl; alkenyl; —(CH$_2$)$_o$(CHR$^{61}$)$_s$OR$^{55}$; —(CH$_2$)$_m$(CHR$^{61}$)$_s$SR$^{56}$; —(CH$_2$)$_o$(CHR$^{61}$)$_s$NR$^{33}$R$^{34}$; —(CH$_2$)$_m$(CHR$^{61}$)$_s$OCONR$^{33}$R$^{75}$; —(CH$_2$)$_o$(CHR$^{61}$)$_s$NR$^{20}$CONR$^{33}$R$^{34}$; (CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)2; CH$_2$)$_o$(CHR$^{61}$)$_s$SO$_2$R$^{62}$; or —(CH$_2$)$_m$(CHR$^{61}$)$_s$C$_6$H$_4$R$^8$;

R$^{23}$ is alkyl; alkenyl; —(CH$_2$)$_o$(CHR$^{61}$)$_s$OR$^{15}$; —(CH$_2$)$_o$(CHR$^{61}$)$_s$SR$^{56}$; —(CH$_2$)$_o$(CHR$^{61}$)$_s$NR$^{33}$R$^{34}$; —(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{24}$ is alkyl; alkenyl; —(CH$_2$)$_o$(CHR$^{61}$)$_s$OR$^{55}$; —(CH$_2$)$_o$(CHR$^{61}$)$_s$SR$^{56}$; —(CH$_2$)$_o$(CHR$^{61}$)$_m$NR$^{33}$R$^{82}$; —(CH$_2$)$_o$(CHR$^{61}$)$_s$OCONR$^{33}$R$^{75}$; —(CH$_2$)$_o$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)PO(OR)$_2$; —(CH$_2$)$_o$(CHR$^{61}$)$_s$SO$_2$R$^{62}$; or —(CH$_2$)$_m$(CHR$^{61}$)C$_6$H$_4$R$^8$;

R$^{25}$ is H; alkyl; alkenyl; —(CH$_2$)$_m$(CHR$^{61}$)$_s$OR$^{55}$; —(CH$_2$)$_m$(CHR$^{61}$)$_s$SR$^{56}$; —(CH$_2$)$_m$(CHR$^{61}$)$_s$NR$^{33}$R$^{34}$; —(CH$_2$)$_m$(CHR$^{61}$)$_s$OCONR$^{33}$R$^{75}$; —(CH$_2$)$_m$(CHR$^{61}$)$_s$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)SO$_2$R$^{62}$; or —(CH$_2$)$_o$(CHR$^{61}$)$_s$C$_6$H$_4$R$^8$;

R$^{26}$ is H; alkyl; alkenyl; —(CH$_2$)$_o$(CHR$^{61}$)$_s$OR$^{55}$; —(CH$_2$)$_m$(CHR$^{61}$)$_s$SR$^{56}$; —(CH$_2$)$_m$(CHR$^{61}$)$_s$NR$^{33}$R$^{34}$; —(CH$_2$)$_m$(CHR$^{61}$)$_s$OCONR$^{33}$R$^{75}$; —(CH$_2$)$_o$(CHR$^{61}$)$_m$NR$^{20}$CONR$^{33}$R$^{82}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)C$_6$H$_4$R$^8$; or R$^{25}$ and R$^{26}$ taken together can form: —(CH$_2$)$_{2-6}$—; —(CH$_2$)$_r$O(CH$_2$)$_r$—; —(CH$_2$)$_r$S(CH$_2$)$_r$—; or (CH$_2$)$_r$NR$^{57}$(CH$_2$)$_r$—;

R$^{27}$ is H; alkyl; alkenyl; —(CH$_2$)$_o$(CHR$^{61}$)$_s$OR$^{55}$; —(CH$_2$)$_o$(CHR$^{61}$)$_s$SR$^{56}$; —(CH$_2$)$_o$(CHR$^{61}$)$_s$NR$^{33}$R$^{34}$; —(CH$_2$)$_o$(CHR$^{61}$)$_s$COOR$^{57}$; —(CH$_2$)$_o$(CHR$^{61}$)$_s$CONR$^{58}$R$^{59}$; —(CH$_2$)$_o$(CHR$^{61}$)$_s$OCONR$^{33}$R$^{75}$; —(CH$_2$)$_m$(CHR$^{61}$)$_s$NR$^{20}$CONR$^{33}$R$^{82}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

R$^{28}$ is alkyl; alkenyl; —(CH$_2$)$_o$(CHR$^{61}$)$_m$—OR$^{55}$; —(CH$_2$)$_o$(CHR$^{61}$)s SR$^{56}$; —(CH$_2$)$_o$(CHR$^{61}$)s NR$^{33}$R$^{34}$; —(CH$_2$)$_m$(CHR$^{61}$)$_s$OCONR$^{33}$R$^{75}$; —(CH$_2$)$_o$(CHR$^{61}$)$_s$NR$^{20}$CONR$^{33}$R$^{82}$—(CH$_2$)$_o$(CHR$^{61}$)$_s$COOR$^{57}$; —(CH$_2$)$_o$(CHR$^{61}$)$_2$CONR$^{58}$R$^{59}$; —(CH$_2$)$_o$(CHR$^{61}$)$_s$PO(OR$^{60}$)$_2$; —(CH$_2$)$_o$(CHR$^{61}$)$_s$SO$_2$R$^{62}$; or —(CH$_2$)$_o$(CHR$^{61}$)$_s$C$_6$H$_4$R$^8$;

$R^{29}$ is alkyl; alkenyl; —$(CH_2)_o(CHR^{61})_sOR^{55}$; —$(CH_2)_o(CHR^{61})_sSR^{56}$; —$(CH_2)_o(CHR^{61})_sNR^{33}R^{34}$; —$(CH_2)_o(CHR^{61})_sOCONR^{33}R^{75}$; —$(CH_2)_o(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^6)_2$; —$(CH_2)_o(CHR^{61})_sSO_2R^{62}$; or —$(CH_2)_m(CHR^{61})_sC_6H_4R^8$;

$R^{30}$ is H; alkyl; alkenyl; or aryl-lower alkyl;

$R^{31}$ is H; alkyl; alkenyl; —$(CH_2)_p(CHR^{61})_sOR^{55}$; —$(CH_2)_p(CHR^{61})_sNR^{33}R^{34}$; —$(CH_2)_p(CHR^{61})_sOCONR^{33}R^{75}$; —$(CH_2)_p(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_m(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{32}$ is H; lower alkyl; or aryl-lower alkyl;

$R^{33}$ is H; alkyl, alkenyl; —$(CH_2)_m(CHR^{61})_sOR^{55}$; —$(CH_2)_m(CHR^{61})_sNR^{34}R^{63}$; —$(CH_2)_o(CHR^{61})_sOCONR^{75}R^{82}$; —$(CH_2)_m(CHR^{61})_sNR^{20}CONR^{78}R^{82}$; —$(CH_2)_o(CHR^{61})_sCOR^{64}$; —$(CH_2)_o(CHR^{61})_s$—$CONR^{58}R^{59}$; —$(CH_2)_o(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{34}$ is H; lower alkyl; aryl, or aryl-lower alkyl;

$R^{33}$ and $R^{34}$ taken together can form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—;

$R^{35}$ is H; alkyl; alkenyl; —$(CH_2)_m(CHR^{61})_sOR^{55}$; —$(CH_2)_m(CHR^{61})_sNR^{33}R^{34}$; —$(CH_2)_m(CHR^{61})_sOCONR^{33}R^{75}$; —$(CH_2)_m(CHR^{61})_sNR^{20}CONR^{33}R^{82}$; —$(CH_2)_p(CHR^{61})_sCOOR^{57}$; —$(CH_2)_p(CHR^{61})_sCONR^{58}R^{59}$; —$(CH_2)_p(CHR^{61})_sPO(OR^{60})_2$; —$(CH_2)_p(CHR^{61})_sSO_2R^{62}$; or —$(CH_2)_p(CHR^{61})_sC_6H_4R^8$;

$R^{36}$ is H, alkyl; alkenyl; —$(CH_2)_o(CHR^{61})_sOR^{55}$; $(CH_2)_p(CHR^{61})_sNR^{33}R^{34}$; —$(CH_2)_p(CHR^{61})_sOCONR^{33}R^{75}$; —$(CH_2)_p(CHR^{61})_sNR^{20}CONR^{33}R^{82}$; —$(CH_2)_p(CHR^{61})_sCOOR^{57}$; —$(CH_2)_m(CHR^{61})_sCONR^{58}R^{59}$; —$(CH_2)_p(CHR^{61})_sPO(OR^{60})_2$; —$(CH_2)_p(CHR^{61})_sSO_2R^{62}$; or —$(CH_2)_o(CHR^{61})_sC_6H_4R^8$;

$R^{37}$ is H; F; Br; Cl; NO$_2$; CF$_3$; lower alkyl; —$(CH_2)_p(CHR^{61})_sOR^{55}$; —$(CH_2)_p(CHR^{61})_sNR^{33}R^{34}$; —$(CH_2)_p(CHR^{61})_sOCONR^{33}R^{75}$; —$(CH_2)_p(CHR^{61})_mNR^{20}CONR^{33}R^{82}$—$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})_sSO_2R^{62}$; or —$(CH_2)$—$(CHR^{61})_sC_6H_4R^8$;

$R^{38}$ is H; F; Br; Cl; NO$_2$; CF$_3$; alkyl; alkenyl; —$(CH_2)_p(CHR^{61})_sOR^{55}$; —$(CH_2)_p(CHR^6.)_sNR^{33}R^{34}$; —$(CH_2)_p(CHR^{61})_sOCONR^{33}R^{75}$; —$(CH_2)_p(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})SO_2R^{62}$; or —$(CH_2)_o(CHR^{61})_sC_6H_4R^8$;

$R^{39}$ is H; alkyl; alkenyl; or aryl-lower alkyl;

$R^{40}$ is H; alkyl; alkenyl; or aryl-lower alkyl;

$R^{41}$ is H; F; Br; Cl; NO$_2$; CF$_3$; alkyl; alkenyl; $(CH_2)_p(CHR^{61})_sOR^{55}$; —$(CH_2)_p(CHR^{61})_sNR^{33}R^{34}$; —$(CH_2)_p(CHR^{61})_sOCONR^{33}R^{75}$; —$(CH_2)_p(CHR^{61})_sNR^{20}CONR^{33}R^{82}$; —$(CH_2)_o(CHR^{61})_sCOOR^{57}$; —$(CH_2)_o(CHR^{61})CONR^{58}R^{59}$; —$(CH_2)_o(CHR^{61})_sPO(OR^{60})_2$; —$(CH_2)_o(CHR^{61})_mSO_2R^{62}$; or —$(CH_2)_o(CHR^{61})_sC_6H_4R^8$;

$R^{42}$ is H; F; Br; Cl; NO$_2$; CF$_3$; alkyl; alkenyl; —$(CH_2)_p(CHR^{61})_sOR^{55}$; —$(CH_2)_p(CHR^{61})_sNR^{33}R^{34}$; —$(CH_2)_p(CHR^{61})OCONR^{33}R^{75}$; —$(CH_2)_p(CHR^{61})_mNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})SO_2R^{62}$; or —$(CH_2)_o(CHR^{61})_sC_6H_4R^8$;

$R^{43}$ is H; alkyl; alkenyl; —$(CH_2)_m(CHR^{61})_sOR^{55}$; —$(CH_2)_r(CHR^{61})_sNR^{33}R^{34}$; —$(CH_2)_o(CHR^{61})_sOCONR^{33}R^{75}$; —$(CH_2)_m(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{60})_2$; —$(CH_2)_o(CHR^{61})SO_2R^{62}$; or —$(CH_2)_o(CHR^{61})_sC_6H_4R^8$;

$R^{44}$ is alkyl; alkenyl; —$(CH_2)_r(CHR^{61})_sOR^{55}$; —$(CH_2)_r(CHR^{61})_sSR^{56}$; —$(CH_2)_r(CHR^{61})_sNR^{33}R^{34}$; —$(CH_2)_r(CHR^{61})_sOCONR^{33}R^{75}$; —$(CH_2)_r(CHR^{61})_sNR^{20}CONR^{33}R^{82}$; —$(CH_2)_r(CHR^{61})_sCOOR^{57}$; —$(CH_2)_r(CHR^{61})_sCONR^{58}R^{59}$; —$(CH_2)_r(CHR^{61})_sPO(OR^6)_2$; —$(CH_2)_m(CHR^{61})_sSO_2R^{62}$; or —$(CH_2)_m(CHR^{61})_sC_6H_4R^8$;

$R^{45}$ is H; alkyl; alkenyl; —$(CH_2)_o(CHR^{61})_sOR^{55}$; —$(CH_2)_o(CHR^{61})SR^{56}$; —$(CH_2)_o(CHR^{61})_sNR^{33}R^{34}$; —$(CH_2)_o(CHR^{61})_sOCONR^{33}R^{75}$; —$(CH_2)_o(CHR^{61})_sNR^{20}CONR^{33}R^{34}$; —$(CH_2)_o(CHR^{61})COOR^{57}$; —$(CH_2)_m(CHR^{61})_sCONR^{58}R^{59}$; —$(CH_2)_m(CHR^{61})_sPO(OR^{60})_2$; —$(CH_2)_o(CHR^{61})_sSO_2R^{62}$; or —$(CH_2)_o(CHR^{61})_sC_6H_4R^8$;

$R^{46}$ is H; alkyl; alkenyl; or —$(CH_2)_o(CHR^{61})_pC_6H_4R^8$;

$R^{47}$ is H; alkyl; alkenyl; or —$(CH_2)_o(CHR^{61})_sOR^{55}$;

$R^{48}$ is H; lower alkyl; lower alkenyl; or aryl-lower alkyl;

$R^{49}$ is H; alkyl; alkenyl; —$(CHR^{61})_sCOOR^{57}$; $(CHR^{61})_sCONR^{58}R^{59}$; $(CHR^{61})_sPO(OR^{82})_2$; —$(CHR^{61})_sSOR^{62}$; or —$(CHR^{61})_sC_6H_4R^8$;

$R^{50}$ is H; lower alkyl; or aryl-lower alkyl;

$R^{51}$ is H; alkyl; alkenyl; —$(CH_2)_m(CHR^{61})_sOR^{55}$; —$(CH_2)_m(CHR^{61})_sSR^{56}$; —$(CH_2)_m(CHR^{61})_sNR^{33}R^{34}$; —$(CH_2)_m(CHR^{61})_sOCONR^{33}R^{75}$; —$(CH_2)_m(CHR^{61})_sNR^{20}CONR^{33}R^{82}$; —$(CH_2)_o(CHR^{61})_sCOOR^{57}$; —$(CH_2)_o(CHR^{61})_sCONR^{58}R^{59}$; —$(CH_2)_o(CHR^{61})_sPO(OR^{61})_2$; —$(CH_2)_o(CHR^{61})_sSO_2R^{62}$; or —$(CH_2)_p(CHR^{61})_sC_6H_1R^8$;

$R^{52}$ is H; alkyl; alkenyl; —$(CH_2)_m(CHR^{61})_sOR^{55}$; —$(CH_2)_m(CHR^{61})_sSR^{56}$; —$(CH_2)_m(CHR^{61})_sNR^{33}R^{34}$; —$(CH_2)_s(CHR^{61})_sOCONR^{33}R^{75}$; —$(CH_2)_o(CHR^{61})_sNR^{20}CONR^{33}R^{82}$; —$(CH_2)_o(CHR^{61})_sCOOR^{57}$; —$(CH_2)_o(CHR^{61})_mCONR^{58}R^{59}$; —$(CH_2)_o(CHR^{61})_pPO(OR^{60})_2$; —$(CH_2)_p(CHR^{61})_sSO_2R^{62}$; or —$(CH_2)_p(CHR^{61})_sC_6H_4R^8$;

$R^{53}$ is H; alkyl; alkenyl; —$(CH_2)_o(CHR^{61})_sOR^{55}$; —$(CH_2)_m(CHR^{61})_sSR^{56}$; —$(CH_2)_m(CHR^{61})_sNR^{33}R^{34}$; —$(CH_2)_m(CHR^{61})_sOCONR^{33}R^{75}$; —$(CH_2)_m(CHR^{61})_sNR^{20}CONR^{33}R^{82}$; —$(CH_2)_o(CHR^{61})_sCOOR^{57}$; —$(CH_2)_o(CHR^{61})CONR^{58}R^{59}$; —$(CH_2)_o(CHR^{61})_pPO(OR^{60})_2$; —$(CH_2)_p(CHR^{61})_sSO_2R^{62}$; or —$(CH_2)_p(CHR^{61})_sC_6H_4R^8$;

$R^{54}$ is H; alkyl; alkenyl; —$(CH_2)_m(CHR^{61})_sOR^{55}$; —$(CH_2)_m(CHR^{61})_sNR^{33}R^{34}$; —$(CH_2)_m(CHR^{61})_sOCONR^{33}R^{75}$; —$(CH_2)_m(CHR^{61})_sNR^{20}CONR^{33}R^{82}$; —$(CH_2)_o(CHR^{61})COOR^{57}$; —$(CH_2)_o(CHR^{61})_sCONR^{58}R^{59}$; or —$(CH_2)_o(CHR^{61})_sC_6H_4R^8$;

$R^{55}$ is H; lower alkyl; lower alkenyl; aryl-lower alkyl; —$(CH_2)_o(CHR^{61})_sOR^{57}$; —$(CH_2)_m(CHR^{61})_sNR^{34}R^{63}$; —$(CH_2)_m(CHR^{61})_sOCONR^{75}R^{82}$; —$(CH_2)_m(CHR^{61})_sNR^{20}CONR^{78}R^{82}$; —$(CH_2)_o(CHR^{61})_m$—$COR^{64}$; —$(CH_2)_o(CHR^{61})_sCOOR^{57}$; or —$(CH_2)_o(CHR^{61})_sCONR^{58}R^{59}$;

$R^{56}$ is H; lower alkyl; lower alkenyl; aryl-lower alkyl; —$(CH_2)_m(CHR^{61})_sOR^{57}$; —$(CH_2)_m(CHR^{61})_sNR^{34}R^{63}$; —$(CH_2)_m(CHR^{61})_sOCONR^{75}R^{82}$; —$(CH_2)_m(CHR^{61})_sNR^{20}CONR^{78}R^{82}$; —$(CH_2)_o(CHR^{61})$—$COR^{64}$; or —$(CH_2)_o(CHR^{61})_sCONR^{58}R^{59}$;

$R^{57}$ is H; lower alkyl; lower alkenyl; aryl lower alkyl; or heteroaryl lower alkyl;

$R^{58}$ is H; lower alkyl; lower alkenyl; aryl; heteroaryl; aryl-lower alkyl; or heteroaryl-lower alkyl;

$R^{59}$ is H; lower alkyl; lower alkenyl; aryl; heteroaryl; aryl-lower alkyl; or heteroaryl-lower alkyl; or $R^{58}$ and $R^{59}$ taken together can form: —$(CH_2)_{2\text{-}6}$—; —$(CH_2)_2O(CH_2)_2$—; —$(CH_2)_2S(CH_2)_2$—; or —$(CH_2)_2NR^{57}(CH_2)_2$—;

$R^{60}$ is H; lower alkyl; lower alkenyl; aryl; or aryl-lower alkyl;

$R^{61}$ is alkyl; alkenyl; aryl; heteroaryl; aryl-lower alkyl; heteroaryl-lower alkyl; —$(CH_2)_mOR^{55}$; —$(CH_2)_mNR^{33}R^{34}$; —$(CH_2)_mOCONR^{75}R^{82}$; —$(CH_2)_mNR^{20}CONR^{78}R^{82}$; —$(CH_2)_oCOOR^{37}$; —$(CH_2)_oNR^{58}R^{59}$; or —$(CH_2)_oPO(COR^{60})_2$;

$R^{62}$ is lower alkyl; lower alkenyl; aryl, heteroaryl; or aryl-lower alkyl;

$R^{63}$ is H; lower alkyl; lower alkenyl; aryl; heteroaryl; aryl-lower alkyl; heteroaryl-lower alkyl; —$COR^{64}$; —$COOR^{57}$; —$CONR^{58}R^{59}$; —$SO_2R^{62}$; or —$PO(OR^{60})_2$;

$R^{34}$ and $R^{63}$ taken together can form: —$(CH_2)_{2\text{-}6}$—; —$(CH_2)_2O(CH_2)_2$—; —$(CH_2)_2S(CH_2)_2$—; or —$(CH_2)_2NR^{57}(CH_2)_2$—;

$R^{64}$ is H; lower alkyl; lower alkenyl; aryl; heteroaryl; aryl-lower alkyl; heteroaryl-lower alkyl; —$(CH_2)_s(CHR^{61})OR^{65}$; —$(CH_2)_p(CHR^{61})_mSR^{66}$; or —$(CH_2)_p(CHR^{61})_sNR^{34}R^{63}$; —$(CH_2)_p(CHR^{61})OCONR^{75}R^{82}$; —$(CH_2)_p(CHR^{61})_sNR^{20}CONR^{78}R^{82}$;

$R^{65}$ is H; lower alkyl; lower alkenyl; aryl, aryl-lower alkyl; heteroaryl-lower alkyl; —$COR^{57}$; —$COOR^{57}$; or —$CONR^{58}R^{59}$;

$R^{66}$ is H; lower alkyl; lower alkenyl; aryl; aryl-lower alkyl; heteroaryl-lower alkyl; or —$CONR^{58}R^{59}$;

m is 2-4; o is 0-4; p is 1-4; q is 0-2; r is 1 or 2; s is 0 or 1;

Z is a chain of 12 α-amino acid residues, the positions of said amino acid residues in said chain being counted starting from the N-terminal amino acid, whereby these amino acid residues are, depending on their position in the chain, Gly or Pro, or of formula —A—CO—, or of formula —B—CO—, or of one of the types

C: $NR^{20}CH(R^{72})CO$—;

D: —$NR^{20}CH(R^{73})CO$—;

E: —$NR^{20}CH(R^{74})CO$—;

F: —$NR^{20}CH(R^{84})CO$—;

H: —$NR^{20}$—$(CH(CO$—$))$—$(CH_2)_{4\text{-}7}$—$(CH(CO$—$))$—$NR^{20}$—; —$NR^{20}$—$(CH(CO$—$))$—$(CH_2)_pSS(CH_2)_p$—$(CH(CO$—$))$—$NR^{20}$—; —$NR^{20}$—$(CH(CO$—$))$—$(-(CH_2)_pNR^{20}CO(CH_2)_p$—$(CH(CO$—$))$—$NR^{20}$—; and —$NR^{20}$—$(CH(CO$—$))$—$(-(CH_2)_pNR^{20}CONR^{20}(CH_2)_m$—$(CH(CO$—$))$—$NR^{20}$—;

$R^{71}$ is H; lower alkyl; lower alkenyl; —$(CH_2)_p(CHR^{61})_sOR^{75}$; —$(CH_2)_p(CHR^{61})_sSR^{75}$; —$(CH_2)_p(CHR^{61})_sNR^{33}R^{34}$; —$(CH_2)_p(CHR^{61})_sOCONR^{33}R^{75}$; —$(CH_2)_p(CHR^{61})_sNR^{20}CONR^{33}R^{82}$; —$(CH_2)_o(CHR^{61})_sCOOR^{75}$; —$(CH_2)_pCONR^{58}R^{59}$; —$(CH_2)_pPO(OR^{62})_2$; —$(CH_2)_pSO_2R^{62}$; or —$(CH_2)_o$—$C_6R^{67}R^{68}R^{69}R^{70}R^{76}$;

$R^{72}$ is H; lower alkyl; lower alkenyl; —$(CH_2)_p(CHR^{61})_sOR^{85}$; or —$(CH_2)_p(CHR^{61})_sSR^{85}$;

$R^{73}$ is —$(CH_2)_oR^{77}$; —$(CH_2)_rO(CH_2)_oR^{77}$; —$(CH_2)_rS(CH_2)_oR^{77}$; or —$(CH_2)_oNR^{20}(CH_2)_oR^{77}$;

$R^{74}$ is —$(CH_2)_pNR^{78}R^{79}$; —$(CH_2)_pNR^{77}R^{80}$; —$(CH_2)_pC(=NR^{80})NR^{78}R^{79}$; —$(CH_2)_pC(=NOR^{50})NR^{78}R^{79}$; —$(CH_2)_pC(=NNR^{78}R^{79})NR^{78}R^{79}$; —$(CH_2)_pNR^{80}C(=NR^{80})NR^{78}, R^{79}$; —$(CH_2)_pN=C(NR^{78}R^{80})NR^{79}R^{80}$; —$(CH_2)_pC_6H_4NR^{78}R^{79}$; —$(CH_2)_pC_6H_4NR^{77}R^{80}$; —$(CH_2)_pC_6H_4C(=NOR^{50})NR^{78}R^{79}$; —$(CH_2)_pC_6H_4C(=NNR^{78}R^{79})NR^{78}R^{79}$; —$(CH_2)_pC_6H_4NR^{80}C(=(=NR^{80})NR^{78}R^{79}$; —$(CH_2)_pC_6H_4N=C(NR^{78}R^{80})NR^{79}R^{80}$; —$(CH_2)_rO$ $(CH_2)_mNR^{78}R^{79}$; —$(CH_2)_rO(CH_2)_mNR^{77}R^{80}$; —$(CH_2)_rO(CH_2)_pC(=NR^{80}NR^{78}R^{79}$; —$(CH_2)_rO(CH_2)_pC(=NOR^{50})NR^{78}R^{79}$; —$(CH_2)_rO(CH_2)_pC(=NNR^{78}R^{79})NR^{78}R^{79}$; —$(CH_2)_rO(CH_2)_mNR^{80}C(=NR^{80})NR^{78}R^{79}$; —$(CH_2)_rO(CH_2)_mN=C(NR^{78}R^{80})NR^{79}R^{80}$; —$(CH_2)_rO(CH_2)_pC_6H_4CNR^{78}R^{79}$; —$(CH_2)_rO(CH_2)_pC_6H_4C(=NR^{80})NR^{78}R^{79}$; —$(CH_2)_rO(CH_2)_pC_6H_4C(=NOR^{50})NR^{78}R^{79}$; —$(CH_2)_rO(CH_2)_pC_6H_4C(=NNR^{78}R^{79})NR^{78}R^{79}$; —$(CH_2)_rO(CH_2)_pC_6H_4R^{80}C(=NR^{80})NR^{78}R^{79}$; —$(CH_2)_rS(CH_2)_mNR^{78}R^{79}$; —$(CH_2)_rS(CH_2)_mNR^{77}R^{80}$; —$(CH_2)_rS(CH_2)_pC(=NR^{80})NR^{78}R^{79}$; —$(CH_2)_rS(CH_2)_pC(=NOR^{50})NR^{78}R^{79}$; —$(CH_2)_rS(CH_2)_pC(=NR^{78}R^{79})NR^{78}R^{79}$; —$(CH_2)_rS(CH_2)_mNR^{80}C(=NR^{80})NR^{78}R^{79}$; —$(CH_2)_rS(CH_2)_mN=C(NR^{78}R^{80})NR^{79}R^{80}$; —$(CH_2)_rS(CH_2)_pC_6H_4CNR^{78}R^{79}$; —$(CH_2)_rS(CH_2)_pC_6H_4C(=NR^{80})NR^{78}R^{79}$; —$(CH_2)_rS(CH_2)_pC_6H_4C(—NOR^{50})NR^{78}R^{79}$; —$(CH_2)_rS(CH_2)_pC_6H_4C(=NNR^{78}R^{79})NR^{78}R^{79}$; —$(CH_2)_rS(CH_2)_pC_6H_4NR^{80}C(=NR^{80}NR^{78}R^{79}$; —$(CH_2)_pNR^{80}COR^{64}$; —$(CH_2)_pNR^{80}COR^{77}$; —$(CH_2)_pNR^{80}CONR^{78}R^{79}$; or —$(CH_2)_pC_6H_4NR^{80}CONR^{78}R^{79}$;

$R^{75}$ is lower alkyl; lower alkenyl; or aryl-lower alkyl;

$R^{33}$ and $R^{75}$ taken together can form: —$(CH_2)_{2\text{-}6}$—; —$(CH_2)_2O(CH_2)_2$—; —$(CH_2)_2S(CH_2)_2$—; or —$(CH_2)_2NR^{57}(CH_2)_2$—;

$R^{75}$ and $R^{82}$ taken together can form: —$(CH_2)_{2\text{-}6}$—; —$(CH_2)_2O(CH_2)_2$—; —$(CH_2)_2S(CH_2)_2$—; or —$(CH_2)_2NR^{57}(CH_2)_2$—;

$R^{76}$ is H; lower alkyl; lower alkenyl; aryl-lower alkyl; —$(CH_2)_oOR^{72}$; —$(CH_2)_oSR^{72}$; —$(CH_2)_oNR^{33}R^{34}$; —$(CH_2)_sOCONR^{33}R^{75}$; —$(CH_2)_oNR^{20}CONR^{33}R^{82}$; —$(CH_2)_sCOOR^{75}$; —$(CH_2)_oCONR^{58}R^{59}$; —$(CH_2)_pPO(OR^{60})_2$; —$(CH_2)_pSO_2R^{62}$; or —$(CH_2)_oCOR^{64}$;

$R^{77}$ is —$C_6R^{67}R^{68}R^{69}R^{70}R^{76}$; or a heteroaryl group of one of the formulae

H1

H2

H3

H4

H5

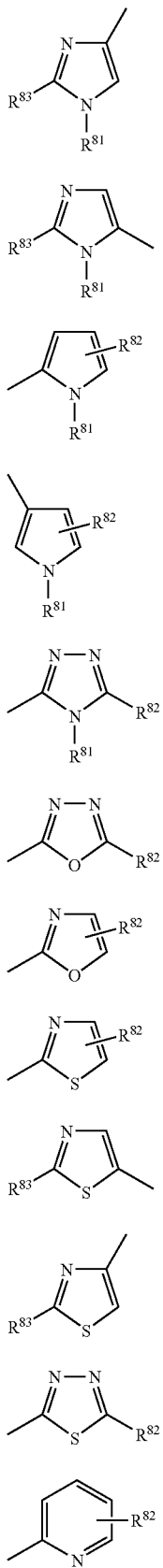
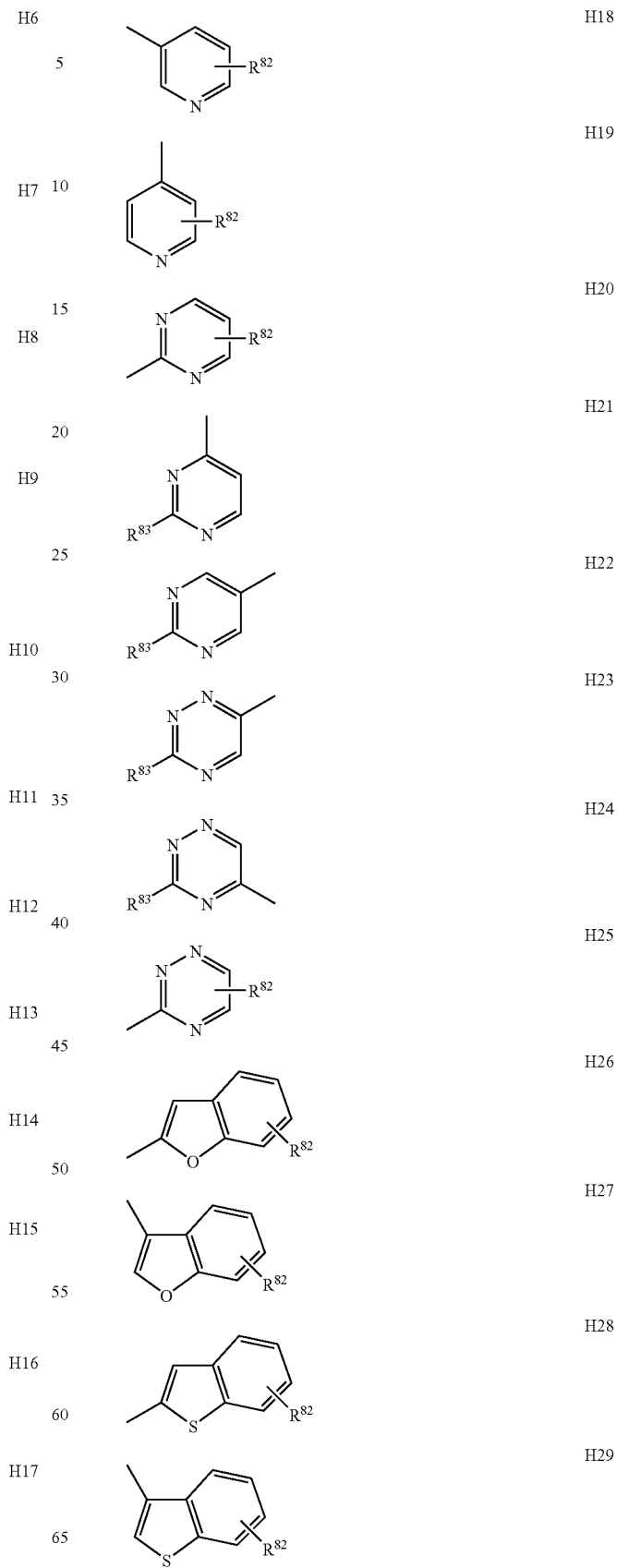

-continued
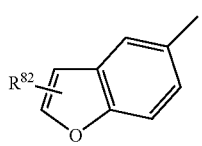
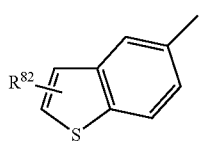
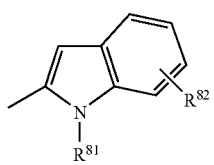
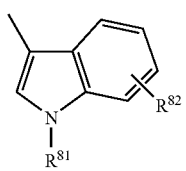
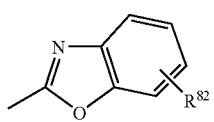
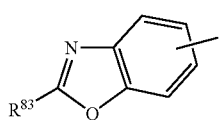
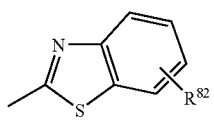
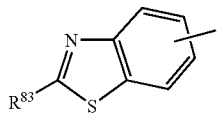
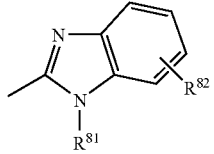
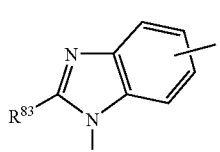
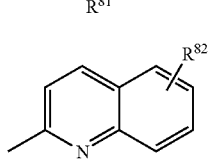
-continued
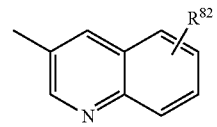 H41
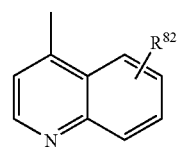 H42
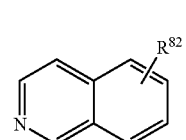 H43
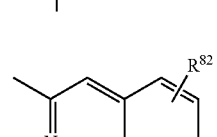 H44
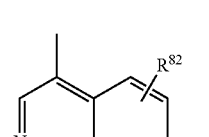 H45
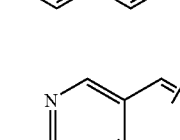 H46
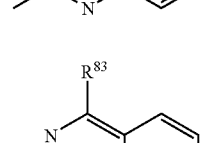 H47
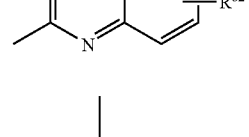 H48
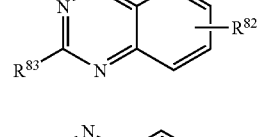 H49
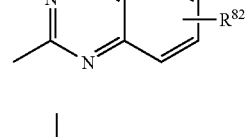 H50
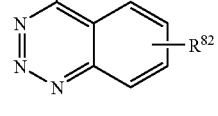

-continued

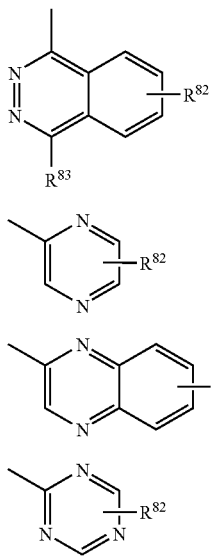

R[78] is H; lower alkyl; aryl; or aryl-lower alkyl;
R[78] and R[82] taken together can form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR[57](CH$_2$)$_2$—;
R[79] is H; lower alkyl; aryl; or aryl-lower alkyl; or
R[78] and R[79], taken together, can be —(CH$_2$)$_{2-7}$—; —(CH$_2$)$_2$O(CH$_2$)$_2$—; or —(CH$_2$)$_2$NR[57](CH$_2$)$_2$—;
R[80] is H; or lower alkyl;
R[81] is H; lower alkyl; or aryl-lower alkyl;
R[82] is H; lower alkyl; aryl; heteroaryl; or aryl-lower alkyl;
R[33] and R[82] taken together can form: —(CH$_2$)$_{2-6}$—; —(CH$_2$)$_2$O(CH$_2$)$_2$—; —(CH$_2$)$_2$S(CH$_2$)$_2$—; or CH$_2$)$_2$NR[57](CH$_2$)$_2$—;
R[83] is H; lower alkyl; aryl; or —NR[78]R[79];
R[84] is —(CH$_2$)$_m$(CHR[61])$_s$OH; —(CH$_2$)$_p$CONR[78]R[79]; —(CH$_2$)$_p$NR[80]CONR[78]R[79]; —(CH$_2$)$_p$C$_6$H$_4$CONR[78]R[79]; or —(CH$_2$)$_p$C$_6$H$_4$NR[80]CONR[78]R[79];
R[85] is lower alkyl; or lower alkenyl;

with the proviso that in said chain of 12 α-amino acid residues Z the amino acid residues in positions 1 to 12 are:
P1: of type C or of type D or of type E or of type F, or the residue is Pro;
P2: of type D;
P3: of type C, or of type D, or the residue is Pro;
P4: of type C, or of type D, or of type E;
P5: of type E, or of type D, or of type C, or of type F, or the residue is Gly or Pro;
P6: of type E, or of type F or of formula —A—CO—, or the residue is Gly;
P7: of type C, or of type E or of type F or of formula —B—CO—;
P8: of type D, or of type C, or of type F, or the residue is Pro;
P9: of type C, or of type E or of type D or of type F;
P10: of type F, or of type D or of type C, or the residue is Pro;
P11: of type E or of type D or of type C or of type F; and
P12: of type C or of type D or of type E or of type F, or the residue is Pro; or
P4 and P9 and/or P2 and P11, taken together, can form a group of type H; and at P6 and P7 also D-isomers being possible;

with the further proviso that
the amino acid residue in P4 is of type C; and/or
the amino acid residue in P5 is of type F; and/or
the amino acid residue in P7 is of type C; and/or
the amino acid residue in P8 is of type F; and/or
the amino acid residue in P9 is of type C; and/or
the amino acid residue in P10 is of type F; and/or
the amino acid residue in P 11 is of type C or of type F;

and pharmaceutically acceptable salts thereof.

In accordance with the present invention these β-hairpin peptidomimetics can be prepared by a process which comprises (a) coupling an appropriately functionalized solid support with an appropriately N-protected derivative of that amino acid which in the desired end-product is in position 5, 6 or 7, any functional group which may be present in said N-protected amino acid derivative being likewise appropriately protected;

(b) removing the N-protecting group from the product thus obtained;

(c) coupling the product thus obtained with an appropriately N-protected derivative of that amino acid which in the desired end-product is one position nearer the N-terminal amino acid residue, any functional group which may be present in said N-protected amino acid derivative being likewise appropriately protected;

(d) removing the N-protecting group from the product thus obtained;

(e) repeating steps (c) and (d) until the N-terminal amino acid residue has been introduced;

(f) coupling the product thus obtained with a compound of the general formula

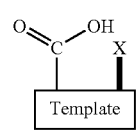
II wherein

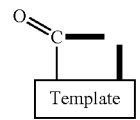

is as defined above and X is an N-protecting group or, if

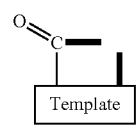

is to be group (a1) or (a2), above, alternatively
(fa) coupling the product obtained in step (e) with an appropriately N-protected derivative of an amino acid of the general formula HOOC—B—H III or HOOC—A—H    IV wherein B and A are as defined above, any functional group which may be present in said N-protected amino acid derivative being likewise appropriately protected;

(fb) removing the N-protecting group from the product thus obtained; and (fc) coupling the product thus obtained with an appropriately N-protected derivative of an amino acid of the above general formula IV and, respectively, III, any functional group which may be present in said N-protected amino acid derivative being likewise appropriately protected;

(g) removing the N-protecting group from the product obtained in step (f) or (fc);

(h) coupling the product thus obtained with an appropriately N-protected derivative of that amino acid which in the desired end-product is in position 12, any functional group which may be present in said N-protected amino acid derivative being likewise appropriately protected;

(i) removing the N-protecting group from the product thus obtained;

(j) coupling the product thus obtained with an appropriately N-protected derivative of that amino acid which in the desired end-product is one position farther away from position 12, any functional group which may be present in said N-protected amino acid derivative being likewise appropriately protected;

(k) removing the N-protecting group from the product thus obtained;

(l) repeating steps (j) and (k) until all amino acid residues have been introduced;

(m) if desired, selectively deprotecting one or several protected functional group(s) present in the molecule and appropriately substituting the reactive group(s) thus liberated;

(o) detaching the product thus obtained from the solid support;

(p) cyclizing the product cleaved from the solid support;

(q) if desired, forming one or two interstrand linkage(s) between side-chains of appropriate amino acid residues at opposite positions of the β-strand region;

(r) removing any protecting groups present on functional groups of any members of the chain of amino acid residues and, if desired, any protecting group(s) which may in addition be present in the molecule; and (s) if desired, converting the product thus obtained into a pharmaceutically acceptable salt or converting a pharmaceutically acceptable, or unacceptable, salt thus obtained into the corresponding free compound of formula I or into a different, pharmaceutically acceptable, salt Alternatively, the peptidomimetics of the present invention can be prepared by (a') coupling an appropriately functionalized solid support with a compound of the general formula

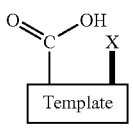

II

-continued
wherein

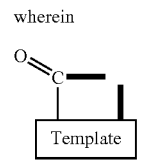

is as defined above and X is an N-protecting group or, if

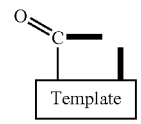

is to be group (a1) or (a2), above, alternatively (a'a) coupling said appropriately functionalized solid support with an appropriately N-protected derivative of an amino acid of the general formula HOOC—B—H III or HOOC—A—H    IV wherein B and A are as defined above, any functional group which may be present in said N-protected amino acid derivative being likewise appropriately protected;

(a'b) removing the N-protecting group from the product thus obtained; and (a'c) coupling the product thus obtained with an appropriately N-protected derivative of an amino acid of the above general formula IV and, respectively, III, any functional group which may be present in said N-protected amino acid derivative being likewise appropriately protected;

(b') removing the N-protecting group from the product obtained in step (a') or (ac);

(c') coupling the product thus obtained with an appropriately N-protected derivative of that amino acid which in the desired end-product is in position 12, any functional group which may be present in said N-protected amino acid derivative being likewise appropriately protected;

(d') removing the N-protecting group from the product thus obtained;

(e') coupling the product thus obtained with an appropriately N-protected derivative of that amino acid which in the desired end-product is one position farther away from position 12, any functional group which may be present in said N-protected amino acid derivative being likewise appropriately protected;

(f') removing the N-protecting group from the product thus obtained;

(g') repeating steps (e') and (f) until all amino acid residues have been introduced;

(h') if desired, selectively deprotecting one or several protected functional group(s) present in the molecule and appropriately substituting the reactive group(s) thus liberated;

(i') detaching the product thus obtained from the solid support;

(j') cyclizing the product cleaved from the solid support;

(k') if desired forming one or two interstrand linkage(s) between side-chains of appropriate amino acid residues at opposite positions of the 1-strand region;

(l') removing any protecting groups present on functional groups of any members of the chain of amino acid residues and, if desired, any protecting group(s) which may in addition be present in the molecule; and (m') if desired, converting the product thus obtained into a pharmaceutically acceptable salt or converting a pharmaceutically acceptable, or unacceptable, salt thus obtained into the corresponding free compound of formula I or into a different, pharmaceutically acceptable, salt.

The peptidomimetics of the present invention can also be enantiomers of the compounds of formula I. These enantiomers can be prepared by a modification of the above processes in which enantiomers of all chiral starting materials are used.

As used in this description, the term "alkyl", taken alone or in combinations, designates saturated, straight-chain or branched hydrocarbon radicals having up to 24, preferably up to 12, carbon atoms. Similarly, the term "alkenyl" designates straight chain or branched hydrocarbon radicals having up to 24, preferably up to 12, carbon atoms and containing at least one or, depending on the chain length, up to four olefinic double bonds. The term "lower" designates radicals and compounds having up to 6 carbon atoms. Thus, for example, the term "lower alkyl" designates saturated, straight-chain or branched hydrocarbon radicals having up to 6 carbon atoms, such as methyl, ethyl, n-propyl, isopropyl, n-butyl, sec.-butyl, isobutyl, tert.-butyl and the like. The term "aryl" designates aromatic carbocyclic hydrocarbon radicals containing one or two six-membered rings, such as phenyl or naphthyl, which may be substituted by up to three substituents such as Br, Cl, F, $CF_3$, $NO_2$, lower alkyl or lower alkenyl. The term "heteroaryl" designates aromatic heterocyclic radicals containing one or two five- and/or six-membered rings, at least one of them containing up to three heteroatoms selected from the group consisting of O, S and N and said ring(s) being optionally substituted; representative examples of such optionally substituted heteroaryl radicals are indicated hereinabove in connection with the definition of $R^{77}$.

The structural element —A—CO— designates amino acid building blocks which in combination with the structural element —B—CO— form templates (a1) and (a2). Templates (a) through (p) constitute building blocks which have an N-terminus and a C-terminus oriented in space in such a way that the distance between those two groups may lie between 4.0-5.5 A. A peptide chain Z is linked to the C-terminus and the N-terminus of the templates (a) through (p) via the corresponding N- and C-termini so that the template and the chain form a cyclic structure such as that depicted in formula I. In a case as here where the distance between the N- and C-termini of the template lies between 4.0-5.5 A the template will induce the H-bond network necessary for the formation of a β-hairpin conformation in the peptide chain Z. Thus template and peptide chain form a β-hairpin mimetic.

The β-hairpin conformation is highly relevant for the antibiotic activity of the β-hairpin mimetics of the present invention. The β-hairpin stabilizing conformational properties of the templates (a) through (p) play a key role not only for the selective antimicrobial activity but also for the synthesis process defined hereinabove, as incorporation of the templates at the beginning of the linear protected peptide precursors enhance significantly cyclization yields.

Building blocks A1-A69 belong to a class of amino acids wherein the N-terminus is a secondary amine forming part of a ring. Among the genetically encoded amino acids only proline falls into this class. The configuration of building block A1 through A69 is (D), and they are combined with a building block —B—CO— of (L)-configuration. Preferred combinations for templates (a1) are —$^D$A1—CO—$^L$B—CO— to —$^D$A69-CO—$^L$B—CO—. Thus, for example, $^D$Pro-$^L$Pro constitutes the prototype of templates (a1). Less preferred, but possible are combinations where templates (a2) are —$^L$—A1—CO—$^D$B—CO— to —$^L$A69-CO—$^D$B—CO—. Thus, for example, $^L$Pro-$^D$Pro constitutes a less preferred prototype of template (a2).

It will be appreciated that building blocks —A1—CO— to —A69-CO— in which A has (D)-configuration, are carrying a group $R^1$ at the α-position to the N-terminus. The preferred values for $R^1$ are H and lower alkyl with the most preferred values for $R^1$ being H and methyl. It will be recognized by those skilled in the art, that A1-A69 are shown in (D)-configuration which, for $R^1$ being H and methyl, corresponds to the (R)-configuration. Depending on the priority of other values for $R^1$ according to the Cahn, Ingold and Prelog-rules, this configuration may also have to be expressed as (S).

In addition to $R^1$ building blocks —A1—CO— to —A69-CO— can carry an additional substituent designated as $R^2$ to $R^{17}$. This additional substituent can be H, and if it is other than H, it is preferably a small to medium-sized aliphatic or aromatic group. Examples of preferred values for $R^2$ to $R^{17}$ are:

$R^2$: H; lower alkyl; lower alkenyl; $(CH_2)_mOR^{55}$ (where $R^{55}$: lower alkyl; or lower alkenyl); $(CH_2)_mSR^{56}$ (where $R^{56}$: lower alkyl; or lower alkenyl); $(CH_2)_mNR^{33}R^{34}$ (where $R^{33}$: lower alkyl; or lower alkenyl; $R^{34}$: H; or lower alkyl; $R^{33}$ and $R^{34}$ taken together form:

—$(CH_1)_{2-6}$—; —$(CH_2)_2O(CH_2)_2$—; —$(CH_2)_2S(CH_2)_2$—; or —$(CH_2)_2NR^{57}(CH_2)_2$—; $R^{57}$: H; or lower alkyl); $(CH_2)_m$ OCONR$^{33}$R$^{75}$ (where $R^{33}$: H; or lower alkyl; or lower alkenyl; $R^{75}$: lower alkyl; or $R^{33}$ and $R^{75}$ taken together form: —$(CH_1)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)NR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^2))COR^{64}$(where: $R^{20}$: H; or lower alkyl; $R^{64}$: lower alkyl; or lower alkenyl); —$(CH_2)_sCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{19}$: H; or lower alkyl; or $R^{58}$ and $R^{59}$ taken together form: —$(CH_2)_{2-6}$—; —$(CH_2)_2O(CH_2)_2$—;

—$(CH_2)_2S(CH_2)_2$—; or —$(CH_2)_2NR^{57}(CH_2)_2$—; where $R^7$: H; or lower alkyl); —$(CH_2) PO(OR^{60})_2$ (where $R^{60}$: lower alkyl; or lower alkenyl); —$(CH_2)_mSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^3$: H; lower alkyl; lower alkenyl; —$(CH_1) OR^{55}$ (where $R^{55}$: lower alkyl; or lower alkenyl); —$(CH_2)_mSR^{56}$ (where $R^{56}$: lower alkyl; or lower alkenyl); —$(CH_2)_m$ NR$^{33}$R$^{34}$ (where $R^{33}$: lower alkyl; or lower alkenyl; $R^{33}$: H; or lower alkyl; or $R^{33}$ and $R^{34}$ taken together form: —$(CH_2)_{2-6}$—; —$(CH_2)_2O(CH_2)_2$—$(CH_2)_2S(CH_1)_2$—; or —$(CH_2)_2NR^{57}(CH_2)_2$—; where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mN(R^{20})COR^{64}$ (where: $R^{20}$: H; or lower alkyl; $R^{64}$: lower alkyl; or lower alkenyl); —$(CH_2)_sCOOR^5$ (where $R^{57}$: lower alkyl; or lower alkenyl); —$(CH_1)_oCONR^{58}R^{59}$ (where $R^5$—: lower alkyl; or lower alkenyl; and $R^{59}$: H; lower alkyl; or $R^{58}$ and $R^{59}$ taken together form: —$(CH_2)_2$.-; —$(CH_1)_2O(CH_2)_2$—;

—$(CH_2)_2S(CH_2)_2$—; or —$(CH_2)_2NR^{57}(CH_2)_2$—; where $R^{57}$: H; or lower alkyl); $(CH_2).PO(OR^{60})_2$ (where $R^{60}$: lower alkyl; or lower alkenyl); —$(CH_2)_oSO_2R^{62}$ (where $R^Q$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^4$: H; lower alkyl; lower alkenyl; —$(CH_2)_mOR^{55}$ (where $R^{55}$: lower alkyl; or lower alkenyl); —$(CH_2)_mSR^{56}$ (where $R^{56}$: lower alkyl; or lower alkenyl); —$(CH_2)$, $NR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$; —$(CH_2)_2S(CH_2)_2$—; or —$(CH_2)_2NR^{57}(CH_2)_2$—; where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_{12})_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_1)_2$—; where $R^{57}$: H; or lower alkyl); —$(CH_2)N(R^{20})COR^{64}$(where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—;

—$(CH_1)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)SO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^5$: lower alkyl; lower alkenyl; —$(CH_2)_mOR^{55}$ (where $R^{55}$: lower alkyl; or lower alkenyl); —$(CH_2)_oSR^{56}$ (where $R^{56}$: lower alkyl; or lower alkenyl); —$(CH_2)_oNR^{33}R^{34}$ (where $R^{33}$: lower alkyl; or lower alkenyl; $R^{34}$: H; or lower alkyl; or $R^{33}$ and $R^{34}$ taken together form:

—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_sOCONR^{33}R^{71}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; $R^{57}$: where H; or lower alkyl); $(CH_2)_mNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); $(CH_2)_oN(R^2)COR^{82}$(where: $R^{20}$: H; or lower alkyl; $R^{64}$: alkyl; alkenyl; aryl; and aryl-lower alkyl; heteroaryl-lower alkyl);

—$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^6$: H; lower alkyl; lower alkenyl; —$(CH_2)_mOR^{55}$ (where $R^{55}$: lower alkyl; or lower alkenyl); —$(CH_2)_mSR^{56}$ (where $R^{56}$: lower alkyl; or lower alkenyl); $(CH_2)_oNR^{31}R^{64}$ (where $R^{33}$: lower alkyl; or lower alkenyl; $R^{34}$: H; or lower alkyl; or $R^{33}$ and $R^{34}$ taken together form:

—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_sCOOR^{57}$ (where $R^{57}$: lower alkyl; or lower alkenyl); —$(CH_2)_mCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—;

—$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^7$: lower alkyl; lower alkenyl; —$(CH_2)_qOR^{55}$ (where $R^{55}$: lower alkyl; or lower alkenyl); —$(CH_2)_qSR^{56}$ (where $R^{56}$: lower alkyl; or lower alkenyl); —$(CH_2)_qNR^{33}R^{34}$ (where $R^{33}$: lower alkyl; or lower alkenyl; $R^{34}$: H; or lower alkyl; or $R^{33}$ and $R^{34}$ taken together form:

—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_qOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); $(CH_2)_qNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_qN(R^{20})COR^{64}$(where: $R^{20}$: H; or lower alkyl; $R^{64}$: lower alkyl; or lower alkenyl); —$(CH_2)_rCOOR^{57}$ (where $R^{57}$: lower alkyl; or lower alkenyl); —$(CH_2)_qCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—;

—$(CH_2)_2S(CH_22$-; or —$(CH_2)_2NR^{57}(CH_2)_2$—; where $R^{57}$: H; or lower alkyl); —$(CH_2)_rPO(OR^{60})_2$ (where $R^{60}$: lower alkyl; or lower alkenyl); $(CH_2)_sSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^8$: H; F; Cl; $CF_3$; lower alkyl; lower alkenyl; —$(CH_2)OR^{55}$(where $R^{55}$: lower alkyl; or lower alkenyl); $(CH_2)_oSR^{56}$ (where $R^{56}$: lower alkyl; or lower alkenyl); —$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H.; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—;

—$CH_2)_2S(CH_2)_2$—; or —$(CH_2)_2NR^{57}(CH_2)_2$—; where $R^{57}$: H; or lower alkyl);

—$(CH_2)_oNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—;

—$(CH_2)_2O(CH_2)_2$—; —$(CH_2)_2S(CH_2)_2$—; or —$(CH_2)_2NR^{57}(CH_2)_2$—; where $R^{57}$: H; or lower alkyl);

—$(CH_2)_oN(R^{20})COR^{64}$ (where: $R^{20}$: H; or lower alkyl; $R^{64}$: lower alkyl; or lower alkenyl);

—$(CH_2)_oCOOR^{57}$ (where $R^{57}$ lower alkyl; or lower alkenyl); —$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form:

—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl);

—$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^9$: lower alkyl; lower alkenyl; —$(CH_2)_mOR^{55}$ (where $R^{55}$: lower alkyl; or lower alkenyl); —$(CH_2)_oSR^{56}$ (where $R^{56}$: lower alkyl; or lower alkenyl); $(CH_2)_oNR^{33}R^{34}$ (where $R^{33}$: lower alkyl; or lower alkenyl; $R^{34}$: H; or lower alkyl; or $R^{33}$ and $R^{34}$ taken together form:

—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl);

—$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mN(R^{20})COR^{64}$(where: $R^{20}$: H; or lower alkyl; $R^{64}$: lower alkyl; or lower alkenyl); —$(CH_2)_oCOOR^{57}$ (where $R^{57}$: lower alkyl; or lower alkenyl);

—$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—;

—$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{10}$: lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_oNR^{33}R^{34}$ (where $R^{33}$: lower alkyl; or lower alkenyl; $R^{34}$: H; or lower alkyl; or $R^{33}$ and $R^{34}$ taken together form:

—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)$—; where $R^{57}$: H; or lower alkyl); —$(CH_2)_oNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$(where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_mCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—;

—$(CH_2)_2S(CH_2)_2$—; or—$(CH_2) NR^{57}(CH_2)_2$—; where $R^{57}$: H; or lower alkyl); —$(CH_1)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{11}$: H; lower alkyl; lower alkenyl; —$(CH_2)_mOR^{55}$ (where $R^{55}$: lower alkyl; or lower alkenyl); —$(CH_2)_mSR^{56}$ (where $R^{56}$: lower alkyl; or lower alkenyl); —$(CH_2)_mNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—;

—$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{12}$: H; lower alkyl; lower alkenyl; —$(CH_2)_mOR^{55}$ (where $R^{55}$: lower alkyl; or lower alkenyl); —$(CH_2)_mSR^{56}$ (where $R^{56}$: lower alkyl; or lower alkenyl); —$(CH_2)_m NR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mN(R^{20})COR^{64}$ (where: $R^{20}$: H; or lower alkyl; $R^{82}$: lower alkyl; or lower alkenyl);.—$(CH_2)_oCOOR^{57}$ (where $R^{57}$: lower alkyl; or lower alkenyl);, —$(CH_2)_rCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—;

—$(CH_2)_2S(CH_2)_2$—; or —$(CH_2)_2NR^{57}(CH_2)_2$—; where $R^{57}$: H; or lower alkyl); —$(CH_2)_rPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{13}$: lower alkyl; lower alkenyl; —$(CH_2)_qOR^{55}$ (where $R^{55}$: lower alkyl; or lower alkenyl); —$(CH_2)_qSR^{56}$ (where $R^{56}$: lower alkyl; or lower alkenyl); —$(CH_2)_q NR^{33}R^{34}$ (where $R^{33}$: lower alkyl; or lower alkenyl; $R^{34}$: H; or lower alkyl; or $R^{33}$ and $R^{34}$ taken together form:

—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_qOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_qNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_qN(R^2O)COR^{64}$ (where: $R^{20}$: H; or lower alkyl; $R^{64}$: lower alkyl; or lower alkenyl); —$(CH_2)_rCOO^{57}$ (where $R^{57}$: lower alkyl; or lower alkenyl); —$(CH_2)_qCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2 O(CH_2)_2$—; —$(CH_2)_2S(CH_2)_2$—; or —$(CH_2)_2NR^{57} (CH_2)_2$—; where $R^{57}$: H; or lower alkyl); —$(CH_2)_rPO (OR^{60})_2$ (where $R^{60}$: lower alkyl; or lower alkenyl); —$(CH_2)_s SO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{14}$: H; lower alkyl; lower alkenyl; —$(CH_2)_mOR^{55}$ (where $R^{55}$: lower alkyl; or lower alkenyl); —$(CH_2)_mSR^{56}$ (where $R^{56}$: lower alkyl; or lower alkenyl); —$(CH_2)_m NR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S (CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O (CH_2)_2$—; —$(CH_2)_2S(CH_2)_2$—; or —$(CH_2)_2NR^{57}(CH_2)_2$—; where $R^{57}$: H; or lower alkyl); —$(CH_2)_mNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mN(R^{20})COR^{64}$ (where: $R^{20}$: H; lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—;

—$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); —$(CH_2)_qC_6H_4R^8$ (where $R^8$: H; F; Cl; $CF_3$; lower alkyl; lower alkenyl; or lower alkoxy).

$R^{15}$: lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_o NR^{33}R^{34}$ (where $R^{33}$: lower alkyl; or lower alkenyl; $R^{34}$: H; or lower alkyl; or $R^{33}$ and $R^{34}$ taken together form:

—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S (CH_2)_2$—; or —$(CH_2)_2NR^{57}(CH_2)_2$—; where $R^{57}$: H; or lower alkyl); —$(CH_2)_mNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); $(CH_2)_oN(R^{20})COR^{64}$ (where: $R^{20}$: H; or lower alkyl; $R^{64}$: lower alkyl; or lower alkenyl); particularly favoured are $NR^{20}CO$ lower alkyl ($R^{20}$=H; or lower alkyl); —$(CH_2)_o COOR^{57}$ (where $R^{57}$: lower alkyl; or lower alkenyl);

—$(CH_2)_oCONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S (CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{16}$: lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_m NR^{33}R^{34}$ (where $R^{33}$: lower alkyl; or lower alkenyl; $R^{34}$: H; or lower alkyl; or $R^{33}$ and $R^{34}$ taken together form:

—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—;

—$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{17}$: lower alkyl; lower alkenyl; —$(CH_2)_qOR^{55}$ (where $R^{55}$: lower alkyl; or lower alkenyl); —$(CH_2)_qSR^{56}$ (where $R^{56}$: lower alkyl; or lower alkenyl); —$(CH_2)_q NR^{33}R^{34}$ (where $R^{33}$: lower alkyl; or lower alkenyl; $R^{34}$: H; or lower alkyl; or $R^{33}$ and $R^{34}$ taken together form:

—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_qOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_qNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_qN(R^{20})COR^{64}$(where: $R^{20}$: H; or lower alkyl; $R^{64}$: lower alkyl; or lower alkenyl); —$(CH_2)_rCOOR^{57}$ (where $R^{57}$: lower alkyl; or lower alkenyl); —$(CH_2)_qCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—;

—$(CH_2)_2S(CH_2)_2$—; or —$(CH_2)_2NR^{57}(CH_2)_2$—; where $R^{57}$: H; or lower alkyl); —$(CH_2)_rPO(OR^{60})_2$ (where $R^{60}$: lower alkyl; or lower alkenyl); —$(CH_2)_mSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

Among the building blocks A1 to A69 the following are preferred: AS with $R^2$ being H, A8, A22, A25, A38 with $R^2$ being H, A42, A47, and A50. Most preferred are building blocks of type A8':

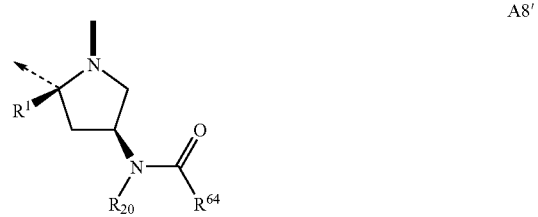

A8' wherein $R^{20}$ is H or lower alkyl; and $R^{64}$ is alkyl; alkenyl; aryl; aryl-lower alkyl; or heteroaryl-lower alkyl; especially those wherein $R^{64}$ is n-heptyl (A8'-1); n-heptyl (A8'-2); 4-(phenyl) benzyl (A8'-3); diphenylmethyl (A8'-4); 3-amino-propyl (A8'-S); 5-amino-pentyl (A8'-6); methyl (A8'-7); ethyl (A8'-8); isopropyl (A8'-9); isobutyl (A8'-10); n-propyl (A8'-11); cyclohexyl (A8'-12); cyclohexylmethyl (A8'-13); n-butyl (A8'-14); phenyl (A8'-15); benzyl (A8'-16); (3-indolyl)methyl (A8'-17); 2-(3-indolyl)ethyl (A8'-18); (4-phenyl)phenyl (A8'-19); and n-nonyl (A8'-20).

Building block A70 belongs to the class of open-chained o-substituted α-amino acids, building blocks A71 and A72 to the corresponding α-amino acid analogues and building blocks A73—A104 to the cyclic analogues of A70. Such amino acid derivatives have been shown to constrain small peptides in well defined reverse turn or U-shaped conformations (C. M. Venkatachalam, *Biopolymers*, 1968, 6, 1425-1434; W. Kabsch, C Sander, *Biopolymers* 1983, 22, 2577). Such building blocks or templates are ideally suited for the stabilization of β-hairpin conformations in peptide loops (D. Obrecht, M. Altorfer, J. A. Robinson, "Novel Peptide Mimetic Building Blocks and Strategies for Efficient Lead Finding", *Adv. Med. Chem.* 1999, Vol. 4, 1-68; P. Balaram, "Non-standard amino acids in peptide design and protein engineering", *Curr. Opin. Struct. Biol.* 1992, 2, 845-851; M. Crisma, G. Valle, C. Toniolo, S. Prasad, R. B. Rao, P. Balaram, "β-turn conformations in crystal structures of model peptides containing α,α-disubstituted amino acids", *Biopolymers* 1995, 35, 1-9; V. J. Hruby, F. Al-Obeidi, W. Kazmierski, *Biochem. J.* 1990, 268, 249-262).

It has been shown that both enantiomers of building blocks —A70-CO— to A104-CO— in combination with a building block —B—CO— of L-configuration can efficiently stabilize and induce β-hairpin conformations (D. Obrecht, M. Altorfer, J. A. Robinson, "Novel Peptide Mimetic Building Blocks and Strategies for Efficient Lead Finding", *Adv. Med. Chem.* 1999, Vol. 4, 1-68; D. Obrecht, C. Spiegler, P. Schönholzer, K. Müller, H. Heimgartner, F. Stierli, *Helv. Chim. Acta* 1992, 75, 1666-1696; D. Obrecht, U. Bohdal, J. Daly, C. Lehmann, P. Schorholzer, K. Müller, *Tetrahedron* 1995,51, 10883-10900; D. Obrecht, C. Lehmann, C. Ruffieux, P. Schönholzer, K. Müller, *Helv. Chim. Acta* 1995, 78, 1567-1587; D. Obrecht, U. Bohdal, C. Broger, D. Bur, C. Lehmann, R. Ruffieux, P. Schönholzer, C. Spiegler, *Helv. Chim. Acta* 1995, 78, 563-580; D. Obrecht, H. Karajiannis, C. Lehmann, P. Schönholzer, C. Spiegler, *Helv. Chim. Acta* 1995, 78, 703-714). Thus, for the purposes of the present invention templates (a1) can also consist of —A70-CO— to A104-CO— where building block A70 to A104 is of either (D)- or (L)-configuration, in combination with a building block —B—CO— of (L)-configuration.

Preferred values for $R^{20}$ in A70 to A104 are H or lower alkyl with methyl being most preferred. Preferred values for $R^{18}$, $R^{19}$ and $R^{21}$-$R^{29}$ in building blocks A70 to A104 are the following:

$R^{18}$: lower alkyl.

$R^{19}$: lower alkyl; lower alkenyl; —$(CH_2)_pOR^{55}$ (where $R^{55}$: lower alkyl; or lower alkenyl); —$(CH_2)_pSR^{56}$ (where $R^{56}$: lower alkyl; or lower alkenyl); —$(CH_2)_p$ $NR^{33}R^{34}$ (where $R^{33}$: lower alkyl; or lower alkenyl; $R^{34}$: H; or lower alkyl; or $R^{33}$ and $R^{34}$ taken together form:

—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pN(R^{20})COR^{64}$ (where: $R^{20}$: H; or lower alkyl; $R^{64}$: lower alkyl; or lower alkenyl); —$(CH_2)_pCOOR^{57}$ (where $R^{57}$: lower alkyl; or lower alkenyl); —$(CH_2)_pCONR^{58}R^{59}$ (where $R^{58}$: lower alkyl; or lower alkenyl; and $R^{59}$: H; or lower alkyl; or $R^{58}$ and $R^{59}$ taken together form: —$(CH_2)_{2-6}$—; —$(CH_2)_2O(CH_2)_2$—;

—$(CH_2)_2S(CH_2)_2$—; or —$(CH_2)_2NR^{57}(CH_2)_2$—; where $R^{57}$: H; or lower alkyl); —$(CH_2)_pPO(OR^{60})_2$ (where $R^{60}$: lower alkyl; or lower alkenyl); —$(CH_2)_pSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{21}$: H; lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_o$ $NR^{33}R^{34}$ (where $R^{33}$: lower alkyl; or lower alkenyl; $R^{34}$: H; or lower alkyl; or $R^{33}$ and $R^{34}$ taken together form:

—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_1)_oCONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2O(CH_2)_2$—;

—$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); $(CH_2)_oSO_2R^{62}$ (where $R^{62}$: lower alkyl; or lower alkenyl); or $(CH_2)_qC_6H_4R^8$ (where $R^8$: H; F; Cl; $CF_3$; lower alkyl; lower alkenyl; or lower alkoxy).

$R^{22}$: lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_o$ $NR^{33}R^{34}$ (where $R^{33}$: lower alkyl; or lower alkenyl; $R^{34}$: H; or lower alkyl; or $R^{33}$ and $R^{34}$ taken together form:

—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_sOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^3$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); —$(CH_2)_oCOOR^{57}$ (where $R^{57}$: lower alkyl; or lower alkenyl); —$(CH_2)_mCONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2O(CH_2)_2$—;

—$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; CF; lower alkyl; lower alkenyl; or lower alkoxy).

$R^{23}$: H; lower alkyl; lower alkenyl; —$(CH_2)_oOR^{55}$ (where $R^{55}$: lower alkyl; or lower alkenyl); —$(CH_2)_oSR^{56}$ (where $R^{56}$: lower alkyl; or lower alkenyl); —$(CH_2)_o$ $NR^{33}R^{34}$ (where $R^{33}$: lower alkyl; or lower alkenyl; $R^{34}$: H; or lower alkyl; or $R^{33}$ and $R^{34}$ taken together form:

—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H.; or lower alkyl); —$(CH_2)_sOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oN(R^{20})COR^{64}$ (where: $R^{20}$: H; or lower alkyl; $R^{64}$: lower alkyl; or lower alkenyl); particularly favoured are $NR^{20}CO$ lower alkyl ($R^{20}$=H; or lower alkyl); —$(CH_2)_o$ $COOR^{57}$ (where $R^{57}$: lower alkyl; or lower alkenyl);

—$(CH_2)_oCONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy);

$R^{24}$: lower alkyl; lower alkenyl; —$(CH_2)_m OR^{55}$ (where $R^{55}$: lower alkyl; or lower alkenyl); —$(CH_2)_o SR^{56}$ (where $R^{56}$: lower alkyl; or lower alkenyl); —$(CH_2)_o NR^{33}R^{34}$ (where $R^{33}$: lower alkyl; or lower alkenyl; $R^{34}$: H; or lower alkyl; or $R^{33}$ and $R^{34}$ taken together form:

—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_o OCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_o NR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_o N(R^{20})COR^{64}$ (where: $R^{20}$: H; or lower alkyl; $R^{64}$: lower alkyl; or lower alkenyl); particularly favoured are $NR^{20}CO$lower alkyl ($R^{20}$=H; or lower alkyl); —$(CH_2)_o COOR^{57}$ (where $R^{57}$: lower alkyl; or lower alkenyl); —$(CH_2)_o CONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_o PO(OR^{60})_2$ (where $R^{60}$: lower alkyl; or lower alkenyl); —$(CH_2)_o SO_2R^{62}$ (where $R^{62}$: lower alkyl; or lower alkenyl); or —$(CH_2)_q C_6H_4R^8$ (where $R^8$: H; F; Cl; $CF_3$; lower alkyl; lower alkenyl; or lower alkoxy);

$R^{25}$: H; lower alkyl; lower alkenyl; —$(CH_2)_m OR^{55}$ (where $R^{55}$: lower alkyl; or lower alkenyl); —$(CH_2)_m NR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$CH_2)_2NR^{57}(CH_2)_2$—; where $R^{57}$: H; or lower alkyl); —$(CH_2)_m OCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; $(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_m NR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_m N(R^{20})COR^{64}$ (where: $R^{20}$: H; or lower alkyl; $R^{64}$: lower alkyl; or lower alkenyl); —$(CH_2)_o COOR^{57}$ (where $R^{57}$: lower alkyl; or lower alkenyl); —$(CH_2)_o CONR^{58}R^{59}$ (where $R^{58}$: lower alkyl; or lower alkenyl; and $R^{59}$: H; lower alkyl; or $R^{58}$ and $R^{59}$ taken together form:

—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_o PO(OR^{60})_2$ (where $R^{60}$: lower alkyl; or lower alkenyl); —$(CH_2)_o SO_2R^{62}$ (where $R^{62}$: lower alkyl; or lower alkenyl); or —$(CH_2)_q C_6H_4R^8$ (where $R^8$: H; F; Cl; $CF_3$; lower alkyl; lower alkenyl; or lower alkoxy).

$R^{26}$: H; lower alkyl; lower alkenyl; —$(CH_2)_m OR^{55}$ (where $R^{55}$: lower alkyl; or lower alkenyl); —$(CH_2)_m NR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_m OCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_m NR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—;

—$(CH_2)_2O(CH_2)_2$—; —$(CH_2)_2S(CH_2)_2$—; or —$(CH_2)_2NR^{57}(CH_1)_2$—; where $R^{57}$: H; or lower alkyl); —$(CH_2)_m N(R^{20})COR^{64}$ (where: $R^{20}$: H; or lower alkyl; $R^{64}$: lower alkyl; or lower alkenyl); —$(CH_2)_o COOR^{57}$ (where $R^{57}$: lower alkyl; or lower alkenyl); —$(CH_2)_o CONR^{58}R^{59}$ (where $R^1B$: lower alkyl; or lower alkenyl; and $R^{59}$: H; lower alkyl; or $R^{58}$ and $R^{59}$ taken together form:

—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_o PO(OR^{60})_2$ (where $R^{60}$: lower alkyl; or lower alkenyl); —$(CH_2)_o SO_2R^{62}$ (where $R^{62}$: lower alkyl; or lower alkenyl); or —$(CH_2)_q C_6H_4R^8$ (where $R^8$: H; F; Cl; $CF_3$; lower alkyl; lower alkenyl; or lower alkoxy).

Alternatively, $R^{25}$ and $R^{26}$ taken together can be —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl).

$R^{27}$: H; lower alkyl; lower alkenyl; —$(CH_2)_m OR^{55}$ (where $R^{55}$: lower alkyl; or lower alkenyl); —$(CH_2)_o SR^{56}$ (where $R^{56}$: lower alkyl; or lower alkenyl); —$(CH_2)oNR^{33}R^{34}$ (where $R^{33}$: lower alkyl; or lower alkenyl; $R^{34}$: H; or lower alkyl; or $R^{33}$ and $R^{34}$ taken together form:

—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)oOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; $(CH_2)_2S(CH_2)_2$—; or —$(CH_2)_2NR^{57}(CH_2)_2$—; where $R^{57}$: H; or lower alkyl); —$(CH_2)_o NR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)N(R^{20})COR^{64}$ (where: $R^{20}$: H; or lower alkyl; $R^{64}$: lower alkyl; or lower alkenyl); —$(CH_2)_o COOR^{57}$ (where $R^{57}$: lower alkyl; or lower alkenyl); —$(CH_2)_o CONR^{58}R^{59}$ (where $R^{58}$: lower alkyl, or lower alkenyl; and $R^{59}$: H; lower alkyl; or $R^{58}$ and $R^{59}$ taken together form: —$(CH_2)_{2-6}$—; —$(CH_2)_2O(CH_2)_2$—;

—$(CH_2)_2S(CH_2)_2$—; or —$(CH_2)_2NR^{57}(CH_2)_2$—; where $R^{57}$: H; or lower alkyl); —$(CH_2)_o PO(OR^{60})_2$ (where $R^{60}$: lower alkyl; or lower alkenyl); —$(CH_2)_o SO_2R^{62}$ (where $R^{62}$: lower alkyl; or lower alkenyl); or —$(CH_2)_q C_6H_4R^8$ (where $R^8$: H; F; Cl; $CF_3$; lower alkyl; lower alkenyl; or lower alkoxy).

$R^{28}$: lower alkyl; lower alkenyl; —$(CH_2)_o OR^{55}$ (where $R^{55}$: lower alkyl; or lower alkenyl); —$(CH_2)_o SR^{56}$ (where $R^{56}$: lower alkyl; or lower alkenyl); —$(CH_2)_o$ NR$^{33}$R$^{34}$ (where R$^{33}$: lower alkyl; or lower alkenyl; R$^{34}$: H; or lower alkyl; or R$^{33}$ and R$^{34}$ taken together form:

—(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —CH$_2$)$_o$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S (CH$_2$)$_2$—; or —(CH$_2$)$_2$NR$^{57}$(CH$_2$)$_2$—; where R$^{57}$: H; or lower alkyl); —(CH$_2$)$_o$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$N(R$^{20}$)COR$^{64}$(where: R$^{20}$: H; or lower alkyl; R$^{64}$: lower alkyl; or lower alkenyl); —(CH$_2$)$_s$COOR$^{57}$ (where R$^{57}$: lower alkyl; or lower alkenyl); —(CH$_2$)$_o$CONR$^{58}$R$^{59}$ (where R$^{58}$: lower alkyl, or lower alkenyl; and R$^{59}$: H; lower alkyl; or R$^{58}$ and R$^{59}$ taken together form: —(CH$_2$)$_{2-6}$—; —(CH$_2$)$_2$O (CH$_2$)$_2$—;

—(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$PO(OR$^{60}$)$_2$ (where R$^{60}$: lower alkyl; or lower alkenyl); —(CH$_2$)$_o$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy).

R$^{29}$: lower alkyl; lower alkenyl; —(CH$_2$)$_o$OR$^{55}$ (where R$^{55}$: lower alkyl; or lower alkenyl); —(CH$_2$)$_o$SR$^{56}$ (where R$^{56}$: lower alkyl; or lower alkenyl); —(CH$_2$)$_o$NR$^{33}$R$^{34}$ (where R$^{33}$: lower alkyl; or lower alkenyl; R$^{34}$: H; or lower alkyl; or R$^{33}$ and R$^{34}$ taken together form:

—(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_s$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S (CH$_2$)$_2$—; or —(CH$_2$)$_2$NR$^{57}$(CH$_2$)$_2$—; where R$^{57}$: H; or lower alkyl); —(CH$_2$)$_o$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$N(R$^{20}$)COR$^{64}$(where: R$^{20}$: H; or lower alkyl; R$^{64}$: lower alkyl; or lower alkenyl); particularly favored are NR$^{20}$COlower-alkyl (R$^{20}$=H; or lower alkyl); —(CH$_2$)$_o$COOR$^{57}$ (where R$^{57}$: lower alkyl; or lower alkenyl);

—(CH$_2$)$_o$CONR$^{58}$R$^{59}$ (where R$^{58}$: lower alkyl, or lower alkenyl; and R$^{59}$: H; lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S (CH$_2$)$_2$—; or —(CH$_2$)$_2$NR$^{57}$(CH$_2$)$_2$—; where R$^{57}$: H; or lower alkyl); —(CH$_2$)$_o$PO(OR$^{60}$)$_2$ (where R$^{60}$: lower alkyl; or lower alkenyl); —(CH$_2$)$_o$SO$_2$R$^{62}$ (where R$^{62}$: lower alkyl; or lower alkenyl); or —(CHz)$_q$C$_6$H$_4$R$^8$ (where R$^8$: H; F; Cl; CF$_3$; lower alkyl; lower alkenyl; or lower alkoxy).

For templates (b) to (p), such as (b1) and (c1), the preferred values for the various symbols are the following:

R$^8$: H; F; Cl; CF$_3$; lower alkyl; lower alkenyl; —(CH$_2$)$_o$OR$^{55}$ (where R$^{55}$: lower alkyl; or lower alkenyl); —(CH$_2$)$_o$SR$^{56}$ (where R$^{56}$: lower alkyl; or lower alkenyl); —(CH$_2$)$_o$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O (CH$_2$)$_2$—; —(CH$_2$)$_2$S(CH$_2$)$_2$—; or —(CH$_2$)$_2$NR$^{57}$ (CH$_2$)$_2$—; where R$^{57}$: H; or lower alkyl); —(CH$_2$)$_o$ OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—;

—(CH$_2$)$_2$S(CH$_2$)$_2$—; or —(CH$_2$)$_2$NR$^{57}$(CH$_2$)$_2$—; where R$^{57}$: H; or lower alkyl);

—(CH$_2$)$_o$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—;

—(CH$_2$)$_2$O(CH$_2$)$_2$—; —(CH$_2$)$_2$S(CH$_2$)$_2$—; or —(CH$_2$)$_2$ NR$^{57}$(CH$_2$)$_2$—; where R$^{57}$: H; or lower alkyl);

—(CH$_2$)$_o$N(R$^{20}$)COR$^{64}$ (where: R$^{20}$: H; or lower alkyl; R$^{64}$: lower alkyl; or lower alkenyl);

—(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl; or lower alkenyl; and R$^{59}$: H; or lower alkyl; or R$^{58}$ and R$^{59}$ taken together form:

—(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl);

—(CH$_2$)$_o$PO(OR$^{60}$)$_2$ (where R$^{60}$: lower alkyl; or lower alkenyl); —(C$_{1-2}$)$_o$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy).

R$^{20}$: H; or lower alkyl.

R$^{30}$: H, methyl.

R$^{31}$: H; lower alkyl; lower alkenyl; —(CH$_2$)$_p$OR$^{55}$ (where R$^{55}$: lower alkyl; or lower alkenyl); —(CH$_2$)$_p$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$S (CH$_2$)$_2$—; or —(CH$_2$)$_2$NR$^{57}$(CH$_2$)$_2$—, where R$^{57}$: H; or lower alkyl); —(CH$_2$)$_p$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S (CH$_2$)$_2$—; or —(CH$_2$)$_2$NR$^{57}$(CH$_2$)$_2$—; where R$^{57}$: H; or lower alkyl); —(CH$_2$)$_p$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—;

—(CH$_2$)$_2$O(CH$_2$)$_2$—; —(CH$_2$)$_2$S(CH$_2$)$_2$—; or —(CH$_2$)$_2$ NR$^{57}$(CH$_2$)$_2$—; where R$^{57}$: H; or lower alkyl);

—(CH$_2$)$_p$N(R$^{20}$)CoR$^{64}$ (where: R$^{20}$: H; or lower alkyl; R$^{64}$: lower alkyl; or lower alkenyl);

—(CH$_2$)$_o$COOR$^{57}$ (where R$^{57}$: lower alkyl; or lower alkenyl); (—(CH$_2$)$_o$CONR$^{58}$R$^{59}$ (where R$^{58}$: lower alkyl, or lower alkenyl; and R$^{59}$: H; lower alkyl; or R$^{58}$ and R$^{59}$ taken together form:

—(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$PO(OR$^{60}$)$_2$ (where R$^{60}$: lower alkyl; or lower alkenyl); —(CH$_2$)$_m$SO$_2$R$^{62}$ (where R$^{62}$: lower alkyl; or lower alkenyl); or —(CH$_2$)$_r$C$_6$H$_4$R$^8$ (where R$^8$: H; F; Cl; CF$_3$; lower alkyl; lower alkenyl; or lower alkoxy); most preferred is —(CH$_2$)CONR$^{58}$R$^{59}$ (R$^{58}$: H; or lower alkyl; R$^{59}$: lower alkyl; or lower alkenyl).

R$^{32}$: H, methyl.

R$^{33}$: lower alkyl; lower alkenyl; —(CH$_2$)$_m$OR$^{55}$ (where R$^{55}$: lower alkyl; or lower alkenyl); —(CH$_2$)$_m$NR$^{34}$R$^{63}$ (where R$^{34}$: lower alkyl; or lower alkenyl; R$^{63}$: H; or lower alkyl; or R$^{34}$ and R$^{63}$ taken together form: —(CH$_2$)$_{2-6}$—;   —(CH$_2$)$_2$O(CH$_2$)$_2$—;   —(CH$_2$)$_2$S(CH$_2$)$_2$—; or —(CH$_2$)$_2$NR$^{57}$(CH$_2$)$_2$—; where R$^{57}$: H; or lower alkyl); (CH$_2$)OCONR$^{75}$R$^{82}$(where R$^{75}$: lower alkyl; or lower alkenyl; R$^{82}$: H; or lower alkyl; or R$^{75}$ and R$^{82}$ taken together form:   —(CH$_2$)$_{2-6}$—;   —(CH$_2$)$_2$O(CH$_2$)$_2$—;   —(CH$_2$)$_2$S(CH$_2$)$_2$—; or —(CH$_2$)$_2$NR$^{57}$(CH$_2$)$_2$—; where R$^{57}$: H; or lower alkyl);

—(CH$_2$)$_m$NR$^{20}$CONR$^{78}$R$^{82}$ (where R$^{20}$: H; or lower lower alkyl; R$^{78}$: H; or lower alkyl; or lower alkenyl; R$^{82}$: H; or lower alkyl; or R$^{78}$ and R$^{82}$ taken together form: —(CH$_2$)$_{2-6}$—;

—(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl);

—(CH$_2$)$_m$N(R$^{20}$)COR$^{64}$ (where: R$^{20}$: H; or lower alkyl; R$^{64}$: lower alkyl; or lower alkenyl);

—(CH$_2$)$_o$COOR$^{57}$ (where R$^{57}$: lower alkyl; or lower alkenyl);   —(CH$_2$)$_m$CONR$^{58}$R$^{59}$ (where R$^{58}$: lower alkyl; or lower alkenyl; and R$^{59}$: H; lower alkyl; or R$^{58}$ and R$^{59}$ taken together form:

—(CH$_2$)$_{2-6}$—;   —(CH$_2$)$_2$O(CH$_2$)$_2$—;   —(CH$_2$)$_2$S(CH$_2$)$_2$—; or —(CH$_2$)$_2$NR$^{57}$(CH$_2$)$_2$—; where R$^{57}$: H; or lower alkyl).

R$^{34}$: H; or lower alkyl.

R$^{35}$: H; lower alkyl; lower alkenyl; —(CH$_2$)$_m$OR$^{15}$ (where R$^{55}$: lower alkyl; or lower alkenyl); —(CH$_2$)$_m$NR$^{33}$R$^{34}$ (where R$^{33}$: lower alkyl; or lower alkenyl; R$^{34}$: H; or lower alkyl; or R$^{33}$ and R$^{34}$ taken together form:   —(CH$_2$)$_{2-6}$—;   —(CH$_2$)$_2$O(CH$_2$)$_2$—;   —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$) OCONR$^{33}$R$^{75}$ (where R$^{33}$: H; or lower alkyl; or lower alkenyl; R$^{75}$: lower alkyl; or R$^{33}$ and R$^{75}$ taken together form:   —(CH$_2$)$_{2-6}$—;   —(CH$_2$)$_2$O(CH$_2$)$_2$—;   —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_m$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—;

—(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl);

—(CH$_2$)$_m$N(R$^{20}$)COR$^{64}$ (where: R$^{20}$: H; or lower alkyl; R$^{64}$: lower alkyl; or lower alkenyl);

—(CH$_2$)$_o$COOR$^{57}$ (where R$^{57}$: lower alkyl; or lower alkenyl);   —(CH$_2$)$_o$CONR$^{58}$R$^{59}$ (where R$^{58}$: lower alkyl; or lower alkenyl; and R$^{59}$: H; lower alkyl; or R$^{58}$ and R$^{59}$ taken together form:

—(CH$_2$)$_{2-6}$—;   —(CH$_2$)$_2$O(CH$_2$)$_2$—;   —(CH$_2$)$_2$S(CH$_2$)$_2$—; or —(CH$_2$)$_2$NR$^{57}$(CH$_2$)$_2$—; where R$^{57}$: H; or lower alkyl).

R$^{36}$: lower alkyl; lower alkenyl; or aryl-lower alkyl.

R$^{37}$: H; lower alkyl; lower alkenyl; —(CH$_2$)$_p$OR$^{55}$ (where R$^{55}$: lower alkyl; or lower alkenyl); —(CH$_2$)$_p$NR$^{33}$R$^{34}$ (where R$^{33}$: lower alkyl; or lower alkenyl; R$^{34}$: H; or lower alkyl; or R$^{33}$ and R$^{34}$ taken together form:   —(CH$_2$)$_{2-6}$—;   —(CH$_2$)$_2$O(CH$_2$)$_2$—;   —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_p$OCONR$^{33}$R$^{75}$ (where R$^{33}$: H; or lower alkyl; or lower alkenyl; R$^{75}$: lower alkyl; or R$^{33}$ and R$^{75}$ taken together form:   —(CH$_2$)$_{2-6}$—;   —(CH$_2$)$_2$O(CH$_2$)$_2$—;   —(CH$_2$)$_2$S(CH$_2$)$_2$—; or —(CH$_2$)$_2$NR$^{57}$(CH$_2$)$_2$—; where R$^{57}$: H; or lower alkyl);

—(CH$_2$)$_p$NR$^{20}$CONR$^{33}$R$^{82}$ (where R$^{20}$: H; or lower alkyl; R$^{33}$: H; or lower alkyl; or lower alkenyl; R$^{82}$: H; or lower alkyl; or R$^{33}$ and R$^{82}$ taken together form: —(CH$_2$)$_2$—;

—(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl);

—(CH$_2$)$_p$N(R$^{20}$)COR$^{64}$ (where: R$^{20}$: H; or lower alkyl; R$^{64}$: lower alkyl; or lower alkenyl);

—(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl, or lower alkenyl; and R$^{59}$: H; lower alkyl; or R$^{58}$ and R$^{59}$ taken together form:

—(CH$_2$)$_{2-6}$—;   —(CH$_2$)$_2$O(CH$_2$)$_2$—;   —(CH$_2$)$_2$S(CH$_2$)$_2$—; or —(CH$_2$)$_2$NR$^{57}$(CH$_2$)$_2$—; where R$^{57}$: H; or lower alkyl);

—(CH$_2$)$_o$PO(OR$^{60}$)$_2$ (where R$^{60}$: lower alkyl; or lower alkenyl); —(CH$_2$)$_o$SO$_2$R$^{62}$ (where R$^{62}$: lower alky; or lower alkenyl); or —(CH$_2$)$_q$C$_6$R$_4$R$^8$ (where R$^8$: H; F; Cl; CF$_3$; lower alkyl; lower alkenyl; or lower alkoxy).

R$^{38}$: H; lower alkyl; lower alkenyl; —(CH$_2$)$_p$OR$^{55}$ (where R$^{55}$: lower alkyl; or lower alkenyl); —(CH$_2$)$_p$NR$^{33}$R$^{34}$ (where R$^{33}$: lower alkyl; or lower alkenyl; R$^{34}$: H; or lower alkyl; or R$^{33}$ and R$^{34}$ taken together form:   —(CH$_2$)$_{2-6}$—;   —(CH$_2$)$_2$O(CH$_2$)$_2$—;   —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_p$OCONR$^{33}$R$^{75}$ (where R$^{33}$: H; or lower alkyl; or lower alkenyl; R$^{75}$: lower alkyl; or R$^{33}$ and R$^{78}$ taken together form:   —(CH$_2$)$_{2-6}$—;   —(CH$_2$)$_2$O(CH$_2$)$_2$—;   —(CH$_2$)$_2$S(CH$_2$)$_2$—; or —(CH$_2$(}$_2$NR$^{57}$(CH$_2$)$_2$—; where R$^{57}$: H; or lower alkyl);

—(CH$_2$)$_p$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—;

—(CH$_2$)O(CH$_2$)$_m$—; —(CH$_2$)$_2$S(CH$_2$)$_2$—; or —(CH$_2$)$_2$NR$^{57}$(CH$_2$)$_2$—; where R$^{57}$: H; or lower alkyl);

—(CH$_2$)$_p$N(R$^{20}$)COR$^{64}$ (where: R$^{20}$: H; or lower alkyl; R$^{64}$: lower alkyl; or lower alkenyl);

—(CH$_2$)$_s$COOR$^7$ (where R$^{57}$: lower alkyl; or lower alkenyl); —(CH$_2$)$_o$CONR$^{58}$R$^{59}$ (where R$^{58}$: lower alkyl, or lower alkenyl; and R$^{59}$: H; lower alkyl; or R$^{58}$ and R$^{59}$ taken together form:

—(CH$_2$)$_{2-6}$—; —(CH$_2$)$_2$O(CH$_2$)$_2$—; —(CH$_2$)S(CH$_2$)$_2$—; or —(CH$_2$)$_2$NR$^{57}$(CH$_2$)$_2$—; where R$^{57}$: H; or lower alkyl);

—(CH$_2$)$_o$PO(OR$^{60}$)$_2$ (where R$^{60}$: lower alkyl; or lower alkenyl); —(CH$_2$)$_o$SO$_2$R$^{62}$ (where R$^{62}$: lower alkyl; or lower alkenyl); or —(CH$_2$)$_q$C$_6$H$_4$R$^8$ (where R$^8$: H; F; Cl; CF$_3$; lower alkyl; lower alkenyl; or lower alkoxy).

R$^{39}$: H; lower alkyl; lower alkenyl; —(CH$_2$)$_m$OR$^{55}$ (where R$^{55}$: lower alkyl; or lower alkenyl); —(CH$_2$)$_m$N(R$^{20}$)COR$^{64}$ (where: R$^{20}$: H; or lower alkyl; R$^{64}$: lower alkyl; or lower alkenyl); —(CH$_2$)$_o$COOR$^{57}$ (where R$^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl).

$R^{40}$: lower alkyl; lower alkenyl; or aryl-lower alkyl.

$R^{41}$: H; lower alkyl; lower alkenyl; —$(CH_2)_pOR^{55}$ (where $R^{55}$: lower alkyl; or lower alkenyl); —$(CH_2)_pNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—;

—$(CH_2)_2O(CH_2)_2$—; —$(CH_2)_2S(CH_2)_2$—; or —$(CH_2)_2NR^{57}(CH_2)_2$—; where $R^{57}$: H; or lower alkyl);

—$(CH_2)_pN(R^{20})COR^{64}$ (where: $R^{20}$: H; or lower alkyl; $R^{64}$: lower alkyl; or lower alkenyl);

—$(CH_2)_oCOOR^{57}$ (where $R^{57}$: lower alkyl; or lower alkenyl); —$(CH_2)_oCONR^{58}R^{59}$ (where $R^{58}$: lower alkyl, or lower alkenyl; and $R^{59}$: H; lower alky; or $R^{58}$ and $R^{59}$ taken together form:

—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{42}$: H; lower alkyl; lower alkenyl; —$(CH_2)_pOR^{55}$ (where $R^{55}$: lower alkyl; or lower alkenyl); —$(CH_2)_pNR^{33}R^{34}$ (where $R^{33}$: lower alkyl; or lower alkenyl; $R^{34}$: H; or lower alkyl; or $R^{33}$ and $R^{34}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_2$—;

—$(CH_2)_2O(CH_2)_2$—; —$(CH_2)_2S(CH_2)_2$—; Or —$(CH_2)_2NR^{57}(CH_2)_2$—; where $R^{57}$: H; or lower alkyl);

—$(CH_2)_pN(R^{20})COR^{64}$ (where: $R^{20}$: H; or lower alkyl; $R^{64}$: lower alkyl; or lower alkenyl);

—$(CH_2)_oCOOR^{57}$ (where $R^{57}$: lower alkyl; or lower alkenyl); —$(CH_2)_oCONR^{58}R^{59}$ (where $R^{58}$: lower alkyl, or lower alkenyl; and $R^{59}$: H; lower alkyl; or $R^{58}$ and $R^{59}$ taken together form:

—$(CH_2)_{2-6}$—; —$(CHZ)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{43}$: H; lower alkyl; lower alkenyl; —$(CH_2)_mOR^{55}$ (where $R^{55}$: lower alkyl; or lower alkenyl); —$(CH_2)_mSR^{56}$ (where $R^8$: lower alkyl; or lower alkenyl); —$(CH_2)_mNR^{33}R^{34}$ (where $R^{33}$: lower alkyl; or lower alkenyl; $R^{34}$: H; or lower alkyl; or $R^{33}$ and $R^{34}$ taken together form:

—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mOCONR^{33}R^{75}$ (where $R^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)$ $NR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mN(R^{20})COR^{64}$ (where: $R^{20}$: H; or lower alkyl; $R^{64}$: lower alkyl; or lower alkenyl); —$(CH_2)_sCOOR^{57}$ (where $R^{57}$: lower alkyl; or lower alkenyl); —$(CH_2)_oCONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—;

—$(CH_2)_2S(CH_2)_2$—; or —$(CH_2)_2NR^{57}(CH_2)_2$—; where $R^{57}$: H; or lower alkyl); —$(CH_2)_oPO(OR^{60})_2$ (where $R^{60}$: lower alkyl; or lower alkenyl); —$(CH_2)_oSO_2R^{62}$ (where $R^{62}$: lower alkyl; or lower alkenyl); or —$(CH_2)_qC_6H_4R^8$ (where $R^8$: H; F; Cl; $CF_3$; lower alkyl; lower alkenyl; or lower alkoxy).

$R^{44}$: lower alkyl; lower alkenyl; —$(CH_2)poR^{55}$ (where $R^{55}$: lower alkyl; or lower alkenyl); —$(CH_2)_pSR^{56}$ (where $R^{56}$: lower alkyl; or lower alkenyl); —$(CH_2)_pNR^{33}R^{34}$ (where $R^{33}$: lower alkyl; or lower alkenyl; $R^{34}$: H; or lower alkyl; or $R^{33}$ and $R^{34}$ taken together form:

—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pOCONR^{33}R^{75}$ (where $R^{33}$: H; or lower alkyl; or lower alkenyl; $R^{75}$: lower alkyl; or $R^{33}$ and $R^{78}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pNR^{20}CONR^{33}R^{82}$ (where $R^{20}$: H; or lower lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_pN(R^{20})COR^{64}$ (where: $R^{20}$: H; or lower alkyl; $R^{64}$: lower alkyl; or lower alkenyl); —$(CH_2)_pCOOR^{57}$ (where $R^{57}$: lower alkyl; or lower alkenyl);

—$(CH_2)CONR^{58}R^{59}$ (where $R^{58}$: lower alkyl; or lower alkenyl; and $R^{59}$: H; lower alkyl; or $R^{58}$ and $R^{59}$ taken together form: —$(CH_2)_{2-6}$—; —$(CH_2)_2O(CH_2)_2$—;

—$(CH_2)_2S(CH_2)_2$—; or —$(CH_2)_2NR^{57}(CH_2)_2$—; where $R^{57}$: H; or lower alkyl); or —$(CH_2)_oC_6H_4R^8$ (where $R^8$: H; F; Cl; $CF_3$; lower alkyl; lower alkenyl; or lower alkoxy).

$R^{45}$: H; lower alkyl; lower alkenyl; —$(CH_2)OOR^{55}$ (where $R^{55}$: lower alkyl; or lower alkenyl); —$(CH_2)_sSR^{56}$ (where $R^{56}$: lower alkyl; or lower alkenyl); —$(CH_2)_m$ NR$^{33}$R$^{34}$ (where R$^{33}$: lower alkyl; or lower alkenyl; R$^{34}$: H; or lower alkyl; or R$^{33}$ and R$^{34}$ taken together form:

—(CH$_2$)$_{2-6}$—; —(CH$_2$)$_2$O(CH$_2$)$_2$—; —(CH$_1$)$_2$S(CH$_2$)$_2$—; or —(CH$_2$)$_2$NR$^{57}$(CH$_2$)$_2$—; where R$^{57}$: H; or lower alkyl); —(CH$_2$)$_s$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$N(R$^{20}$)COR$^{64}$ (where: R$^{20}$: H; or lower alkyl; R$^{64}$: lower alkyl; or lower alkenyl); —(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl; or lower alkenyl; and R$^{59}$: H; lower alkyl; or R$^{58}$ and R$^{59}$ taken together form: —(CH$_2$)$_{2-6}$—; —(CH$_2$)$_2$O(CH$_2$)$_2$—;

—(CH$_2$)$_2$S(CH$_{12}$)$_2$—; or —(CH$_2$)$_2$NR$^{57}$(CH$_2$)$_2$—; where R$^{57}$: H; or lower alkyl); or —(CH$_2$)$_s$C$_6$H$_4$R$^{8}$ (where R$^{8}$: H; F; Cl; CF$_3$; lower alkyl; lower alkenyl; or lower alkoxy).

R$^{46}$: H; lower alkyl; lower alkenyl; —(CH$_2$)$_s$OR$^{55}$ (where R$^{55}$: lower alkyl; or lower alkenyl); —(CH$_2$)$_s$SR$^{56}$ (where R$^{56}$: lower alkyl; or lower alkenyl); —(CH$_2$)$_s$NR$^{33}$R$^{34}$ (where R$^{33}$: lower alkyl: or lower alkenyl; R$^{34}$: H; or lower alkyl; or R$^{33}$ and R$^{34}$ taken together form:

—(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_s$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_o$NR$^{20}$CoNR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together formi: —(CH$_2$)$_{2-6}$—; —(CH$_2$)$_2$O(CH$_1$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_s$N(R$^{20}$)COR$^{64}$ (where: R$^{20}$: H; or lower alkyl; R$^{64}$: lower alkyl; or lower alkenyl); —(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl; or lower alkenyl; and R$^{59}$: H; lower alkyl; or R$^{58}$ and R$^{59}$ taken together form: —(CH$_2$)$_{2-6}$—; —(CH$_2$)$_2$O(CH$_2$)$_2$—;

—(CH$_2$)$_2$S(CH$_2$)$_2$—; or —(CH$_2$)$_2$NR$^{57}$(CH$_2$)$_2$—; where R$^{57}$: H; or lower alkyl); or —(CH$_2$)$_s$C$_6$H$_4$R$^{8}$ (where R$^{8}$: H; F; Cl; CF$_3$; lower alkyl; lower alkenyl; or lower alkoxy).

R$^{47}$: H; or OR$^{55}$ (where R$^{55}$: lower alkyl; or lower alkenyl).

R$^{48}$: H; or lower alkyl.

R$^{49}$: H; lower alkyl; —(CH$_2$)$_o$COOR$^{57}$ (where R$^{57}$: lower alkyl; or lower alkenyl); —(CH$_2$)$_o$CONR$^{58}$R$^{59}$ (where R$^{58}$: lower alkyl; or lower alkenyl; and R$^{59}$: H; lower alkyl; or R$^{58}$ and R$^{59}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); or (CH$_2$)$_s$C$_6$H$_4$R$^{8}$ (where R$^{8}$: H; F; Cl; CF$_3$; lower alkyl; lower alkenyl; or lower alkoxy).

R$^{50}$: H; methyl.

R$^{51}$: H; lower alkyl; lower alkenyl; —(CH$_2$)$_m$OR$^{55}$ (where R$^{55}$: lower alkyl; or lower alkenyl); —(CH$_2$)$_m$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); (CH$_2$)$_m$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)S(CH$_2$)$_2$—; or —(CH$_2$)$_2$NR$^{57}$(CH$_2$)$_2$—; where R$^{57}$: H; or lower alkyl); —(CH$_2$)$_m$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—;

—(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl);

—(CH$_2$)$_m$N(R$^{20}$)COR$^{64}$ (where: R$^{20}$: H; or lower alkyl; R$^{82}$: lower alkyl; or lower alkenyl);

—(CH$_2$)$_m$COOR$^{57}$ (where R$^{57}$: lower alkyl; or lower alkenyl); —(CH$_2$)$_p$CONR$^{58}$sR$^{59}$ (where R$^{59}$: lower alkyl; or lower alkenyl; and R$^{59}$: H; lower alkyl; or R$^{58}$ and R$^{59}$ taken together form:

—(CH$_2$H)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); or —(CH$_2$)$_r$C$_6$H$_4$R$^{8}$ (where R$^{8}$: H; F; Cl; CF$_3$; lower alkyl; lower alkenyl; or lower alkoxy).

R$^{52}$: H; lower alkyl; lower alkenyl; —(CH$_2$)$_m$OR$^{55}$ (where R$^{55}$: lower alkyl; or lower alkenyl); —(CH$_2$)$_m$NR$^{33}$R$^{34}$ (where R$^{33}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_s$OCONR$^{33}$R$^{75}$ (where R$^{33}$: H; or lower alkyl; or lower alkenyl; R$^{75}$: lower alkyl; or R$^{33}$ and R$^{75}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); —(CH$_2$)$_m$NR$^{20}$CONR$^{33}$R$^{82}$ (where R$^{20}$: H; or lower lower alkyl; R$^{33}$: H; or lower alkyl; or lower alkenyl; R$^{82}$: H; or lower alkyl; or R$^{33}$ and R$^{82}$ taken together form: —(CH$_2$)$_{2-6}$—;

—(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; R$^{57}$: H; or lower alkyl);

—(CH$_2$)$_m$N(R$^{20}$)COR$^{64}$ (where: R$^{20}$: H; or lower alkyl; R$^{64}$: lower alkyl; or lower alkenyl);

—(CH$_2$)$_p$COOR$^{57}$ (where R$^{57}$: lower alkyl; or lower alkenyl); —(CH$_2$)$_p$CONR$^{58}$R$^{59}$ (where R$^{58}$: lower alkyl; or lower alkenyl; and R$^{59}$: H; lower alkyl; or R$^{58}$ and R$^{59}$ taken together form:

—(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); or —(CH$_2$)$_r$C$_6$H$_4$R$^{8}$ (where R$^{8}$: H; F; Cl; CF$_3$; lower alkyl; lower alkenyl; or lower alkoxy).

R$^{53}$: H; lower alkyl; lower alkenyl; —(CH$_2$)$_m$OR$^{55}$ (where R$^{55}$: lower alkyl; or lower alkenyl); —(CH$_2$)$_m$NR$^{33}$R$^{34}$ (where R$^{34}$: lower alkyl; or lower alkenyl; R$^{34}$: H; or lower alkyl; or R$^{33}$ and R$^{34}$ taken together form: —(CH$_2$)$_{2-6}$—; —(CH$_2$)$_2$O(CH$_2$)$_2$—; —(CH$_2$)$_2$S(CH$_2$)$_2$—; or —(CH$_2$)$_2$NR$^{57}$(CH$_2$)$_2$—; where R$^{57}$: H; or lower alkyl); (CH$_2$)$_m$OCONRW$^{33}$R$^{75}$ (where R$^{33}$: H; or lower alkyl; or lower alkenyl; $R^{75}$: lower alkyl; or $R^{33}$ and $R^{75}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mNR^{20}CONR^{33}R^{82}$ (where $R^{20}$: H; or lower alkyl; $R^{33}$: H; or lower alkyl; or lower alkenyl; $R^{82}$: H; or lower alkyl; or $R^{33}$ and $R^{82}$ taken together form: —$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); —$(CH_2)_mN(R^{20})COR^{64}$ (where: $R^{20}$: H; or lower alkyl; $R^{64}$: lower alkyl; or lower alkenyl); —$(CH_2)_pCOOR^{57}$ (where $R^{57}$: lower alkyl; or lower alkenyl); —$(CH_2)_pCONR^{58}R^{59}$ (where $R^{58}$: lower alkyl; or lower alkenyl; and $R^{59}$: H; lower alkyl; or $R^{58}$ and $R^{59}$ taken together form:

—$(CH_2)_{2-6}$—; —$(CH_2)_2O(CH_2)_2$—; —$(CH_2)_2S(CH_2)_2$—; or —$(CH_2)_2NR^{57}(CH_2)_2$—; where $R^{57}$: H; or lower alkyl); or —$(CH_2)_rC_6H_4R^8$ (where $R^8$: H; F; Cl; $CF_3$; lower alkyl; lower alkenyl; or lower alkoxy).

$R^{54}$: lower alkyl; lower alkenyl; or aryl-lower alkyl.

Among the building blocks A70 to A104 the following are preferred: A74 with $R^{22}$ being H, A75, A76, A77 with $R^{22}$ being H, A78 and A79.

The building block —B—CO— within template (a1) and (a2) designates an L-amino acid residue.

Preferred values for B are: —$NR^{20}CH(R^{71})$— and enantiomers of groups A5 with $R^2$ being H, A8, A22, A25, A38 with $R^2$ being H, A42, A47, and A50. Most preferred are

| | |
|---|---|
| Ala | L-Alanine |
| Arg | L-Arginine |
| Asn | L-Asparagine |
| Cys | L-Cysteine |
| Gln | L-Glutamine |
| Gly | Glycine |
| His | L-Histidine |
| Ile | L-Isoleucine |
| Leu | L-Leucine |
| Lys | L-Lysine |
| Met | L-Methionine |
| Phe | L-Phenylalanine |
| Pro | L-Proline |
| Ser | L-Serine |
| Thr | L-Threonine |
| Trp | L-Tryptophan |
| Tyr | L-Tyrosine |
| Val | L-Valine |
| Cit | L-Citrulline |
| Orn | L-Ornithine |
| tBuA | L-t-Butylalanine |
| Sar | Sarcosine |
| t-BuG | L-tert.-Butylglycine |
| 4AmPhe | L-para-Aminophenylalanine |
| 3AmPhe | L-meta-Aminophenylalanine |
| 2AmPhe | L-ortho-Aminophenylalanine |
| Phe(mC(NH$_2$)=NH) | L-meta-Amidinophenylalanine |
| Phe(pC(NH$_2$)=NH) | L-para-Amidinophenylalanine |
| Phe(mNHC(NH$_2$)=NH) | L-meta-Guanidinophenylalanine |
| Phe(pNHC(NH$_2$)=NH) | L-para-Guanidinophenylalanine |
| Phg | L-Phenylglycine |
| Cha | L-Cyclohexylalanine |
| C$_4$al | L-3-Cyclobutylalanine |
| C$_5$al | L-3-Cyclopentylalanine |
| Nle | L-Norleucine |
| 2-Nal | L-2-Naphthylalanine |
| 1-Nal | L-1-Naphthylalanine |
| 4Cl-Phe | L-4-Chlorophenylalanine |
| 3Cl-Phe | L-3-Chlorophenylalanine |
| 2Cl-Phe | L-2-Chlorophenylalanine |
| 3,4Cl$_2$-Phe | L-3,4-Dichlorophenylalanine |
| 4F-Phe | L-4-Fluorophenylalanine |
| 3F-Phe | L-3-Fluorophenylalanine |
| 2F-Phe | L-2-Fluorophenylalanine |
| Tic | L-1,2,3,4-Tetrahydroisoquinoline-3-carboxylic acid |
| Thi | L-β-2-Thienylalanine |
| Tza | L-2-Thiazolylalanine |
| Mso | L-Methionine sulfoxide |
| AcLys | L-N-Acetyllysine |
| Dpr | L-2,3-Diaminopropionic acid |
| A$_2$Bu | L-2,4-Diaminobutyric acid |
| Dbu | (S)-2,3-Diaminobutyric acid |
| Abu | γ-Aminobutyric acid (GABA) |
| Aha | ε-Aminohexanoic acid |
| Aib | α-Aminoisobutyric acid |
| Y(Bzl) | L-O-Benzyltyrosine |
| Bip | L-Biphenylalanine |
| S(Bzl) | L-O-Benzylserine |
| T(Bzl) | L-O-Benzylthreonine |
| hCha | L-Homo-cyclohexylalanine |
| hCys | L-Homo-cysteine |
| hSer | L-Homo-serine |
| hArg | L-Homo-arginine |
| hPhe | L-Homo-phenylalanine |
| Bpa | L-4-Benzoylphenylalanine |
| Pip | L-Pipecolic acid |
| OctG | L-Octylglycine |
| MePhe | L-N-Methylphenylalanine |
| MeNle | L-N-Methylnorleucine |
| MeAla | L-N-Methylalanine |
| MeIle | L-N-Methylisoleucine |
| MeVal | L-N-Methvaline |
| MeLeu | L-N-Methylleucine |

In addition, the most preferred values for B also include groups of type A8″ of (L)-configuration:

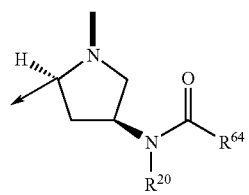

A8″ wherein $R^{20}$ is H or lower alkyl and $R^{64}$ is alkyl; alkenyl; aryl; aryl-lower alkyl; or heteroaryl-lower alkyl; especially those wherein $R^{64}$ is n-hexyl (A8″-21); n-heptyl (A8″-22); 4-(phenyl)benzyl (A8″-23); diphenylmethyl (A8″-24); 3-aminopropyl (A8″-25); 5-amino-pentyl (A8″-26); methyl (A8″-27); ethyl (A8″-28); isopropyl (A8″-29); isobutyl (A8″-30); n-propyl (A8″-31); cyclohexyl (A8″-32); cyclohexylmethyl (A8″-33); n-butyl (A8″-34); phenyl (A8″-35); benzyl (A8″-36); (3-indolyl)methyl (A8″-37); 2-(3-indolyl)ethyl (A8″-38); (4-phenyl)phenyl (A8″-39); and n-nonyl (A8″-40).

The peptidic chain Z of the β-hairpin mimetics described herein is generally defined in terms of amino acid residues belonging to one of the following groups:

| | |
|---|---|
| Group C | —$NR^{20}CH(R^{72})CO$—; "hydrophobic: small to medium-sized" |
| Group D | —$NR^{20}CH(R^{73})CO$—; "hydrophobic: large aromatic or heteroaromatic" |
| Group E | —$NR^{20}CH(R^{74})CO$—; "polar-cationic" and "urea-derived" |
| Group F | —$NR^{20}CH(R^{84})CO$—; "polar-non-charged" |
| Group H | —$NR^{20}$—CH(CO—)—$(CH_2)_{4-7}$—CH(CO—)—$NR^{20}$—; |
| | —$NR^{20}$—CH(CO—)—$(CH_2)_pSS(CH_2)_p$-CH(CO—)—$NR^{20}$—; |
| | —$NR^{20}$—CH(CO—)—(—$(CH_2)_pNR^{20}CO(CH_2)_p$-CH(CO—)—$NR^{20}$—; and |
| | —$NR^{20}$—CH(CO—)—(—$(CH_2)_pNR^{20}CONR^{20}(CH_2)_p$-CH(CO—)—$NR^2$—; |
| | "interstrand linkage" |

Furthermore, the amino acid residues in chain Z can also be of formula —A—CO— or of formula —B—CO— wherein A and B are as defined above. Finally, Gly can also be an amino acid residue in chain Z, and Pro can be an amino acid residue in chain Z, too, with the exception of positions where interstrand linkages (H) are possible.

Group C comprises amino acid residues with small to medium-sized hydrophobic side chain groups according to the general definition for substituent $R^{72}$. A hydrophobic residue refers to an amino acid side chain that is uncharged at physiological pH and that is repelled by aqueous solution. Furthermore these side chains generally do not contain hydrogen bond donor groups, such as (but not limited to) primary and secondary amides, primary and secondary amines and the corresponding protonated salts thereof, thiols, alcohols, phosphonates, phosphates, ureas or thioureas. However, they may contain hydrogen bond acceptor groups such as ethers, thioethers, esters, tertiary amides, alkyl- or aryl phosphonates and phosphates or tertiary amines. Genetically encoded small-to-medium-sized amino acids include alanine, isoleucine, leucine, methionine and valine.

Group D comprises amino acid residues with aromatic and heteroaromatic side chain groups according to the general definition for substituent $R^{73}$. An aromatic amino acid residue refers to a hydrophobic amino acid having a side chain containing at least one ring having a conjugated π-electron system (aromatic group). In addition they may contain hydrogen bond donor groups such as (but not limited to) primary and secondary amides, primary and secondary amines and the corresponding protonated salts thereof, thiols, alcohols, phosphonates, phosphates, ureas or thioureas, and hydrogen bond acceptor groups such as (but not limited to) ethers, thioethers, esters, tertiary amides, alkyl- or aryl phosphonates- and phosphates or tertiary amines. Genetically encoded aromatic amino acids include phenylalanine and tyrosine.

A heteroaromatic amino acid residue refers to a hydrophobic amino acid having a side chain containing at least one ring having a conjugated π-system incorporating at least one heteroatom such as (but not limited to) O, S and N according to the general definition for substituent $R^{77}$. In addition such residues may contain hydrogen bond donor groups such as (but not limited to) primary and secondary amides, primary and secondary amines and the corresponding protonated salts thereof, thiols, alcohols, phosphonates, phosphates, ureas or thioureas, and hydrogen bond acceptor groups such as (but not limited to) ethers, thioethers, esters, tertiary amides, alkyl- or aryl phosphonates- and phosphates or tertiary amines. Genetically encoded heteroaromatic amino acids include tryptophan and histidine.

Group E comprises amino acids containing side chains with polar-cationic, acylamino- and urea-derived residues according to the general definition for substituen $R^{74}$. Polar-cationic refers to a basic side chain which is protonated at physiological pH. Genetically encoded polar-cationic amino acids include arginine, lysine and histidine. Citrulline is an example for an urea derived amino acid residue.

Group F comprises amino acids containing side chains with polar-non-charged residues according to the general definition for substituent $R^{84}$. A polar-non-charged residue refers to a hydrophilic side chain that is uncharged at physiological pH, but that is not repelled by aqueous solutions. Such side chains typically contain hydrogen bond donor groups such as (but not limited to) primary and secondary amides, primary and secondary amines, thiols, alcohols, phosphonates, phosphates, ureas or thioureas. These groups can form hydrogen bond networks with water molecules. In addition they may also contain hydrogen bond acceptor groups such as (but not limited to) ethers, thioethers, esters, tetriary amides, alkyl- or aryl phosphonates- and phosphates or tertiary amines. Genetically encoded polar-non-charged amino acids include asparagine, cysteine, glutamine, serine and threonine.

Group H comprises side chains of preferably (L)-amino acids at opposite positions of the β-strand region that can form an interstrand linkage. The most widely known linkage is the disulfide bridge formed by cysteines and homo-cysteines positioned at opposite positions of the α-strand. Various methods are known to form disulfide linkages including those described by: J. P. Tam et al. *Synthesis* 1979, 955-957; Stewart et al., *Solid Phase Peptide Synthesis,* 2d Ed., Pierce Chemical Company, III., 1984; Ahmed et al. *J. Biol. Chem.* 1975, 250, 8477-8482; and Pennington et al., Peptides, pages 164-166, Giralt and Andreu, Eds., ESCOM Leiden, The Netherlands, 1990. Most advantageously, for the scope of the present invention, disulfide linkages can be prepared using acetamidomethyl (Acm)-protective groups for cysteine. A well established interstrand linkage consists in linking ornithines and lysines, respectively, with glutamic and aspartic acid residues located at opposite β-strand positions by means of an amide bond formation. Preferred protective groups for the side chain amino-groups of ornithine and lysine are allyloxycarbonyl (Alloc) and allylesters for aspartic and glutamic acid. Finally, interstrand linkages can also be established by linking the amino groups of lysine and ornithine located at opposite β-strand positions with reagents such as N,N-carbonylimidazole to form cyclic ureas.

As mentioned earlier, positions for interstrand linkages are positions P4 and P9; and/or P2 and P 11 taken together. Such interstrand linkages are known to stabilize the β-hairpin conformations and thus constitute an important structural element for the design of β-hairpin mimetics.

Most preferred amino acid residues in chain Z are those derived from natural α-amino acids. Hereinafter follows a list of amino acids which, or the residues of which, are suitable for the purposes of the present invention, the abbreviations corresponding to generally adopted usual practice:

| three letter code | | one letter code |
| --- | --- | --- |
| Ala | L-Alanine | A |
| Arg | L-Arginine | R |
| Asn | L-Asparagine | N |
| Asp | L-Aspartic acid | D |
| Cys | L-Cysteine | C |
| Glu | L-Glutamic acid | E |
| Gln | L-Glutamine | Q |
| Gly | Glycine | G |
| His | L-Histidine | H |
| Ile | L-Isoleucine | I |
| Leu | L-Leucine | L |
| Lys | L-Lysine | K |
| Met | L-Methionine | M |
| Phe | L-Phenylalanine | F |
| Pro | L-Proline | P |
| $^D$Pro | D-Proline | $^D$P |
| Ser | L-Serine | S |
| Thr | L-Threonine | T |
| Trp | L-Tryptophan | W |
| Tyr | L-Tyrosine | Y |
| Val | L-Valine | V |

Other α-amino acids which, or the residues of which, are suitable for the purposes of the present invention include:

| | |
|---|---|
| Cit | L-Citrulline |
| Orn | L-Ornithine |
| tBuA | L-t-Butylalanine |
| Sar | Sarcosine |
| Pen | L-Penicillamine |
| t-BuG | L-tert.-Butylglycine |
| 4AmPhe | L-para-Aminophenylalanine |
| 3AmPhe | L-meta-Aminophenylalanine |
| 2AmPhe | L-ortho-Aminophenylalanine |
| Phe(mC(NH$_2$)=NH) | L-meta-Amidinophenylalanine |
| Phe(pC(NH$_2$)=NH) | L-para-Amidinophenylalanine |
| Phe(mNHC (NH$_2$)=NH) | L-meta-Guanidinophenylalanine |
| Phe(pNHC (NH$_2$)=NH) | L-para-Guanidinophenylalanine |
| Phg | L-Phenylglycine |
| Cha | L-Cyclohexylalanine |
| C$_4$al | L-3-Cyclobutylalanine |
| C$_5$al | L-3-Cyclopentylalanine |
| Nle | L-Norleucine |
| 2-Nal | L-2-Naphthylalanine |
| 1-Nal | L-1-Naphthylalanine |
| 4Cl-Phe | L-4-Chlorophenylalanine |
| 3Cl-Phe | L-3-Chlorophenylalanine |
| 2Cl-Phe | L-2-Chlorophenylalanine |
| 3,4Cl$_2$-Phe | L-3,4-Dichlorophenylalanine |
| 4F-Phe | L-4-Fluorophenylalanine |
| 3F-Phe | L-3-Fluorophenylalanine |
| 2F-Phe | L-2-Fluorophenylalanine |
| Tic | 1,2,3,4-Tetrahydroisoquinoline-3-carboxylic acid |
| Thi | L-β-2-Thienylalanine |
| Tza | L-2-Thiazolylalanine |
| Mso | L-Methionine sulfoxide |
| AcLys | N-Acetyllysine |
| Dpr | 2,3-Diaminopropionic acid |
| A$_2$Bu | 2,4-Diaminobutyric acid |
| Dbu | (S)-2,3-Diaminobutyric acid |
| Abu | γ-Aminobutyric acid (GABA) |
| Aha | ε-Aminohexanoic acid |
| Aib | α-Aminoisobutyric acid |
| Y(Bzl) | L-O-Benzyltyrosine |
| Bip | L-(4-phenyl)phenylalanine |
| S(Bzl) | L-O-Benzylserine |
| T(Bzl) | L-O-Benzylthreonine |
| hCha | L-Homo-cyclohexylalanine |
| hCys | L-Homo-cysteine |
| hSer | L-Homo-serine |
| hArg | L-Homo-arginine |
| hPhe | L-Homo-phenylalanine |
| Bpa | L-4-Benzoylphenylalanine |
| 4-AmPyrr1 | (2S,4S)-4-Amino-pyrrolidine-L-carboxylic acid |
| 4-AmPyrr2 | (2S,4R)-4-Amino-pyrrolidine-L-carboxylic acid |
| 4-PhePyrr1 | (2S,5R)-4-Phenyl-pyrrolidine-L-carboxylic acid |
| 4-PhePyrr2 | (2S,5S)-4-Phenyl-pyrrolidine-L-carboxylic acid |
| 5-PhePyrr1 | (2S,5R)-5-Phenyl-pyrrolidine-L-carboxylic acid |
| 5-PhePyrr2 | (2S,5S)-5-Phenyl-pyrrolidine-L-carboxylic acid |
| Pro(4-OH)1 | (4S)-L-Hydroxyproline |
| Pro(4-OH)2 | (4R)-L-Hydroxyproline |
| Pip | L-Pipecolic acid |
| $^D$Pip | D-Pipecolic acid |
| OctG | L-Octylglycine |
| MePhe | L-N-Methylphenylalanine |
| MeNle | L-N-Methylnorleucine |
| MeAla | L-N-Methylalanine |
| MeIle | L-N-Methylisoleucine |
| MeVal | L-N-Methylvaline |
| MeLeu | L-N-Methylleucine |

Particularly preferred residues for group C are:

| | |
|---|---|
| Ala | L-Alanine |
| Ile | L-Isoleucine |
| Leu | L-Leucine |
| Met | L-Methionine |
| Val | L-Valine |
| tBuA | L-t-Butylalanine |
| t-BuG | L-tert.-Butylglycine |
| Cha | L-Cyclohexylalanine |
| C$_4$al | L-3-Cyclobutylalanine |
| C$_5$al | L-3-Cyclopentylalanine |
| Nle | L-Norleucine |
| hCha | L-Homo-cyclohexylalanine |
| OctG | L-Octylglycine |
| MePhe | L-N-Methylphenylalanine |
| MeNle | L-N-Methylnorleucine |
| MeAla | L-N-Methylalanine |
| MeIle | L-N-Methylisoleucine |
| MeVal | L-N-Methylvaline |
| MeLeu | L-N-Methylleucine |

Particularly preferred residues for group C are:
Particularly preferred residues for group D are:

| | |
|---|---|
| His | L-Histidine |
| Phe | L-Phenylalanine |
| Trp | L-Tryptophan |
| Tyr | L-Tyrosine |
| Phg | L-Phenylglycine |
| 2-Nal | L-2-Naphthylalanine |
| 1-Nal | L-1-Naphthylalanine |
| 4Cl-Phe | L-4-Chlorophenylalanine |
| 3Cl-Phe | L-3-Chlorophenylalanine |
| 2Cl-Phe | L-2-Chlorophenylalanine |
| 3,4Cl$_2$-Phe | L-3,4-Dichlorophenylalanine |
| 4F-Phe | L-4-Fluorophenylalanine |
| 3F-Phe | L-3-Fluorophenylalanine |
| 2F-Phe | L-2-Fluorophenylalanine |
| Thi | L-β-2-Thienylalanine |
| Tza | L-2-Thiazolylalanine |
| Y(Bzl) | L-O-Benzyltyrosine |
| Bip | L-Biphenylalanine |
| S(Bzl) | L-O-Benzylserine |
| T(Bzl) | L-O-Benzylthreonine |
| hPhe | L-Homo-phenylalanine |
| Bpa | L-4-Benzoylphenylalanine |

Particularly preferred residues for group E are

| | |
|---|---|
| Arg | L-Arginine |
| Lys | L-Lysine |
| Orn | L-Ornithine |
| Dpr | L-2,3-Diaminopropionic acid |
| A$_2$Bu | L-2,4-Diaminobutyric acid |
| Dbu | (S)-2,3-Diaminobutyric acid |
| Phe(pNH$_2$) | L-para-Aminophenylalanine |
| Phe(mNH$_2$) | L-meta-Aminophenylalanine |
| Phe(oNH$_2$) | L-ortho-Aminophenylalanine |
| hArg | L-Homo-arginine |
| Phe(mC(NH$_2$)=NH) | L-meta-Amidinophenylalanine |
| Phe(pC(NH$_2$)=NH) | L-para-Amidinophenylalanine |
| Phe(mNHC (NH$_2$)=NH) | L-meta-Guanidinophenylalanine |
| Phe(pNHC (NH$_2$)=NH) | L-para-Guanidinophenylalanine |
| Cit | L-Citrulline |

Particularly preferred residues for group F are

| | |
|---|---|
| Asn | L-Asparagine |
| Cys | L-Cysteine |
| Gln | L-Glutamine |
| Ser | L-Serine |
| Thr | L-Threonine |
| Cit | L-Citrulline |
| Pen | L-Penicillamine |
| AcLys | L-$N^\varepsilon$-Acetyllysine |
| hCys | L-Homo-cysteine |
| hSer | L-Homo-serine |

Generally, the peptidic chain Z within the β-hairpin mimetics of the invention comprises 12 amino acid residues. The positions P1 to P12 of each amino acid residue in the chain Z are unequivocally defined as follows: P1 represents the first amino acid in the chain Z that is coupled with its N-terminus to the C-terminus of the templates (b)-(p) or of group —B—CO— in template (a1), or of group —A—CO— in template a2, and P12 represents the last amino acid in the chain Z that is coupled with its C-terminus to the N-terminus of the templates (b)-(p) or of group —A—CO— in template (a1) or of group —B—CO— in template (a2). Each of the positions P1 to P12 will preferably contain an amino acid residue belonging to one of the above types C to F, or of formula —A—CO— or of formula —B—CO— as follows:

P1: of type C or of type D or of type E or of type F;
P2: of type D;
P3: of type C;
P4: of type E, or of type C;
P5: of type E, or of type F;
P6: of type E, or of type F, or of formula —A—CO—;
P7: of type E, or of type F, or of formula —B—CO—;
P8: of type D, or of type C, or of Type F;
P9: of type C, or of type E;
P10: of type F, or of type D, or of type C;
P11: of type D, or of type C, or of type F;
P12: of type C or of type D or of type E or of type F;

at P6 and P7 also D-isomers being possible;

with the proviso that
the amino acid residue in position P4 is of type C; and/or
the amino acid residue in position P5 is of type F; and/or
the amino acid residue in position P8 is of type F; and/or
the amino acid residue in position P9 is of type C; and/or
the amino acid residue in position P10 is of type F; and/or
the amino acid residue in position P11 is of type C or F.

Most preferably, the amino acid residues in positions P1 to P12 are:
P1: Arg;
P2: Trp;
P3: Leu;
P4: Lys or Val;
P5: Lys;
P6: Arg;
P7: Arg;
P8: Trp;
P9: Leu, Val or Lys;
P10: Tyr, Thr or Gln;
P11: Val, Leu, Tyr or Gln; and
P12: Arg;
with the proviso that
the amino acid residue in position P4 is Val; and/or
the amino acid residue in position P9 is Leu or Val; and/or
the amino acid residue in position P10 is Thr or Gln; and/or
the amino acid residue in position P11 is Val or Leu or Gln.

Particularly preferred β-peptidomimetics of the invention include those described in Examples 1, to 8.

The processes of the invention can advantageously be carried out as parallel array syntheses to yield libraries of template-fixed β-hairpin peptidomimetics of the above general formula I. Such parallel syntheses allow one to obtain arrays of numerous (normally 24 to 192, typically 96) compounds of general formula I in high yields and defined purities, minimizing the formation of dimeric and polymeric by-products. The proper choice of the functionalized solid-support (i.e. solid support plus linker molecule), templates and site of cyclization play thereby key roles.

The functionalized solid support is conveniently derived from polystyrene crosslinked with, 20 preferably 1-5%, divinylbenzene; polystyrene coated with polyethyleneglycol spacers (Tentagel®); and polyacrylamide resins (see also Obrecht, D.; Villalgordo, J.-M, "Solid-Supported Combinatorial and Parallel Synthesis of Small-Molecular-Weight Compound Libraries", *Tetrahedron Organic Chemistry Series*, Vol. 17, Pergamon, Elsevier Science, 1998).

The solid support is functionalized by means of a linker, i.e. a bifunctional spacer molecule which contains on one end an anchoring group for attachment to the solid support and on the other end a selectively cleavable functional group used for the subsequent chemical transformations and cleavage procedures. For the purposes of the present invention the linker must be designed to eventually release the carboxyl group under mild acidic conditions which do not affect protecting groups present on any functional group in the side-chains of the various amino acids. Linkers which are suitable for the purposes of the present invention form acid-labile esters with the carboxyl group of the amino acids, usually acid-labile benzyl, benzhydryl and trityl esters; examples of linker structures of this kind include 2-methoxy-4-hydroxymethylphenoxy (Sasrin® linker), 4-(2,4-dimethoxyphenyl-hydroxymethyl)-phenoxy (Rink linker), 4-(4-hydroxymethyl-3-methoxyphenoxy)butyric acid (HMPB linker), trityl and 2-chlorotrityl.

Preferably, the support is derived from polystyrene crosslinked with, most preferably 1-5%, divinylbenzene and functionalized by means of the 2-chlorotrityl linker.

When carried out as a parallel array syntheses the processes of the invention can be advantageously carried out as described herein below but it will be immediately apparent to those skilled in the art how these procedures will have to be modified in case it is desired to synthesize one single compound of the above formula I A number of reaction vessels (normally 24 to 192, typically 96) equal to the total number of compounds to be synthesized by the parallel method are loaded with 25 to 1000 mg, preferably 100 mg, of the appropriate functionalized solid support, preferably 1 to 3% cross linked polystyrene or tentagel resin.

The solvent to be used must be capable of swelling the resin and includes, but is not limited to, dichloromethane (DCM), dimethylformamide (DMF), N-methylpyrrolidone (NMP), dioxane, toluene, tetrahydrofuran (THF), ethanol (EtOH), trifluoroethanol (TFE), isopropylalcohol and the like. Solvent mixtures containing as at least one component a polar solvent (e.g. 20% TFE/DCM, 35% THF/NMP) are beneficial for ensuring high reactivity and solvation of the resin-bound peptide chains (Fields, G. B., Fields, C. G., *J. Am. Chem. Soc.* 1991, 113, 4202-4207).

With the development of various linkers that release the C-terminal carboxylic acid group under mild acidic conditions, not affecting acid-labile groups protecting functional groups in the side chain(s), considerable progresses have been made in the synthesis of protected peptide fragments. The 2-methoxy-4-hydroxybenzylalcohol-derived linker (Sasrin® linker, Mergler et al., *Tetrahedron Lett.* 1988, 29 4005-4008) is cleavable with diluted trifluoroacetic acid (0.5-1% TFA in DCM) and is stable to Fmoc deprotection conditions during the peptide synthesis, Boc/tBu-based additional protecting groups being compatible with this protection scheme. Other linkers which are suitable for the process of the invention include the super acid labile 4-(2,4-dimethoxyphenyl-hydroxymethyl)-phenoxy linker (Rink linker, Rink, H. *Tetrahedron Lett.* 1987, 28, 3787-3790), where the removal of the peptide requires 10% acetic acid in DCM or 0.2% trifluoroacetic acid in DCM; the 4-(4-hydroxymethyl-3-methoxyphenoxy)butyric acid-derived linker (HMPB-linker, Flörsheimer & Riniker, *Peptides* 1991,1990 131) which is also cleaved with 1% TFA/DCM in order to yield a peptide fragment containing all acid labile side-chain protective groups; and, in addition, the 2-chlorotritylchloride linker (Barlos et al., *Tetrahedron Lett.* 1989, 30, 3943-3946), which allows the peptide detachment using a mixture of glacial acetic acid/trifluoroethanol/DCM (1:2:7) for 30 min.

Suitable protecting groups for amino acids and, respectively, for their residues are, for example, for the amino group (as is present e.g. also in the side-chain of lysine)

| Cbz | benzyloxycarbonyl |
|---|---|
| Boc | tert.-butyloxycarbonyl |
| Fmoc | 9-fluorenylmethoxycarbonyl |
| Alloc | allyloxycarbonyl |
| Teoc | trimethylsilylethoxycarbonyl |
| Tcc | trichloroethoxycarbonyl |
| Nps | o-nitrophenylsulfonyl; |
| Trt | triphenymethyl or trityl | for the carboxyl group (as is present e.g. also in the side-chain of aspartic and glutamic acid) by conversion into esters with the alcohol components

| tBu | tert.-butyl |
|---|---|
| Bn | benzyl |
| Me | methyl |
| Ph | phenyl |
| Pac | Phenacyl |
| | Allyl |
| Tse | trimethylsilylethyl |
| Tce | trichloroethyl; | for the guanidino group (as is present e.g. in the side-chain of arginine)

| Pmc | 2,2,5,7,8-pentamethylchroman-6-sulfonyl |
|---|---|
| Ts | tosyl (i.e. p-toluenesulfonyl) |
| Cbz | benzyloxycarbonyl |
| Pbf | pentamethyldihydrobenzofuran-5-sulfonyl | for the hydroxy group (as is present e.g. in the side-chain of threonine and serine)

| tBu | tert.-butyl |
|---|---|
| Bn | benzyl |
| Trt | trityl | and for the mercapto group (as is present e.g. in the side-chain of cysteine)

| Acm | acetamidomethyl |
|---|---|
| tBu | tert.-butyl |
| Bn | benzyl |
| Trt | trityl |
| Mtr | 4-methoxytrityl. |

The 9-fluorenylmethoxycarbonyl-(Fmoc)-protected amino acid derivatives are preferably used as the building blocks for the construction of the template-fixed β-hairpin loop mimetics of formula I. For the deprotection, i.e. cleaving off of the Fmoc group, 20% piperidine in DM or 2% DBU/2% piperidine in DMF can be used.

The quantity of the reactant, i.e. of the amino acid derivative, is usually 1 to 20 equivalents based on the milliequivalents per gram (meq/g) loading of the functionalized solid support (typically 0.1 to 2.85 meq/g for polystyrene resins) originally weighed into the reaction tube. Additional equivalents of reactants can be used if required to drive the reaction to completion in a reasonable time. The reaction tubes, in combination with the holder block and the manifold, are reinserted into the reservoir block and the apparatus is fastened together. Gas flow through the manifold is initiated to provide a controlled environment, for example, nitrogen, argon, air and the like. The gas flow may also be heated or chilled prior to flow through the manifold. Heating or cooling of the reaction wells is achieved by heating the reaction block or cooling externally with isopropanol/dry ice and the like to bring about the desired synthetic reactions. Agitation is achieved by shaking or magnetic stirring (within the reaction tube). The preferred workstations (without, however, being limited thereto) are Labsource's Combi-chem station and MultiSyn Tech's-Syro synthesizer.

Amide bond formation requires the activation of the c-carboxyl group for the acylation step. When this activation is being carried out by means of the commonly used carbodiimides such as dicyclohexylcarbodiimide (DCC, Sheehan & Hess, *J. Am. Chem. Soc.* 1955, 77, 1067-1068) or diisopropylcarbodiimide (DIC, Sarantakis et al *Biochem. Biophys. Res. Commun.* 1976, 73, 336-342), the resulting dicyclohexylurea is insoluble and, respectively, diisopropylurea is soluble in the solvents generally used. In a variation of the carbodiimide method 1-hydroxybenzotriazole (HOBt, König & Geiger, *Chem. Ber* 1970, 103, 788-798) is included as an additive to the coupling mixture. HOBt prevents dehydration, suppresses racemization of the activated amino acids and acts as a catalyst to improve the sluggish coupling reactions. Certain phosphonium reagents have been used as direct coupling reagents, such as benzotriazol-1-yl-oxy-tris-(dimethylamino)-phosphonium hexafluorophosphate (BOP) (Castro et al., *Tetrahedron Lett.* 1975, 14, 1219-1222; *Synthesis*, 1976, 751-752), or benzotriazol-1-yl-oxy-tris-pyrrolidino-phosphonium hexafluorophoshate (Py-BOP, Coste et al., *Tetrahedron Lett.* 1990, 31, 205-208), or 2-(1H-benzotriazol-1-yl-)1,1,3,3-tetramethyluronium terafluoroborate (TBTU), or hexafluorophosphate (HBTU, Knorr et al., *Tetrahedron Lett.* 1989, 30, 1927-1930); these phosphonium reagents are also suitable for in situ formation of HOBt esters with the protected amino acid derivatives. More recently diphenoxyphosphoryl azide (DPPA) or O-(7-aza-benzotriazol-1-yl)-N,N,N',N'-tetramethyluronium tetrafluoroborate (TATU) or O-(7-aza-benzotriazol-1-yl)-N,N,N',N'-tetramethyluronium hexafluorophosphate (HATU)/7-aza-1-hydroxy benzotriazole (HOAt, Carpino et al., *Tetrahedron Lett.* 1994, 35, 2279-2281) have also been used as coupling reagents.

Due to the fact that near-quantitative coupling reactions are essential it is desirable to have experimental evidence for completion of the reactions. The ninhydrin test (Kaiser et al., *Anal. Biochemistry* 1970, 34, 595), where a positive calorimetric response to an aliquot of resin-bound peptide indicates qualitatively the presence of the primary amine, can easily and quickly be performed after each coupling step. Fmoc chemistry allows the spectrophotometric detection of the Fmoc chromophore when it is released with the base (Meienhofer et al., *Int. J. Peptide Protein Res.* 1979, 13, 3542).

The resin-bound intermediate within each reaction tube is washed free of excess of retained reagents, of solvents, and of by-products by repetitive exposure to pure solvent(s) by one of the two following methods:

1) The reaction wells are filled with solvent (preferably 5 ml), the reaction tubes, in combination with the holder block and manifold, are immersed and agitated for 5 to 300 minutes, preferably 15 minutes, and drained by gravity followed by gas pressure applied through the manifold inlet (while closing the outlet) to expel the solvent;

2) The manifold is removed from the holder block, aliquots of solvent (preferably 5 ml) are dispensed through the top of the reaction tubes and drained by gravity through a filter into a receiving vessel such as a test tube or vial.

Both of the above washing procedures are repeated up to about 50 times (preferably about 10 times), monitoring the efficiency of reagent, solvent, and byproduct removal by methods such as TLC, GC, or inspection of the washings.

The above described procedure of reacting the resin-bound compound with reagents within the reaction wells followed by removal of excess reagents, by-products, and solvents is repeated with each successive transformation until the final resin-bound fully protected linear peptide has been obtained.

Before this fully protected linear peptide is detached from the solid support, it is possible, if desired, to selectively deprotect one or several protected functional group(s) present in the molecule and to appropriately substitute the reactive group(s) thus liberated. To this effect, the functional group(s) in question must initially be protected by a protecting group which can be selectively removed without affecting the remaining protecting groups present. Alloc (allyloxycarbonyl) is an example for such a protecting group for amino which can be selectively removed, e.g. by means of $Pd^o$ and phenylsilane in $CH_2Cl_2$, without affecting the remaining protecting groups, such as Fmoc, present in the molecule. The reactive group thus liberated can then be treated with an agent suitable for introducing the desired substituent. Thus, for example, an amino group can be acylated by means of an acylating agent corresponding to the acyl substituent to be introduced.

Detachment of the fully protected linear peptide from the solid support is achieved by immersion of the reaction tubes, in combination with the holder block and manifold, in reaction wells containing a solution of the cleavage reagent (preferably 3 to 5 ml). Gas flow, temperature control, agitation, and reaction monitoring are implemented as described above and as desired to effect the detachment reaction. The reaction tubes, in combination with the holder block and manifold, are disassembled from the reservoir block and raised above the solution level but below the upper lip of the reaction wells, and gas pressure is applied through the manifold inlet (while closing the outlet) to efficiently expel the final product solution into the reservoir wells. The resin remaining in the reaction tubes is then washed 2 to 5 times as above with 3 to 5 ml of an appropriate solvent to extract (wash out) as much of the detached product as possible. The product solutions thus obtained are combined, taking care to avoid cross-mixing. The individual solutions/extracts are then manipulated as needed to isolate the final compounds. Typical manipulations include, but are not limited to, evaporation, concentration, liquid/liquid extraction, acidification, basification, neutralization or additional reactions in solution.

The solutions containing fully protected linear peptide derivatives which have been cleaved off from the solid support and neutralized with a base, are evaporated. Cyclization is then effected in solution using solvents such as DCM, DMF, dioxane, THF and the like. Various coupling reagents which were mentioned earlier can be used for the cyclization. The duration of the cyclization is about 6-48 hours, preferably about 24 hours. The progress of the reaction is followed, e.g. by RP-HPLC (Reverse Phase High Performance Liquid Chromatography). Then the solvent is removed by evaporation, the fully protected cyclic peptide derivative is dissolved in a solvent which is not miscible with water, such as DCM, and the solution is extracted with water or a mixture of water-miscible solvents, in order to remove any excess of the coupling reagent.

Before removing the protecting groups from the fully protected cyclic peptide, it is possible, if desired, to form an interstrand linkage between side-chains of appropriate amino acid residues at opposite positions of the β-strand region.

Interstrand linkages and their formation have been discussed above, in connection with the explanations made regarding groups of the type H which can, for example, be disulfide bridges formed by cysteines and homocysteines at opposite positions of the α-strand, or glutamic and aspartic acid residues linking ornithines and, respectively, lysines located at opposite N-strand positions by amide bond formation. The formation of such interstrand linkages can be effected by methods well known in the art.

Finally, the fully protected peptide derivative of type I is treated with 95% TFA, 2.5% $H_2O$, 2.5% TIS or another combination of scavengers for effecting the cleavage of protecting groups. The cleavage reaction time is commonly 30 minutes to 12 hours, preferably about 2 hours. Thereafter most of the TFA is evaporated and the product is precipitated with ether/hexane (1:1) or other solvents which are suitable therefor. After careful removal of the solvent, the cyclic peptide derivative obtained as end-product can be isolated. Depending on its purity, this peptide derivative can be used directly for biological assays, or it has to be further purified, for example by preparative HPLC.

As mentioned earlier, it is thereafter possible, if desired, to convert a fully deprotected product thus obtained into a pharmaceutically acceptable salt or to convert a pharmaceutically acceptable, or unacceptable, salt thus obtained into the corresponding free compound of formula I or into a different, pharmaceutically acceptable, salt. Any of these operations can be carried out by methods well known in the art.

The starting materials used in the process of the invention, pre-starting materials therefore, and the preparation of these starting and pre-starting materials will now be discussed in detail.

Building blocks of type A can be synthesized according to the literature methods described below. The corresponding amino acids have been described either as unprotected or as Boc- or Fmoc-protected racemates, (D)- or (L)-isomers. It will be appreciated that unprotected amino acid building blocks can be easily transformed into the corresponding Fmoc-protected amino acid building blocks required for the present invention by standard protecting group manipulations. Reviews describing general methods for the synthesis of o-amino acids include: R. Duthaler, *Tetrahedron (Report)* 1994, 349, 1540-1650; R. M. Williams, "Synthesis of-optically active c-amino acids", *Tetrahedron Organic Chemistry Series, Vol.* 7, J. E. Baldwin, P. D. Magnus (Eds.), Pergamon Press., Oxford 1989. An especially useful method for the synthesis of optically active α-amino acids relevant for this invention includes kinetic resolution using hydrolytic enzymes (M. A. Verhovskaya, 1. A. Yamskov, *Russian Chem. Rev.* 1991, 60, 1163-1179; R. M. Williams, "Synthesis of optically active α-amino acids", *Tetrahedron Organic Chemistry Series, Vol.* 7, J. E. Baldwin, P. D. Magnus (Eds.), Pergamon Press., Oxford 1989, Chapter 7, p. 257-279). Hydrolytic enzymes involve hydrolysis of amides and nitriles by aminopeptidases or nitrilases, cleavage of N-acyl groups by acylases, and ester hydrolysis by lipases or proteases. It is well documented that certain enzymes will lead specifically to pure (L)-enantiomers whereas others yield the corresponding (D)-enantiomers (e.g.: R. Duthaler, *Tetrahedron Report* 1994, 349, 1540-1650; R. M. Williams, "Synthesis of optically active α-amino acids", *Tetrahedron Organic Chemistry Series, Vol.* 7, J. E. Baldwin, P. D. Magnus (Eds.), Pergamon Press., Oxford 1989).

A1: See D. Ben-Ishai, *Tetrahedron* 1977, 33, 881-883; K. Sato, A. P. Kozikowski, *Tetrahedron Lett.* 1989, 30, 4073-4076; J. E. Baldwin, C. N. Farthing, A. T. Russell, C. J. Schofield, A. C. Spirey, *Tetrahedron Lett.* 1996, 37, 3761-3767; J. E. Baldwin, R. M. Adlington, N. G. Robinson, *J. Chem. Soc. Chem. Commun.* 1987, 153-157; P. Wipf, Y. Uto, *Tetrahedron Lett.* 1999, 40, 5165-5170; J. E. Baldwin, R. M. Adlington, A. O'Neil, A. C. Spirey, J. B. Sweeney, *J. Chem. Soc. Chem. Commun.* 1989, 1852-1854 (for $R^1$=H, $R^1$=H); T. Hiyama, *Bull. Chem. Soc. Jpn.* 1974, 47, 2909-2910; T. Wakarniya, K. Shimbo, T. Shiba, K. Nakajima, M. Neya, K. Okawa, *Bull. Chem. Soc. Jpn.* 1982, 55, 3878-3881; 1. Shima, N. Shimazaki, K. Imai, K. Hemmi, M. Hashimoto, *Chem. Pharm. Bull.* 1990, 38, 564-566; H. Han, J. Yoon, K. D. Janda, *J. Org. Chem.* 1998, 63, 2045-2048 ($R^1$=H, $R^2$=Me); J. Legters, G. H. Willemis, L. Thijs, B. Zwannenburg, *Recl. Trav. Chim. Pays-Bas* 1992, 111, 59-68 ($R^1$=H, $R^2$=hexyl); J. Legters, L. Thijs, B. Zwannenburg, *Recl. Trav. Chim. Pays-Bas* 1992, 111, 16-21; G. A. Molander, P. J. Stengel, *J. Org. Chem.* 1995, 21, 6660-6661 ($R^1$=H, $R^1$=Ph); I. Funaki, L. Thijs, B. Zwannenburg, *Tetrahedron* 1996, 52, 9909-9924 ($R^1$=H, R=Bn); A. S. Pepito, D.C. Dittmer, *J. Org. Chem.* 1997, 62, 7920-7925; ($R^1$=H, $R^2$=CH$_2$OH); M. Egli, A. S. Dreiding, *Helv. Chim. Acta* 1986, 69, 1442-1460 ($R^2$=CH(OH)CH$_2$OH); M. Carduccu, S. Fioravanti, M. A. Loreto, L. Pellacani, P. A. Tardella, *Tetrahedron Lett.* 1996, 37, 3777-3778; F. J. Lalmer, L. P. Hager, *Tetrahedron: Asymmetry* 1997, 21, 3547-3550 ($R^1$=Me, $R^2$=H, Me); G. A. Molander, P. J. Stengel, *Tetrahedron* 1997, 26, 8887-8912; M. A. Loreto, F. Pompei, P. A. Tardella, D). Tofani, *Tetrahedron* 1997, 53, 15853-15858 ($R^1$=Me, R=CH$_2$SiMe$_3$); H. Shao, J. K. Rueter, M. Goodman, *J. Org. Chem.* 1998, 63, 5240-5244 ($R^1$=Me, $R^2$=Me).

A2: See A. Rao, M. K. Gujär, V. Vivarr, *Tetrahedron: Asymmetry* 1992, 3, 859-862; R. L. Johnson, G. Rayakumar, K.-L. Yu, R. K. Misra, *J. Med. Chem.* 1986, 29, 2104-2107 ($R^1$=H, $R^2$=H); J. E. Baldwin, R. M. Adlington, R. H. Jones, C. J. Schofield, C. Zarcostas, *J. Chem. Soc. Chem. Commun.* 1985, 194-196; J. E. Baldwin, R. M. Adlington, R. H. Jones, C. J. Schofield, C. Zarcostas, *Tetrahedron* 1986, 42, 4879-4888 ($R^1$=H, $R^2$=CH$_2$OH, CH$_2$CHO, CH$_2$CH$_2$COOH, CH$_2$CH$_2$OH); A. P. Kozikowski, W. Tueckmantel, I. J. Reynolds, J. T. Wroblewski, *J. Med. Chem.* 1990, 33, 1561-1571; A. P. Kozikowski, W. Tueckmantel, Y. Liao, H. Manev, S. Ikonomovic J. T. Wroblenski, *J. Med. Chem.* 1993, 36, 2706-2708 ($R^1$=H, $R^2$=CH$_2$OH, CHCONH$_2$, CONHCH$_2$COOH, COOtBu); D. Seebach, T. Vettiger, H.-M. Müller, D. Plattner, W. Petter, *Liebigs Ann. Chem.* 1990, 687-695 ($R^1$=ArylCH(OH), $R^2$=H); D. Seebach, E. Dziadulewicz, L. Behrendt, S. Cantoreggi, R. Fitzi, *Liebigs Ann. Chem.* 1989, 1215-1232 ($R^1$=Me, Et, $R^2$=H).

A3: See A. P. Kozikowski, Y. Liao, W. Tueckmantel, S. Wang, S. Pshsenichkin, *Bioorg. Med. Chem. Lett.* 1996, 6, 2559-2564 ($R^1$=H; $R^2$=CHCHO, CH$_2$OH, CH$_2$CH$_2$OH, CH$_2$COOH, COOH); Isono, *J. Am. Chem. Soc,* 1969, 91, 7490 ($R^1$=H; $R^2$=Et); P. J. Blythin, M. J. Green, M. J. Mary, H. Shue, *J. Org. Chem.* 1994, 59, 6098-6100; S. Hanessian, N. Bernstein, R.-Y. Yang, R. Maquire, *Bioorg. Chem. Lett.* 1994, 9, 1437-1442 ($R^1$=H; $R^2$=Ph).

A4: See G. Emmer, *Tetrahedron* 1992, 48, 7165-7172; M. P. Meyer, P. L. Feldman, H. Rapoport, *J. Org. Chem.* 1985, 50, 5223-5230 ($R^1$=H; $R^2$=H); A. J. Bose, M. S. Manhas, J. E. Vincent, I. F. Fernandez, *J. Org. Chem.* 1982, 47, 4075-4081 ($R^1$=H; $R^2$=NHCOCH$_2$OPh); D. L. Boger, J. B. Meyers, *J. Org. Chem.* 1991, 56, 5385-5390 ($R^1$=H; $R^2$=NHCOCH$_2$Ph); K.-D. Kampe, *Tetrahedron Lett.* 1969, 117-120 ($R^1$=CH$_2$OH; $R^2$=Ph); M. D. Andrews, M. G. Maloney, K. L. Owen, *J. Chem. Soc. Perkin Trans.* 1, 1996, 227-228 ($R^1$=CH$_2$OH; $R^2$=H).

A5: See C. Bisang, C. Weber, J. Inglis, C. A. Schiffer, W. F. van Gunsteren, J. A. Robinson *J. Am. Chem. Soc.* 1995, 117, 7904 ($R^1$=CH$_3$; $R^2$=H); S. Takano, M. Morija, Y. Iwabuki, K. Ogasawara, *Tetrahedron Lett.* 1989, 30, 3805-3806 ($R^1$=H; $R^2$=COOH); M. D. Bachi, R. Breiman, H. Meshulam, *J. Org. Chem.* 1983, 48, 1439-1444 ($R^1$=H; $R^2$=CH(Et)COOH); D. S. Kemp, T. P. Curran, *Tetrahedron Lett.* 1988, 29, 4931-4934; D. S. Kemp, T. P. Curran, W. M. Davies, *J. Org. Chem.* 1991, 56, 6672-6682 ($R^1$=H; $R^2$=CH$_2$OH); F. Manfre, J.-M. Kern, J.-F. Biellmann, *J. Org. Chem.* 1992, 57, 2060-2065 ($R^1$=H; $R^2$=H, CH=CH$_2$, CCH); B. W. Bycroft, S. R. Chabra, *J. Chem. Soc. Chem. Commun.* 1989, 423-425 ($R^1$=H; $R^2$=CH$_2$COOtBu; Y. Xu, J. Choi, M. 1. Calaza, S. Turner, H. Rapoport, *J. Org. Chem.* 1999, 64, 40694078 ($R^1$=H; $R^2$=3-pyridyl); E. M. Khalil, W. J. Ojala, A. Pradhamn, V. D. Nair, W. B. Gleason, *J. Med. Chem.* 1999, 42, 628-637; E. M. Khalil, N. L. Subasinghe, R. L. Johnson, *Tetrahedron Lett.* 1996, 37, 3441-3444 ($R^1$=allyl; $R^2$=H); A. DeNicola, J.-L. Luche, *Tetrahedron Lett.* 1992, 33, 6461-6464; S. Thaisrivongs, D. T. Pals, J. A. Lawson, S. Turner, D. W. Harris, *J. Med. Chem.* 1987, 30, 536-541; E. M. Khalil, N. L. Subasinghe, R. L. Johnson, *Tetrahedron Lett.* 1996, 37, 3441-3444; A. Lewis, J. Wilkie, T. J. Rutherford, D. Gani, *J. Chem. Soc. Perkin Trans.* 1, 1998, 3777-3794 ($R^1$=Me; $R^2$=H); A. Lewis, J. Wilkie, T. J. Rutherford, D. Gani, *J. Chem. Soc. Perkin Trans.* 1, 1998, 3777-3794 ($R^1$=CH$_2$COOMe; $R^2$=H); N. L. Subasinghe, E. M. Khalil, R. L. Johnson, *Tetrahedron Lett.* 1997, 38, 1317-1320 ($R^1$=CH$_2$CHO; $R^2$=H); D. J. Witter, S. J. Farniglietti, J. C. Gambier, A. L. Castelhano, *Bioorg. Med. Chem. Lett.* 1998, 8, 3137-3142; E. H. Khalil, W. H. Ojada, A. Pradham, V. D. Nair, W. B. Gleason, *J. Med. Chem.* 1999, 42, 628-637 ($R^1$=CH$_2$CH$_2$CHO; $R^2$=H).

A6: See DeNardo, Farnaco Ed. Sci. 1977, 32, 522-529 ($R^1$=H; $R^3$=H); P. J. T. Floris, N. Terhuis, H. Hiemstra, N. W. Speckarnp, *Tetrahedron,* 1993, 49, 8605-8628; S. Kanemasa, N. Tomoshige, O. Tsuge, *Bull. Chem. Soc. Jpn.* 1989, 62, 3944-3949 ($R^1$=H; $R^3$=H); Sucrow, *Chem. Ber.* 1979, 112, 1719.

A7: See Fichter, J. *Prakt. Chem.* 1906, 74, 310 ($R^1$=Me; $R^4$=Ph).

A8: See L. Lapantsanis, G. Milias, K. Froussios, M. Kolovos, *Synthesis* 1983, 641-673; H. Nedev, H. Naharisoa, *Tetrahedron Lett.* 1993, 34,42014204; D. Y. Jackson, C. Quan, D. R. Artis, T. Rawson, B. Blackburn, *J. Med. Chem.* 1997, 40, 3359-3368; D. Konopinska, H. Bartosz-Bechowski, G. Rosinski, W. Sobotka, *Bull. Pol. Acad. Sci. Chem.* 1993, 41, 2740; J. Hondrelis, G. Lonergan, S. Voliotis, J. Matsukas, *Tetrahedron* 1990, 46, 565-576; T. Nakamura, H. Matsuyama, H. Kanigata, M. Iyoda, *J. Org. Chem.* 1992, 57, 3783-3789; C. E. O'Connell, K. Ackermann, C. A. Rowell, A. Garcia, M. D. Lewis, C. E. Schwartz, *Bioorg. Med. Chem. Lett.* 1999, 9, 2095-2100; G. Lowe, T. Vilaivan, *J. Chem. Soc. Perkin Trans.* 1997, 547-554; B. Bellier, l. McCourt-Tranchepain, B. Ducos, S. Danascimenta, H. Mundal, *J. Med. Chem.* 1997, 40, 3947-3956; M. Peterson, R. Vince *J. Med. Chem.* 1991, 34, 2787-2797; E. M. Smith, G. F. Swiss, B. R. Neustadt, E. H. Gold, l. A. Sommer, *J. Med. Chem.* 1988, 31, 875-885; E. Rubini, C. Gilon, Z. Selinger, M. Chorev, *Tetrahedron* 1986, 42, 6039-6045 ($R^1$=H; $R^5$=OH); C. R. Noe, M. Knollmueller, H. Voellenkle, M. Noe-Letschnig, A. Weigand, J. Mühl, *Pharmazie*, 1996, 51, 800-804 ($R^1$=$CH_3$; $R^5$=OH); J. Kitchin, R. C. Berthell, N. Canunack, S. Dolan, D. N. Evans, *J. Med. Chem.* 1994, 37, 3703-3716; D. Y. Jackson, C. Quan, D. R. Artis, T. Rawson, B. Blackburn, *J. Med. Chem.* 1997,40, 3359-3368 ($R^1$=H; $R^5$=OBn); J. E. Baldwin, A. R. Field, C. C. Lawrence, K. D. Merritt, C. J. Schofield, *Tetrahedron Lett.* 1993, 34, 7489-7492; K. Hashimoto, Y. Shima, H.'Shirahara, *Helerocycles* 1996, 42,-489-492 ($R^1$=H; R5=OTs); T. R. Webb, C. Eigenbrot, *J. Org. Chem.* 1991, 56, 3009-3016; D.C. Cafferty, C. A. Slate, B. M. Nakhle, H. D. Graham, T. L. Anstell, *Tetrahedron* 1995, 51, 9859-9872 ($R^1$=H; $R^5$=$NH_2$); T. R. Webb, C. Eigenbrot, *J. Org. Chem.* 1991, 56, 3009-3016 ($R^1$=H; $R^5$=$CH_2NH_2$); J. K. Thottathil, J. L. Moniot, *Tetrahedron Leti.* 1986, 27, 151-154 ($R^1$=H; $R^5$=Ph); K. Plucinska, T. Kataoka, M. Yodo, W. Cody, *J. Med. Chem.* 1993, 36, 1902-1913 ($R^1$=H; $R^5$=SBn); J. Krapcho, C. Turk, D. W. Cushman, J. R. Powell, *J. Med. Chem.* 1988, 31, 1148-1160 ($R^1$=H; $R^5$=SPh); A. J. Verbiscar, B. Witkop, *J. Org. Chem.* 1970, 35, 1924-1927 ($R^1$=H; $R^5$=$SCH_2$(4-OMe)$C_6H_4$); S. 1. Klein, J. M. Denner, B. F. Molino, C. Gardner, R. D'Alisa, *Bioorg. Med. Chem. Lett.* 1996, 6, 2225-2230 ($R^1$=H; $R^5$=O($CH_2)_3$Ph); R. Zhang, F. Brownewell, J. S. Madalengoita, *Tetrahedron Lett.* 1999, 40, 2707-2710 ($R^1$=H; $R^5$=$CH_2COOBn$).

A9: See Blake, *J. Am. Chem. Soc.* 1964, 86, 5293-5297; J. Cooper, R. T. Gallagher, D. T. Knight, *J. Chem. Soc. Chem. Perkin Trans.*1, 1993, 1313-1318; D. W. Knight, A. W. Sibley, *J. Chem. Soc. Perkin Trans.*1, 1997, 2179, 2188 ($R^1$=H; $R^6$=H); Blake,*J. Am. Chem. Soc.* 1964, 86, 5293-5297; Y. Yamada, T. Ishii, M. Kimura, K. Hosaka, *Tetrahedron Let.* 1981, 1353-1354 ($R^1$=H; $R^6$=OH); Y. Umio, *Yakugaku Zasshi*, 1958, 78, 727 ($R^1$=H; $R^6$=iPr); Miyamoto, *Yakugaku Zasshi*, 1957, 77, 580-584; Tanaka, *Proc. Jpn. Acad.* 1957, 33, 47-50 ($R^1$=H; $R^6$=$CH(CH_3)CH_2N(CH_3)_2$); L. E. Overman, B. N. Rodgers, J. E. Tellew, W. C. Trenkle, *J. Am. Chem. Soc.* 1997, 119, 7159-7160 ($R^1$=H; $R^6$=allyl); Ohki, *Chem. Pharm. Bull.* 1976, 24, 1362-1369 ($R^1$=$CH_3$; $R^6$=H).

A10: See J. Mulzer, A. Meier, J. Buschmann, P. Luger, *Synthesis* 1996, 123-132 ($R^1$=H; $R^7$=CH=$CH_2$); J. Cooper, P. T. Gallagher, D. W. Knight, *J. Chem. Soc. Chem. Commun.* 1988, 509-510; E. Götschi, C. Jenny, P. Reindl, F. Ricklin, *Helv. Chim. Acta* 1996, 79, 2219-2234 ($R^1$=H; $R^7$=OH); N. A. Sasaki, R. Pauli, C. Fontaine, A. Chiaroni, C. Riche, P. Potier, *Tetrahedron Lett.* 1994, 35, 241-244 ($R^1$=H; $R^7$=COOH); R. Cotton, A. N.C. Johnstone, M. North, *Tetrahedron* 1995, 51, 8525-8544 ($R^1$=H; $R^7$=COOMe); J. S. Sabol, G. A. Flynn, D. Friedrich, E. W. Huber, *Tetrahedron Lett.* 1997, 38, 3687-3690 ($R^1$=H; $R^1$=$CONH_2$); P. P. Waid, G. A. Flyrn, E. W. Huber, J. S. Sabol, *Tetrahedron Lett.* 1996, 37, 4091-4094 ($R^1$=H; $R^7$=(4-BnO)$C_6H_4$); N. A. Sasaki, R. Pauli, P. Potier, *Tetrahedron Let.* 1994, 35, 237-240 ($R^1$=H; $R^7$=$SO_2Ph$); R. J. Heffner, J. Jiang, M. Jouillie, *J. Am. Chem. Soc.* 1992, 114, 10181-10189; U. Schmidt, H. Griesser, A. Lieberknecht, J. Häusler, *Angew. Chem.* 1981, 20-93, 272-273 ($R^1$=H; $R^7$=OAryl); H. Mosberg, A. L. Lomize, C. Wang, H. Kroona, D. L. Heyl, *J. Med. Chem.* 1994,37,43714383 ($R^1$=H; $R^7$=4-$OHC_6H4$); S. A. Kolodziej, G. V. Nikiforovich, R. Sceean, M.-F. Lignon, J. Martinez, G. R. Marshall,*J. Med. Chem.* 1995, 38, 137-149 ($R^1$=H; $R^7$=$SCH_2$(4-Me)$C_6H_4$).

A11: See Kuhn, Osswald, *Chem. Ber.* 1956, 89, 1423-1434; Patchett, Witkop, *J. Am. Chem. Soc.* 1957, 79, 185-189; Benz, *Helv. Chim. Acta* 1974, 57, 2459-2475; P. Wessig, *Synlett*, 1999, 9, 1465-1467; E. M. Smit, G. F. Swiss, B. R. Neustadt, E. H. Gold, J. A. Somrner, *J. Med. Chem.* 1988,31, 875-885; J. Krapcho, C. Turk, D. W. Cushman, J. R. Powell, J. M. DeForrest, *J. Med. Chem.* 1988, 31, 1148 ($R^1$=H; $R^6$=H); D. Benlshai, S. Hirsh, *Tetrahedron* 1988, 44, 5441-5450 ($R^1$=H; $R^6$=$CH_3$); M. W. Holladay, C. W. Lin, C. S. Garvey, D. G. Witte, *J. Med. Chem.* 1991, 34,455457 ($R^1$=H; $R^6$=allyl); P. Barralough, P. Hudhonune, C. A. Spray, D. W. Young, *Tetrahedron* 1995, 51, 4195-4212 ($R^1$=H; $R^6$=Et); J. E. Baldwin, M. Rudolf, *Tetrahedron Lett.* 1994, 35, 6163-6166; J. E. Baldwin, S. J. Bamford, A. M. Fryer, M. Rudolf, M. E. Wood, *Tetrahedron* 1997, 53, 5233-5254 ($R^1$=H; $R^6$=$CH_2COOtBu$); P. Gill, W. D. Lubell, *J. Org. Chem.* 1995, 60, 2658-2659 ($R^1$=H; $R^6$=$CH_3$; Bn; allyl; $CH_2COOMe$); M. J. Blanco, F. J. Sardina, *J. Org. Chem.* 1998, 63, 3411-3466 ($R^1$=H; $R^6$=$OCH_2OMe$).

A12: See Ahmed, Cheeseman, *Tetrahedron* 1977, 33, 2255-2257; J. S, New, J. P. Yevich, *J. Heterocycl. Chem.* 1984, 21, 1355-1360; R. Kikumoto, Y. Tamao, K. Ohkubo, T. Tezuka, S. Tonomura, *J. Med. Chem.* 1980, 23, 1293-1299; C. J. Blankley, J. S. Kaltenbronn, D. E. DeJolin, A. Werner, L. R. Bennett, *J. Med. Chem.* 1987, 30, 992-998; S. Klutcho, C. J. Blankley, R. W. Fleming, J. M. Hinkley, R. E. Werner, *J. Med. Chem.* 1986, 29, 1953-1961 ($R^a$=H; $R^8$=H); L. J. Beeley, C. J. M. Rockwell, *Tetrahedron Lett.* 1990, 31, 417-420 ($R^1$=COOEt; $R^1$=H).

A13: See G. Flouret, W. Brieher, T. Majewski, K. Mahan, *J. Med. Chem.* 1991, 43, 2089-2094; G. Galiendo, P. Grieco, E. Perissuti, V. Santagada, *Farmaco*, 1996, 51, 197-202; D. F. McComsey, M. J. Hawkins, P. Andrade-Gordon, M. F. Addo, B. E. Maryanoff, *Bioorg. Med. Chem. Lett.* 1999, 9, 1423-1428; G. B. Jones, S. B. Heaton, B. J. Chapman, M. Guzel, *Tetrahedron: Asymmetry* 1997, 8, 3625-3636; M. Asani, H. Watanabe, K. Honda, S. Inoue, *Tetrahedron: Asymmetry* 1998, 9,4165-4174; K. Gross, Y. M. Yun, P. Beak, *J. Org. Chem.* 1997, 62, 7679-7689 ($R^1$=H; $R^6$=H; $R^8$=H); K. Gross, Y. M. Yun, P. Beak, *J. Org. Chem.* 1997, 62, 7679-7689 ($R^1$=H; $R^6$=H; $R^8$=6-Cl); Ch. Noe, M. Knollmueller, C. Schoedl, M. L. Berger, *Sci. Pharm.* 1996, 64, 577-590; E. Reiman, W. Erdle, H. Unger, *Pharmazie*, 1994, 54, 418-421 ($R^1$=H; $R^6$=$CH_2COOH$; $R^8$=H); V. Collot, M. Schmitt, A. K. Marwah, B. Norberg, J.-J. Bourgignon, *Tetrahedron Lett.* 1997, 38, 8033-8036 ($R^1$=H; $R^6$=Ph; $R^8$=H); L. V. Dunkerton, H. Chen, B. P. McKillican, *Tetrahedron Lett.* 1988, 29, 2539-2542 ($R^1$=$C(CH_3)_2CH=CH_2$; $R^6$=H; $R^8$=H); E. J.

Corey, *J. Am. Chem. Soc.* 1970, 92, 2476-2488; Neunhoeffer, Lehmann, *Chem. Ber.* 1961, 94, 2960-2963 ($R^1=CH_3$; $R^6=H$; $R^8=H$).

A14: Amino acids of type A14 can be made according to Scheme 1.

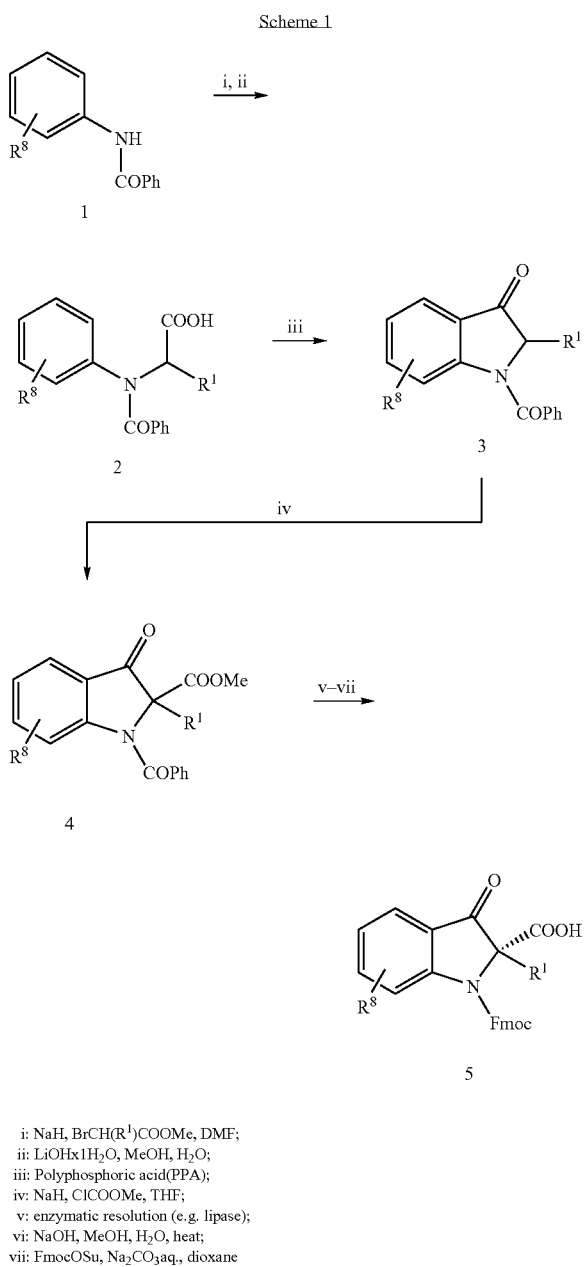

i: NaH, BrCH($R^1$)COOMe, DMF;
ii: LiOHx1H$_2$O, MeOH, H$_2$O;
iii: Polyphosphoric acid(PPA);
iv: NaH, ClCOOMe, THF;
v: enzymatic resolution (e.g. lipase);
vi: NaOH, MeOH, H$_2$O, heat;
vii: FmocOSu, Na$_2$CO$_3$aq., dioxane A15: See D. S. Perlow, J. M. Erb, N. P. Gould, R. D. Tung, R. M. Freidinger, *J. Org. Chem.* 1992, 57, 439-44400; D. Y. Jackson, C. Quan, D. R. Artis, T. Rawson, B. Blackburn, *J. Med. Chem.* 1997, 40, 3359-3368 ($R^1=H$; $R^2=H$); H. H. Wasserman, K. Rodrigues, K. Kucharczyk, *Tetrahedron Lett.* 1989, 30, 6077-6080 ($R^1=H$; $R^2=COOH$).

A16: See Beyerman, Boekee, *Recl. Trav. Chim. Pays-Bas,* 1959, 78, 648-653; M. E. Freed, A. R. Day, *J. Org. Chem.* 1960, 25, 2105-2107; D. R. Adams, P. D. Bailey, I. D. Collier, J. D. Hefer-man, S. Slokes, *J. Chem. Soc. Chem. Commun.* 1996, 349-350; J. E. Baldwin, R. M. Adlington, C. R. A. Godfrey, D. W. Collins, J. D. Vaughan, *J. Chem. Soc. Chem. Commun.* 1993, 1434-1435; Y. Matsumura, Y. Takeshima, H. Ohita, *Bull. Chem. Soc. Jpn.* 1994, 67, 304-306 ($R^1=H$; $R^6=H$); C. Herdeis, W. Engel, *Arch. Pharm.* 1991, 324, 670 ($R^1=COOMe$; $R^6=CH_3$).

A17, A18: See C. R. Davies, J. S. Davies, *J. Chem. Soc. Perkin Trans 1*, 1976, 2390-2394; K. Bevan, *J. Chem. Soc. C,* 1971, 514-522; K. Umezawa, K. Nakazawa, Y. Ikeda, H. Naganawa, S. Kondo, *J. Org. Chem.* 1999, 64, 3034-3038 ($R^1=R^3=H$); P. D. Williams, M. G. Bock, R. D. Tung, V. M. Garsky, D. S. Parlow, *J. Med. Chem.,* 1992, 35, 3905-3918; K. Tamaki, K. Tanzawa, S. Kurihara, T. Oikawa, S. Monrma, *Chem. Pharm. Bull.* 1995, 43, 1883-1893 ($R^1=R^5=H$; $R^3=COOBn$); K. J. Hale, J. Cai, V. Delisser, S. Manaviazar, S. A. Peak, *Tetrahedron* 1996, 52, 1047-1068; M. H. Chen, O. P. Goel, J.-W. Hyun, J. Magano, J. R. Rubin, *Bioorg. Med. Chem. Lett.* 1999, 9, 1587-1592 ($R^1=R^5=H$; $R^3=COOtBu$); R. Baenteli, 1. Brun, P. Hall, R. Metternich, *Tetrahedron Lett.* 1999, 40, 2109-2112 ($R^1=R^5=H$; $R^3=COR$); K. J. Hale, N. Jogiya, S. Manaviazar, *Tetrahedron* 1998, 39, 7163-7166 ($R^1=H$; $R^3=COOBn$; $R^5=OBn$); T. Kamenecka, S. J. Danishewsky, *Angew. Chem. Int. Ed. Engl.* 1998, 37, 2995-2998 ($R^1=H$; $R^3=COO(CH_2)_2SiMe_3$; $R^5=OSiMe_2tBu$).

A19: See Beilstein, Registry Number 648833 ($R^1=R^4=R^8=H$). Compounds of this type can be prepared according to Scheme 2.

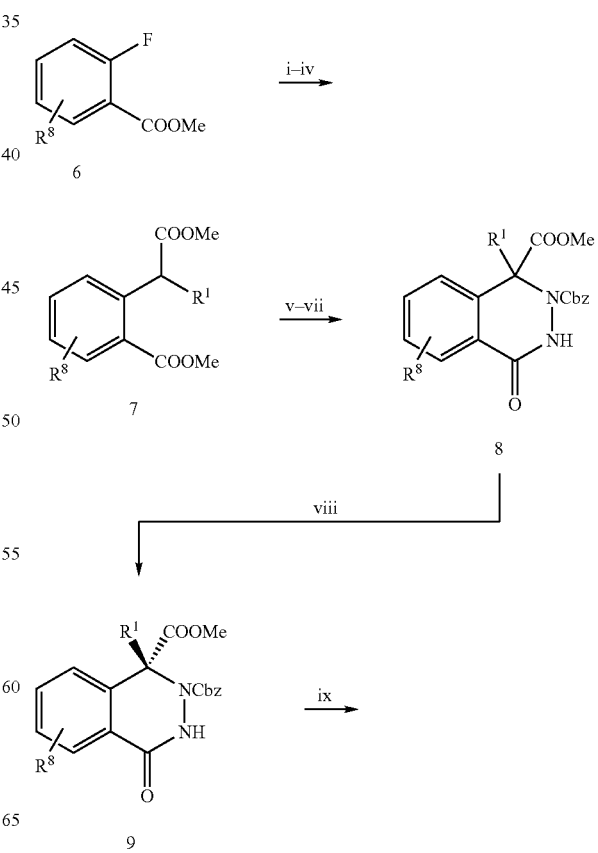

-continued

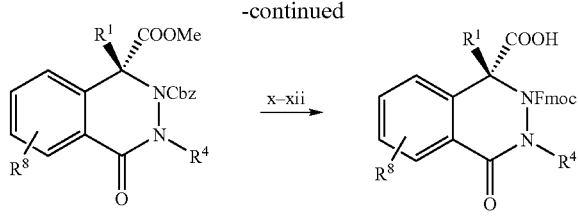

i: NaH, CH$_2$(COOMe)$_2$, DMSO;
ii: NaH, R$^1$—X, DMSO;
iii: NaOHaq., MeOH, 75°;
iv: DBU, MeI, DMF;
v: LDA, BocN═NBoc;
vi: TFA, CH$_2$Cl$_2$;
vii: CbzCl, Na$_2$CO$_3$aq., dioxane;
viii: enzymatic resolution (e.g. lipase); then DBU, MeI, DMF:
ix: NaH, R$^4$—X, THF;
x: Pd/C, H$_2$, EtOH;
xi: LiOHx1H$_2$O, MeOH, H$_2$O
xii: FmocOSu, Na$_2$CO$_3$aq., dioxane A20: See D. Hagiwara, H. Miyake, N. Igari, M. Karino, Y. Maeda, *J. Med. Chem.* 1994, 37, 2090-2099 (R$^1$=H; R$^9$=OH); Y. Arakawa, M. Yasuda, M. Ohnishi, S. Yoshifuiji, *Chem. Pharm. Bull.* 1997, 45, 255-259 (R$^1$=H; R$^9$=COOH); P. J. Murray, I. D. Starkey, *Tetrahedron Leti.* 1996, 37, 1875-1878 (R$^1$=H; R$^9$=(CH$_2$)$_2$NHCOCH$_2$Ph); K. Clinch, A. Vasella, R. Schauer, *Tetrahedron Lett.* 1987, 28, 6425-6428 (R$^1$=H; R$^9$=NHAC).

A21: See A. Golubev, N. Sewald, K. Burger, *Tetrahedron Lett.* 1995, 36, 2037-2040; F. Macbetti, F. M. Cordero, F. DeSario, A. Guarna, A. Brandi, *Tetrahedron Lett.* 1996, 37, 42054208; P. L. Ornstein, D. D. Schoepp, M. B. Arnold, J. D. Leander, D. Lodge, *J. Med. Chem.* 1991, 34, 90-97; R$^1$=R$^6$=H); P. D. Leeson, B. J. Williams, R. Baker, T. Ludduwahetty, K. W. Moore, M. Rowley, *J. Chem. Soc. Chem. Commun.* 1990, 1578-1580; D. I. C. Scopes, N. F. Hayes, D. E. Bays, D. Belton, J. Brain, *J. Med. Chem.* 1992, 35, 490-501; H. Kessler, M. Kuehn, T. Löschner, *Liebigs Anil. Chem.* 1986, 1-20 (R$^1$=R$^6$=H); C. Herdeis, W. Engel, *Arch. Pharm.* 1992, 7, 419-424 (R$^1$=R$^6$=Bn); C. Herdeis, W. Engel, *Arch. Pharm.* 1992,411418 (R$^1$=COOMe; R$^6$=H); C. Herdeis, W. Engel, *Arch. Phamm.* 1992, 419-424 (R$^1$=COOMe; R$^6$=Bn).

A22: See P. D. Leeson, B. J. Williams, R. Baker, T. Ladduwahetty, K. W. Moore, M. Rowley, *J. Chem. Soc. Chem. Comm.* 1990, 1578-1580 (R$^1$=H; R$^{10}$=NHOBn).

A23: See Beyemman, Boekee, *Recl. Trav. Chim. Pays-Bos* 1959, 78, 648-653; D. R. Adams, P. D. Bailey, 1. D. Collier, J. D. Heffernan, S. Stokes *J. Chem. Soc. Chem. Commun.* 1996, 349-350; J. E. Baldwin, R. M. Adlington, C. Godfrey, D. W. Collins, J. G. Vaughan, *J. Chem. Soc. Chem. Comm.* 1993, 1434-1435 (R$^1$=R$^6$=H); C. Herdeis, W. Engel, *Arch. Pharm.* 1993, 297-302 (R$^1$=COOMe; R$^6$=H).

A24: See Plieninger, Leonhauser, *Chem. Ber.* 1959, 92, 1579-1584; D. W. Knight, N. Lewis, A. C. Share, D. Haigh, *J. Chem. Soc. Perkin Trans.*1 1998, 22, 3673-3684; J. Drumrnond, G. Johnson, D. G. Nickell, D. F. Ortwine, R. F. Bruns, B. Welbaum, *J. Med. Chem.* 1989, 32, 2116-2128; M. P. Moyer, P. L. Feldman, H. Rapoport, *J. Org. Chem.* 1985, 50, 5223-5230 (R$^1$=R$^6$=H); McElvain, Laughton, *J. Am. Chem. Soc.* 1951, 73, 448-451 (R$^1$=H; R$^6$=Ph); McElvain, Laughton, *J. Am. Chem. Soc.* 1951, 73, 448-451 (R$^1$=Ph; R$^6$=H);

A25: See L.-Y. Hu, T. R. Ryder, S. S, Nikarn, E. Millernan, B. G. Szoke, M. F. Rafferty, *Bioorg. Med. Chem. Lett.* 1999, 9, 1121-1126; W. C. Lunma, R. D. Hartman, W. S. Saari, E. L. Engelhardt, V. J. Lotti, C. K Stone, *J. Med. Chem.* 1981, 24, 93-101; N. Hosten, M. J. O. Antenuis, *Bull. Soc. Chim. Belg.* 1988, 97, 48-50; C. F. Bigge, S. J. Hays, P. M. Novak, J. T. Drummond, G. Johnson, T. P. Bobovski, *Tetrahedron Lett.* 1989, 30, 5193-5191; B. Aebischer, P. Frey, H.-P. Haerter, P. L. Hemming, W. Müller, *Helv. Chim. Acta* 1989, 72, 1043-1051; W. J. Hoeckstra, B. E. Maryanoff, B. P. Damiano, P. Andrade-Gordon, J. H. Cohen, M. J. Constanzo, B. J. Haertlein, L. R. Hecker, B. L. Hulshizer, J. A. Kauffman, P. Keane, *J. Med. Chem.* 1999, 42, 5254-5265 (R$^1$=H; R$^{11}$=H); B. D. Dorsey, R. B. Levin, S. L. McDaniel, J. P. Vacca, J. P. Guare, *J. Med. Chem.* 1994, 37, 3443-3451; M. Cheng, B. De, S. Pikul, N. G. Almstaed, M. G. Natchus, M. V. Anastasio, S. J. McPhail, C. J. Snider, Y. O. Taiwo, L. Chen, C. M. Dunaway, *J. Med. Chem.* 2000, 43, 369-380; R. Kuwano, Y. Ito, *J. Org. ChenL* 1999, 64, 1232-1237 (R$^1$=H; R$^{11}$=COOtBu); J. Kitchin, R. C. Bethell, N. Cammack, S. Dolan, D. N. Evans, *J. Med. Chem.* 1994, 37, 3707-3716 (R$^1$=H; R$^{11}$=COOPh); C. F. Bigge, S. J. Hays, P. M. Novak, J. T. Drummond, G. Johnson, T. P. Bobovski, *J. Med. Chem.* 1990, 33, 2916-2924 (R$^1$=H; R$^{11}$=COOtBu; (CH$_2$)$_3$COOEt; (CH$_2$)$_3$PO(Me)OH; CH$_2$PO(OH)$_2$; (CH$_2$)$_2$PO(OEt)$_2$; (CH$_2$)$_2$PO(OH)$_2$).

Compounds of type A25 can also be prepared according to Scheme 3:

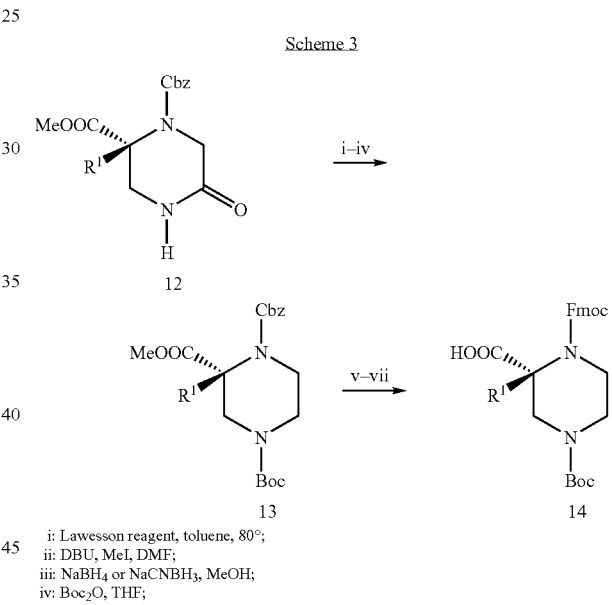

i: Lawesson reagent, toluene, 80°;
ii: DBU, MeI, DMF;
iii: NaBH$_4$ or NaCNBH$_3$, MeOH;
iv: Boc$_2$O, THF;
v: LiOHx1H$_2$O, MeOH, H$_2$O;
vi: Pd/C, H$_2$, EtOH;
vii: FmocOSu, Na$_2$CO$_3$aq., dioxane A26: See Koegel, *J. Biol. Chem.* 1953, 201, 547 (R$^1$=R$^{12}$=H).

A27: See G. Makara, G. R. Marshall, *Tetrahedron Lett.* 1997, 38, 5069-5072; R. N. Patel, A. Banerjee, R. L. Hanson, D. B. Brzozowski, L. W. Parker, L. J. Szarka, *Tetrahedron: Asymmetry* 1999, 10, 31-36 (R$^1$=H; R$^{13}$O=OH, OtBu); J. E. Johanson, B. D. Christie, H. Rapoport, *J. Org. Chem.* 1981, 46,49144920; N. Moss, J.-S. Duceppe, J.-M- Ferland, J. Gauthier, *J. Med. Chem.* 1996, 39, 2178-2187 (R$^1$=H; R$^{13}$=CONHMe); G. M. Makara, G. R. Marshall, *Tetrahedron Lett.* 1997, 38, 5069-5072 (R$^1$=H; R$^{13}$=SCH$_2$(4-MeO)C$_6$H$_4$).

A28: See A. Golubev, N. Sewald, K. Burger, *Tetrahedron Lett.* 1995, 36, 2037-2040; P. L. Ornstein, D. D. Schoepp, M. B. Arnold, J. D. Leander, D. Lodge, *J. Med. Chem.* 1991, 34, 90-97 (R$^1$=R$^6$=H); P. D. Leeson, B. J. Williams, R. Baker, T. Ladduwahetty, K. W. Moore, M. Rowley, *J. Chem. Soc.*

Chem. Commun. 1990, 22, 1578-1580; C. Herdeis, W. Engel, Arch. Pharm. 1991, 324, 670 ($R^1$=H; $R^6$=Me); C. Herdeis, W. Engel, Arch. Pharm. 1991, 324, 670 ($R^1$=COOMe; $R^6$=H, Me).

A29: See Kawase, Masami, Chem. Pharm. Bull. 1997, 45, 1248-1253; 1. G. C. Coutts, J. A. Hadfield, P. R. Huddleston, J. Chem. Res. Miniprint, 1987, 9, 2472-2500; 1. G. C. Coutts, J. A. Hadfield, P. R. Huddleston, J. Chem. Res. Miniprint, 1987, 9, 2472-2500; V. J. Hrubi, W. L. Cody, A. M. Castrucci, M. E. Hadley, Collect. Czech. Chem. Commun. 1988, 53, 2549-2573; R. T. Shuman, R. B. Rothenberger, C. S. Campbell, G. F. Smith, D. S. Gifford-Moore, P. D. Gesellchen, J. Med. Chem. 1993, 36, 314-319; M. Kawase, Y. Okada, H. Miyamae, Heterocycles, 1998, 48, 285-294 ($R^1$=$R^5$=H); Kawase, Masami, Chem. Pharm. Bull. 1997, 45, 1248-1253 ($R^1$=H; $R^8$=6,7-(MeO$_2$)); D. F. Ortwine, T. C. Malone, C. F. Bigge, J. T. Drummond, C. Humblet, J. Med. Chem. 1992, 35, 1345-1370 ($R^1$=H; $R^8$=7-CH$_2$PO(OEt)$_2$); E. J. Corey, D. Y. Gin, Tetrahedron Lett. 1996, 37, 7163-7166 ($R^1$=CH$_2$SCOOtBu); P. Dostert, M. Varasi, A. DellaTorre, C. Monti, V. Rizzo, Eur. J. Med. Chim. Ther. 1992, 27, 57-59 ($R^1$=Me; $R^8$=6,7-(OH)$_2$); Z. Czarnocki, D. Suh, D. B. McLean, P. G. Hultin, W. A. Szarek, Can. J. Chem. 1992, 70, 1555-1561; B. Schbnenberger, A. Brossi, Helv. Chim. Acta 1986, 69, 1486-1497 ($R^1$=Me; $R^8$=6-OH; 7-MeO); Hahn, Stiel, Chem. Ber. 1936, 69, 2627; M. Chrzanowska, B. Schönenberger, A. Brossi, J. L. Flippen—Anderson, Helv. Chim. Acta 1987, 70, 1721-1731; T. Hudlicky, J. Org. Chem. i981, 46, 1738-1741 ($R^1$=Bn; $R^8$=6,7-(OH)$_2$); A. l. Meyers, M. A. Gonzalez, V. Struzka, A. Akahane, J. Guiles, J. S. Warmus, Tetrahedron Lett. 1991, 32, 5501-5504 ($R^1$=CH$_2$(3, 4-methylenedioxy)C$_6$H$_3$; $R^8$=6,7AOMe)$_2$).

A30 and A31 can be prepared according to Schemes 4 and 5.

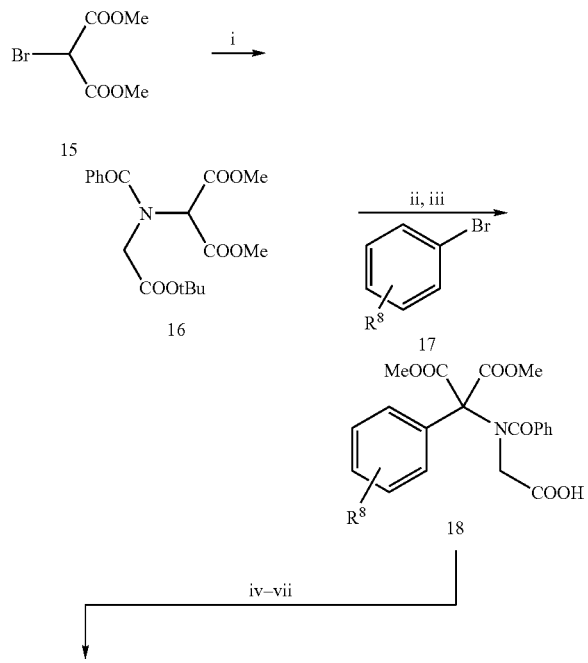

Scheme 4

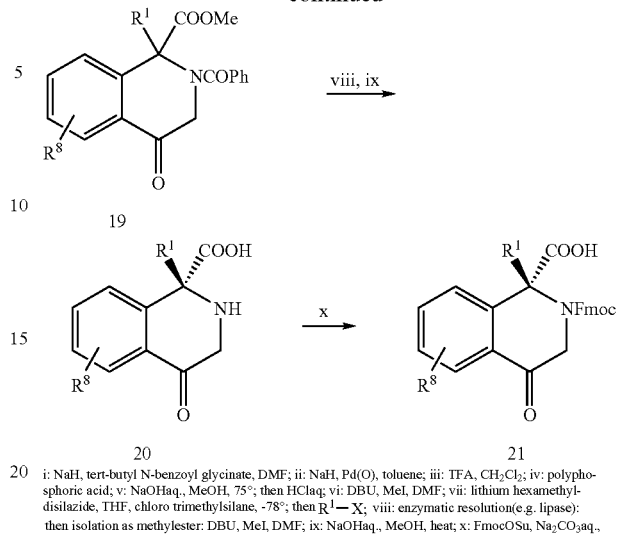

i: NaH, tert-butyl N-benzoyl glycinate, DMF; ii: NaH, Pd(O), toluene; iii: TFA, CH$_2$Cl$_2$; iv: polyphosphoric acid; v: NaOHaq., MeOH, 75°; then HClaq; vi: DBU, MeI, DMF; vii: lithium hexamethyldisilazide, THF, chloro trimethylsilane, -78°; then $R^1$—X; viii: enzymatic resolution(e.g. lipase): then isolation as methylester: DBU, MeI, DMF; ix: NaOHaq., MeOH, heat; x: FmocOSu, Na$_2$CO$_3$aq., dioxane Scheme 5

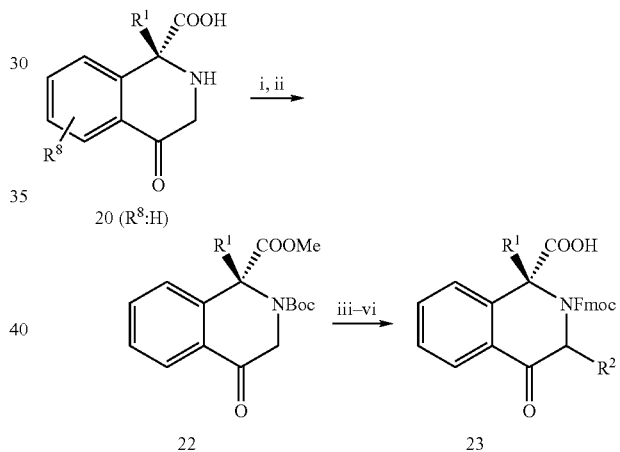

i: Boc$_2$O, Na$_2$CO$_3$aq., dioxane; ii: DBU, MeI, DMF; iii: lithium hexamethyldisilazide, THF, chlorotrimethylsilane, -78°; then $R^2$—X; iv: LiOHx1H$_2$O, MeOH, H$_2$O; v: TFA, CH$_2$Cl$_2$; vi: FmocOSu, Na$_2$CO$_3$aq., dioxane A32 can be prepared according to P. W. Schiller, G. Weltrowska, T. M.-D. Nguyen, C. Lemieux, N. Nga, J. Med. Chem. 1991, 34, 3125-3132; V. S. Goodfellow, M. V. Marathe, K. G. Kuhiman, T. D. Fitzpatrick, D. Cuadrato, J. Med. Chem. 1996, 39, 1472-1484; G. Caliendo, F. Fiorino, P. Grieco, E. Perissutti, S. DeLuca, A. Guiliano, G. Santelli, D. Califano, B. Severino, V. Santagada, Farmacao, 1999, 54, 785-790; V. S. Goodfellow, M. V. Marathe, K. G. Kuhlman, T. D. Fitzpatrick, D. Cuadro, J. Med. Chem. 1996, 39, 1472-1484 ($R^1$=$R^8$=H); D. Tourwe, E. Mannekens, N. T. Trang, P. Verheyden, H. Jaspers, J. Med. Chem. 1998, 41, 5167-5176; A.-K. Szardenings, M. Gordeev, D. V. Patel, Tetrahedron Lett. 1996, 37, 3635-3638; W. Wiczk, K. Stachowiak, P. Skurski, L. Lankiewicz, A. Michniewicz, A. Roy, J. Am. Chem. Soc. 1996, 118, 8300-8307; K. Verschuren, G. Toth, D. Tourwe, M. Lebi., G. van Binst, V. Hrubi, Synthesis 1992, 458-460 ($R^1$=H; $R^8$=6-OH); P. L. Ornstein, M. B. Arnold, N. K. Augenstein, J. W. Paschal, J. Org. Chem. 1991, 56, 43884392 ($R^1$=H; $R^8$=6-MeO); D. Ma, Z. Ma, A. P. Kozikowski, S. Pshenichkin, J. T. Wroblenski, *Bioorg. Med. Leit.* 1998, 8, 2447-2450 ($R^1$=H; R=6-COOH); U. Schöllkopf, R. Hinrichs, R. Lonsky, *Angew. Chem.* 1987, 99, 137-138 ($R^1$=Me; $R^8$=H); B. O. Kammermeier, U. Lerch, C. Sommer, *Synthesis* 1992, 1157-1160 ($R^1$=COOMe; $R^8$=H); T. Gees, W. B. Schweizer, D. Seebach, *Helv. Chim. Acta* 1993, 76, 2640-2653 (R1=Me; $R^8$=6,7-(MeO$_2$)).

A33: See Hinton, Mann, *J. Chem. Soc.* 1959, 599-608.

A34: See G. P. Zecchini, M. P. Paradisi, *J. Heterocycl. Chem.* 1979, 16, 1589-1597; S. Cerrini, *J. Chem. Soc. Perkin Trans.*1, 1979, 1013-1019; P. L. Omstein, J. W. Paschal, P. D. Geselichen, *J. Org. Chem.* 1990, 55, 738-741; G. M. Ksander, A. M. Yan, C. G. Diefenbacher, J. L. Stanton, *J. Med. Chem.* 1985, 28, 1606-1611; J. A. Robl, D. S. Karanewsky, M. M. Asaad, *Tetrahedron Lett.* 1995, 36, 1593-1596; S. Katayama, N. Ae, R. Nagata, *Tetrahedron: Asymmetry* 1998, 9, 4295-4300 ($R^1$=$R^8$=H); K. Hino, Y. Nagai, H. Uno, *Chem. Pharm. Bull.* 1988, 36, 2386-2400 ($R^1$=Me; $R^8$=H).

A35: See Beilstein Registry Numbers: 530775, 883013 ($R^1$=$R^8$=H).

A36: See R. W. Carling, P. D. Leeson, A. M. Moseley, R. Baker, A. C. Foster, *J. Med. Chem.* 1992, 35, 1942-1953; S. Kano, T. Ebata, S. Shibuya, *J. Chem. Soc. Perkin Trans.*1, 1980, 2105-2111 ($R^1$=$R^8$=H); R. W. Carling, P. D. Leeson, A. M. Moseley, R. Baker, A. C. Foster, *J. Med. Chem.* 1992, 35, 1942-1953 ($R^1$=H; $R^8$=5-Cl; 7-Cl).

A37: See Nagarajan, *Indian J. Chem.* 1973, 11, 112 ($R^1$=CH$_2$COOMe; $R^8$=H).

A38: See R. Pauly, N. A. Sasaki, P. Potire, *Tetrahedron Lett.* 1994, 35, 237-240; J. Podlech, D. Seebach, Liebigs Ann. Org. *Bioorg. Chem.* 1995, 7, 1217-1228; K. C. Nicolaou, G.-Q. Shi, K. Namoto, F. Bernal, *J. Chem. Soc. Chem. Commun.* 1998, 1757-1758 ($R^1$=H; $R^2$=H).

A39: See Beilstein, Registry Number 782885.

A40: See F. P. J. C. Rutjes, N. M. Terhuis, H. Hiemstra, N. W. Speckamp, *Tetrahedron* 1993, 49, 8605-8628 ($R^1$=H; R=Bn); compounds of this type can be prepared according to Scheme 6.

A41: Compounds of this type can be prepared according to Scheme 7.

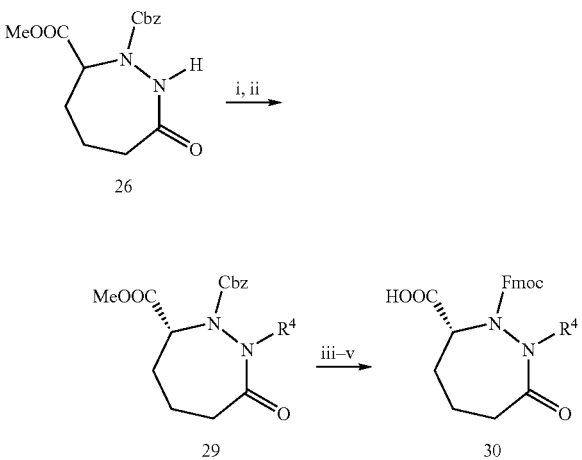

i: resolution (e.g. lipase); then isolation as methylester: DBU, MeI, DMF;
ii: NaH, $R^4$—X, THF; iii: LiOHx1H$_2$O, MeOH, H$_2$O; iv: Pd/C, H$_2$, EtOH; v: FmocOSu, Na$_2$CO$_3$aq., dioxane A42 to A46: Compounds of this type can be prepared according to Schemes 8 to 12. Key intermediate 34 and α-amino acid synthesis involving this building block include: R. M. Williams, M.-N. Im, *Tetrahedron Lett.* 1988, 29, 6079-6082; R. M. Williams, M.-N. Im, *J. Am. Chem. Soc.*1991, 113, 9276-9286; J. F. Dellaria, B. D. Santarsiero, *Tetrahedron Lett.* 1988, 29, 6079-6082; J. F. Dellaria, B. D. Santarsiero, *J. Org. Chem.* 1989, 54, 3916-3926; J. E. Baldwin, V. Lee, C. J. Schofield, *Synlett* 1992, 249-251; J. E. Baldwin, V. Lee, C. J. Schofield, *Heterocycles* 1992, 34, 903-906.

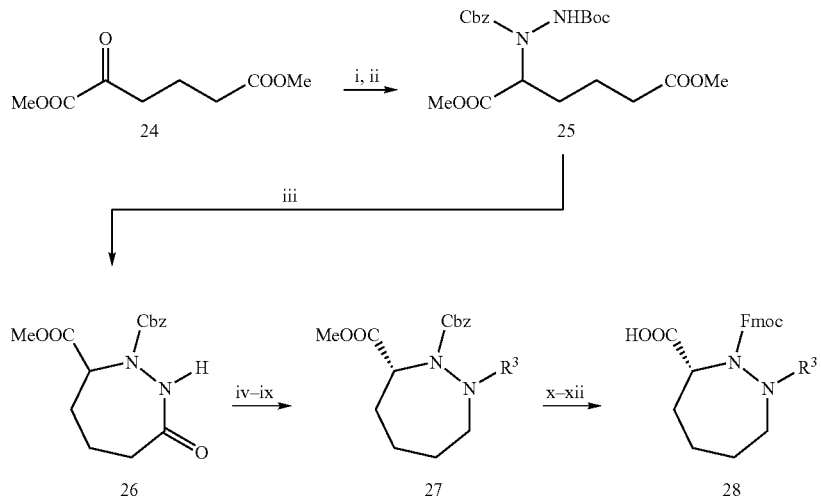

i: BocNHNH$_2$, NaCNBH$_3$, MeOH, AcOH; ii: CbzCl, Et$_3$N, CH$_2$Cl$_2$; iii: TFA, CH$_2$Cl$_2$; then pyridine, DMAP, heat; iv: resolution (e.g. lipase); v: DBU, MeI, DMF; vi: Lawesson reagent, toluene, 75°; vii: DBU, MeI, DMF; viii: NaBH$_4$ or NaCNBH$_3$, MeOH; ix: $R^3$ introduced by reductive amination, alkylation or acylation; x: LiOHx1H$_2$O, MeOH, H$_2$O; xi: Pd/C, H$_2$, EtOH; xii: FmocOSu, Na$_2$CO$_3$aq., dioxane

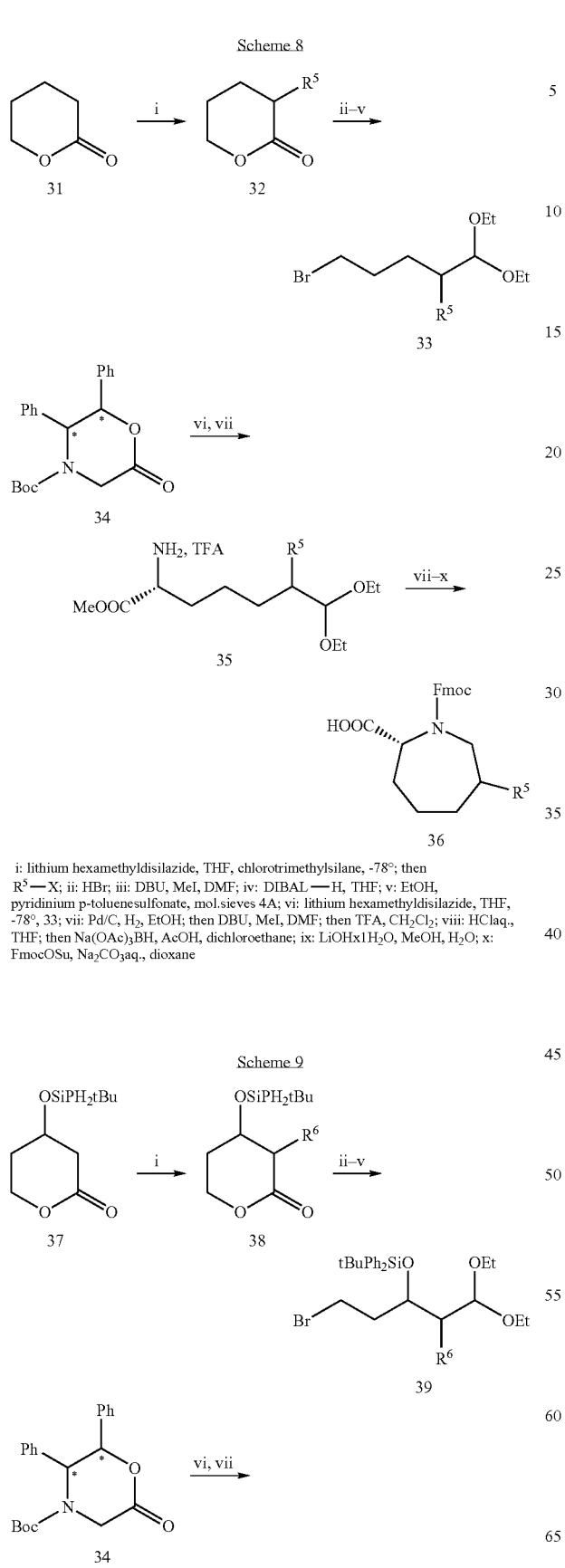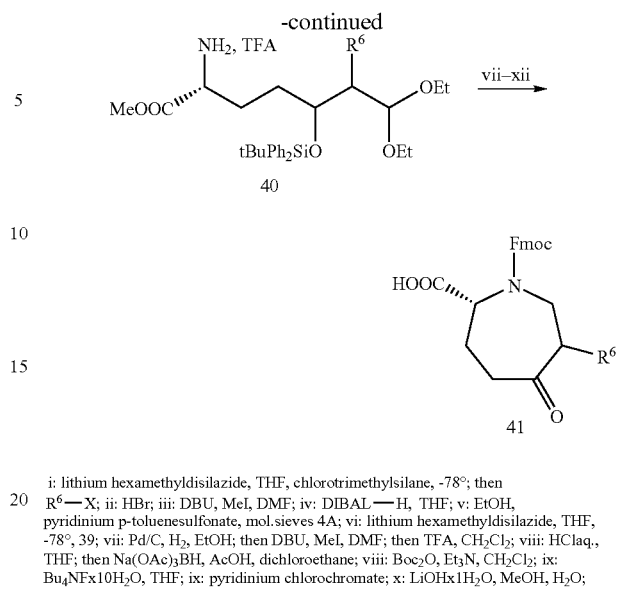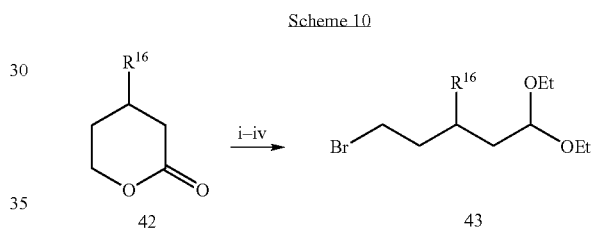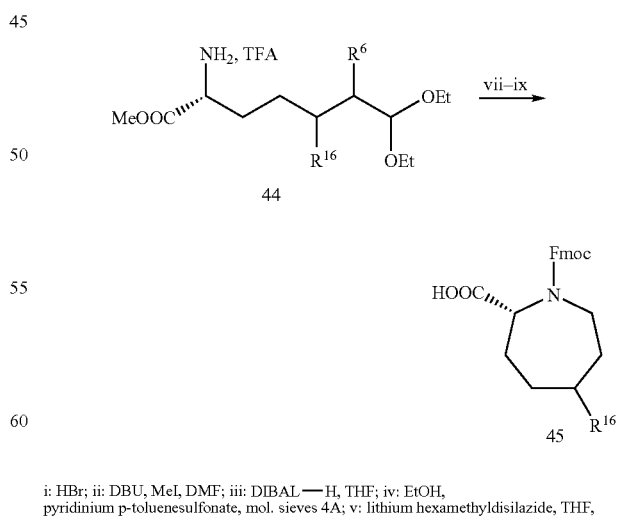

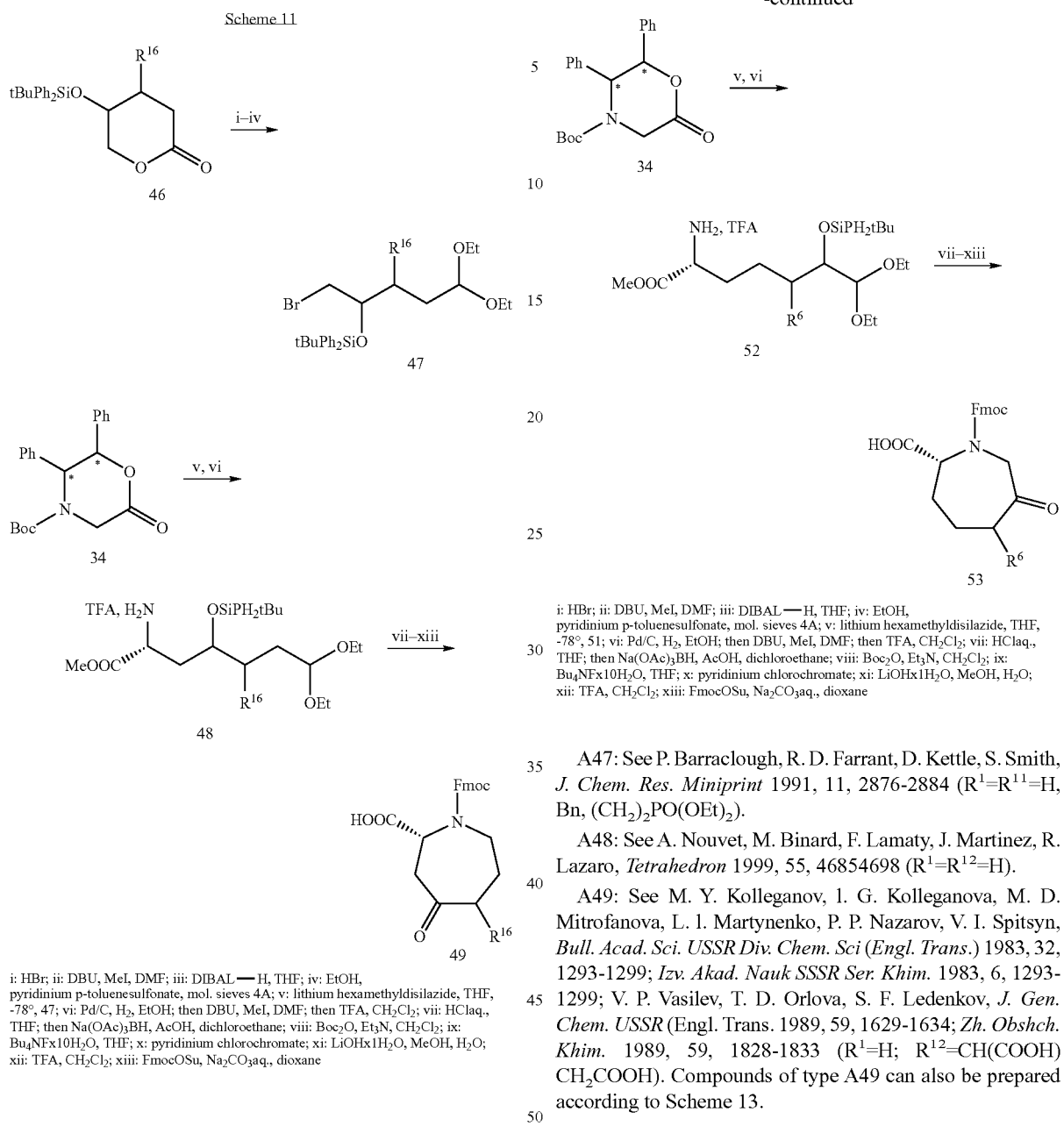

A47: See P. Barraclough, R. D. Farrant, D. Kettle, S. Smith, *J. Chem. Res. Miniprint* 1991, 11, 2876-2884 ($R^1=R^{11}=H$, Bn, $(CH_2)_2PO(OEt)_2$).

A48: See A. Nouvet, M. Binard, F. Lamaty, J. Martinez, R. Lazaro, *Tetrahedron* 1999, 55, 46854698 ($R^1=R^{12}=H$).

A49: See M. Y. Kolleganov, I. G. Kolleganova, M. D. Mitrofanova, L. I. Martynenko, P. P. Nazarov, V. I. Spitsyn, *Bull. Acad. Sci. USSR Div. Chem. Sci (Engl. Trans.)* 1983, 32, 1293-1299; *Izv. Akad. Nauk SSSR Ser. Khim.* 1983, 6, 1293-1299; V. P. Vasilev, T. D. Orlova, S. F. Ledenkov, *J. Gen. Chem. USSR* (Engl. Trans. 1989, 59, 1629-1634; *Zh. Obshch. Khim.* 1989, 59, 1828-1833 ($R^1=H$; $R^{12}=CH(COOH)CH_2COOH$). Compounds of type A49 can also be prepared according to Scheme 13.

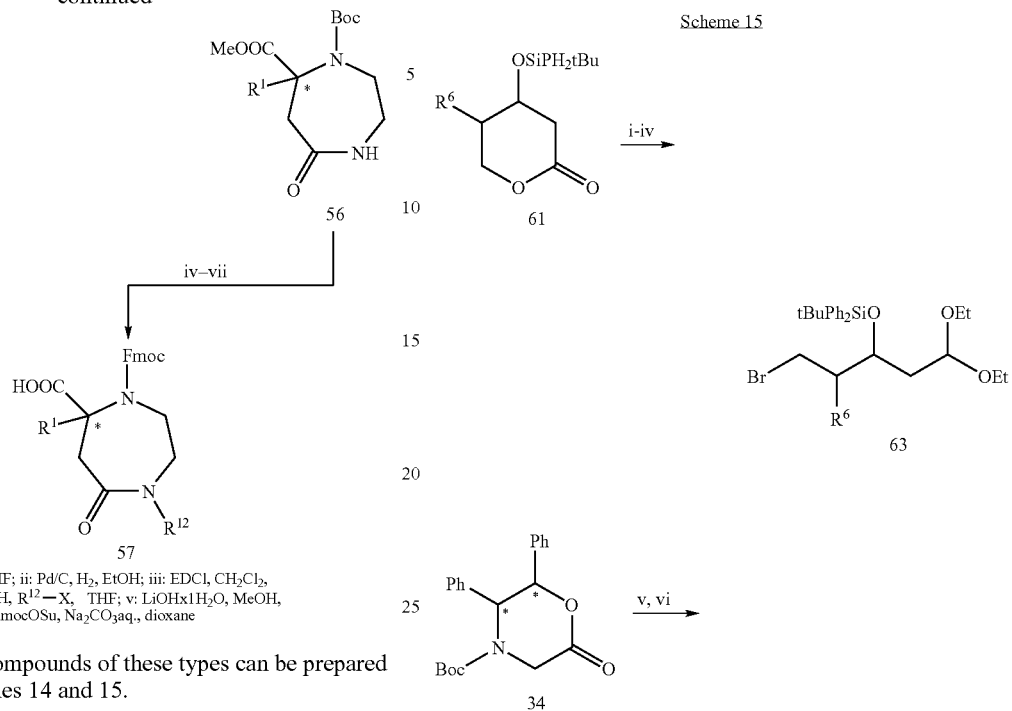

Scheme 15 i: NaH, CbzNH(CH₂)₂Br, THF; ii: Pd/C, H₂, EtOH; iii: EDCl, CH₂Cl₂, diisopropylethylamin; iv: NaH, R¹²—X, THF; v: LiOHx1H₂O, MeOH, H₂O; vi: TFA, CH₂Cl₂; vii: FmocOSu, Na₂CO₃aq., dioxane A50 and A51: Compounds of these types can be prepared according to Schemes 14 and 15.

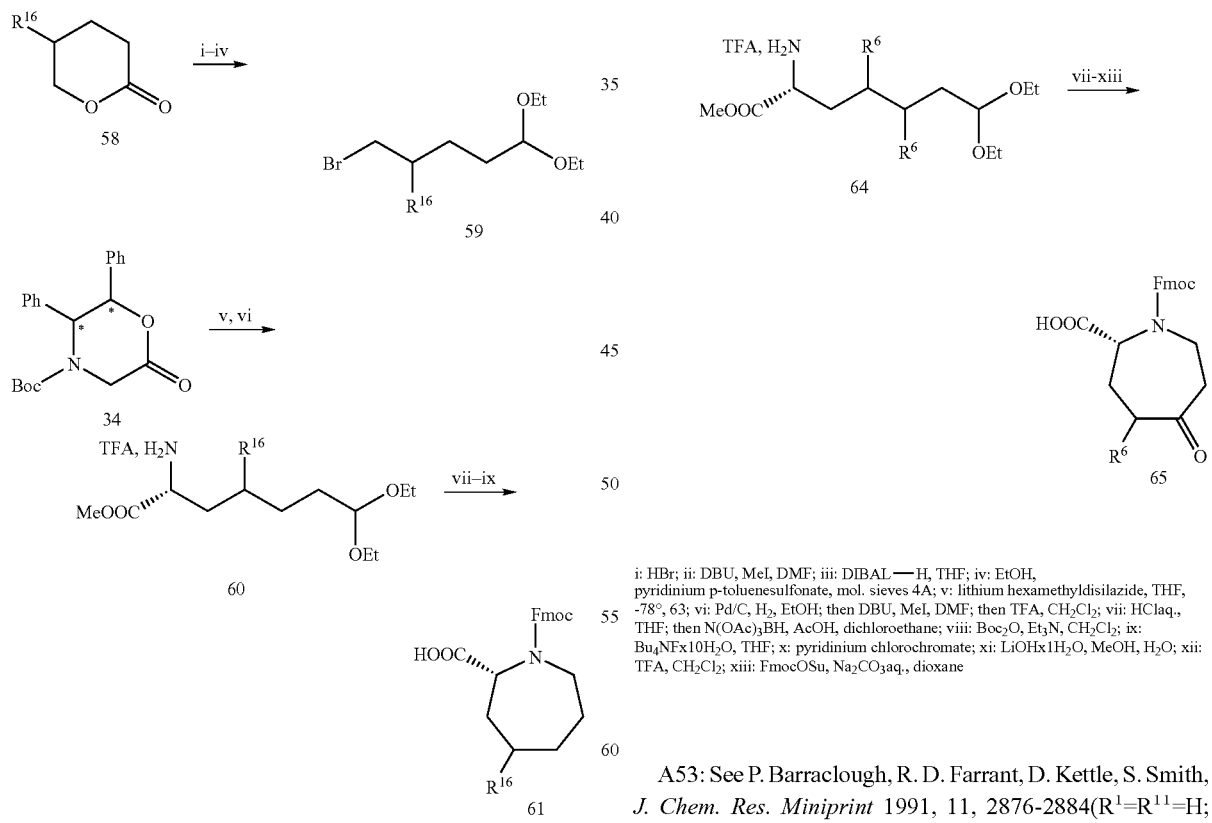

Scheme 14 i: HBr; ii: DBU, MeI, DMF; iii: DIBAL—H, THF; iv: EtOH, pyridinium p-toluenesulfonate, mol. sieves 4A; v: lithium hexamethyldisilazide, THF, -78°, 59; vi: Pd/C, H₂, EtOH; then DBU, MeI, DMF; then TFA, CH₂Cl₂; vii: HClaq., THF; then Na(OAc)₃BH, AcOH, dichloroethane; viii: LiOHx1H₂O, MeOH, H₂O; ix: FmocOSu, Na₂CO₃aq., dioxane i: HBr; ii: DBU, MeI, DMF; iii: DIBAL—H, THF; iv: EtOH, pyridinium p-toluenesulfonate, mol. sieves 4A; v: lithium hexamethyldisilazide, THF, -78°, 63; vi: Pd/C, H₂, EtOH; then DBU, MeI, DMF; then TFA, CH₂Cl₂; vii: HClaq., THF; then N(OAc)₃BH, AcOH, dichloroethane; viii: Boc₂O, Et₃N, CH₂Cl₂; ix: Bu₄NFx10H₂O, THF; x: pyridinium chlorochromate; xi: LiOHx1H₂O, MeOH, H₂O; xii: TFA, CH₂Cl₂; xiii: FmocOSu, Na₂CO₃aq., dioxane A53: See P. Barraclough, R. D. Farrant, D. Kettle, S. Smith, *J. Chem. Res. Miniprint* 1991, 11, 2876-2884(R¹=R¹¹=H; R¹=H; R¹¹=Bn, (CH₂)₃PO(OH)₂); (CH₂)₃PO(Et)₂); J. 1. Levin, J. F. DiJoseph, L. M. Killar; A. Sung, T. Walter, *Bioorg. Med. Chem. Lett.* 1998, 8, 2657-2662 (R¹=H; R¹¹=4CF₃OC₆H₄CO).

A 52 and A54: Compounds of this type can be prepared according to Schemes 16 and 17.

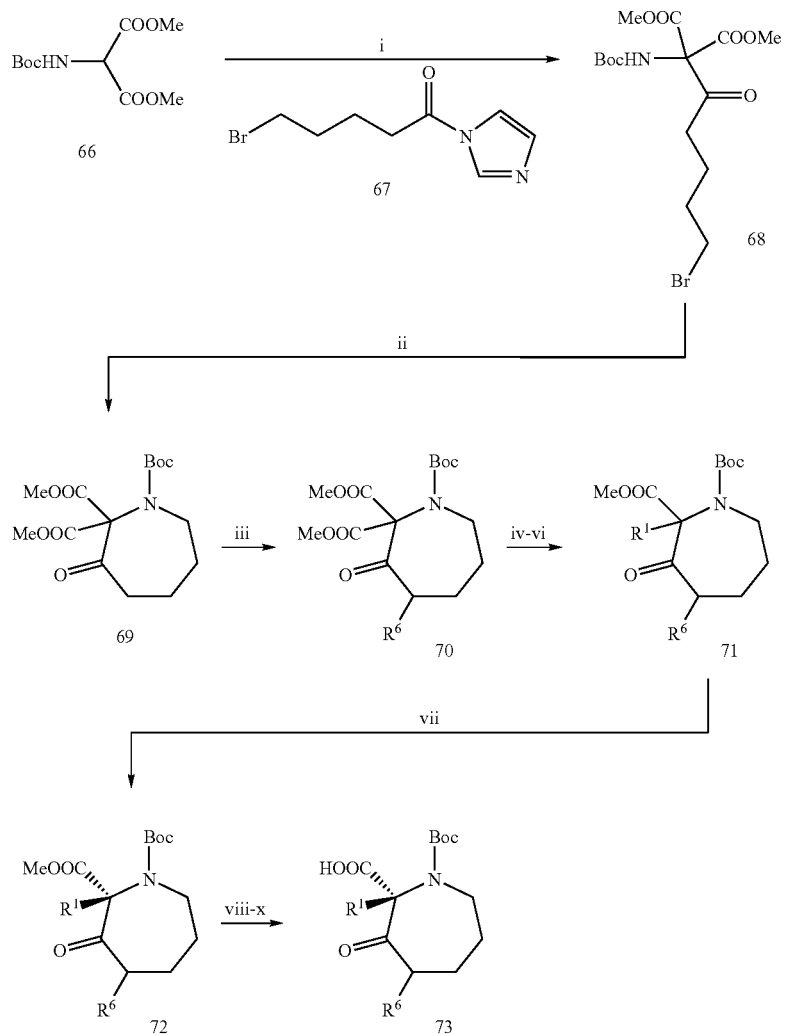

i: iBuMgCl, THF; ii: NaH, THF; iii: lithium hexamethyldisilazide, THF, chlorotrimetylsilane, -78°; then R⁶—X; iv: NaOHaq., MeOH, 75°; then HClaq; v: DBU, MeI, DMF; vi: lithium hexamethyl-disilazide, THF, chlorotrimetylsilane, -78°; then R¹—X; vii: resolution (e.g. lipase); then DBU, MeI, DMF; viii: LiOHx1H₂O, MeOH, H₂O; ix: TFA, CH₂Cl₂; x: FmocOSu, Na₂CO₃aq., dioxne

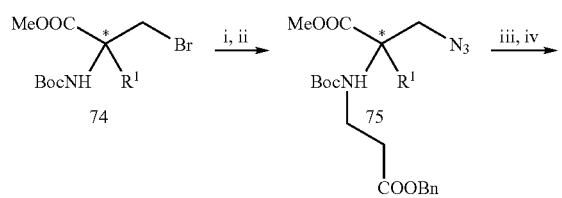

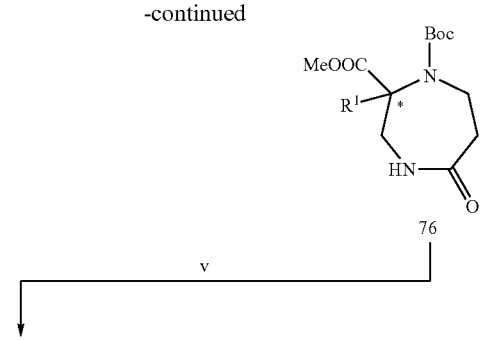

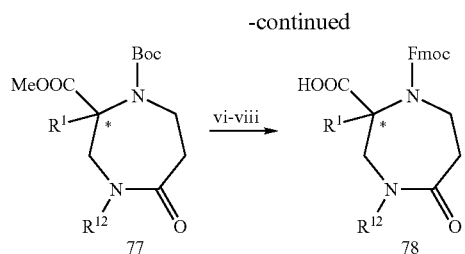

i: NaN₃, DMSO; ii: NaH, THF, CH₂=CHCOOBn; iii: Pd/C, H₂, EtOH;
iv: EDCl, CH₂Cl₂, diisopropylethylamine; v: NaH, $R^{12}$—X, THF;
vi: LiOHx1H₂O; vii: TFA, CH₂Cl₂; viii: FmocOSu, Na₂CO₃aq., dioxane A55 and A56: Compounds of this type can be prepared according to Schemes 18 and 19.

Scheme 18

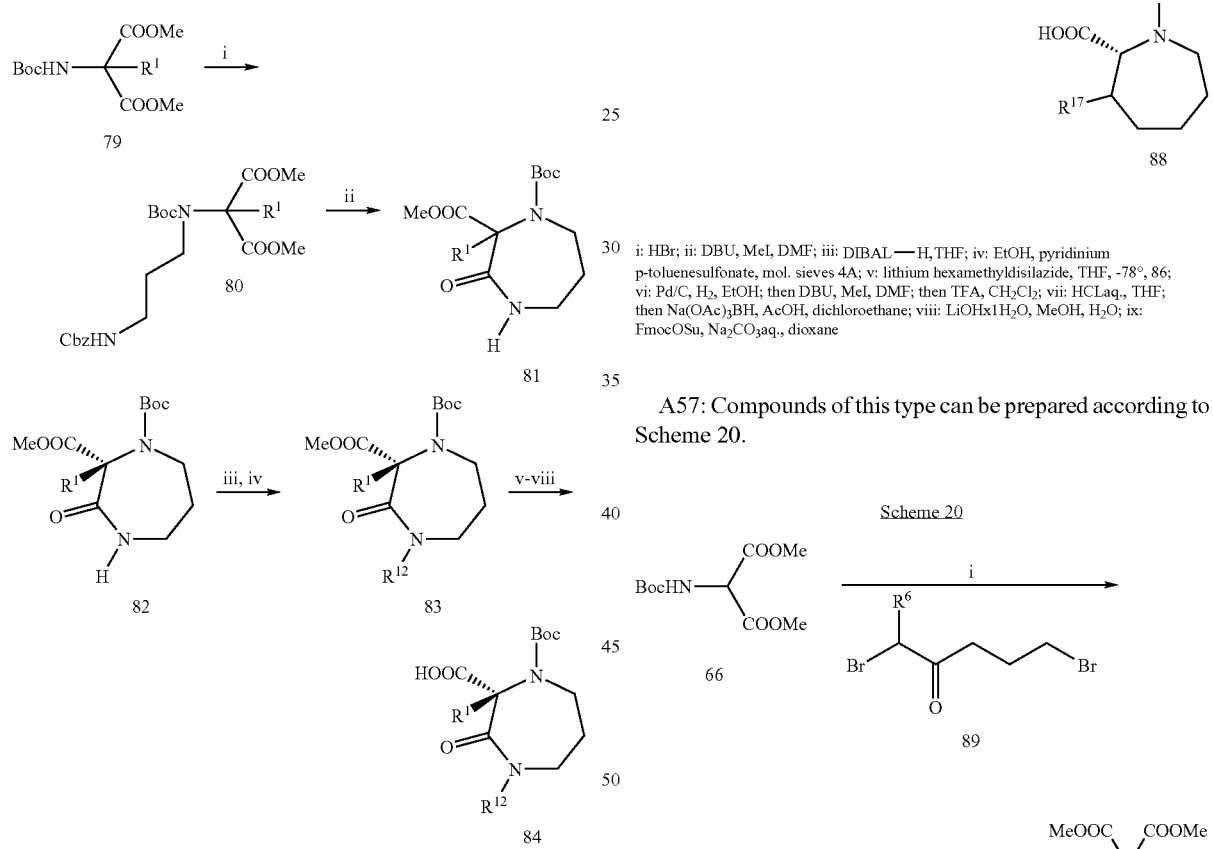

i: NaH, THF, CbzNH(CH₂)₃Br; ii: Pd/C, H₂, EtOH; then toluene, heat;
iii: resolution (e.g. lipase); iv: DBU, MeI, DMF; v: NAH, $R^{12}$—X, THF;
vi: LiOHx1H₂O, MeOH, H₂O; vii: TFA, CH₂Cl₂; viii: FmocOSu, Na₂CO₃aq., dioxane

Scheme 19

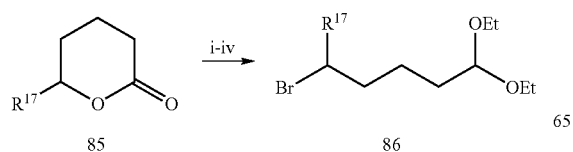

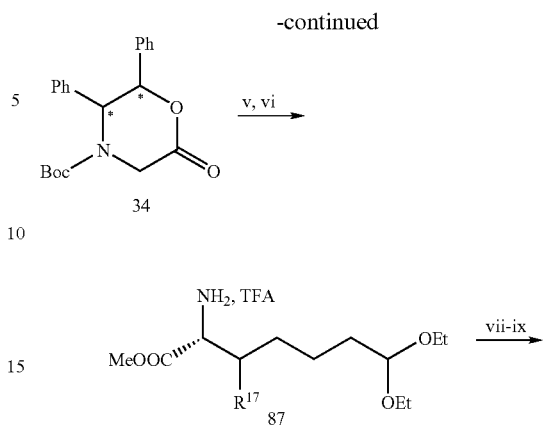

i: HBr; ii: DBU, MeI, DMF; iii: DIBAL—H,THF; iv: EtOH, pyridinium p-toluenesulfonate, mol. sieves 4A; v: lithium hexamethyldisilazide, THF, -78°, 86; vi: Pd/C, H₂, EtOH; then DBU, MeI, DMF; then TFA, CH₂Cl₂; vii: HCLaq., THF; then Na(OAc)₃BH, AcOH, dichloroethane; viii: LiOHx1H₂O, MeOH, H₂O; ix: FmocOSu, Na₂CO₃aq., dioxane A57: Compounds of this type can be prepared according to Scheme 20.

Scheme 20

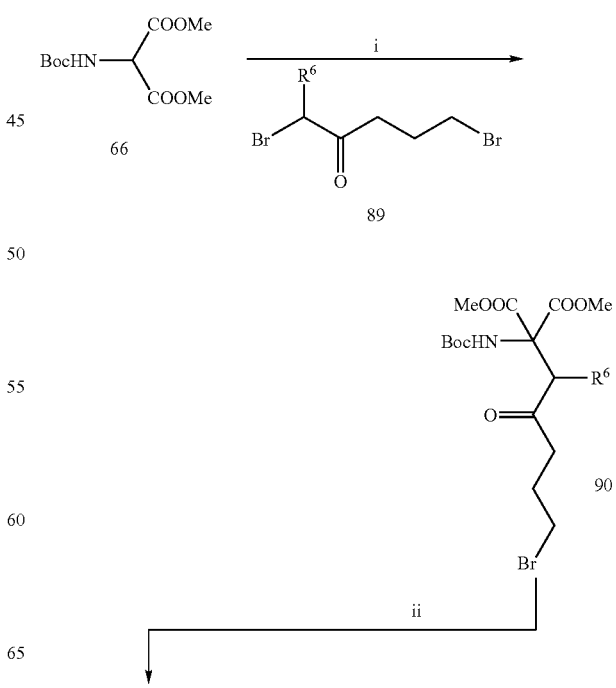

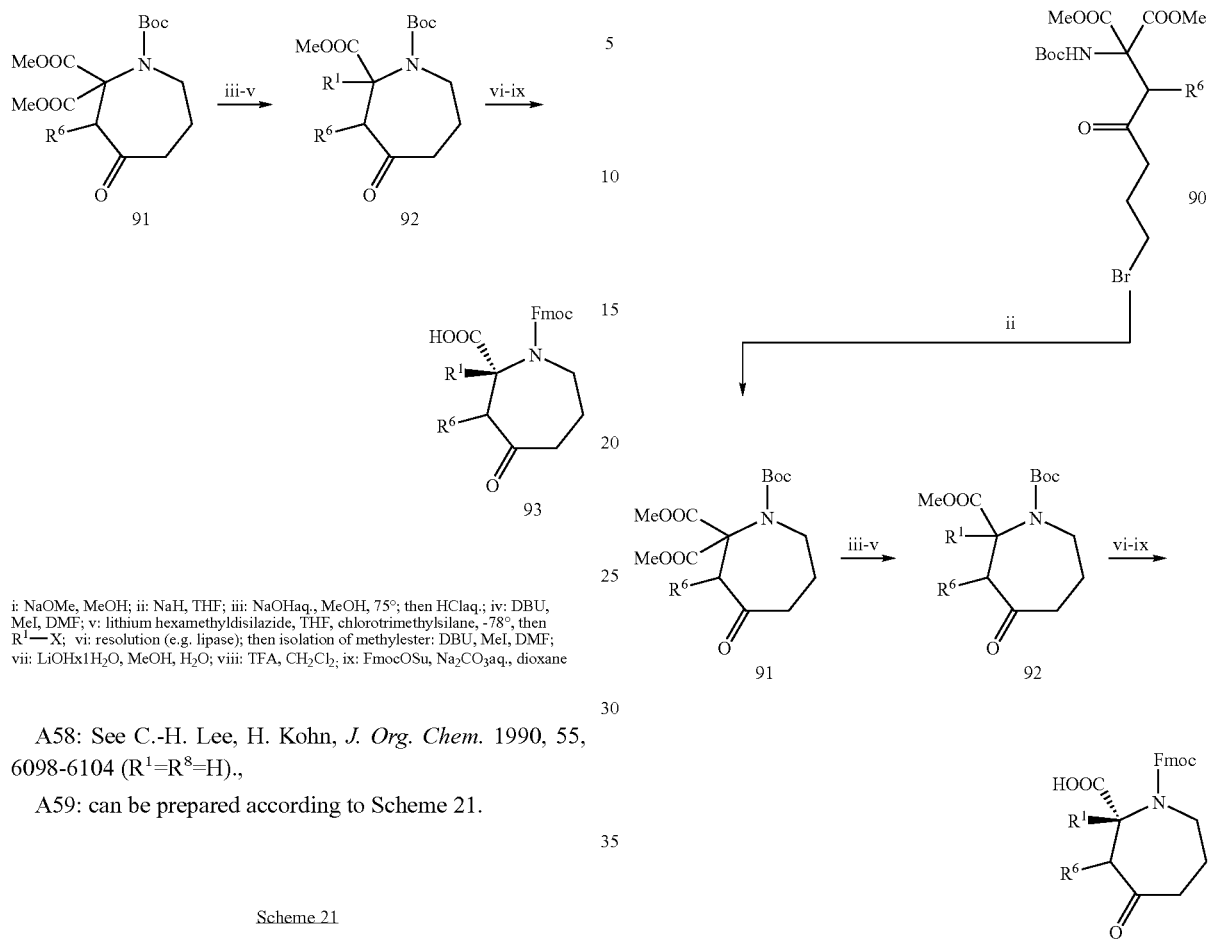

i: NaOMe, MeOH; ii: NaH, THF; iii: NaOHaq., MeOH, 75°; then HClaq.; iv: DBU, MeI, DMF; v: lithium hexamethyldisilazide, THF, chlorotrimethylsilane, -78°, then R¹—X; vi: resolution (e.g. lipase); then isolation of methylester: DBU, MeI, DMF; vii: LiOHx1H₂O, MeOH, H₂O; viii: TFA, CH₂Cl₂; ix: FmocOSu, Na₂CO₃aq., dioxane A58: See C.-H. Lee, H. Kohn, *J. Org. Chem.* 1990, 55, 6098-6104 ($R^1=R^8=H$)., A59: can be prepared according to Scheme 21.

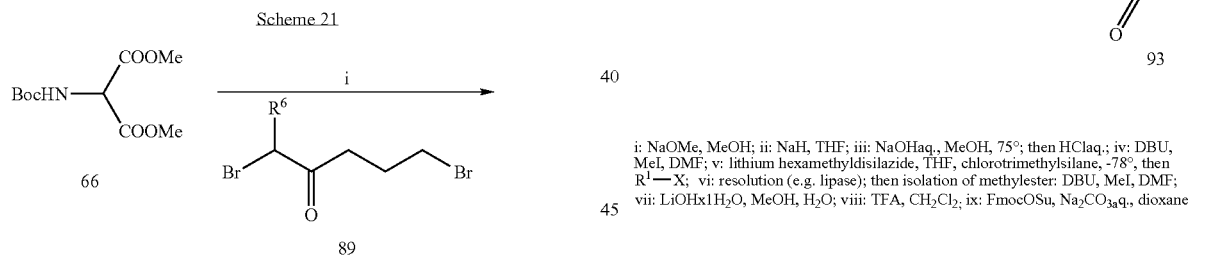

i: NaOMe, MeOH; ii: NaH, THF; iii: NaOHaq., MeOH, 75°; then HClaq.; iv: DBU, MeI, DMF; v: lithium hexamethyldisilazide, THF, chlorotrimethylsilane, -78°, then R¹—X; vi: resolution (e.g. lipase); then isolation of methylester: DBU, MeI, DMF; vii: LiOHx1H₂O, MeOH, H₂O; viii: TFA, CH₂Cl₂; ix: FmocOSu, Na₂CO₃aq., dioxane A60: Compounds of this type can be prepared according to Scheme 22.

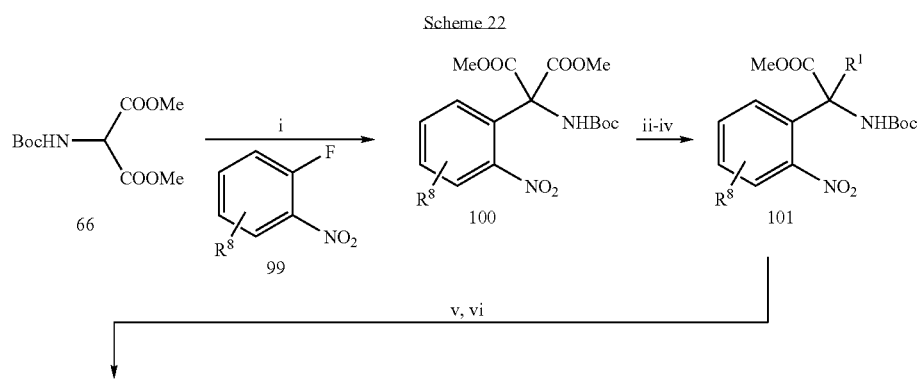

-continued

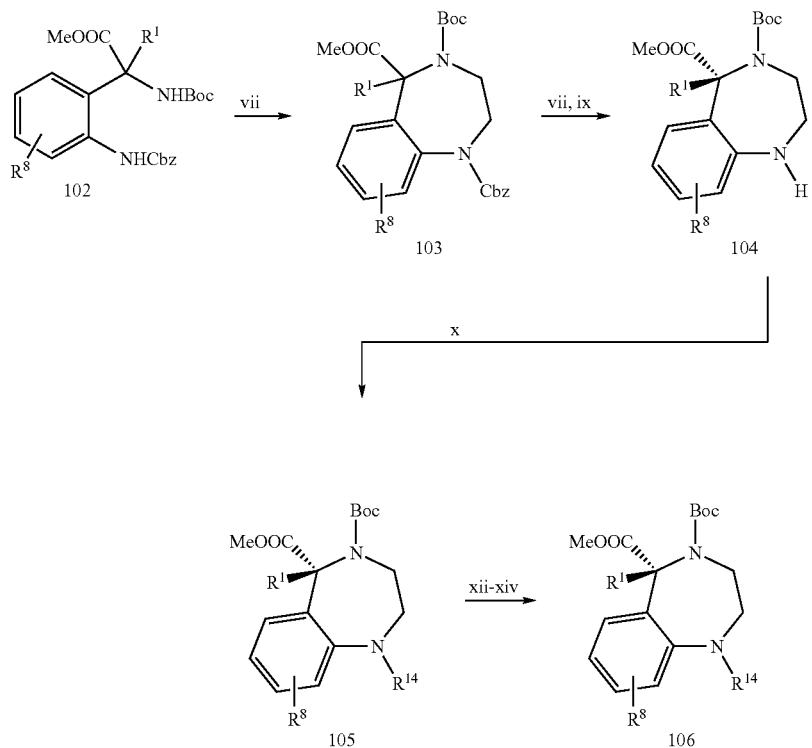

i: NaH, DMSO; ii: NaOHaq., MeOH, 75°; then HClaq.; iii: DBU, MeI, DMF; iv: NaOMe (2.2equiv.), R¹—X; v: Raney-Ni, H₂, EtOH; vi: CbzCl, Et₃N, CH₂Cl₂; vii: NaH, Br(CH₂)₂Br, THF; viii: resolution (e.g. lipase); then DBU, MeI, DMF; ix: Pd/C, H₂, EtOH; x: NaH,R¹⁴—X; THF; xi: LiOHx1H₂O, MeOH, H₂O; xii: FA, CH₂Cl₂; xiii: FmocOSu, Na₂CO₃aq., dioxane A61: See D. R. Armour, K. M. Morriss, M. S. Congreve, A. B. Hawcock, *Bioorg. Med. Chem. Lett.* 1997, 7, 2037-2042 (R¹=R¹²=H).

A62: Compounds of this type can be prepared according to Scheme 23.

Scheme 23

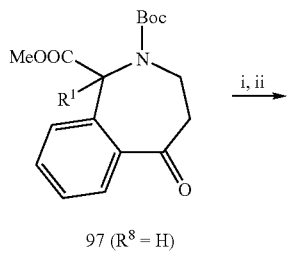

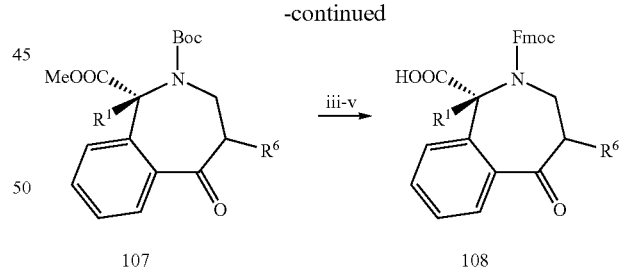

i: resolution (e.g. lipase); then DBU, MeI, DMF; ii: lithium hexamethyldisilazide, THF, chlorotrimethylsilane, -78°; then R⁶—X; iii: LiOHx1H₂O, MeOH, H₂O; iv: TFA, CH₂Cl₂; v: FmocOSu, Na₂CO₃aq., dioxane A63: See S. E. Gibson, N. Guillo, R. J. Middleton, A. Thuilliez, M. J. Tozer, *J. Chem. Soc. Perkin Trans.*1, 1997, 4, 447-456; S. E. Gibson, N. Guillo, S. B. Kalindjan, M. J. Tozer, *Bioorg. Med. Chem. Lett.*, 1997, 7, 1289-1292 (R¹=H; R⁸=H); Bejistein Registry Number: 459155 (R¹=H; R⁸=4,5-MeO₂).

A64: Compounds of this type can be prepared according to Scheme 24.

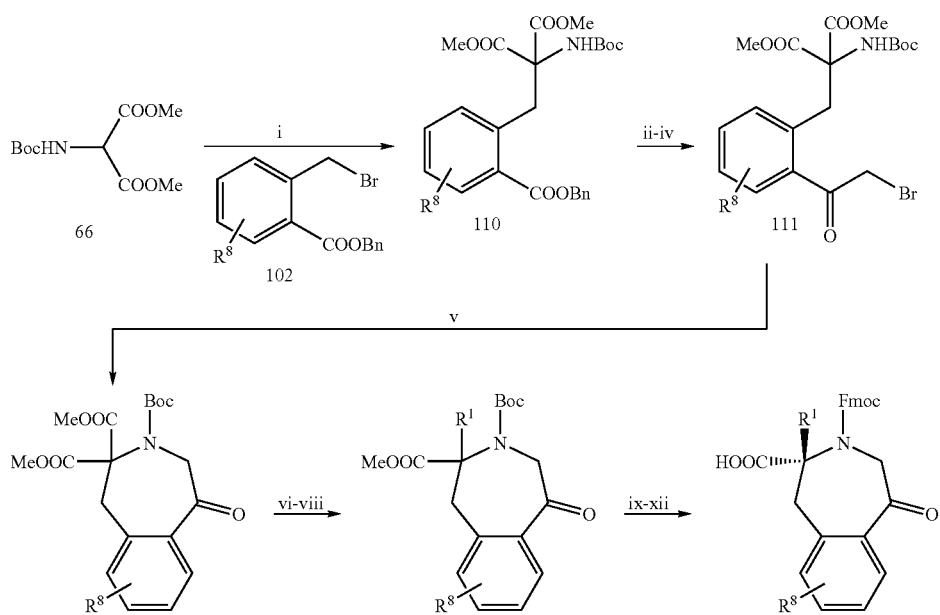

i: NaH, DMSO; ii: Pd/C, H₂, EtOH; iii: iBuOCOCl, diisopropylethylamine, CH₂Cl₂; then diazomethane; iv: HBr, CH₂Cl₂; v: NaH, THF; vi: NaOHaq., MeOH, 75°; then HClaq.; vii: DBU, MeI, DMF; viii: lithium diisopropylamide, THF, chlorotrimethylsilane, -78°; then R¹—X; ix: resolution (e.g. lipase); then isolation of methylester: DBU, MeI, DMF; x: LiOHx1H₂O, MeOH, H₂O; xi: TFA, CH₂Cl₂; xii: FmocOSu, Na₂CO₃aq., dioxane A65 and A 67: Compounds of these types can be prepared according to Schemes 25 and 26.

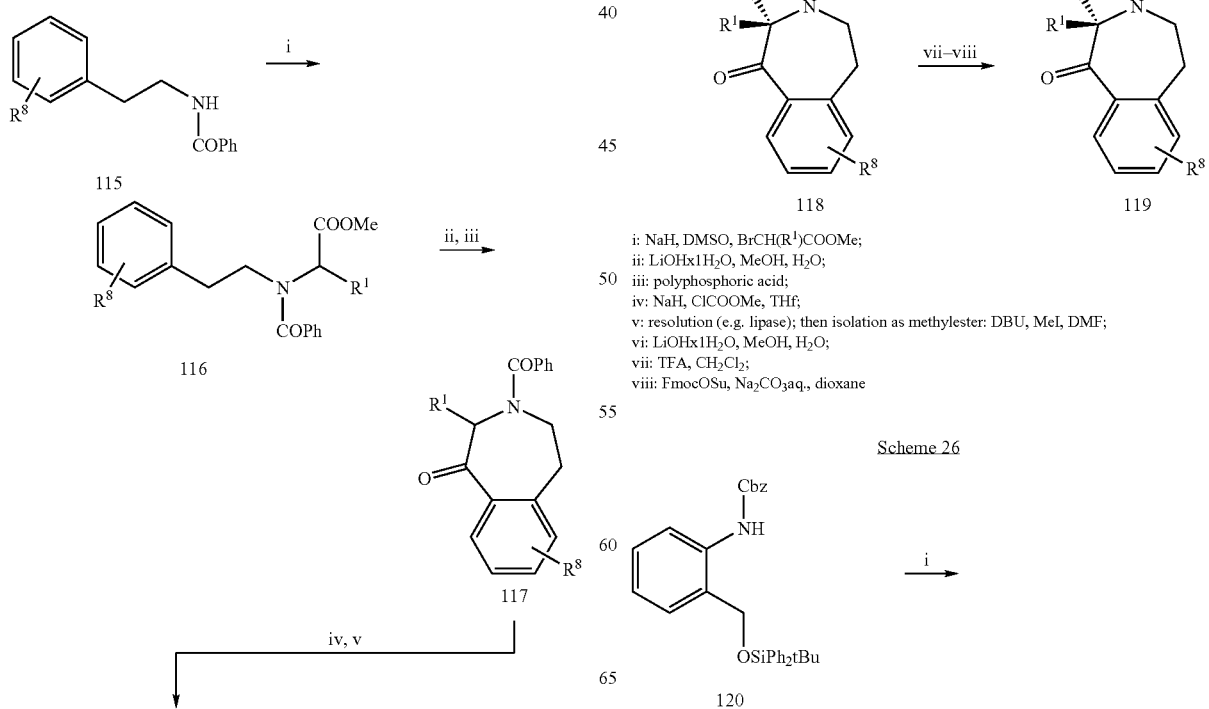

i: NaH, DMSO, BrCH(R¹)COOMe;
ii: LiOHx1H₂O, MeOH, H₂O;
iii: polyphosphoric acid;
iv: NaH, ClCOOMe, THf;
v: resolution (e.g. lipase); then isolation as methylester: DBU, MeI, DMF;
vi: LiOHx1H₂O, MeOH, H₂O;
vii: TFA, CH₂Cl₂;
viii: FmocOSu, Na₂CO₃aq., dioxane -continued

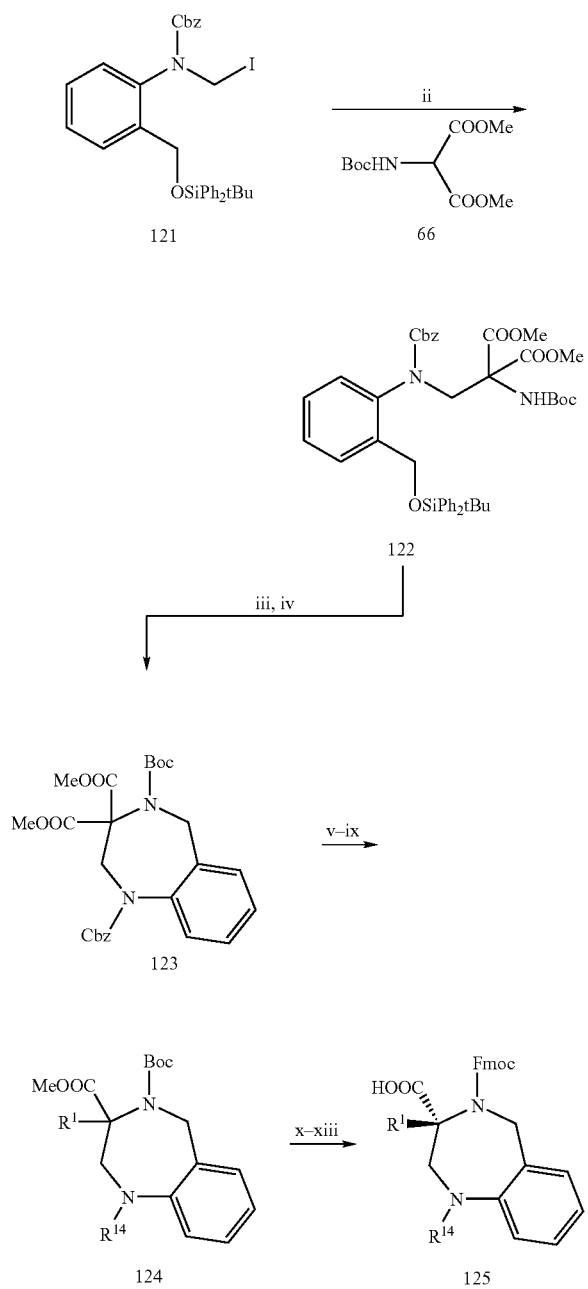

i: NaH, THF, CH$_2$I$_2$;
ii: NaH, DMSO;
iii: Bu$_4$NFx10H$_2$O, THF;
iv: methanesulfonylchloride, Et$_3$N, CH$_2$Cl$_2$; then NaH, THF;
v: NaOHaq., MeOH, 75°; then HClaq.;
vi: DBU, MeI, DMF;
vii: lithium hexamethyldisilazide, THF, chlorotrimethylsilane, -78°; then R$^{14}$—X;
viii: Pd/C, H$_2$, EtOH;
ix: NaH, THF, R$^{14}$—X;
x: resolution (e.g. lipase); then isolation of methylester: DBU, MeI, DMF;
xi: LiOHx1H$_2$O, MeOH, H$_2$O;
xii: TFA, CH$_2$Cl$_2$;
xiii: FmocOSu, Na$_2$CO$_3$aq., dioxane A66: See G. L. Grunewald, L. H. Dahanukar, *J. Heterocycl. Chem.* 1994, 31, 1609-1618 (R$^1$=H; R$^8$=H, 8-NO$_2$; C(l)=O).

A68: See Griesbeck, H. Mauder, 1. Müeller, *Chem. Ber.* 1992, 11, 2467-2476; (R$^1$=R$^8$=H; C(1)=O).

A69: R. Kreber, W. Gerhardt, *Liebigs Ann. Chem.* 1981, 240-247 (R$^1$=R$^8$=H).

As explained above, building blocks A70 belong to the class of open-chain α-substituted α-amino acids, A71 and A72 to the class of the corresponding β-amino acid analogues and A73—A104 to the class of the cyclic analogues of A70.

Building blocks of types A70 and A73—A104 have been synthesized by several different general methods: by [2+2] cycloaddition of ketenes with imines (I. Ojima, H. J. C. Chen, X. Quin, *Tetrahedron Lett.* 1988, 44, 5307-5318); by asymmetric aldol reaction (Y. Ito, M. Sawamura, E. Shirakawa, K. Hayashikazi, T. Hayashi, *Tetrahedron Lett.* 1988, 29, 235-238; by the oxazolidinone method (J. S. Amato, L h Weinstock, S. Karady, U.S. Pat. No. 4,508,921 A; M. Gander-Coquoz, D. Seebach, *Helv. Chim. Acta* 1988, 71, 224-236; A. K. Beck, D. Seebach, *Chimia* 1988, 42, 142-144; D. Seebach, J. D. Aebi, M. Gander-Coquoz, R. Naef, *Helv. Chim. Acta* 1987, 70, 1194-1216; D. Seebach, A. Fadel, *Helv. Chim. Acta* 1995, 68, 1243-1250; J. D. Aebi, D. Seebach, *Helv. Chim. Acaa* 1985, 68, 1507-1518; A. Fadel, J. Salaun, *Tetrahedron Lett.* 1987, 28, 2243-2246); by Schmidt-rearrangement of α,α-isubstituted α-ketoesters (G. I. Georg, X. Guan, J. Kant, *Tetrahedron Leit.* 1988, 29, 403-406); asynunetric synthesis via chiral Ni(II)— derived Schiff-bases (Y. N. Belokon, V. 1. Baklhmutov, N. I. Chemoglawva, K. A. Kochetov, S. V. Vitt, N. S. Garbalinskaya, V. M. Belikov, *J. Chem. Soc. Perkin Trans.* 1, 1988, 305-312; M. Kolb, J. Barth, *Liebigs Ann. Chem.* 1983, 1668-1688); by the bis-lactim ether synthesis (U. Schöllkopf, R. Hinrichs, R. Lonsky, *Angew. Chem.* 1987, 99, 137-138); by microbial resolution (K. Sakashita, I. Watanabe, JP 62/253397A2) and by the hydantoin method combined with resolution of the racemic amino acids with chiral auxilliaries derived from L-phenylalanine amides (D. Obrecht, C. Spiegler, P. Schönholzer, K. Müeller, H. Heimgartner, F. Stierli, *Helv. Chim. Acta* 1992, 75, 1666-1696; D. Obrecht, U. Bohdal, J. Daly, C. Lehmann, P. Schönholzer, K. Müller, *Tetrahedron* 1995, 51, 10883-10900; D. Obrecht, C. Lehmann, C. Ruffieux, P. Schönholzer, K. Müller, *Helv. Chim. Acta* 1995, 78, 1567-1587; D. Obrecht, U. Bohdal, C. Broger, D. Bur, C. Lehmann, R. Ruffleux, P. Schönholzer, C. Spiegler, *Helv. Chim. Acta* 1995, 78, 563-580; D. Obrecht, H. Karajiannis, C. Lehmann, P. Schönholzer, C. Spiegler, *Helv. Chim. Acta* 1995, 78, 703-714; D. Obrecht, M. Altorfer, C. Lehmann, P. Schönholzer, K. Müller, *J. Org. Chem.* 1996, 61, 4080-4086; D. Obrecht, C. Abrecht, M. Altorfer, U. Bohdal, A. Grieder, P. Pfyffer, K. Müller, *Helv. Chim. Acta* 1996, 79, 1315-1337). The latter method has been especially useful in preparing both enantiomers of building blocks of type A70 (see Scheme 27) and A73—A104 (see Scheme 28) in pure form.

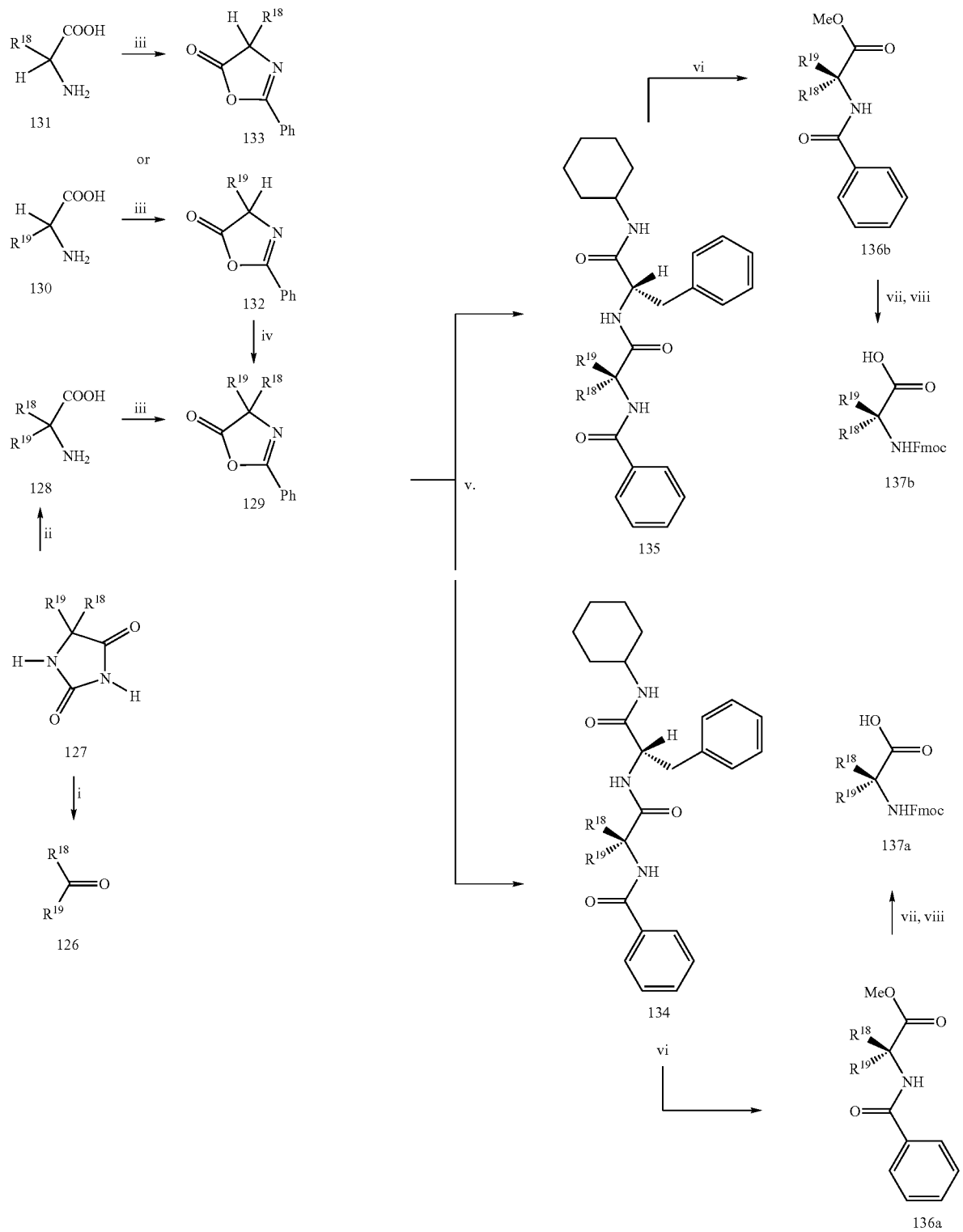

The method depicted in Scheme 27 consists in treatment of the appropriate ketones 126 with KCN, (NH$_4$)CO$_3$ in a mixture of ethanol/water (E. Ware, *J. Chem. Res.* 1950, 46, 403; L. H. Goodson, I. L. Honigberg, J. J. Lehmann, W. H. Burton, *J. Org. Chem.* 1960, 25, 1920; S, N. Rastogi, J. S. Bindra, N. Anand, *Ind. J. Chem.* 1971, 1175) to yield the corresponding hydantoins 127, which were hydrolyzed with Ba(OH)$_2$ in water at 120-140° (R. Sarges, R. C. Schur, J. L. Belletire, M. J. Paterson, *J. Med. Chem.* 1988, 31, 230) to give 128 in high yields. Schotten-Baurnann acylation (Houben-Weyl, 'Methoden der Organischen Chemie', Volume XI/2, Stickstoff-Verbindungen II und III, Georg Tieme Verlag, Stuttgart, pp 339) followed by cyclization with N,N'-dicyclohexyl carbodiimide gave azlactones 129 (D. Obrecht, U. Bohdal, C. Broger, D. Bur, C. Lehmann, R. Ruffieux, P. Schönholzer, C. Spiegler, *Helv. Chim. Acta* 1995, 78, 563-580; D. Obrecht, C. Spiegler, P. Schönholzer, K. Müller, H. Heimgartner, F. Stierli, *Helv. Chim. Acta* 1992, 75, 1666-1696). Alternatively, azlactones 129 could also be prepared starting from amino acids 130 and 131, Schotten-Baurmann acylation and cyclization with N,N'-dicyclohexyl carbodiimide to azlactones 132 and 133 and alkylation to yield 129 (D. Obrecht, U. Bohdal, C. Broger, D. Bur, C. Lehmann, R. Ruffieux, P. Schönholzer, C. Spiegler, *Helv. Chim. Acta* 1995, 78, 563-580; D. Obrecht, C Spiegler, P. Schönholzer, KI Müller, H. Heimgartner, F. Stierli, *Helv. Chim. Acta* 1992, 7S, 1666-1696)(see Scheme 1). Treatment of 129 with L-phenylalanine cyclohexylamide (D. Obrecht, U. Bohdal, C. Broger, D. Bur, C. Lehmann, R. Ruflieux, P. Schönholzer, C. Spiegler, *Helv. Chim. Acta* 1995, 78, 563-580) gave diastereomeric peptides 134 and 135, which could be conveniently separated by flash-chromatography or crystallisation. Treatment of 134 and 135 with methanesulphonic acid in methanol at 80° gave esters 136a and 136b which were converted into the corresponding Fmoc-protected final building blocks 137a and 137b.

Scheme 28

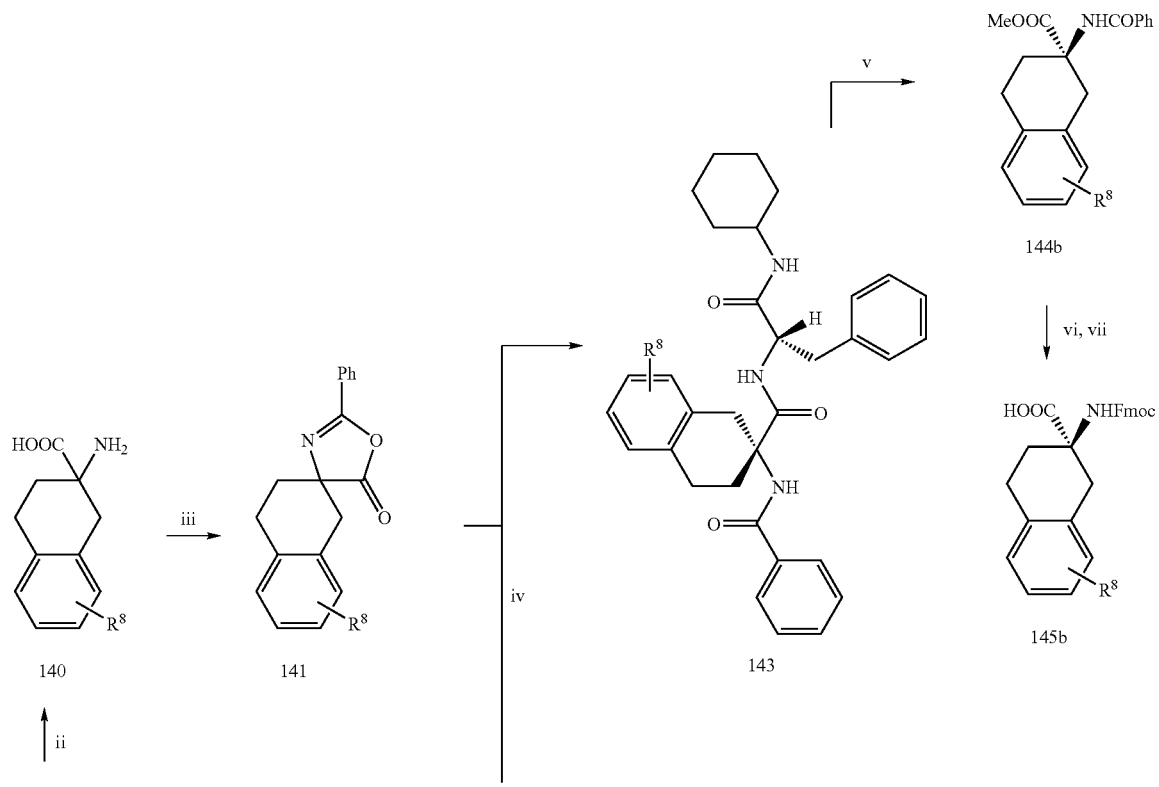

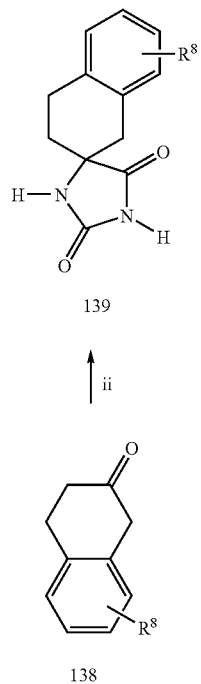

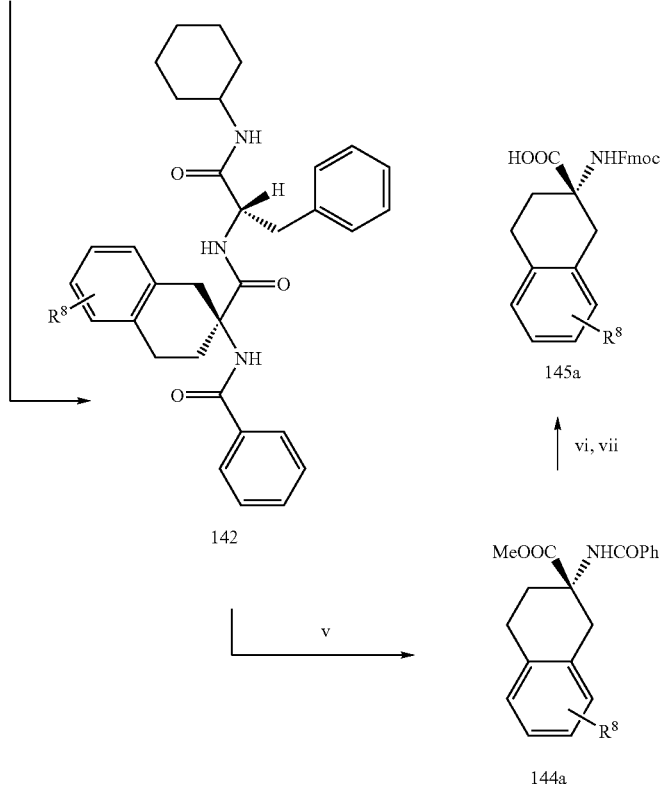

i: KCN, (NH₄)₂CO₃, EtOH/H₂O; ii: Ba(OH)₂, H₂O; iii: aq. NaOH, PhCOCl, dioxane; then DCC, CH₂Cl₂; iv: L-phenylalanine cyclohexylamide, N-methylpyrrolidone, 70°; v: CH₃SO₃H, MeOH, 80°; vi: 6N HClaq., dioxane, 100°; vii: Me₃SiCl, DIEA, CH₂Cl₂; the FmocCl According to the general method described in Scheme 28 (D. Obrecht, U. Bohdal, C. Broger, D. Bur, C. Lehmann, R. Ruffieux, P. Schönholzer, C. Spiegler, *Helv. Chim. Acta* 1995, 78, 563-580; D. Obrecht, C. Spiegler, P. Schönholzer, K. Müller, H. Heimgartner, F. Stierli, *Helv. Chim. Acta* 1992, 75, 1666-1696) A73—A104 can be prepared starting from the corresponding ketones 138, hydantoin formation (139) (E. Ware, *J. Chem. Res.* 1950, 46, 403; L. H. Goodson, 1. L. Honigberg, J. J. Lehmann, W. H. Burton, *J. Org. Chem.* 1960, 25, 1920; S, N. Rastogi, J. S. Bindra, N. Anand, *Ind. J. Chem.* 1971, 1175; D. Obrecht, U. Bohdal, C. Broger, D. Bur, C. Lehmann, R. Ruffieux, P. Schönholzer, C. Spiegler, *Helv. Chim. Acta* 1995, 78, 563-580) and saponification (Ba(OH)₂) to yield the racemic amino acids 140, which upon Schotten-Baumann-acylation and cyclization with N,N'-dicyclohexyl-carbodiimide gave azlactones 141. Reaction with L-phenylalanine cyclohexylamide (D. Obrecht, U. Bohdal, C. Broger, D. Bur, C. Lehmann, R. Ruffieux, P. Schönholzer, C. Spiegler, Helv. Chim. Acta 1995, 78, 563-580) gave the diastereomeric peptides 142 and 143, which were separated by flash-chromatography or crystallization. Treatment of 142 and 143 with methanesulphonic acid in methanol at 80° gave esters 144a and 144b which were converted into the corresponding suitably protected amino acid precursors 145a and 145b, ready for peptide synthesis.

A71: Amino acid building blocks of this type (see formula 147) can be conveniently prepared from the corresponding disubstituted succinates 146 by Curtius-rearrangement as shown in Scheme 29.

Scheme 29

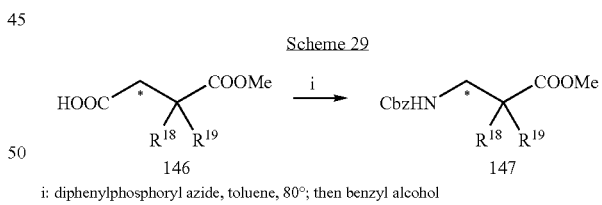

i: diphenylphosphoryl azide, toluene, 80°; then benzyl alcohol

A71: See D. Seebach, S. Abele. T. Sifferlen, M. Haenggi, S. Gruner, P. Seiler, *Helv. Chim. Acta* 1998, 81, 2218-2243 ($R^{18}$ and $R^{19}$ form: —(CH₂)₂—; —(CH₂)₃—; —(CH₂)₄—; —(CH₂)₅—; $R^{20}$=H); L. Ducrie, S. Reinelt, P. Seiler, F. Diederich, D. R. Bolin, R. M. Campbell, G. L. Olson, *Helv. Chim. Acta* 1999, 82, 2432-2447; C. N.C. Drey, R. J. Ridge,*J. Chem. Soc. Perkin Trans.*1, 1981, 2468-2471; U. P. Dhokte, V. V. Khau, D. R. Hutchinson, M. J. Martinelli, *Tetrahedron Lett.* 1998, 39, 8771-8774 ($R^{18}$=$R^{19}$=Me; $R^{20}$=H); D. L. Varie, D. A. Hay, S. L. Andis, T. H. Corbett, *Bioorg. Med. Chem. Lett.* 1999, 9, 369-374 ($R^{18}$=$R^{19}$=Et); Testa, *J. Org. Chem.* 1959, 24, 1928-1936 ($R^{1'''}$=Et; $R^{19}$=Ph); M. Haddad, C. Wakselman, J Fluorine Chem. 1995, 73, 57-60 ($R^{18}$=Me;

$R^{19}$=CF$_3$; $R^{20}$=H); T. Shono, K. Tsubata, N. Okinaga, *J. Org. Chem.* 1984, 49, 1056-1059 ($R^{18}$=$R^{19}$=$R^{82}$=Me); K. Ikeda, Y. Terao, M. Sekiya, *Chem. Pharm. Bull.* 1981, 29, 1747-1749 ($R^{18}$ and $R^{19}$ form: —(CH$_2$)$_s$—; $R^{20}$=Me). Amino acid building blocks of type A72 can be conveniently prepared by Arndt-Eistert C1-homologation of compounds of type A70 according to Scheme 30.

Scheme 30

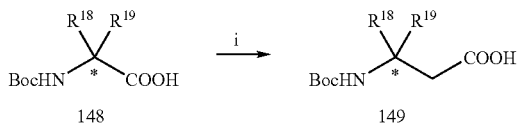

148    149 i: iBuOCOCl, diisopropylethylamine, CH$_2$Cl$_2$; then diazomethane, hv or Cu(I)

A72: See Y. V. Zeifman, *J. Gen. Chem. USSR* (Engl.Trans.) 1967, 37, 2355-2363 ($R^{18}$=$R^{19}$=CF$_3$); W. R. Schoen, J. M. Pisano, K. Pendergast, M. J. Wyvratt, M. H. Fisher, *J. Med. Chem.* 1994, 37, 897-906; S. Thaisrivongs, D. T. Pals, D. W. DuCharme, S. Turner, G. L. DeGraaf, *J. Med. Chem.* 1991, 34, 655-642; T. K. Hansen, H. Thoegersen, B. S. Hansen, *Bioorg. Med. Chem. Lett.* 1997, 7, 2951-2954; R. J. DeVita, R. Bochis, A. J. Frontier, A. Kotliar, M. H. Fisher, *J. Med. Chem.* 1998, 41, 1716-1728; D. Seebach, P. E. Ciceri, M. Overhand, B. Jaun, D. Rigo, *Helv. Chim. Acta* 1996, 79, 2043-2066; R. P. Nargund, K. H. Barakat, K. Cheng, W. Chan, B. R. Butler, A. A. Patchett, *Bioorg. Med. Chem. Lett.* 1996, 6, 1265-1270 ($R^{18}$=$R^{19}$=Me); E. Altmann, K. Nebel, M. Mutter, *Helv. Chim. Acta* 1991, 74, 800-806 ($R^{18}$=Me; $R^{19}$=COOMe).

A73: Compounds of this type can be prepared according to C. Mapelli, G. Tarocy, F. Schwitzer, C. H. Stammer, *J. Org. Chem.* 1989, 54, 145-149 ($R^{21}$=4-OHC$_6$H$_4$); F. Elrod, E. M. Holt, C. Mapelli, C. H. Stammer. *J. Chem. Soc. Chem. Commun.* 1988, 252-253 ($R^{21}$=CH$_2$COOMe); R. E. Mitchell, M. C. Pirrung, G. M. McGeehan, *Phytochemistry* 1987, 26, 2695 ($R^{21}$=CH$_2$OH), J. Bland, A. Batolussi, C. H. Stanuner, *J. Org. Chem.* 1988, 53, 992-995 ($R^{21}$=CH$_2$NH$_2$). Additional derivatives of A73 have been described by T. Wakamiya, Y. Oda, H. Fujita, T. Shiba, *Tetrahedron Lett.* 1986, 27, 2143-2134; U. Schöllkopf, B. Hupfeld, R. Gull, *Angew. Chem.* 1986, 98, 755-756; J. E. Baldwin, R. M. Adlington, B. J. Rawlings, *Tetrahedron Lett.* 1985, 26, 481-484; D. Kalvin, K. Ranalingam, R. Woodard, *Synth. Comm.* 1985, 15, 267-272 and L. M. Izquierdo, I. Arenal, M. Bernabe, E. Alvarez, *Tetrahedron Lett.* 1985, 41, 215-220.

A74: Compounds of this type can be prepared according to general method described in Scheme 28 starting from the corresponding cyclobutanones.

A75 and A76: Compounds of this type can be prepared using the following methods: P. Hughes, J. Clardy, *J. Org. Chem.* 1988, 53, 47934796; E. A. Bell, M. Y. Qureshi, R. J. Pryce, D. H. Janzen, P. Lemke, J. Clardy, *J. Am. Chem. Soc.* 1980, 102, 1409; Y. Gaoni, *Tetrahedron Lett.* 1988, 29, 1591-1594; R. D. Allan, J. R. Haurahan, T. W. Harnbley, G. A R. Johnston, K. N. Mewett, A. D. Mitrovic, *J. Med. Chem.* 1990, 33, 2905-2915 ($R^{23}$=COOH); G. W. Fleet, J. A. Seijas, M. Vasquez Tato, *Tetrahedron* 1988, 44, 2077-2080 ($R^{23}$=CH$_2$OH).

A77: Compounds of this type can be prepared according to J. H. Burckhalter, G. Schined, *J. Pharm. Sci.* 1966, 55, 443-445 ($R^{23}$=aryl).

A78: Compounds of this type can be prepared according to J. C. Watkins, P. Kroosgard-Larsen, T. Honoré, *TIPS* 1990, 11, 25-33; F. Trigalo, D. Brisson, R. Azerad, *Tetrahedron Lett.* 1988, 29, 6109 ($R^{24}$=COOH).

A79: Compounds of this type can be prepared according to general method described in Scheme 28 starting from the corresponding pyrrolidine-3-ones.

A80—A82: Compounds of this type can be prepared according to D. M. Walker, E. W. Logusch, *Tetrahedron Lett.* 1989, 30, 1181-1184; Y. Morimoto, K. Achiwa, *Chem. Pharm. Bull.* 1989, 35, 3845-3849; J. Yoshimura, S. Kondo, M. Ihara, H. Hashimoto, *Carbohydrate Res.* 1982, 99, 129-142.

A83: Compounds of this type can be prepared according to general method described in Scheme 28 starting from the corresponding pyrazoline-4-ones.

A84: Compounds of this type can be prepared according to R. M. Pinder, B. H. Butcher, D. H. Buxton, D. J. Howells, *J. Med. Chem.* 1971, 14, 892-893; D. Obrecht, U. Bohdal, C. Broger, D. Bur, C. Lehmann, R. Ruffieux, P. Schönholzer, C. Spiegler, *Helv. Chim. Acta* 1995, 78, 563-580.

A85: Compounds of this type can be prepared according to general method described in Scheme 28 starting from the corresponding indane-1,3-diones.

A86: Compounds of this type can be prepared according to general method described in Scheme 28 starting from the corresponding indane-2-ones.

A87: Compounds of this type and analogues thereof can be prepared according to C. Cativiela, M. D. Diaz de Villegas, A. Avenoza, J. M. Peregrina, *Tetrahedron* 1993, 47, 10987-10996; C. Cativiela, P. Lopez, J. A. Mayoral, *Tetrahedron Assymmetry* 1990, 1, 379; C. Cativiela, 1. A. Mayoral, A. Avenoza, M. Gonzalez, M. A. Rey, *Synthesis* 1990, 1114.

A87 and A88: Compounds of this type can be prepared according to L. Munday, *J. Chem. Soc.* 1961, 4372; J. Ansell, D. Morgan, H. C. Price, *Tetrahedron Lett.* 1978, 47,46154616.

A89: Compounds of this type can be prepared according to general method described in Scheme 28 starting from the corresponding piperidine-3-ones.

A90: Compounds of this type can be prepared according to general method described in Scheme 28 starting from the corresponding tetrahydrothiapyran-3-ones.

A91: Compounds of this type can be prepared according to general method described in Scheme 28 starting from the corresponding tetrahydropyran-3-ones.

A92: Compounds of this type can be prepared according to general method described in Scheme 28 starting from the corresponding piperidine-2,5-diones.

A93: Compounds of this type can be prepared according to general method described in Scheme 28 starting from the corresponding cyclohexanones.

A94: Compounds of this type can be prepared according to *J. Org. Chem.* 1990, 55, 4208.

A95: Compounds of this type can be prepared according to N.J. Lewis, R. L. Inloes, J. Hes, R. H. Matthews, G. Milo, *J. Med. Chem.* 1978, 21, 1070-1073.

A96: Compounds of this type can be prepared according to general method described in Scheme 28 starting from the corresponding tetrahydropyran4-ones.

A97: Compounds of this type can be prepared according to general method described in Scheme 28 starting from the corresponding piperidine-2,4-diones.

A98: Compounds of this type can be prepared according to general method described in Scheme 28 starting from the corresponding 1-tetralones (D. Obrecht, C. Spiegler, P. Schönholzer, K. Müller, H. Heimgartner, F. Stierli, *Helv. Chim. Acta* 1992, 75, 1666-1696).

A99: Compounds of this type can be prepared according to general method described in Scheme 28 starting from the corresponding tetraline-1,4-dione mono-diethylacetals.

A100: Compounds of this type can be prepared according to general method described in Scheme 28 starting from the corresponding tetrahydroquinolin-4-ones.

A101: Compounds of this type can be prepared according to general method described in Scheme 28 starting from the corresponding tetrahydroquinoline-2,4-diones.

A102: Compounds of this type can be prepared according to K. Ishizumi, N. Ohashi, N. Tanno, *J. Org. Chem.* 1987, 52, 4477-4485; D. Obrecht, U. Bohdal, C. Broger, D. Bur, C. Lehmann, R. Ruffieux, P. Schönholzer, C. Spiegler, *Helv. Chim. Acta* 1995, 78, 563-580; D. Obrecht, C. Spiegler, P. Schönholzer, K. Müller, H. Heimgartner, F. Stierli, *Helv. Chim. Acta* 1992, 75, 1666-1696; D. R. Haines, R. W. Fuller, S. Ahmad, D. T. Vistica, V. E. Marquez, *J. Med. Chem.* 1987, 30, 542-547; T. Decks, P. A Crooks, R. D. Waigh, *J. Pharm. Sci* 1984, 73, 457-460; I. A. Blair, L. N. Mander, *Austr. J. Chem.* 1979, 32, 1055-1065.

Overviews dealing with building blocks of types (b)Ap) are: S. Hanessian, G. McNaughton-Smith, H.-G. Lombart, W. D. Lubell, *Tetrahedron* 1997, 38, 12789-12854; D. Obrecht, M. Altorfer, J. A. Robinson, "Novel Peptide Mimetic Building Blocks and Strategies for Efficient Lead Finding", *Adv. Med. Chem.* 1999, Vol. 4, 1-68

Templates of type (b1) can be prepared according to Schemes 31 and 32.

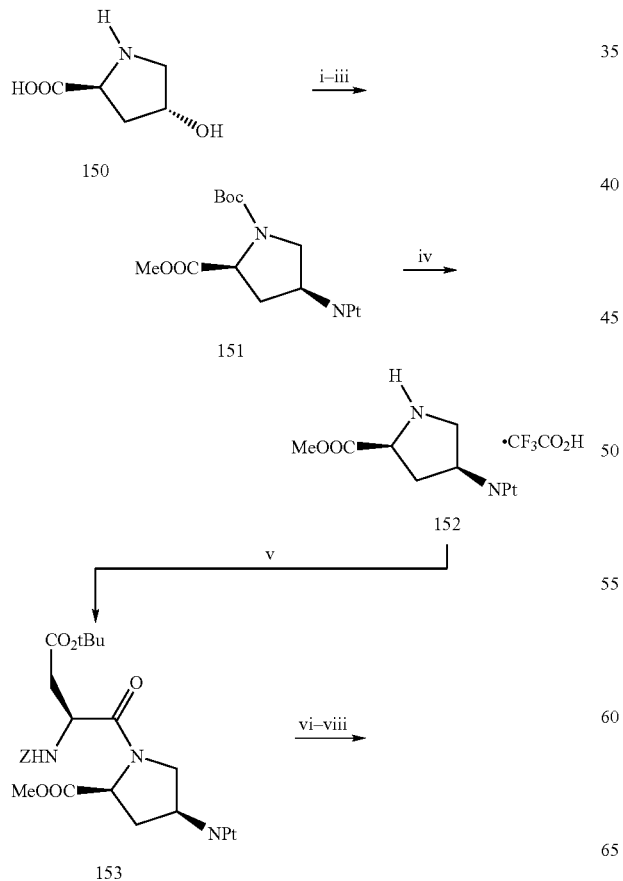

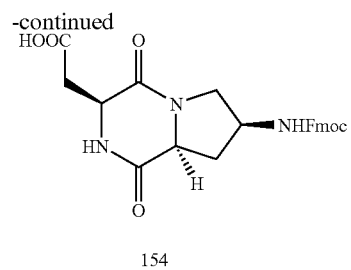

i: Treatment of 150 with a dehydrating reagent such as thionylchloride in methanol at an elevated temperature, conveniently at reflux.

ii: Introduction of Boc, e.g. using di-tert.-butyl dicarbonate and triethylamine in a suitable solvent such as dichloromethane; any other suitable N-protecting group (not shown in Reaction Scheme 31) can be introduced in an analogous manner.

iii: Reaction of formed product with phthalimide, diethyl diazodicarboxylate and triphenylphoshine under standard Mitsunobu conditions (Mitsunobu, O.; Wada, M.; Sano, T. J. *J. Am. Chem. Soc.* 1972, 94, 672) to conveniently yield 151.

iv: Treatment of 151 with trifluoracetic acid in dichloromethane.

v: 152 is coupled under standard peptide coupling conditions with Cbz-Asp(tBu)OH in DMF with reagents such as HBTU and 1-hydroxybenztriazole (HOBt) with a base such as diisopropylethylamine to yield 153.

vi: Removal of the Cbz-group, conveniently by hydrogenation using $H_2$ and a catalyst such as Palladium on charcoal, in solvents such as ethanol, DMF and ethyl acetate.

vii: The phthalimide group is cleaved off from the resulting product, conveniently by treatment with hydrazine in a suitable solvent such as ethanol at an elevated temperature, suitably at about 80° C. and cleavage of the formed product with trifluoracetic acid in $CH_2Cl_2$.

viii: The formed amino acid is conveniently protected with reagents such as 9-fluorenylmethoxcarbonyl chloride or 9-fluorenylmethoxcarbonyl succinimide using a base such as sodium carbonate or triethylamine in a suitable solvent or mixture of solvents such as dioxane and water, or dichloromethane to yield 154 as described by Bisang, C.; Weber, C.; Robinson, J. A. *Helv. Chim. Acta* 1996, 79, 1825-1842.

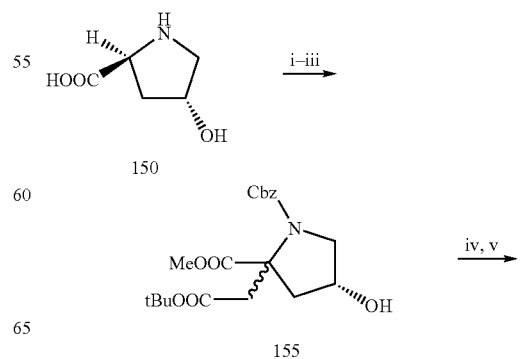

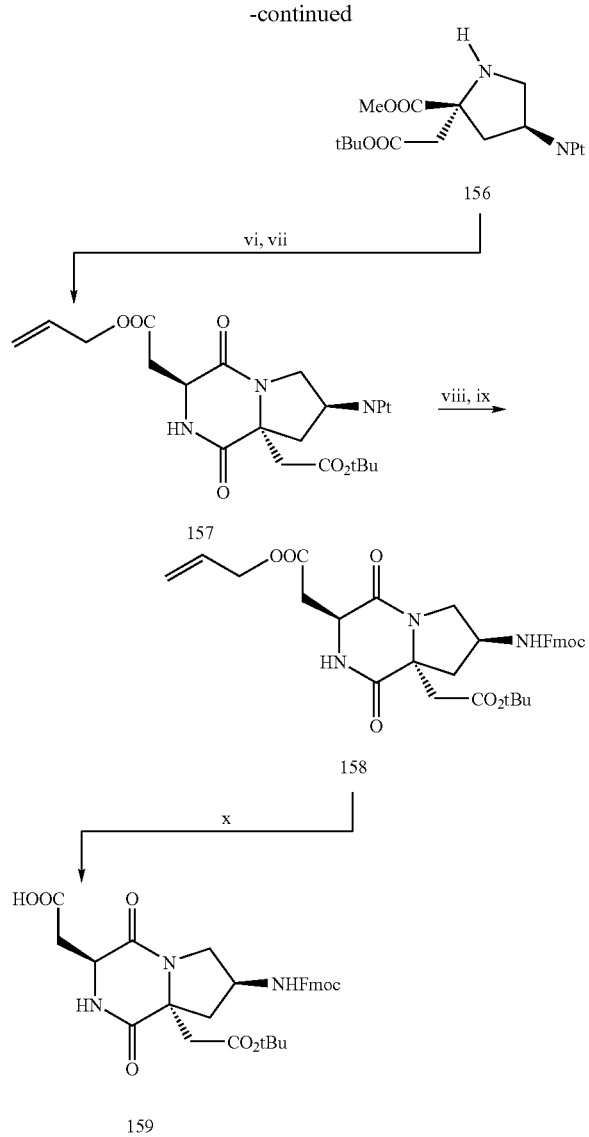

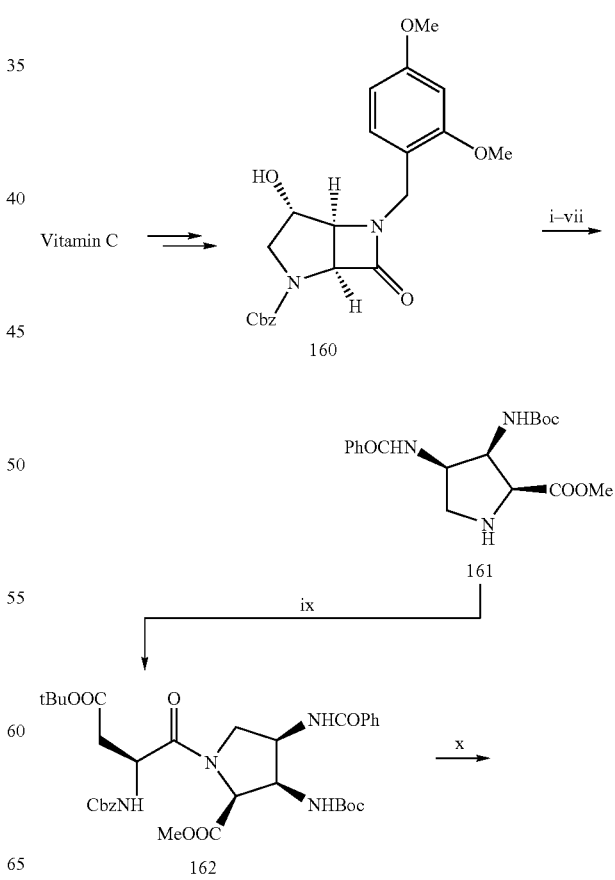

sunobu conditions (Mitsunobu, O.; Wada, M.; Sano, T. J. *J. Am. Chem. Soc.* 1972, 94, 672).

v: The resulting product is hydrogenated using $H_2$ and a suitable catalyst such as palladium on charcoal in a solvent such as ethyl acetate, DMF or ethanol; subsequently separation of diastereomers takes place and yields 156.

vi: 156 is coupled with Fmoc—Asp(allyl)OH under standard peptide coupling conditions using reagents such as HATU, HOAt and a base such as diisopropylethylamine in a suitable solvent such as DMF.

vii: Cyclization, conveniently with DBU in DWF to yield 157.

viii: The phthalimide group is cleaved off from resulting product, conveniently by hydrazinolysis, e.g. treatment with methylhydrazine in a suitable solvent such as DMF.

ix: The formed product is conveniently protected with reagents such as 9-fluorenylmethoxcarbonyl chloride or 9-fluorenylmethoxcarbonyl succinimide using a base such as sodium carbonate or triethylamine in a suitable solvent or mixture of solvents such as dioxane and water, or dichloromethane to yield 158.

x: Standard removal of an allyl ester group using e.g. palladium(0) as catalyst gives 159.

Templates of type (b2) can be prepared according to Scheme 33.

i: Treatment of 150 with a dehydrating reagent such as thionyl chloride in a suitable solvent such as methanol at an elevated temperature, conveniently at reflux.

ii: The resulting amino acid ester is N-protected under standard conditions for introducing the Cbz-group, e.g. using benzyloxycarbonyl chloride and triethylamine in a suitable solvent such as dichloromethane.

iii: The Cbz-protected amino acid methyl ester is treated with trimethylsilylchloride and a base such as triethylamine in a solvent such as tetrahydrofuran, cooled, conveniently to about −78° C., followed by reaction with a strong base such as lithium diisopropylamide or lithium hexamethyldisilylazide and tert.-butyl bromoacetate yielding 155 as a mixture of diastereomers as described by Bisang, C.; Jiang, L.; Freund, E.; Emery, F.; Bauch, C.; Matile, H.; Pluschke, G.; Robinson, J. A. *J. Am. Chem. Soc.* 1998, 120, 7439-7449; Emery, F.; Bisang, C.; Favre, M.; Jiang, L.; Robinson, J. AL *J. Chem. Soc. Chem. Commun.* 1996, 2155-2156.

iv: Reaction of 155 with phthalimide, diethyl diazodicarboxylate and triphenylphosphine under standard Mit-

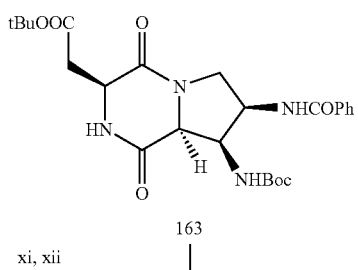

163 xi, xii

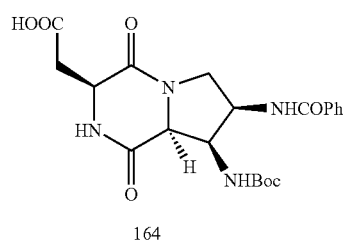

164 i: 160 (obtainable from Vitamin C as described by Hubschwerlen, C. (*Synthesis* 1986, 962) is treated with phthalimide, diethyl diazodicarboxylate and triphenylphoshine under standard Mitsunobu conditions (Mitsunobu, O.; Wada, M.; Sano, T. J. *J. Am. Chem. Soc.* 1972, 94, 672).

ii: The phthalimide group is cleaved off from the product, conveniently by hydrazinolysis, e.g. by treatment with methylhydrazine in a suitable solvent such as DMF.

iii: The amino group is protected by treatment with a benzoylating reagent such as benzoic acid anhydride or benzoylchloride and a base such as triethylamine or 4-dimethylaminopyridine in a suitable solvent such as dichloromethane or DMF.

iv: Removal of the 2,4-dimethoxybenzyl group, e.g. with $K_2S_2O_8$ and $Na_2HPO_4$ in aqueous acetonitrile at an elevated temperature, e.g. at about 80° C.

v: Introduction of a tert-butoxycarbonyl group using e.g. di-tert.-butyloxycarbonyl dicarbonate, triethylamine and a catalytic amount of 4-dimethylaminopyridine in a suitable solvent such as dichloromethane.

vi: Reaction with aqueous sodium carbonate in tetrahydrofuran followed by acidification.

vii: Esterification of the carboxylic acid group, conveniently with diazomethane in a suitable solvent such as diethylether yielding 161.

viii Removal of the Cbz-group, conveniently by hydrogenation with $H_2$ in the presence of a catalyst such as palladium on charcoal in a solvent such as DMF to yield 161 as described by Pfeifer, M.; Robinson, J. A. *J. Chem. Soc. Chem. Commun.* 1998, 1977.

ix: 161 is coupled under standard peptide cgupling conditions with Cbz—Asp(tBu)OH in DMF with reagents such as HBTU and 1-hydroxybenztriazole with a base such as diisopropylethylamine to yield 162 as described by Pfeifer, M.; Robinson, J. A. *J. Chem. Soc. Chem. Commun.* 1998, 1977.

x: Removal of the Cbz-group, e.g. by hydrogenation using $H_2$ and a catalyst such as palladium on charcoal under standard conditions, yields 163 as described by Pfeifer, M.; Robinson, J. A. *J. Chem. Soc. Chem. Commun.* 1998, 1977.

xi: Cleavage of the tert.-butyl ester and tert.-butyloxycarbonyl groups, conveniently using trifluoracetic acid in dichlorometihane or 4N hydrochloric acid in dioxane.

xii: The intermediate free amino acid formed is conveniently protected with reagents such as 9-fluorenylmethoxcarbonyl chloride or 9-fluorenylmethoxycarbonyl succinimide using a base such as sodium carbonate or triethylamine in a suitable solvent or mixture of solvents such as dioxane and water, or dichloromethane to yield 164 as described by Pfeifer, M.; Robinson, J. A. *J. Chem. Soc. Chem. Commun.* 1998, 1977.

Templates of type (c1) can be prepared according to Schenies 34 to 37.

Scheme 34

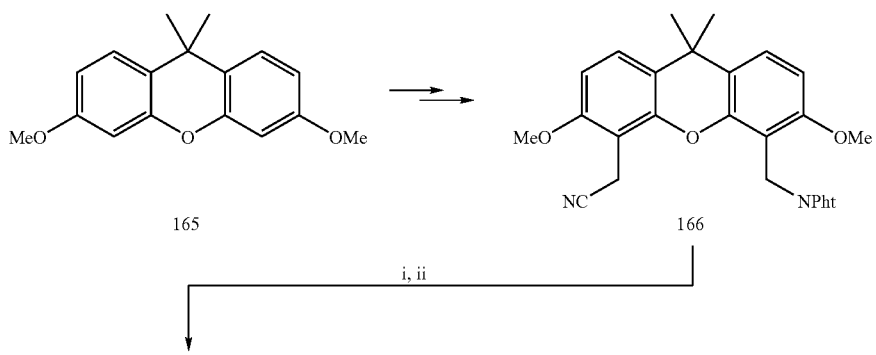

i, ii

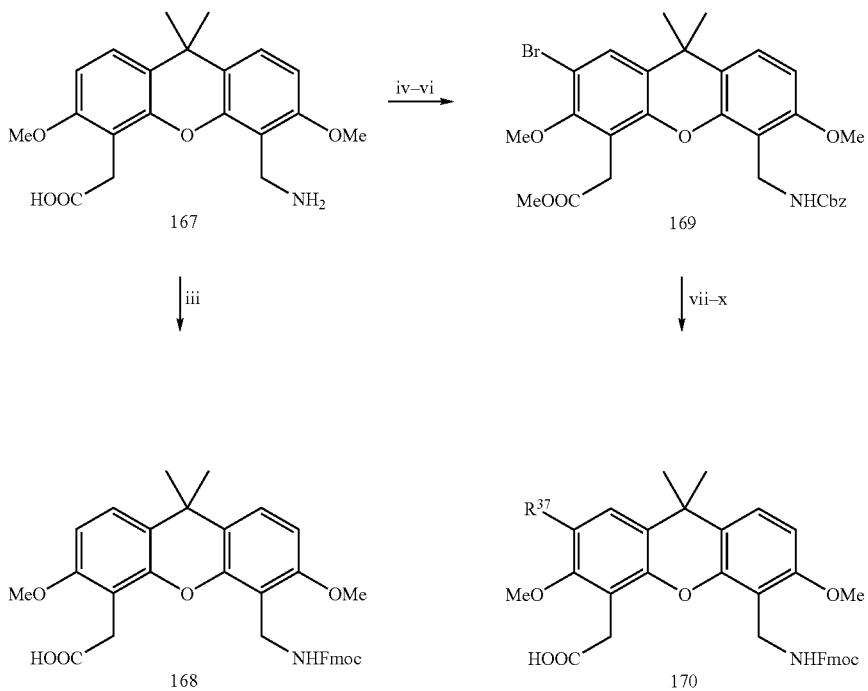

i: 166 can be synthesized from 165 according to P. Waldmeier, "Solid-supported synthesis of highly substituted xanthene-derived templates for the synthesis of aturn stabilized cyclic peptide libraries", PhD-thesis, University of Zurich, 1996. For cleaving the phthalimide group 166 is conveniently submitted to hydrazinolysis, e.g. by treatment with hydrazine hydrate in a suitable solvent such as ethanol at an elevated temperature, e.g. at about 80° C.

ii: The intermediate aminonitrile is saponified, conveniently under basic conditions, e.g. with aqueous sodium hydroxide in a suitable solvent such as ethanol at an elevated temperature, conveniently under reflux, to yield 167.

iii: The intermediate free amino acid formed is conveniently protected with reagents such as 9-fluorenylmethoxcarbonyl chloride or 9-fluorenylmethoxcarbonyl succinimide using a base such as sodium carbonate or triethylamine in a suitable solvent or mixture of solvents such as dioxane and water, or dichloromethane to yield 168 as described by P. Waldmeier, "Solid-supported synthesis of highly substituted xanthene-derived templates for the synthesis of β-turn stabilized cyclic peptide libraries", PhD-thesis, University of Zurich, 1996.

iv: Regioselective bromination of 167 is performed preferably with bromine in acetic acid and dichloromethane. In a similar fashion $R^{37}$=NO, can be introduced by treatment with $HNO_3$ in acetic acid and $R^{37}$=$CH_2$—NPht by treatment with hydroxymethyl phthalimide in $H_2SO_4$.

v: The amino group is conveniently Cbz-protected with reagents such as benzyloxycarbonyl chloride or succinimide in a suitable solvent such as dioxane in presence of a base such as aqueous sodium hydroxide.

vi: The carboxylic acid group is esterified, preferably with DBU and methyl iodide in DMF to yield 169.

vii: Introduction of lower alkyl, substituted lower alkyl and aryl substituents ($R^{37}$), conveniently by palladium(0)-catalyzed Stille-(Stille, J. K. *Angew. Chem.* 1986, 68, 504) and Suzuki-couplings (Oh-e, T.; Mijaura, N.; Suzuki, A. *J. Org. Chem.* 1993, 58, 2201). Any other functionalization known for aryl bromides can be employed for introduction of substituents $R^{37}$.

viii: Removal of the Cbz-group, e.g. by hydrogenation using $H_2$ and a catalyst such as palladium on charcoal in a suitable solvent such as ethanol, DMF and ethyl acetate.

ix: Hydrolysis of the ester group, conveniently under acidic conditions, e.g. with 25% aqueous hydrochloric acid in a suitable solvent such as dioxane at an elevated temperature, preferably at about 100° C.

x: The intermediate free amino acid formed is conveniently protected with reagents such as 9-fluorenylinethoxcarbonyl chloride or 9-fluorenylmethoxcarbonyl succinimide using a base such as sodium carbonate or triethylamine in a suitable solvent or mixture of solvents such as dioxane and water, or dichloromethane to yield 170.

Scheme 35

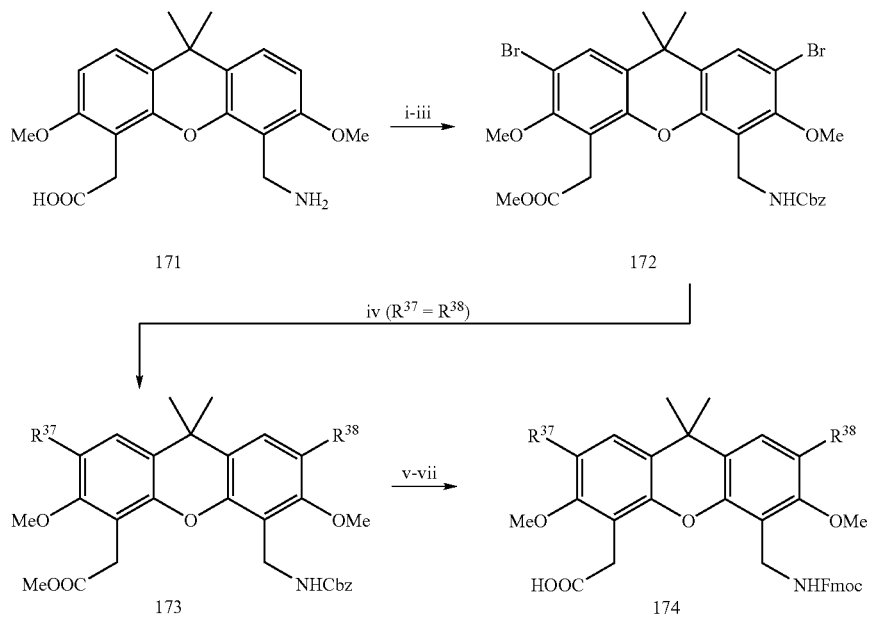

i: Double ortho-bromination of 171 is performed preferably with excess bromine in acetic acid and dichloromethane. In a similar fashion $R^{37}=R^{38}=NO_2$ can be introduced by treatment with $HNO_3$ in acetic acid and $R^{37}=R^{38}=CH_2$—NPht by treatment with hydroxymethyl phthalimide in $H_2SO_4$.

ii: The amino group is protected, conveniently Cbz-protected, with reagents such as benzyloxycarbonyl chloride or succinimide in a suitable solvent such as dioxane in the presence of a base such as aqueous sodium hydroxide.

iii: The carboxylic acid group is esterified, preferably with DBU and methyl iodide in DMF to yield 172.

iv: Introduction of lower alkyl, substituted lower alkyl and aryl substituents ($R^{37}=R^{38}$), e.g. by palladium(0)-catalyzed Stille-(Stille, J. K. Angew. Chem. 1986, 68, 504) and Suzuki-couplings (Oh-e, T.; Mijaura, N.; Suzuki, A. J. Org. Chem. 1993, 58, 2201). Any other functionalization known for aryl bromides can be employed for introduction of substituents $R^{37}$ and $R^{38}$.

v: Removal of the Cbz-group of 173, e.g. by hydrogenation using $H_2$ and a catalyst such as palladium on charcoal in a suitable solvent such as ethanol, DMF or ethyl acetate.

vi: Hydrolysis of the ester group, conveniently under acidic conditions, e.g. with 25% aqueous hydrochloric acid in a suitable solvent such as dioxane at an elevated temperature, conveniently at about 100° C.

vii: The intermediate free amino acid formed is conveniently protected with reagents such as 9-fluorenylmethoxycarbonyl chloride or 9-fluorenylmethoxycarbonyl succinimide using a base such as sodium carbonate or triethylamine in a suitable solvent or mixture of solvents such as dioxane and water, or dichloromethane to yield 174.

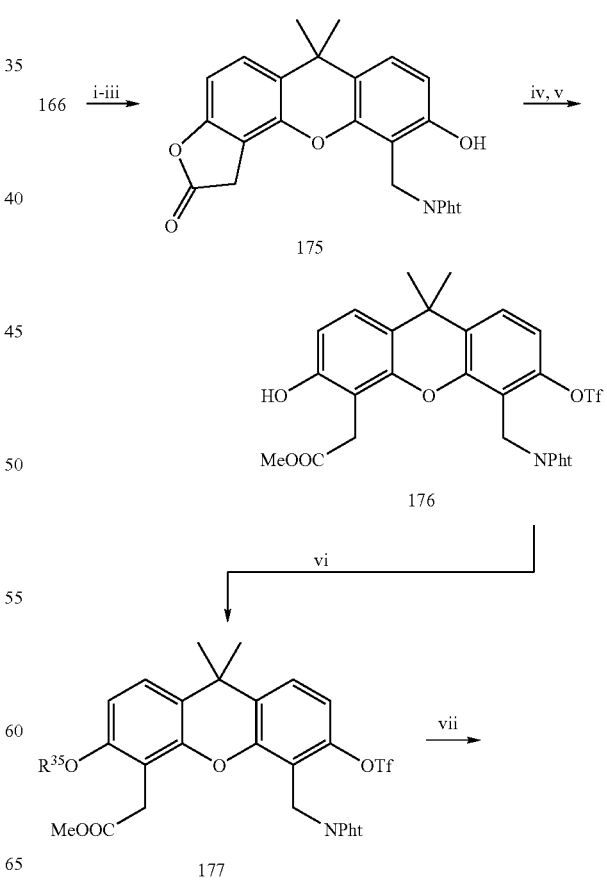

Scheme 36

Scheme 37

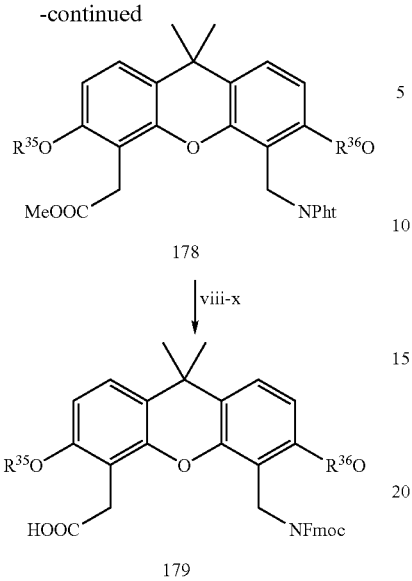

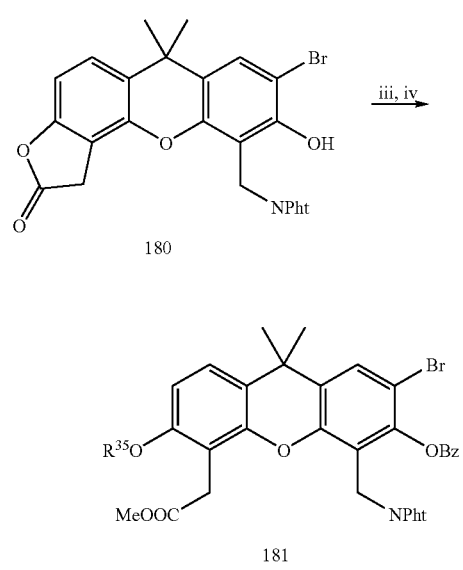

i: Cleavage of the methoxy groups of 166, preferably by treatment with an excess of boron tribromide in a suitable solvent such as dichloromethane.

ii: Hydrolysis of the cyano group under acidic conditions, preferably with 25% aqueous hydrochloric acid in a suitable solvent such as dioxane at an elevated temperature, conveniently at about 100° C.

iii: The resulting acid is treated with a dehydrating agent such as thionyl chloride in a suitable solvent such as dioxane to yield 175.

iv: Treatment of 175 with an appropriate triflating reagent, preferably trifluoromethanesulfonic acid anhydride in the presence of a base such as 2,6-di-tert.-butyl-pyridine in a suitable solvent such as dichloromethane.

v: Heating of the intermediate, conveniently in a suitable solvent such as methanol.

vi: Introduction of lower alkyl or aryl-lower alkyl ($R^{35}$) by alkylation to yield 177. Any other functionalization known for phenol groups can be employed for introduction of substituents $R^{35}$.

vii: Introduction of lower alkyl or aryl ($R^{36}$), conveniently by palladium(0)-catalyzed Suzuki-coupling (Oh-e, T.; Mijaura, N.; Suzuki, A. *J. Org. Chem.* 1993, 58, 2201) to yield 178. Any other functionalization known for aryl bromides can be employed for introduction of substituents $R^{36}$.

viii: Hydrolysis of the ester group under acidic conditions, conveniently with 25% aqueous hydrochloric acid in a suitable solvent such as dioxane at an elevated temperature, e.g. at about 100° C.

ix: Cleavage of the phthalimido group, conveniently by hydrazinolysis, e.g. with hydrazine hydrate in a suitable solvent such as ethanol.

x: The intermediate free amino acid formed is conveniently protected with reagents such as 9-fluorenylmethoxycarbonyl chloride or 9-fluorenylmethoxycarbonyl succinimide using a base such as sodium carbonate or triethylamine in a suitable solvent or mixture of solvents such as dioxane and water, or dichloromethane to yield 179.

-continued

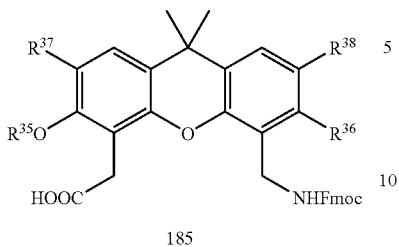

185 i: Bromination of 175 using reagents such as bromine in a mixture of acetic acid and dichloromethane at temperatures ranging from about 0° C. to about room temperature.
ii: Benzoylation of the hydroxy group using an appropriate acylating agent such as benzoyl chloride or benzoic acid anhydride, a base such as pyridine or triethylamine and a suitable solvent such as dichloromethane to yield 180.
iii: 180 is treated with methanol and a catalytic amount of an acidic catalyst such as camphor sulfonic acid under heating.
iv: Introduction of lower alkyl or aryl-lower alkyl ($R^{35}$) by alkylation using a base such as sodium hydride or potassium tert.-butoxide in a solvent such as tetrahydrofuran, dimethoxyethane or DMF gives 181.
v: Lower alkyl, substituted lower alkyl and aryl substituents ($R^{38}$) are introduced, e.g. by palladium(0)-catalyzed Stille-(Stille, J. K. *Angew. Chem.*1986, 68, 504) and Suzuki-couplings (Ob-e, T.; Mijaura, N.; Suzuki, A. *J. Org. Chem.* 1993, 58, 2201). Any other functionalization known for aryl bromides can be employed for introduction of substituents $R^{38}$.
vi: For cleaving the benzyloxy group the intermediate is conveniently heated with sodium cyanide adsorbed on aluminum oxide and methanol.
vii: Treatment with an appropriate triflating reagent, preferably trifluoromethanesulfonic acid anhydride, in the presence of a base such as 2,6-di-tert.-butyl-pyridine in a suitable solvent such as dichloromethane.
viii: Introduction of lower alkyl and aryl substituents ($R^{36}$), e.g. by palladium(0)-catalyzed Stille-(Stille, J. K. *Angew. Chem.*1986, 68, 504) and Suzuki-couplings (Oh-e, T.; Mijaura, N.; Suzuki, A. *J. Org. Chem.* 1993, 58, 2201) yields 182. Any other functionalization known for aryl bromides can be employed for introduction of substituents $R^{36}$.
ix: Bromination under standard conditions such as using bromine in acetic acid and dichloromethane at temperatures ranging from about 0° C. to about room temperature.
x: Lower alkyl, substituted lower alkyl and aryl substituents ($R^{37}$) are introduced, e.g. by palladium(0)-catalyzed Stille-(Stille, J. K. *Angew. Chem.*1986, 68, 504) and Suzuki-couplings (Oh-e, T.; Mijaura, N.; Suzuki, A. *J. Org. Chem.* 1993, 58, 2201) to yield 184. Any other functionalization known for aryl bromides can be employed for introduction of substituents $R^{33}$.
xi: The ester group is hydrolyzed under acidic conditions, conveniently with 25% aqueous hydrochloric acid in a suitable solvent such as dioxane at an elevated temperature, e.g. at about 100° C.
xii: The phthalimido group is cleaved, e.g. by hydrazinolysis, conveniently with hydrazine hydrate in a suitable solvent such as ethanol.
xiii: The intemmediate free amino acid formed is conveniently protected with reagents such as 9-fluorenylmethoxcarbonyl chloride or 9-fluorenylmethoxcarbonyl succinimide using a base such as sodium carbonate or triethylamine in a suitable solvent or mixture of solvents such as dioxane and water, or dichloromethane to yield 185.

Templates of type (c2) can be prepared as shown in Schemes 38 and 39.

Scheme 38

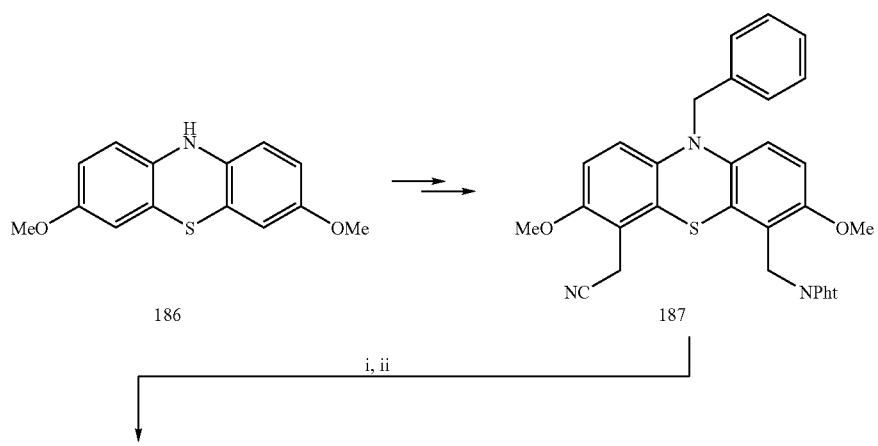

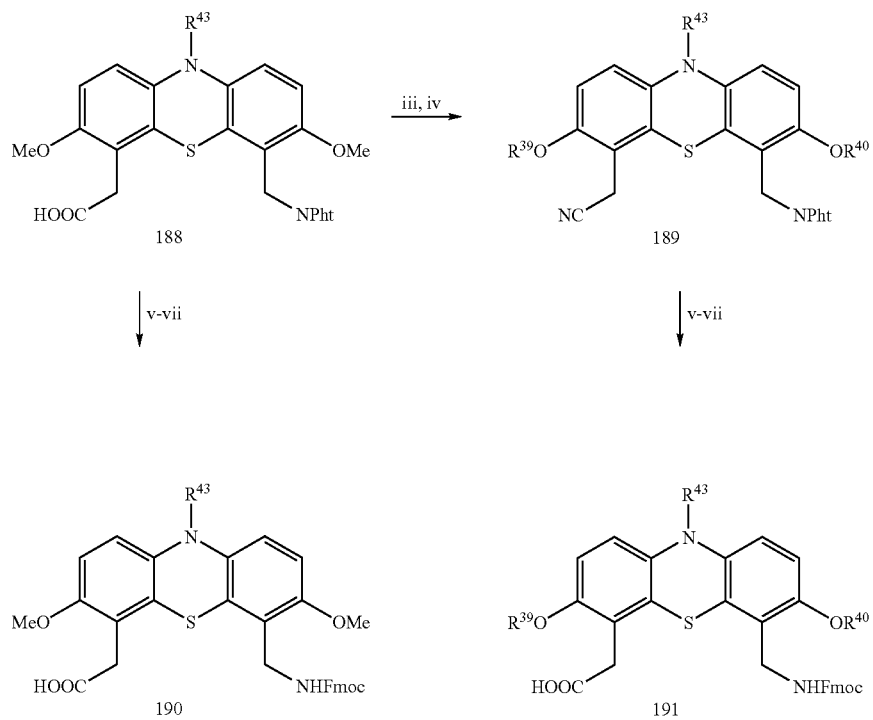

i: 3,7-Dimethoxyphenothiazine 186 is prepared and converted into 187 according to Müller, K.; Obrecht, D.; Knierzinger, A.; Spiegler, C.; Bannwarth, W.; Trzeciak, A.; Englert, G.; Labhardt, A.; Schönholzer, P. *Perspectives in Medicinal Chemistry*, Editor Testa, B.; Kyburz, E.; Fuhrer, W.; Giger, R., Weinheim, New York, Basel, Cambridge: Verlag Helvetica Chimica Acta, 1993, 513-531; Bannwarth, W.; Gerber, F.; Grieder, A.; Knierzinger, A.; Müller, K.; Obrecht. D.; Trzeciak, A. *Can. Pat. Appl.* CA2101599(131 pages). The benzyl group is cleaved off from 187 conveniently by hydrogenation, e.g. with $H_2$ and a catalyst such as palladium on charcoal in a suitable solvent such as ethanol, DMF or ethyl acetate.

ii: Introduction of lower alkyl ($R^{43}$) by alkylation using an appropriate alkylating agent ($R^{43}$—X'; X'=OTf, Br, I) and strong bases such as sodium amide in liquid ammonia or sodium hydride in tetrahydrofuran, dioxan or DMF in the presence of a phase transfer catalyst such as TDA-I. In a similar manner substituted lower alkyl ($R^{43}$) can be introduced; thus, for example $R^{43}$=$CH_2COOR^{55}$ and $CH_2CH_2COOR^{55}$ can be introduced by treatment with the appropriate 2-halo acetic and, respectively, 3-halo propionic acid derivatives. Any other functionalization known for diarylamines can be employed for introduction of substituents $R^{43}$.

iii: Cleavage of the methoxy groups of 188,:conveniently by treatment with an excess of boron tribromide in a suitable solvent such as dichloromethane at temperatures ranging from about −20° C. to about room temperature.

iv: For the introduction of lower alkyl, substituted lower alkyl or aryl-lower alkyl substituents ($R^{39}$ and $R^{40}$) the intermediate bis-phenol derivative is conveniently reacted with a reagent of the formula $R^{39}$- and $R^{40}$-X' (X'=OTf, Br, I) in the presence of strong bases such as sodium hydride in tetaahydrofuran, dioxan or DMF in the presence of a phase transfer catalyst such as TDA-I. Any other functionalization known for phenol groups can be employed for introduction of substituents $R^{39}$ and $R^{40}$.

v: The cyano group of 188 and, respectively, 189 is hydrolyzed, conveniently under acidic conditions, e.g. with 25% aqueous hydrochloric acid in a suitable solvent such as dioxane at an elevated temperature, e.g. at about 100° C.

vi: The phthalimide group of the intermediate is cleaved, conveniently by hydrazinolysis, e.g. with hydrazine hydrate in a suitable solvent such as ethanol.

vii: The free amino group is conveniently protected with reagents such as 9-fluorenylmethoxcarbonyl chloride or 9-fluorenylmethoxcarbonyl succinimide using a base such as sodium carbonate or triethylamine in a suitable solvent or mixture of solvents such as dioxane and water, or dichloromethane to yield 190 and, respectively, 191.

Scheme 39

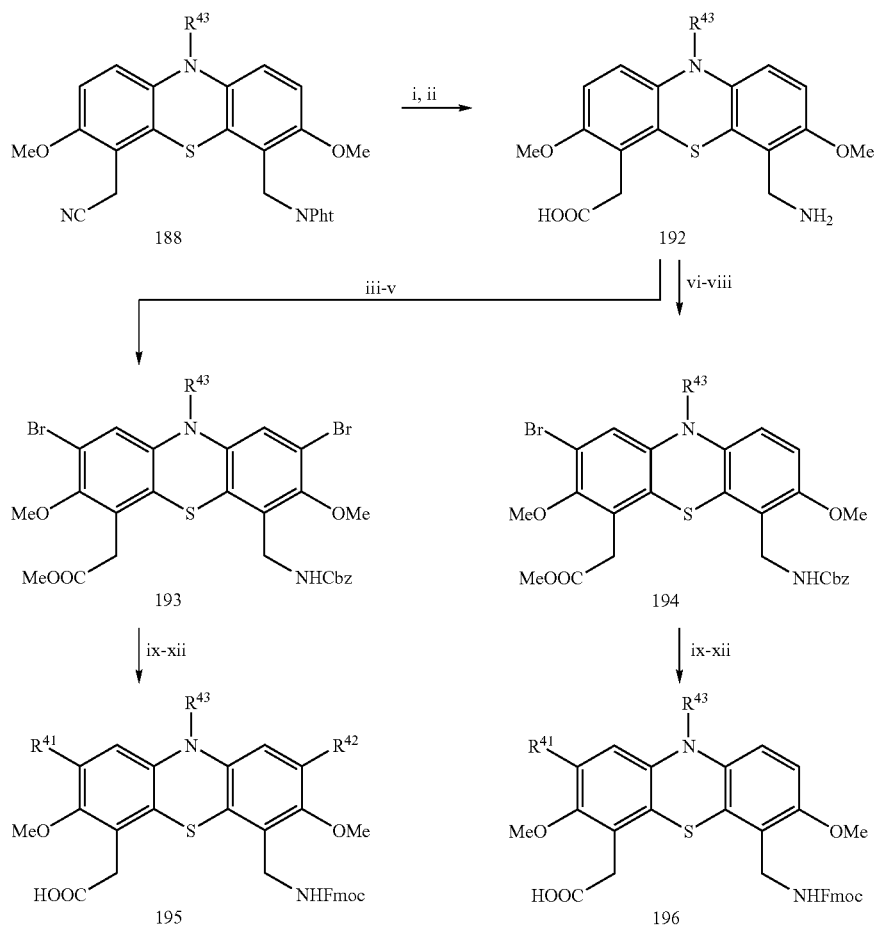

i: The cyano group of 188 is hydrolyzed, conveniently under acidic conditions, e.g. with 25% aqueous hydrochloric acid in a suitable solvent such as dioxane at an elevated temperature, e.g. at about 100° C.

ii: The phthalimide group of the intermediate is cleaved, conveniently by hydrazinolysis, e.g. with hydrazine hydrate in a suitable solvent such as ethanol to yield 192.

iii: Double ortho-bromination of 192 is performed preferably with excess bromine in acetic acid and dichloromethane. In a similar fashion $R^{41}=R^{42}=NO_2$ can be introduced by treatment with $HNO_3$ in acetic acid and $R^{41}=R^{42}=CH_2$—NPht by treatment with hydroxymethyl phthalimide in $H_2SO_4$. Any other functionalization by electrophilic aromatic substitution known can be employed for introduction of substituents $R^{41}$ and $R^{42}$.

iv: The amino group is protected, conveniently Cbz-protected, with reagents such as benzyloxycarbonyl chloride or succinimide in a suitable solvent such as dioxane in the presence of a base such as aqueous sodium. hydroxide.

v: The carboxylic acid group is esterified, preferably with DBU and methyl iodide in DMF to yield 193.

vi: Regioselective bromination of 192 is performed preferably with bromine in acetic acid and dichloromethane. In a similar fashion $R^{41}=NO_2$ can be introduced by treatment with $HNO_3$ in acetic acid and $R^{41}=CH_2$—NPt by treatment with hydroxymethyl phthalimide in $H_2SO_4$. Any other functionalization by electrophilic aromatic substitution known can be employed for introduction of substituents $R^{41}$.

vii: The amino group is conveniently Cbz-protected with reagents such as benzyloxycarbonyl chloride or succinimide in a suitable solvent such as dioxane in presence of a base such as aqueous sodium hydroxide.

viii: The carboxylic acid group is esterified, preferably with DBU and methyl iodide in DMF to yield 194.

ix: Introduction of lower alkyl, substituted lower alkyl and aryl substituents ($R^{41}$) for 194 and ($R^{41}$ and $R^{42}$) for 193, conveniently by palladium(0)-catalyzed Stille-(Stille, J. K. Angew. Chem.1986, 68, 504) and Suzuki-couplings (Oh-e, T.; Mijaura, N.; Suzuki, A. J. Org. Chem. 1993, 58, 2201). Any other functionalization known for aryl bromides can be employed for introduction of substituents $R^{41}$ and $R^{42}$.

x: Removal of the Cbz-group, e.g. by hydrogenation using $H_2$ and a catalyst such as palladium on charcoal in a suitable solvent such as ethanol, DMF and ethyl acetate.

xi: Hydrolysis of the ester group, conveniently under acidic conditions, e.g. with 25% aqueous hydrochloric acid in a suitable solvent such as dioxane at an elevated temperature, preferably at about 100° C.

xii: The intermediate free amino acid formed is conveniently protected with reagents such as 9-fluorenylmethoxcarbonyl chloride or 9-fluorenylmethoxcarbonyl succinimide using a base such as sodium carbonate or triethylamine in a suitable solvent or mixture of solvents such as dioxane and water, or dichloromethane to yield 195 and 196.

Templates of type (c3) can be prepared as shown in Schemes 40 and 41.

ii: Introduction of lower alkyl ($R^{43}$) by alkylation with $R^{43}$-X' (X'=OTf, Br, I) using strong bases such as sodium amide in liquid ammonia or sodium hydride in tetrahydrofuran, dioxan or DMF in the presence of a phase transfer catalyst such as TDA-I to yield 199. In a similar manner substituted

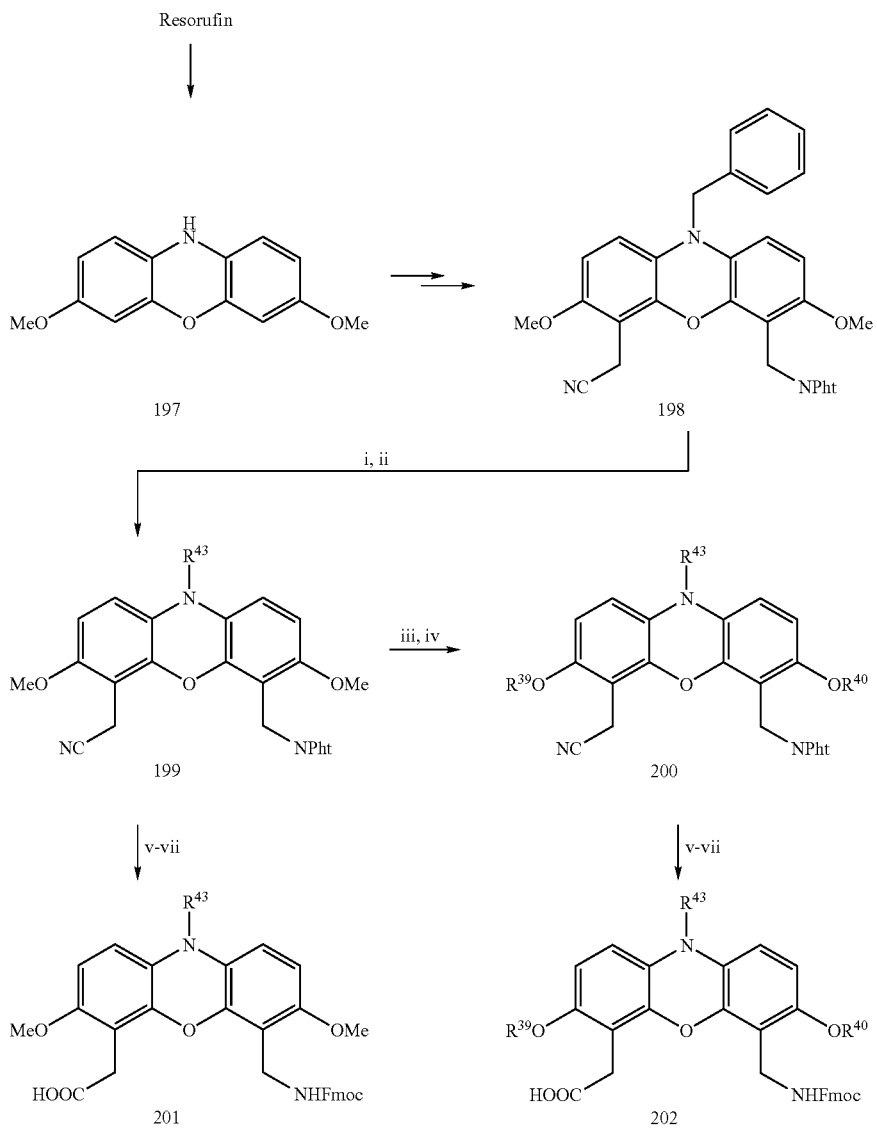

Scheme 40 i: 197 can be prepared from comunercial resorufin and coverted into 198 according to Müller, K.; Obrecht, D.; Knierzinger, A.; Spiegler, C.; Bannwarth, W.; Trzeciak, A.; Englert, G.; Labhardt, A.; Schönholzer, P. *Perspectives in Medicinal Chemistry*, Editor Testa, B.; Kyburz, E.; Fuhrer, W.; Giger, R., Weinheim, New York, Basel, Cambridge: Verlag Helvetica Chimica Acta, 1993, 513-531; Bannwarth, W.; Gerber, F.; Grieder, A.; Knierzinger, A.; Müller, K.; Obrecht. D.; Trzeciak, A. *Can. Pat. Appl.* CA2101599(131 pages). For splitting off the benzyl group 198 is conveniently hydrogenated e.g. with $H_2$ and a catalyst such as palladium on charcoal in a suitable solvent such as ethanol, DMF or ethyl acetate.

lower alkyl ($R^{43}$) can be introduced; thus, for example, $R^{43}$=$CH_2COOR^{55}$ and $CH_2CH_2COOR^{55}$ can be introduced by treatment with the appropriate 2-halo acetic and, respectively, 3-halo propionic acid derivatives. Any other functionalization of diarylamino groups known can be employed for introduction of substituents $R^{43}$.

iii: Cleavage of the methoxy groups of 199, conveniently by treatment with excess boron tribromide in dichloromethane at temperatures ranging from about −20° to about room temperature.

iv: The intermediate bis-phenol derivative is preferably reacted with $R^{39}$ and $R^{40}$—X' (X'=OTf, Br, I) in the presence of strong bases such as sodium hydride in tetrahydrofuran, dioxan or DMF in the presence of a phase transfer catalyst such as TDA-1. Any other functionalization for phenol groups can be employed for introduction of substituents $R^{39}$ and $R^{40}$.

v: The cyano group of 199 and, respectively, 200 is hydrolyzed under acidic conditions, e.g. with 25% aqueous hydrochloric acid in a suitable solvent such as dioxane at an elevated temperature, conveniently at about 100° C.

vi: The phthalimide group is cleaved, conveniently by hydrazinolysis, e.g. with hydrazine hydrate in suitable solvent such as ethanol.

vii: The free amino group is conveniently protected with reagents such as 9-fluorenylmethoxcarbonyl chloride or 9-fluorenylmethoxycarbonyl succinimide using a base such as sodium carbonate or triethylamine in suitable solvent or mixture of solvents such as dioxane and water, or dichloromethane to yield 201 and, respectively, 202.

iii: Double ortho bromination of 203 is performed preferably with excess bromine in acetic acid and dichloromethane. In a similar fashion $R^{41}=R^{42}=NO_2$ can be introduced by treatment with $HNO_3$ in acetic acid and $R^{41}=R^{42}=CH_2-NPht$ by treatment with hydroxymethyl phthalimide in $H_2SO_4$. Any other functionalization by electrophilic aromatic substitution can be employed for introduction of substituents $R^{41}$ and $R^{42}$.

iv: The amino group is protected, conveniently Cbz-protected, with reagents such as benzyloxycarbonyl chloride or succinimide in a suitable solvent such as dioxane in the presence of a base such as aqueous sodium hydroxide.

v: The carboxylic acid group is esterified, preferably with DBU and methyl iodide in DMF to yield 204.

vi: Regioselective bromination of 203 is performed preferably with bromine in acetic acid and dichloromethane. In a similar fashion $R^{41}=NO_2$ can be introduced by treatment

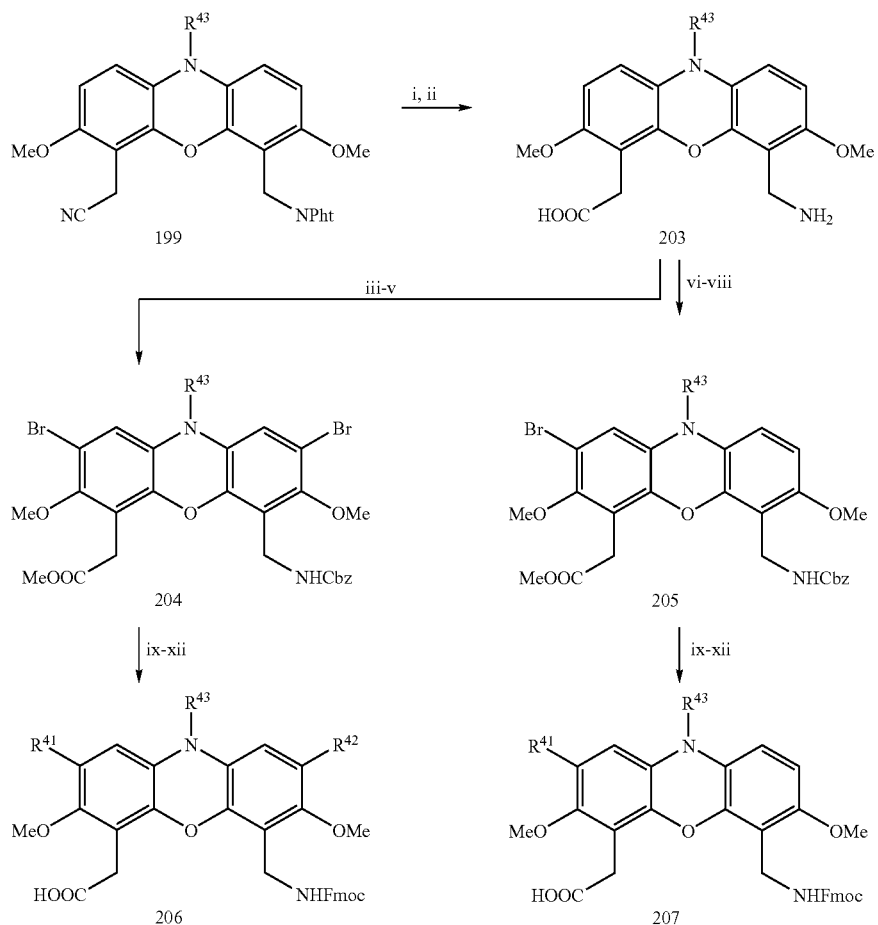

Scheme 41 i: The cyano group of 199 is hydrolyzed, conveniently under acidic conditions, e.g. with 25% aqueous hydrochloric acid in a suitable solvent such as dioxane at an elevated temperature, e.g. at about 100° C.

ii: The phthalimide group of the intermediate is cleaved, conveniently by hydrazinolysis, e.g. with hydrazine hydrate in a suitable solvent such as ethanol to yield 203.

with $HNO_3$ in acetic acid and $R^{41}=CH_2-NPht$ by treatment with hydroxymethyl phthalimide in $H_2SO_4$.

vii: The amino group is conveniently Cbz-protected with reagents such as benzyloxycarbonyl chloride or succinimide in a suitable solvent such as dioxane in presence of a base such as aqueous sodium hydroxide.

viii: The carboxylic acid group is esterified, preferably with DBU and methyl iodide in DMF to yield 205.

ix: Introduction of lower alkyl, substituted lower alkyl and aryl substituents ($R^{41}$)for 205 and ($R^{41}$ and $R^{42}$) for 204, conveniently by palladium(0)-catalyzed Stille-(Stille, J. K. *Angew. Chem.* 1986, 68, 504) and Suzuki-couplings (Oh-e, T.; Mijaura, N.; Suzuki, A. *J. Org. Chem.* 1993, 58, 2201). Any other functionalization known for aryl bromides can be employed for introduction of substituents $R^{41}$ and $R^{42}$.

x: Removal of the Cbz-group, e.g. by hydrogenation using $H_2$ and a catalyst such as palladium on charcoal in a suitable solvent such as ethanol, DMF and ethyl acetate.

xi: Hydrolysis of the ester group, conveniently under acidic conditions, e.g. with 25% aqueous hydrochloric acid in a suitable solvent such as dioxane at an elevated temperature, preferably at about 100° C.

xii: The intermediate free amino acid formed is conveniently protected with reagents such as 9-fluorenylmethoxcarbonyl chloride or 9-fluorenylmethoxcarbonyl succinimide using a base such as sodium carbonate or triethyl amine in a suitable solvent or mixture of solvents such as dioxane and water, or dichloromethane to yield 206 and 207.

Templates(d) can be prepared according to D. Obrecht, U. Bohdal, C. Lehmann, P. Schönholzer, K. Müller, *Tetrahedron* 1995, 51, 10883; D. Obrecht, C. Abrecht, M. Altorfer, U. Bohdal, A. Grieder, M. Kleber, P. Pfyffer, K. Müller, *Helv. Chim. Acta* 1996, 79, 1315-1337.

Templates (e1) and (e2): See R. Müller, L. Revesz, *Tetrahedron Lett.* 1994, 35,4091; H.-G. Lubell, W. D. Lubell, *J. Org. Chem.* 1996, 61, 9437; L. Colombo, M. DiGiacomo, G. Papeo, O. Carugo, C. Scolastico, L. Manzoni, *Tetrahedron Lett.* 1994, 35,4031.

Templates (e3): See S. Hanessian, B. Ronan, A. Laoui, *Bioorg. Med. Chem. Lett.* 1994, 4, 1397.

Templates (e4): See S. Hanessian, G. McNaughton-Smith, *Bioorg. Med. Chem. Lett.* 1996, 6, 1567.

Templates (f): See T.P. Curran, P. M. McEnay, *Tetrahedron Lett.* 1995, 36, 191-194.

Templates (g): See D. Grarnberg, C. Weber, R. Beeli, J. Inglis, C. Bruns, J. A. Robinson, *Helv. Chem. Acta* 1995, 78, 1588-1606; K. H. Kim, J. P. Durnas, J. P. Gennanas, *J. Org. Chem.* 1996, 61, 3138-3144.

Templates (h): See S. de Lombart, L. Blanchard, L. B. Stamford, D. M. Sperbeck, M. D. Grim, T. M. Jenson, H. R. Rodriguez, *Tetrahedron Lett.* 1994, 35, 7513-7516.

Templates (i1): See J. A. Robl, D. S. Karanewski, M. M. Asaad, *Tetrahedron Lett.* 1995, 5, 773-758.

Templates (i2): See T. P. Burkholder, T.-B. Le, E. L. Giroux, G. A. Flynn, *Bioorg. Med. Chem. Lett.* 1992, 2, 579.

Templates (i3) and (i4): See L. M. Simpkins, J. A. Robl, M. P. Cimarusti, D. E. Ryono, J. Stevenson, C.-Q. Sun, E. W. Petrillo, D. S. Karanewski, M. M. Asaad, J. E. Bird, T. R. Schaeffer, N.C. Trippodo, Abstracts of papers, 210th Am. Chem. Soc Meeting, Chicago, Ill., MEDI 064 (1995).

Templates (k): See D. Benlshai, A. R. McMurray, *Tetrahedron* 1993, 49, 6399.

Templates (l): See E. G. von Roedem, H. Kessler, *Angew. Chem. Int. Ed. Engl.* 1994, 33, 687-689.

Templates (m): See R. Gonzalez-Muniz, M. J. Dominguez, M. T. Garcia-Lopez, *Tetrahedron* 1992, 48, 5191-5198.

Templates (n): See F. Esser, A. Carpy, H. Briem, H. Köppen, K.-H. Pook, *Int. J. Pept. Res.* 1995, 45, 540-546.

Templates (o): See N. De la Figuera, I. Alkorta, T. Garcia-Lopez, R. Herranz, R. Gonzalez-Muniz, *Tetrahedron* 1995, 51, 7841.

Templates (p): See U. Slomcynska, D. K. Chalmers, F. Comille, M. L. Smythe, D. D. Benson, K. D. Moeller, G. R. Marshall, *J. Org. Chem.* 1996, 61, 1198-1204.

The β-hairpin peptidomimetics of the invention can be used in a wide range of applications in order to inhibit the growth of or to kill microorganisms. In particular they can be used to selectively inhibit the growth of or to kill microorganisms such as *Pseudomonas aeruginosa* and *Acinetobacter*.

They can be used for example as disinfectants or as preservatives for materials such as foodstuffs, cosmetics, medicaments and other nutrient-containing materials. The β-hairpin peptidomimetics of the invention can also be used to treat or prevent diseases related to microbial infection in plants and animals.

For use as disinfectants or preservatives the β-hairpin peptidomimetics can be added to the desired material singly, as mixtures of several β-hairpin peptidomirnmetics or in combination with other antimicrobial agents. The β-hairpin peptidomimetics may be administered per se or may be applied as an appropriate formulation together with carriers, diluents or excipients well known in the art.

When used to treat or prevent infections or diseases related to such infections, particularly infections related to respiratory diseases such as cystic fibrosis, emphysema and asthma, infections related to skin or soft tissue diseases such as surgical wounds, traumatic wounds and burn wounds, infections related to gastrointestinal diseases such as epidemic diarrhea, necrotizing enterocolitis and typhlitis, infections related to eye diseases such as keratitis and endophtbalmitis, infections related to ear diseases such as otitis, infections related to CNS diseases such as brain abscess and meningitis, infections related to bone diseases such as osteochondritis and osteomyelitis, infections related to cardiovascular diseases such as endocartitis and pericarditis, infections related to gastrourinal diseases such as epididymitis, prostatitis and urethritis, the β-hairpin peptidomimetics can be administered singly, as mixtures of several β-hairpin peptidomimetics, in combination with other antimicrobial or antibiotic agents, or anti cancer agents, or antiviral (e.g. anti-HIV) agents, or in combination with other pharmaceutically active agents. The β-hairpin peptidomimetics can be administered per se or as pharmaceutical compositions.

Pharmaceutical compositions comprising β-hairpin peptidomimetics of the invention may be manufactured by means of conventional mixing, dissolving, granulating, coated tablet-making, levigating, emulsifying, encapsulating, entrapping or lyophilizing processes. Pharmaceutical compositions may be formulated in conventional manner using one or more physiologically acceptable carriers, diluents, excipients or auxilliaries which facilitate processing of the active β-hairpin peptidomimetics into preparations which can be used pharmaceutically. Proper formulation depends upon the method of administration chosen.

For topical administration the β-hairpin peptidomimetics of the invention may be formulated as solutions, gels, ointrnents, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injections, the β-hairpin peptidomimetics of the invention may be formulated in adequate solutions, preferably in physiologically compatible buffers such as Hink's solution, Ringer's solution, or physiological saline buffer. The solution may contain formulatory agents such as suspending, stabilizing and/or dispersing agents. Alternatively, the β-hairpin peptidomimetics of the invention may be in powder form for combination with a suitable vehicle, e.g., sterile pyrogen-free water, before use.

For transmucosal administration, penetrants appropriate to the barrier to be permeated are used in the formulation as known in the art.

For oral administration, the compounds can be readily formulated by combining the active β-hairpin peptidomimetics of the invention with pharmaceutically acceptable carriers well known in the art. Such carriers enable the β-hairpin peptidomimetics of the invention to be formulated as tablets, pills, dragees, capsules, liquids, gels, syrups, slurries, suspensions etc., for oral ingestion of a patient to be treated. For oral formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP); granulating agents; and binding agents. If desired, desintegrating agents may be added, such as cross-linked polyvinylpyrrolidones, agar, or alginic acid or a salt thereof, such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. In addition, flavoring agents, preservatives, coloring agents and the like may be added.

For buccal administration, the composition may take the form of tablets, lozenges, etc. formulated as usual.

For administration by inhalation, the β-hairpin peptidomimetics of the invention are conveniently delivered in form of an aeorosol spray from pressurized packs or a nebulizer, with the use of a suitable propellant, e.g. dichlorodifluoromethane, trichlorofluoromethane, carbon dioxide or another suitable gas. In the case of a pressurized aerosol the dose unit may be determined by providing a valve to deliver a metered amount. Capsules and cartridges of e.g. gelatin for use in an inhaler or insufflator may be formulated containing a powder mix of the β-hairpin peptidomimetics of the invention and a suitable powder base such as lactose or starch.

The compounds may also be formulated in rectal or vaginal compositions such as suppositories together with appropriate suppository bases such as cocoa butter or other glycerides.

In addition to the formulations described previously, the β-hairpin peptidomimetics of the invention may also be formulated as depot preparations. Such long acting formulations may be administered by implantation (e.g. subcutaneously or intranuscularly) or by intramuscular injection. For the manufacture of such depot preparations the β-hairpin peptidomimetics of the invention may be formulated with suitable polymeric or hydrophobic materials (e.g. as an emulsion in an acceptable oil) or ion exchange resins, or as sparingly soluble salts.

In addition, other pharmaceutical delivery systems may be employed such as liposomes and emulsions well known in the art. Certain organic solvents such as dimethylsulfoxide also may be employed. Additionally, the β-hairpin peptidomimetics of the invention may be delivered using a sustained-release system, such as semipermeable matrices of solid polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic agent, additional strategies for protein stabilization may be employed.

As the β-hairpin pepdidomimetics of the invention may contain charged residues, they may be included in any of the above-described formulations as such or as pharmaceutically acceptable salts. Pharmaceutically acceptable salts tend to be more soluble in aqueous and other protic solvents than are the corresponding free base forms.

The β-hairpin peptidomimetics of the invention, or compositions thereof, will generally be used in an amount effective to achieve the intended purpose. It is to be understood that the amount used will depend on a particular application.

For example, for use as a desinfectant or preservative, an antimicrobially effective amount of a β-hairpin peptidomimetic of the invention, or a composition thereof, is applied or added to the material to be desinfected or preserved. By antimicrobially effective amount is meant an amount of a β-hairpin peptidomimetic of the invention or composition that inhibits the growth of, or is lethal to, a target microbe population. While the antimicrobially effective amount will depend on a particular application, for use as desinfectants or preservatives the β-hairpin peptidomimetics of the invention, or compositions thereof, are usually added or applied to the material to be desinfected or preserved in relatively low amounts. Typically, the β-hairpin peptidomimetics of the invention comprise less than about 5% by weight of a desinfectant solution or material to be preserved, preferably less than 1% by weight and more preferably less than 0.1% by weight. An ordinary skilled expert will be able to determine antimicrobially effective amounts of particular β-hairpin peptidomimetics of the invention for particular applications without undue experimentation using, for example, the in vitro assays provided in the examples.

For use to treat or prevent microbial infections or diseases related to such infections, the β-hairpin pepidomimetics of the invention, or compositions thereof, are administered or applied in a therapeutically effective amount. By therapeutically effective amount is meant an amount effective in ameliorating the symptoms of, or in ameliorating, treating or preventing microbial infections or diseases related thereto. Determination of a therapeutically effective amount is well within the t: capacities of those skilled in the art, especially in view of the detailed disclosure provided herein.

As in the case of desinfectants and preservatives, for topical administration to treat or prevent bacterial infections a therapeutically effective dose can be determined using, for example, the in vitro assays provided in the examples. The treatment may be applied while the infection is visible, or even when it is not visible. An ordinary skilled expert will be able to determine therapeutically effective amounts to treat topical infections without undue experimentation.

For systemic administration, a therapeutically effective dose can be estimated initially from in vitro assays. For example, a dose can be formulated in animal models to achieve a circulating β-hairpin 30 peptidomimetic concentration range that includes the $IC_{50}$ as determined in the cell culture (i.e. the concentration of a test compound that is lethal to 50% of a cell culture), the MIC, as determined in cell culture (i.e. the concentration of a test compound that is lethal to 100% of a cell culture). Such information can be used to more accurately determine useful doses in humans.

Initial dosages can also be determined from in vivo data, e.g. animal models, using techniques that are well known in the art. One having ordinary skills in the art could readily optimize administration to humans based on animal data.

Dosage amount for applications as antimicrobial agents may be adjusted individually to provide plasma levels of the β-hairpin peptidomimetics of the invention which are sufficient to maintain the therapeutic effect. Therapeutically effective serum levels may be achieved by administering multiple doses each day.

In cases of local administration or selective uptake, the effective local concentration of the β-hairpin peptidomimetics of the invention may not be related to plasma concentration. One having the skills in the art will be able to optimize therapeutically effective local dosages without undue experimentation.

The amount of β-hairpin peptidomimetics administered will, of course, be dependent on the subject being treated, on the subject's weight, the severity of the affliction, the manner of administration and the judgement of the prescribing physician.

The antimicrobial therapy may be repeated intermittently while infections are detectable or even when they are not detectable. The therapy may be provided alone or in combination with other drugs, such as for example antibiotics or other antimicrobial agents.

Normally, a therapeutically effective dose of the β-hairpin peptidomimetics described herein will provide therapeutic benefit without causing substantial toxicity.

Hemolysis of red blood cells is often employed for assessment of toxicity of related compounds such as prolegrin or fachyplesin. Values are given as %-lysis of red blood cells observed at a concentration of 100 μg/ml. Typical values determined for cationic peptides such as protegrin and iachyplesin range between 30-40% with average MIC-values of 1-5 μg/ml over a wide range of pathogens. Normally, β-hairpin peptidomimetics of the invention will show hemolysis in a range of 0.5-10%, often in a range of 1-5%, at activity levels comparable to those mentioned above for protegrin and tachyplesin. Thus preferred compounds exhibit low MIC-values and low %-hemolysis of red blood cells observed at a concentration of 100 μg/ml.

Toxicity of the β-hairpin peptidomimetics of the invention herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in humans. The dosage of the β-hairpin peptidomimetics of the invention lies preferably within a range of circulating concentrations that include the effective dose with little or no toxicity. The dosage may vary within the range depending upon the dosage form employed and the route of administration utilized. The exact formulation, route of administration and dose can be chosen by the individual physician in view of the patient's condition (see, e.g. Fingl et al. 1975, In: *The Pharmacological Basis of Therapeutics*, Ch.1, p.1).

The following Examples illustrate the invention in more detail but are not intended to limit its scope in any way. The following abbreviations are used in these Examples:

HBTU: 1-benzotriazol-1-yl-tetramethylurounium hexafluorophosphate (Knorr et al. *Tetrahedron Lett.* 1989, 30, 1927-1930);
HOBt: 1-hydroxybenzotriazole;
DIEA: diisopropylethylamine;
HOAT: 7-aza-1-hydroxybenzotriazole;
HATU: O-(7-aza-benzotriazole-1-yl)-N,N,N',N'-tetramethyluronoium hexafluorophosphate (Carpino et al. *Tetrahedron Lett.* 1994, 35, 2279-2281).

EXAMPLES

1. Peptide Synthesis

Coupling of the First Protected Amino Acid Residue to the Resin 0.5 g of 2-chlorotritylchloride resin (Barlos et al. *Tetrahedron Lett.* 1989, 30, 3943-3946) (0.83 mMol/g, 0.415 mmol) was filled into a dried flask. The resin was suspended in $CH_2Cl_2$ (2.5 ml) and allowed to swell at room temperature under constant stirring for 30 min. The resin was treated with 0.415 rnMol (1 eq) of the first suitably protected amino acid residue (see below) and 284 μl (4 eq) of diisopropylethylamine (DIEA) in $CH_2Cl_2$ (2.5·ml), the mixture was shaken at 25° C. for 4 hours. The resin colour changed to purple and the solution remained yellowish. The resin was shaken ($CH_2Cl_2$/MeOH/DIEA:17/2/1), 30 mnl for 30 rmin; then washed in the following order with $CH_2Cl_2$ (1×), DMF (1×), $CH_2Cl_2$ (1×), MeOH (1×), $CH_2Cl_2$(1 x), MeOH (1×), $CH_2Cl_2$ (2×), $Et_2O$ (2×) and dried under vacuum for 6 hours.

Loading was typically 0.6-0.7 mMol/g.

The following preloaded resin was prepared: Fmoc-ProO-chlorotritylresin.

Synthesis of the Fully Protected Peptide Fragment

The synthesis was carried out using a Syro-peptide synthesizer (Multisyntech) using 24 to 96 reaction vessels. In each vessel was placed 60 mg (weight of the resin before loading) of the above resin. The following reaction cycles were programmed and carried out:

| Step | Reagent | Time |
| --- | --- | --- |
| 1 | $CH_2Cl_2$, wash and swell (manual) | 3 × 1 min. |
| 2 | DMF, wash and swell | 1 × 5 min |
| 3 | 40% piperidine/DMF | 1 × 5 min. |
| 4 | DMF, wash | 5 × 2 min. |
| 5 | 5 equiv. Fmoc amino acid/DMF + 5 eq. HBTU + 5 eq. HOBt + 5 eq. DIEA | 1 × 120 min. |
| 6 | DMF, wash | 4 × 2 min. |
| 7 | $CH_2Cl_2$, wash (at the end of the synthesis) | 3 × 2 min. |

Steps 3 to 6 are repeated to add each amino-acid.

Cleavage of the Fully Protected Peptide Fragment

After completion of the synthesis, the resin was suspended in 1 ml (0.39 mMol) of 1% TFA in $CH_2Cl_2$ (v/v) for 3 minutes, filtered and the filtrate was neutralized with 1 ml (1.17 mMol, 3 eq.) of 20% DIEA in $CH_2Cl_2$ (v/v). This procedure was repeated twice to ensure completion of the cleavage. The filtrate was evaporated to dryness and the product was fully deprotected [cleavage mixture containing 95% trifluoroacetic acid (TFA), 2.5% water and 2.5% triisopropylsilane (TIS)] to be analyzed by reverse phase-HPLC (column Cls) and ESI-MS to monitor the efficiency of the linear peptide synthesis.

Cyclization of the Linear Peptide 100 mg of the fully protected linear peptide were dissolved in DMF (9 ml, conc. 10 mg/ml). Then 41.8 mg (0.110 mMol, 3 eq.) of HATU, 14.9 mg (0.110 mMol, 3 eq) of HOAt and 1 ml (0.584 mMol) of 10% DIEA in DMF (v/v) were added and the mixture vortexed at 20° C. for 16 hours and subsequently concentrated under high vacuum. The residue was partitioned between $CH_2Cl_2$ and $H_2O/CH_3CN$ (90/10: v/v). The $CH_2Cl_2$ phase was evaporated to yield the fully protected cyclic peptide.

Deprotection and Purification of the Cyclic Peptide:

The cyclic peptide obtained was dissolved in 1 ml of the cleavage mixture containing 95% trifluoroacetic acid (TFA), 2.5% water and 2.5% triisopropylsilane (TIS). The mixture was left to stand at 20° C. for 2.5 hours and then concentrated under vacuum. The residue was dissolved in a solution of H₂O/acetic acid (75/25: v/v) and the mixture extracted with di-isopropylether.

The water phase was dried under vacuum and then the product purified by preparative reverse phase HPLC.

After lyophilisation products were obtained as a white powder and analysed by ESI-MS. The analytical data comprising HPLC retention times and ESI-MS are shown in table 1.

Analytical HPLC retention times (RT, in minutes) were determined using a VYDAC 218MS5215 column with the following solvents A (H₂O+0.02% TFA) and B (CH₃CN) and the gradient: 0 min: 92% A, 8% B; 8 min: 62% A 38% B; 9-12 min: 0% A, 100% B.

Examples 1-7

(n=12) are shown in table 1. The peptides were synthesized starting with the amino acid Pro which was grafted to the resin. Starting resin was Fmoc-ProO-chlorotrityl resin, which was prepared as described above. The linear peptides were synthesized on solid support according to procedure described above in the following sequence: Resin-Pro-$^D$Pro-P12-P11-P10-P9-P8-P7-P6-P5-P4-P3-P2-P1, cleaved from the resin, cyclized, deprotected and purified as indicated.

HPLC-retention times (minutes) were determined using the gradient described above:

Ex.1 (5.73; 6.29)*; Ex.2 (5.13; 5.51; 5.75)*; Ex.3 (4.83; 5.37)*; Ex.4 (4.79; 5.43)*; Ex.5 (5.27; 5.85)* Ex.6 (5.3 1; 6.03); Ex.7 (4.59).

* double peaks which show both correct MS and chiral amino acid analysis. At 60° only one peak is observed.

method (see ref 1, below) examined in sterile 96-wells plates (Nunclon polystyrene microtiter plates) in a total volume of 100 µl. Innocula of the microorganisms were prepared with 0.5 Mcfarland standard and then diluted into Müeller-Hinton (MH⁺) broth to give appr. $10^6$ colony forming units (CFU)/ml for bacteria Aliquots (50 µl) of the innocula were added to 50 µl of MH broth containing the peptide in serial twofold dilutions. For the screening of the peptides displaying selectivity, the following microorganisms were used: *Escherichia coli* (ATCC 25922), *Pseudomonas aeruginosa* (*P. aeruginosa*) (ATCC 27853), *Staphylococcus aureus* (ATCC 29213 and ATCC 25923), and clinical isolates of *Pseudomonas aeruginosa* (*P. aeruginosa*) V02 16085 and *Acinetobacter* (Acinetobacter V04 19905/1, *Acinetobacter* V12 21143/1 and *Acinetobacter* V12 21193/1). Antimicrobial activities of the peptides were expressed as the minimal inhibitory concentration (MIC) in µg/ml at which no visible growth was observed after 18-20 hours of incubation of the microtiter plates at 37° C.

2.3. Antimicrobial Activity of the Peptides in 0.9% Saline

Salt sensitivity of the peptides was tested by the microtiter serial dilution assay as described above. Only MH broth was replaced by MH broth containing 0.9% NaCl.

2.4. Antimicrobial Activity of the Peptides in Human Serum

Serum binding of the peptides was tested by the microtiter serial dilution assay as described above. Only MH broth was replaced by MH broth containing 90% human serum (BioWhittaker).

TABLE 1

Examples (Ex)

| Ex. | SEQ ID | P1 | P2 | P3 | P4 | P5 | P6 | P7 | P8 | P9 | P10 | P11 | P12 | Template | Purity %[a] | [m/z], z = 2 |
|---|---|---|---|---|---|---|---|---|---|---|---|---|---|---|---|---|
| 1 | SEQ ID NO:1 | Arg | Trp | Leu | Lys | Lys | Arg | Arg | Trp | Leu | Tyr | Tyr | Arg | $^D$Pro$^L$Pro | 100 | 1000.3 |
| 2 | SEQ ID NO:2 | Arg | Trp | Leu | Lys | Lys | Arg | Arg | Trp | Lys | Tyr | Val | Arg | $^D$Pro$^L$Pro | 100 | 976.1 |
| 3 | SEQ ID NO:3 | Arg | Trp | Leu | Lys | Lys | Arg | Arg | Trp | Lys | Thr | Tyr | Arg | $^D$Pro$^L$Pro | 54 | 977.0 |
| 4 | SEQ ID NO:4 | Arg | Trp | Leu | Lys | Lys | Arg | Arg | Trp | Lys | Gln | Tyr | Arg | $^D$Pro$^L$Pro | 100 | 991.1 |
| 5 | SEQ ID NO:5 | Arg | Trp | Leu | Val | Lys | Arg | Arg | Trp | Lys | Tyr | Tyr | Arg | $^D$Pro$^L$Pro | 100 | 993.4 |
| 6 | SEQ ID NO:6 | Arg | Trp | Leu | Lys | Lys | Arg | Arg | Trp | Val | Tyr | Tyr | Arg | $^D$Pro$^L$Pro | 100 | 993.5 |
| 7 | SEQ ID NO:7 | Arg | Trp | Leu | Lys | Lys | Arg | Arg | Trp | Lys | Tyr | Gln | Arg | $^D$Pro$^L$Pro | 100 | 991.2 |
| 8 | SEQ ID NO:8 | Arg | Trp | Leu | Lys | Lys | Arg | Arg | Trp | Lys | Tyr | Leu | Arg | $^D$Pro$^L$Pro | 24 | 983.1 |

[a] %-puritiy of compounds after prep. HPLC.

2. Biological Methods 2.1. Preparation of the Peptides.

Lyophilized peptides were weighed on a Microbalance (Mettler MT5) and dissolved in sterile water containing 0.01% acetic acid.

2.2. Antimicrobial Activity of the Peptides.

The selective antimicrobial activities of the peptides were determined by the standard NCCLS broth microdilution 2.5. Hemolysis The peptides were tested for their hemolytic activity against human red blood cells (hRBC). Fresh hRBC were washed three times with phosphate buffered saline (PBS) by centrifugation for 10 min at 2000×g. Peptides at a concentration of 100 µg/ml were incubated with 20% v/v hRBC for 1 hour at 37° C. The final erythrocyte concentration was appr. $0.9 \times 10^9$/ml. A value of 0% resp. 100% cell lysis was determined by incubation of the hRBC in the presence of PBS alone and resp. 0.1% Triton X-100 in H₂O. The samples were centrifuged and the supernatant was 20 fold diluted in PBS buffer and the optical density (OD) of the sample at 540 nM was measured. The 100% lysis value ($OD_{540}H_2O$) gave an OD of approximately 1.6-2.0. Percent hemolysis was calculated as follows:

($OD_{540}$peptide/$OD_{540}H_2O$)×100%.

2.6. Results

The results of the experiments described above are indicated in Table 2 and Table 3, herein below.

REFERENCES

1. National Committee for Clinical Laboratory Standards. 1993. Methods for dilution antimicrobial susceptibility tests for bacteria that grow aerobically, 3rd ed. Approved standard M7-A3. National Committee for Clinical laboratory standards, Villanova, Pa.
2. Mossman T. J Immunol Meth 1983, 65, 55-63
3. Berridge M V, Tan A S. *Archives of Biochemistry & Biophysics* 1993, 303, 474-482

TABLE 2

Minimal inhibitory concentrations (MIC in μg/ml) in Mueller-Hinton broth and percentage hemolyses at a concentration of 100 μg/ml of peptide

| Ex. | *Escherichia coli* ATCC 25922 | *Escherichia coli* ATCC 43827 | *Staphylococcus attreus* ATCC 29213 | *Staphylococcus aureus* ATCC 25923 | *P. aeruginosa* ATCC 27853 | *P. aeruginosa* VO216085 | *Acinetobacter* V1221143/1 | *Acinetobacter* V1221193/1 | Hemolysis at 100 μg/ml |
|---|---|---|---|---|---|---|---|---|---|
| 1 | 25 | 25 | 25 | 50 | 12.5 | 9.4 | 6.2 | 6.2 | 0.5 |
| 2 | 50 | 100 | 100 | 100 | 3.1 | 3.1 | 6.2 | 6.2 | 0.5 |
| 3 | 100 | 200 | 100 | 100 | 6.2 | 6.2 | 25 | 100 | 1.5 |
| 4 | 100 | 100 | 100 | 200 | 3.1 | 3.1 | 6.2 | 12.5 | 0.6 |
| 5 | 25 | n.d. | 100 | 100 | 6.2 | n.d. | n.d. | n.d. | 0.5 |
| 6 | 12.5 | n.d. | 100 | 100 | 6.2 | n.d. | n.d. | n.d. | 0.5 |
| 7 | 100 | n.d. | 200 | 25 | 9.4 | n.d. | n.d. | n.d | 0.7 |
| 8 | 50 | n.d. | 100 | 100 | 6.2 | n.d. | n.d. | n.d. | 0.4 | n.d.: not determined

TABLE 3

Minimal inhibitory concentrations (MIC in μg/ml) in Mueller-Hinton broth containing 0.9% NaCl

| Ex. | *Escherichia coli* ATCC 25922 | *Escherichia coli* ATCC 43827 | *P. aeruginosa* ATCC 278853 | *P. aeruginosa* VO216085 | *Acinetobacter* V12 21143/1 | *Acinetobacter* V12 21193/1 |
|---|---|---|---|---|---|---|
| 1 | 100 | 200 | 50 | 50 | 6.2 | 6.2 |
| 2 | 100 | 100 | 9.4 | 6.2 | 12.5 | 25 |
| 3 | 200 | 200 | 200 | 9.4 | 25 | 100 |
| 4 | 100 | 200 | 6.2 | 3.1 | 12.5 | 25 |

The invention claimed is:

1. A compound of the general formula

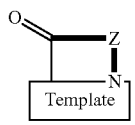

(I)

wherein the template is $^D$Pro-$^L$Pro

Z is a chain of 12 α-amino acid residues, the positions of said amino acid residues in said chain being counted starting from the N-terminal amino acid, wherein the amino acids in positions 1-12 are:
P1: Arg;
P2: Trp;
P3: Leu;
P4: Lys or Val;
P5: Lys;
P6: Arg;
P7: Arg;
P8: Trp;
P9: Leu, Val or Lys;
P10: Tyr or Gln;
P11: Val, Leu, Tyr or Gln; and
P12: Arg;
with the proviso that
the amino acid residue in position P4 is Val; and/or
the amino acid residue in position P9 is Leu or Val; and/or
the amino acid residue in position P10 is Gln; and/or
the amino acid residue in position P11 is Val or Leu or Gln;
and the enantiomer thereof and pharmaceutically acceptable salts thereof.

2. The compound of claim 1 wherein the amino acid residues in position 1-12 are:
P1: Arg;
P2: Trp;
P3: Leu;
P4: Lys;
P5: Lys;
P6: Arg;
P7: Arg;
P8: Trp;
P9: Leu;
P10: Tyr;
P11: Tyr; and
P12: Arg.

3. The compound of claim 1 wherein the amino acid residues in position 1-12 are:
P1: Arg;
P2: Trp;
P3: Leu;
P4: Lys;
P5: Lys;
P6: Arg;
P7: Arg;
P8: Trp;
P9: Lys;
P10: Tyr;

P11: Val; and
P12: Arg.

4. The compound of claim 1 wherein the amino acid residues in position 1-12 are:
P1: Arg;
P2: Trp;
P3: Leu;
P4: Lys;
P5: Lys;
P6: Arg;
P7: Arg;
P8: Trp;
P9: Lys;
P10: Gln;
P11: Tyr; and
P12: Arg.

5. The compound of claim 1 wherein the amino acid residues in position 1-12 are:
P1: Arg;
P2: Trp;
P3: Leu;
P4: Val;
P5: Lys;
P6: Arg;
P7: Arg;
P8: Trp;
P9: Lys;
P10: Tyr;
P11: Tyr; and
P12: Arg.

6. The compound of claim 1 wherein the amino acid residues in position 1-12 are:
P1: Arg;
P2: Trp;
P3: Leu;
P4: Lys;
P5: Lys;
P6: Arg;
P7: Arg;
P8: Trp;
P9: Val;
P10: Tyr;
P11: Tyr; and
P12: Arg.

7. The compound of claim 1 wherein the amino acid residues in position 1-12 are:
P1: Arg;
P2: Trp;
P3: Leu;
P4: Lys;
P5: Lys;
P6: Arg;
P7: Arg;
P8: Trp;
P9: Lys;
P10: Tyr;
P11: Gln; and
P12: Arg.

8. A pharmaceutical composition containing a compound according to claim 1 and a pharmaceutically inert carrier.

9. The pharmaceutical composition of claim 8 which is in a form suitable for oral, topical, transdermal, injection, buccal, transmucosal, pulmonary or inhalation administration.

10. The pharmaceutical composition of claim 8 which is in the form of a tablet, dragee, capsule, solution, liquid, gel, plaster, cream, ointment, syrup, slurry, suspension, spray, nebulizer or suppository.

11. A method for treating an infection, comprising administering a compound of claim 1 to a patient in need thereof.

12. The method of claim 11, wherein said infection is related to cystic fibrosis, emphysema, asthma, skin or soft tissue diseases; surgical wounds, traumatic wounds, burns, epidemic diarrhea, necrotizing enterocolitis, typhlitis, keratitis, endophthalmitis, otitis, brain abscess, meningitis, osteochondritis, osteomyelitis, endocarditis, pericarditis, epididymitis, prostatitis or urethritis.

13. A method for disinfecting or preserving foodstuffs, cosmetics, medicaments and other nutrient-containing materials comprising adding an effective amount of a compound of claim 1 as a disinfectant or preservative to such foodstuffs, cosmetics, medicaments and other nutrient-containing materials.

* * * * *

UNITED STATES PATENT AND TRADEMARK OFFICE
CERTIFICATE OF CORRECTION

| | | |
|---|---|---|
| PATENT NO. | : 7,582,604 B2 | Page 1 of 1 |
| APPLICATION NO. | : 11/062021 | |
| DATED | : September 1, 2009 | |
| INVENTOR(S) | : Vrijbloed et al. | |

It is certified that error appears in the above-identified patent and that said Letters Patent is hereby corrected as shown below:

On the title page,

[*] Notice: Subject to any disclaimer, the term of this patent is extended or adjusted under 35 USC 154(b) by 289 days Delete the phrase "by 289 days" and insert -- by 566 days --

Signed and Sealed this

Fourth Day of May, 2010

David J. Kappos
*Director of the United States Patent and Trademark Office*